US007029861B1

(12) United States Patent
Beutler et al.

(10) Patent No.: US 7,029,861 B1

(45) Date of Patent: Apr. 18, 2006

(54) LPS-RESPONSE GENE COMPOSITIONS AND METHODS

(75) Inventors: Bruce A. Beutler, Dallas, TX (US); Alexander Poltorak, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 526 days.

(21) Appl. No.: 09/396,985

(22) Filed: Sep. 15, 1999

Related U.S. Application Data

(60) Provisional application No. 60/100,403, filed on Sep. 15, 1998, provisional application No. 60/102,392, filed on Sep. 29, 1998.

(51) Int. Cl.

| | |
|---|---|
| ***G01N 33/50*** | (2006.01) |
| ***C12Q 1/68*** | (2006.01) |
| ***C07H 21/04*** | (2006.01) |
| ***C07K 14/00*** | (2006.01) |
| ***C12N 5/00*** | (2006.01) |

(52) U.S. Cl. ............................ 435/7.2; 435/6; 435/7.1; 435/69.1; 435/320.1; 435/172.3; 435/325; 435/235.1; 435/375; 530/300; 530/350; 530/351; 536/23.1

(58) Field of Classification Search .................... 435/6, 435/7.1, 22, 69.1, 320.1, 7.2, 172.3, 325, 435/235.1, 375; 530/300, 350, 351; 576/23.1
See application file for complete search history.

(56) References Cited

U.S. PATENT DOCUMENTS

| | | | | |
|---|---|---|---|---|
| 4,215,051 | A | 7/1980 | Schroeder et al. | 260/346.7 |
| 4,554,101 | A | 11/1985 | Hopp | 260/112.5 |
| 4,603,102 | A | 7/1986 | Himmelmann et al. | 430/523 |
| 4,683,195 | A | 7/1987 | Mullis et al. | 435/6 |
| 4,683,202 | A | 7/1987 | Mullis | 435/91 |
| 4,800,159 | A | 1/1989 | Mullis et al. | 435/172.3 |
| 4,883,750 | A | 11/1989 | Whiteley et al. | 435/6 |
| 5,464,937 | A | 11/1995 | Sims et al. | 530/350 |
| 5,488,032 | A | 1/1996 | Dower et al. | 514/2 |
| 5,508,262 | A | 4/1996 | Norman, Jr. | 514/8 |
| 5,608,035 | A | 3/1997 | Yanofsky et al. | 530/324 |
| 5,726,148 | A | 3/1998 | Katoh et al. | 514/2 |
| 5,767,064 | A | 6/1998 | Sims et al. | 514/2 |
| 5,767,234 | A | 6/1998 | Yanofsky et al. | 530/327 |
| 5,776,731 | A | 7/1998 | Parnet et al. | 435/69.1 |
| 5,786,331 | A | 7/1998 | Barrett et al. | 514/15 |

FOREIGN PATENT DOCUMENTS

| | | |
|---|---|---|
| EP | 320 308 | 6/1989 |
| EP | 329 822 | 10/1990 |
| WO | WO 89/06700 | 7/1989 |
| WO | WO 90/07641 | 7/1990 |

OTHER PUBLICATIONS

Bell, et al., "A high-resolution map of the brown (b, Tyrp1) deletion complex of mouse Chromosome 4," *Mammalian Genome*. 6, 389-395, 1995.

Beutler et al., "Cachectin/tumor necrosis factor: Production, distribution and metabolic fate in vivo," *J. Immunol.*, 135: 3972-3977, 1985.

Beutler et al., "Passive immunization against cachetin/tumor necrosis factor protects mice from lethal effect of endotoxin, " *Science*, 229:869-871, 1985.

Beutler et al., "Control of cachectin (tumor necrosis factor) synthesis: mechanisms of endotoxin resistance," *Science*, 232:977-980, 1986.

Burn et al., "Increased exon-trapping efficency through modifications to the pSPL3 splicing vector," *Gene*. 161, 183-187, 1995.

Chaudhary et al. "Cloning and characterization of two toll/interleukin-1 receptor-like genes TIL3 and TIL4: evidence for a multi-gene receptor family in humans," *Blood*. 91, 4020-4027, 1998.

Cseh and Beutler, "Alternate cleavage of the cachectin/ tumor necrosis factor propeptide results in a larger, inactive form of secreted protein, " *J. Biol. Chem.* 264, 16256-16260, 1989.

Geppert et al., "Lipopolysaccharide signals activation of tumor necrosis factor biosynthesis through the ras/raf-1/ MEK/MAPK pathway," *Mol. Med.*, 1:93-103, 1994.

Gerard, "For whom the bell tolls," *Nature*, 395:217-219, 1998.

Han et al., "Endotoxin-responsive sequences control cachectin/tumor necrosis factor biosynthesis at the translation level," *J. Exp. Med.*, 171:465-475, 1990.

(Continued)

*Primary Examiner*—Joseph Murphy
*Assistant Examiner*—Nirmal S. Basi
(74) *Attorney, Agent, or Firm*—Fulbright & Jaworski

(57) ABSTRACT

The present invention describes a mutant TLR-4 in mice that does not recognize endotoxin and therefore does not stimulate the secretion of TNF from macrophages. Methods of detecting the mutation are provided; as are methods screening for drugs that may stimulate TNF production. Finally methods of incorporating and expressing the mutant TLR-4 genes into a host cell are contemplated.

26 Claims, 21 Drawing Sheets

OTHER PUBLICATIONS

Hayes and Zoon, "Priming of human monocytes for enhanced lipopolysaccharide responses: expression of alpha interferon, interferon regulatory factors, and tumor necrosis factor," *Infec. Immun.,* 61:3222-3227, 1993.

Haziot et al., "Resistance to endotoxin shock and reduced dissemination of gram-negative bacteria in CD 14-deficient mice," *Immunity,* 4:407-414, 1996.

Heine et al., "Cutting edge: cells that carry a null allele for toll-like receptor 2 are capable of responding to endotoxin," *J. Immunology,* 162:6971-6975, 1999.

Hirsch et al., "Identifcation of positive and negative regulatory elements governing cell-type-specific expression of the neural cell adhesion molecule gene," *Mol Cell Biol.* May 1990; 10(5):1959-1968, 1990.

Hoshino et al., "Cutting Edge: Toll-Like Receptor 4 (TLR4) —Deficient Mice Are Hyporesponsive to Lipoplysaccharide: Evidence for TLR4 as the Lps Gene Product," *Journal of Immunology,* 162:3749-3752, 1999.

Hu et al., "Resistance to salmonellosis in the chicken is linked to NRAMPI and TNC," *Genome Research.* 7, 693-704, 1997.

Kawai et al., "Unresponsiveness of MyD88-deficient mice to endotoxin," *Immunity,* 11(1):115-122, 1999.

Kirkland et al., Identification of lipopolysaccharide-binding proteins in 70Z/3 cells of photoaffinity cross-linking, *J. Biol. Chem.,* 265:9520-9525, 1990.

Kirschning et al., "human toll-like receptor 2 confers responsiveness to bacterial lipopolysaccharide," *J. Exp. Med.,* 188:2091-2097, 1998.

Kruys et al., "Constitutive activity of the tumor necrosis factor promoter is canceled by the 3' untranslated region in nonmacrophage cell lines; a transdominant factor overcomes this suppressive effect," *Proc. Natl. Acad. Sci. USA,* 89:673-677, 1992.

Kuhns et al., "Endotoxin and IL-1 hyporesponsiveness in a patient with recurrent bacterial infections," ABSTRACT, *J. Immunol.* 158, 3959-3964, 1997.

Lemaitre et al., "The dorsoventral regulatory gene cassette *spatzle/Toll/cactus* controls the potent antifungal response in *drosophilia* adults," *Cell.* 86, 973-983, 1996.

Macela et al., "The immune response against *Francisella tularensis* live vaccine strain in $Lps^n$ and $Lps^d$ mice," *FEMS Immunol. Med. Microbiol.* 13, 235-238, 1996.

Matsuura and Galanos, "Induction of hypersensitivity to endotoxin and tumor necrosis factor by sublethal infection with *Salmonella typhimurium," Infec. Immun.,* 58:935-937, 1990.

Medzhitov et al., "A human homologue of the *Drosophilia* Toll protein signals activation of adaptive immunity," *Nature,* 388:394-397, 1997.

Medzhitov et al., "MyD88 is an adaptor protein in the hToll/IL-1 receptor family signaling pathways," *Molecular Cell,* 2:253-258, 1998.

Modlin et al., "The toll of innate immunity on microbial pathogens," *N. Engl. J. Med.,* 340:1834-1835, 1999.

Muzio et al., "The human toll signaling pathway: divergence of nuclear factor κB and JNK/SAPK activation upstream of tumor necrosis factor receptor-associated factor 6 (TRAF6), " *J. Exp. Med.* 187, 2097-2101, 1998.

Poltorak et al., "Genetic and physical mapping of the Lps locus: identification of the Toll-4 receptor as a candidate gene in the critical region," *Blood Cells Molecules & Diseases,* 240(170):340-355, 1998.

Poltorak et al., "Defective LPS signaling in C3H/HeJ and C57BL/10ScCr mice: mutations in Tlr4 gene," *Science,* 282:2085-2088, 1998.

Qureshi et al., "Endotoxin-tolerant mice have mutations in toll-like receptor 4 (Tlr4)," *J Exp. Med.,* 189:615-625, 1999.

Rock et al., "A family of human receptors structurally related to *Drosophila* Toll," *Proc. Natl. Acad. Sci. U.S.A.* 95, 588-593, 1998.

Rommens et al., In: Hochgeschwender, U., Gardiner, K., eds., *Identification of Transcribed Sequences,* "Towards a transcriptional map of the q21-q22 region of chromosome 7," New York, N.Y., Plenum Press, 1998, p. 65.

Rosetto et al., "Signals from the IL-1 receptor homolog, toll, can activate an immune response in a *drosophila* hemocyte cell line," *Biochem. Biophys. Res. Commun.* 209, 111-116, 1995.

Schneider et al., "Dominant and recessive mutations define functional domains of *Toll,* a transmembrane protien required for dorsal-ventral polarity in the *Drosophilia* embryo," *Genes Dev.,* 5:797-807, 1991.

Shimazu et al., "MD-2, a molecule that confers lipopolysaccharide responsiveness on Toll-like receptor 4," *J. Exp. Med.,* 189(11):1777-1782, 1999.

Tracey et al., "Shock and tissue induced by recombinant human cachectin," *Science,* 234:470-474, 1986.

Vogel et al., "Construction of a BALB/c congenic mouse, C.C3H-$Lps^d$, that expresses the $Lps^d$ allele: analysis of chromosome 4 markers surrounding the Lps gene," *Infect. Immun.* 62, 4454-4459, 1994.

Wright et al., "CD14, a receptor for complexes of lipopolysaccharide (LPS) and LPS binding protein," *Science,* 249:1431-1433, 1990.

Yang et al., "Toll-like receptor-2 mediates lipopolysaccharide-induced cellular signalling," *Nature,* 395:284-288, 1998.

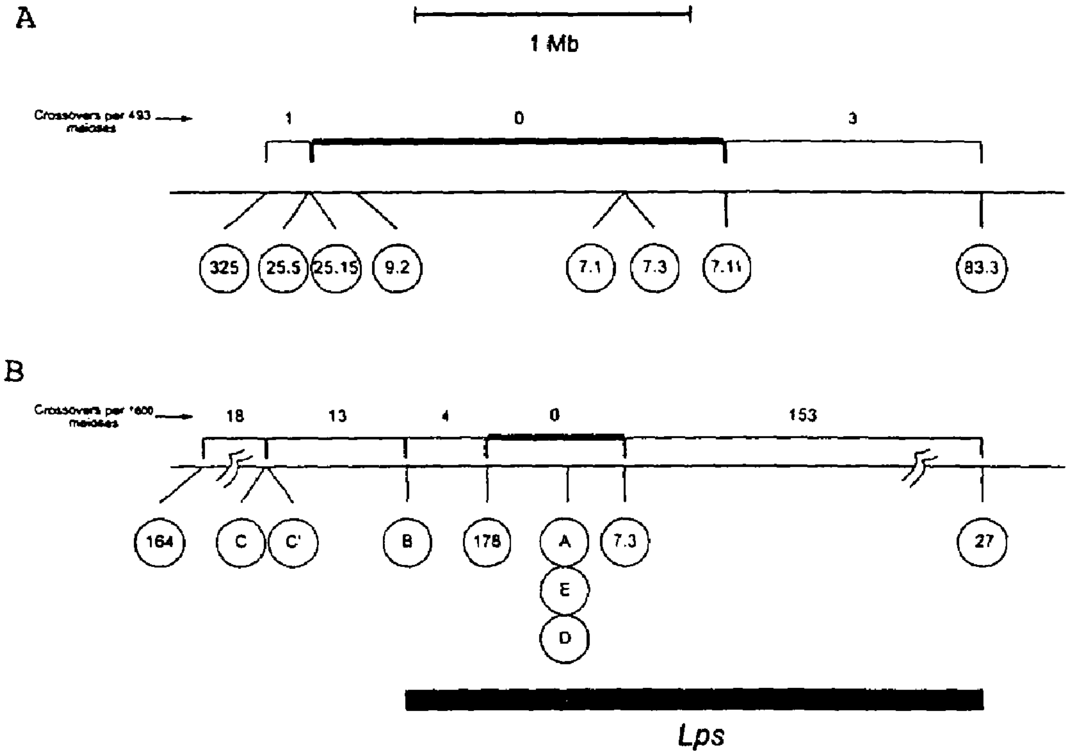
FIG. 2A-B

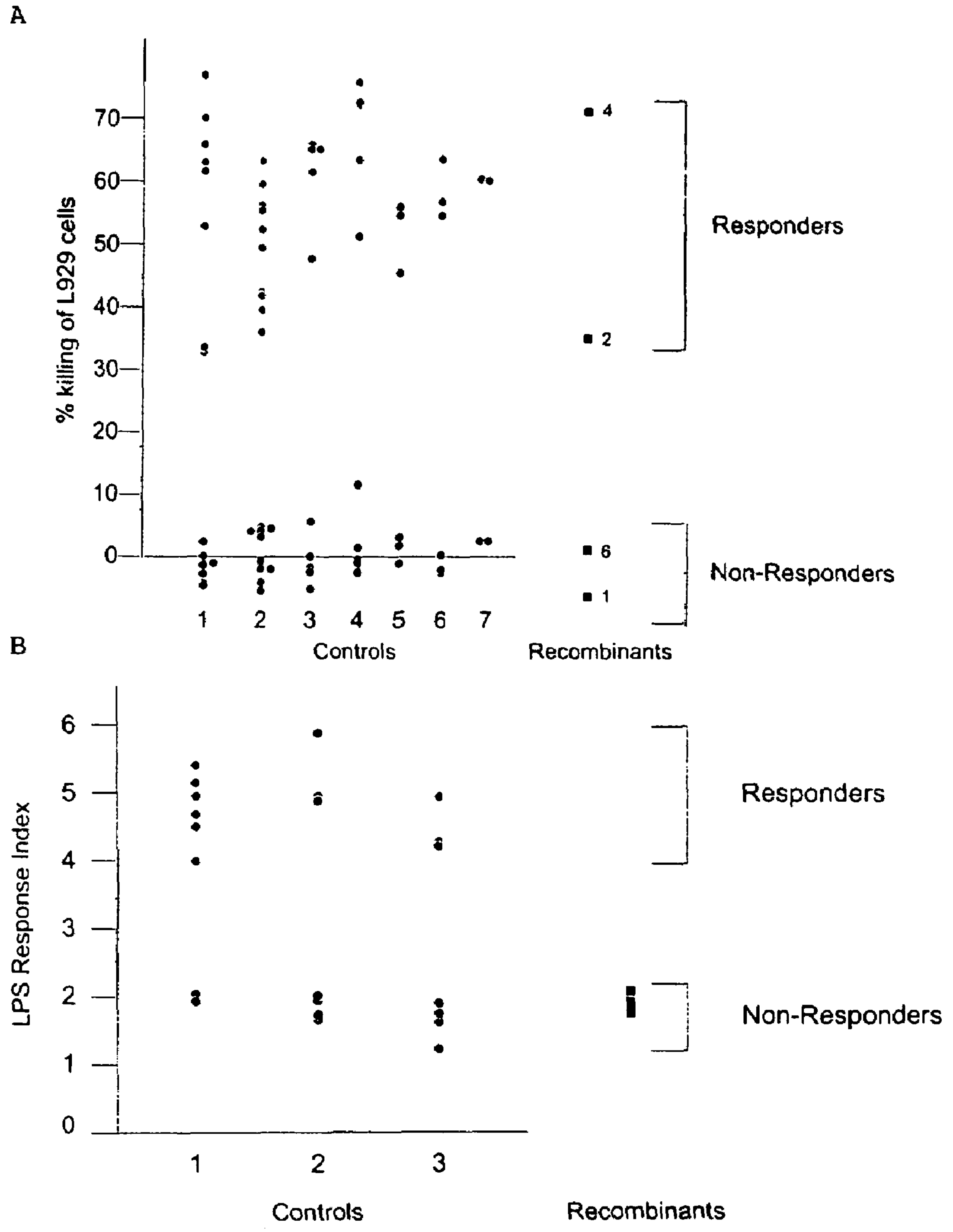
FIG. 3A-B

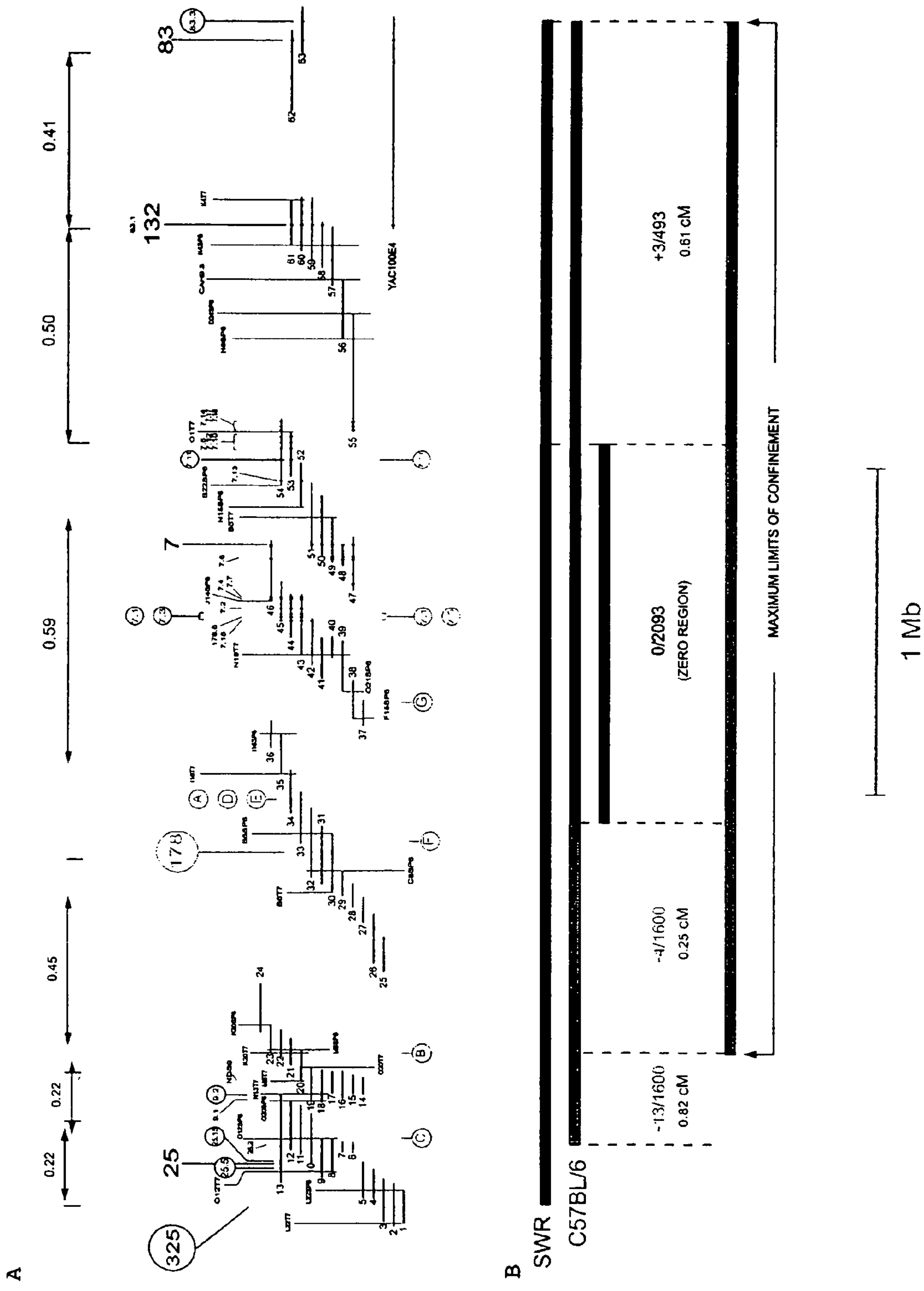
FIG. 4A-B

```
         1                                                    50
jtoll    MMPPWLLART LIMAL.FFSC LTPGSLNPCI EVVPNITYQC MDQKLSKVPD
ntoll    MMPPWLLART LIMAL.FFSC LTPGSLNPCI EVVPNITYQC MDQKLSKVPD
           ***  *         *    *            *          *  * *
rattlr4  MMPLLHLAGT LIMAL.FLSC LRPGSLNPCI EVLPNITYQC MDQNLSKIPH
           ****       *  **    *  * **  *   *         ** **   *
humtlr4  MMSASRLAGT LIPAMAFLSC VRPESWEPCV EVVPNITYQC MELNFYKIPD

         51                                                  100
jtoll    DIPSSTKNID LSFNPLKILK SYSFSNFSEL QWLDLSRCEI ETIEDKAWHG
ntoll    DIPSSTKNID LSFNPLKILK SYSFSNFSEL QWLDLSRCEI ETIEDKAWHG
            *   *            *     *  *
rattlr4  DIPYSTKNLD LSFNPLKILR SYSFTNFSQL QWLDLSRCEI ETIEDKAWHG
         ** *             ** *     ** **   *          *    * ***
humtlr4  NLPFSTKNLD LSFNPLRHLG SYSFFSFPEL QVLDLSRCEI QTIEDGAYQS

         101                                                 150
jtoll    LHHLSNLILT GNPIQSFSPG SFSGLTSLEN LVAVETKLAS LESFPIGQLI
ntoll    LHHLSNLILT GNPIQSFSPG SFSGLTSLEN LVAVETKLAS LESFPIGQLI
          **  **         *           *           **     * *
rattlr4  LNQLSTLVLT GNPIKSFSPG SFSGLTNLEN LVAVETKMTS LEGFHIGQLI
           *  *          * ***      ** **       ***     * *  *  *
humtlr4  LSHLSTLILT GNPIQSLALG AFSGLSSLQK LVAVETNLAS LENFPIGHLK

         151                                                 200
jtoll    TLKKLNVAHN FIHSCKLPAY FSNLTNLVHV DLSYNYIQTI TVNDLQFLRE
ntoll    TLKKLNVAHN FIHSCKLPAY FSNLTNLVHV DLSYNYIQTI TVNDLQFLRE
         *          *   * *          *              * *
rattlr4  SLKKLNVAHN LIHSFKLPEY FSNLTNLEHV DLSYNYIQTI SVKDLQFLRE
         *  *         *             *       *  *  *   ***  ** **
humtlr4  TLKELNVAHN LIQSFKLPEY FSNLTNLEHL DLSSNKIQSI YCTDLRVLHQ

         201                                                 250
jtoll    NPQVNLSLDM SLNPIDFIQD QAFQGIKLHE LTLRGNFNSS NIMKTCLQNL
ntoll    NPQVNLSLDM SLNPIDFIQD QAFQGIKLHE LTLRGNFNSS NIMKTCLQNL
                 *       *  *       *        *        ** *  *
rattlr4  NPQVNLSLDL SLNPIDSIQA QAFQGIRLHE LTLRSNFNSS NVLKMCLQNM
         * **           ***    * **     *       *  *  *   * *  **
humtlr4  MPLLNLSLDL SLNPMNFIQP GAFKEIRLHK LTLRNNFDSL NVMKTCIQGL

         251                                                 300
jtoll    AGLHVHRLIL GEFKDERNLE IFEPSIMEGL CDVTIDEFRL TYTNDFSDDI
ntoll    AGLHVHRLIL GEFKDERNLE IFEPSIMEGL CDVTIDEFRL TYTNDFSDDI
         *              *     * **  *     **            *  *
rattlr4  TGLHVHRLIL GEFKNERNLE SFDRSVMEGL CNVSIDEFRL TYINHFSDDI
         *  *    *      *     *  *  **      **  *     *  *****
humtlr4  AGLEVHRLVL GEFRNEGNLE KFDKSALEGL CNLTIEEFRL AYLDYYLDDI

         301                                                 350
jtoll    VK.FHCLANV SAMSLAGVSI KYLEDVPKHF KWQSLSIIRC QLKQFPTLDL
ntoll    VK.FHCLANV SAMSLAGVSI KYLEDVPKHF KWQSLSIIRC QLKQFPTLDL
         *****   *      **  *   ***   *             *  *  * *
rattlr4  YN.LNCLANI SAMSFTGVHI KHIADVPRHF KWQSLSIIRC HLKPFPKLSL
         ****   **   **  *** * **** ****  *  *  ****  ****  *  *
humtlr4  IDLFNCLTNV SSFSLVSVTI ERVKDFSYNF GWQHLELVNC KFGQFPTLKL

         351                                                 400
jtoll    PFLKSLTLTM NKGSISFKKV ALPSLSYLDL SRNALSFSGC CSYSDLGTNS
ntoll    PFLKSLTLTM NKGSISFKKV ALPSLSYLDL SRNALSFSGC CSYSDLGTNS
              *  *   ***  ***       *        **          *   *
rattlr4  PFLKSWTLTT NREDISFGQL ALPSLRYLDL SRNAMSFRGC CSYSDFGTNN
         ** **  * *  ***** *** *     **        **  *        *  **
humtlr4  KSLKRLTFTS NKGGNAFSEV DLPSLEFLDL SRNGLSFKGC CSQSDFGTTS

         401                                                 450
jtoll    LRHLDLSFNG AIIMSANFMG LEELQHLDFQ HSTLKRVTEF SAFLSLEKLL
ntoll    LRHLDLSFNG AIIMSANFMG LEELQHLDFQ HSTLKRVTEF SAFLSLEKLL
         **         * *            **          *       *
rattlr4  LKYLDLSFNG VILMSANFMG LEELEYLDFQ HSTLKKVTEF SVFLSLEKLL
                      *  *  *    *  *       *  ***          ** *
humtlr4  LKYLDLSFNG VITMSSNFLG LEQLEHLDFQ HSNLKQMSEF SVFLSLRNLI
```

FIG. 7A

```
         451                                             500
jtoll    YLDISYTNTK IDFDGIFLGL TSLNTLKMAG NSFKDNTLSN VFANTTNLTF
ntoll    YLDISYTNTK IDFDGIFLGL TSLNTLKMAG NSFKDNTLSN VFANTTNLTF
                               *
rattlr4  YLDISYTNTK IDFDGIFLGL ISLNTLKMAG NSFKDNTLSN VFTNTTNLTF
              * * * ** *   *   *  **         ** * ** *  ***
humtlr4  YLDISHTHTR VAFNGIFNGL SSLEVLKMAG NSFQENFLPD IFTELRNLTF

         501                                             550
jtoll    LDLSKCQLEQ ISWGVFDTLH RLQLLNMSHN NLLFLDSSHY NQLYSLSTLD
ntoll    LDLSKCQLEQ ISWGVFDTLH RLQLLNMSHN NLLFLDSSHY NQLYSLSTLD
                      *     **                  *    *     *
rattlr4  LDLSKCQLEQ ISRGVFDTLY RLQLLNMSHN NLLFLDPSHY KQLYSLRTLD
             *      * *** ** * *  *        ***  ***   * *  **
humtlr4  LDLSQCQLEQ LSPTAFNSLS SLQVLNMSHN NFFSLDTFPY KCLNSLQVLD

         551                                             600
jtoll    CSFNRIETS. KGILQHFPKS LAFFNLTNNS VACICEHQKF LQWVKEQKQF
ntoll    CSFNRIETS. KGILQHFPKS LAFFNLTNNS VACICEHQKF LQWVKEQKQF
                                 *              * *       *  *
rattlr4  CSFNRIETS. KGILQHFPKS LAVFNLTNNS VACICEYQNF LQWVKDQKMF
         * * * *  *  **     *    **   * * *  *  * *     *   ***
humtlr4  YSLNHIMTSK KQELQHFPSS LAFLNLTQND FACTCEHQSF LQWIKDQRQL

         601                                             650
jtoll    LVNVEQMTCA TPVEMNTSLV LDFNNSTCYM YKTIISVSVV SVIVVSTVAF
ntoll    LVNVEQMTCA TPVEMNTSLV LDFNNSTCYM YKTIISVSVV SVIVVSTVAF
                *   * ** **        *     *              *  *
rattlr4  LVNVEQMKCA SPIDMKASLV LDFTNSTCYI YKTIISVSVV SVLVVATVAF
           *  * *   * * *****   *** *  ** *    *   *      **  *
humtlr4  LVEVERMECA TPSDKQGMPV LSL.NITCQM NKTIIGVSVL SVLVVSVVAV

         651                                             700
jtoll    LIYHFYFHLI LIAGCKKYSR GESIYDAFVI YSSQNEDWVR NELVKNLEEG
ntoll    LIYHFYFHLI LIAGCKKYSR GESIYDAFVI YSSQNEDWVR NELVKNLEEG
rattlr4  LIYHFYFHLI LIAGCKKYSR GESIYDAFVI YSSQNEDWVR NELVKNLEEG
          * *     *  *   *  *    *            *
humtlr4  LVYKFYFHLM LLAGCIKYGR GENIYDAFVI YSSQDEDWVR NELVKNLEEG

         701                                             750
jtoll    VPRFHLCLHY RDFIHGVAIA ANIIQEGFHK SRKVIVVVSR HFIQSRWCIF
                        *
ntoll    VPRFHLCLHY RDFIPGVAIA ANIIQEGFHK SRKVIVVVSR HFIQSRWCIF
             *
rattlr4  VPRFQLCLHY RDFIPGVAIA ANIIQEGFHK SRKVIVVVSR HFIQSRWCIF
           *                       *               *
humtlr4  VPPFQLCLHY RDFIPGVAIA ANIIHEGFHK SRKVIVVVSQ HFIQSRWCIF

         751                                             800
jtoll    EYEIAQTWQF LSSRSGIIFI VLEKVEKSLL RQQVELYRLL SRNTYLEWED
ntoll    EYEIAQTWQF LSSRSGIIFI VLEKVEKSLL RQQVELYRLL SRNTYLEWED
rattlr4  EYEIAQTWQF LSSRSGIIFI VLEKVEKSLL RQQVELYRLL SRNTYLEWED
                                 *    *
humtlr4  EYEIAQTWQF LSSRAGIIFI VLQKVEKTLL RQQVELYRLL SRNTYLEWED

         801                                  840
jtoll    NPLGRHIFWR RLKNALLDGK ASNPEQTAEE EQETATWT~~
ntoll    NPLGRHIFWR RLKNALLDGK ASNPEQTAEE EQETATWT~~
          *            *        *  ** *         *
rattlr4  NALGRHIFWR RLKKALLDGK ALNPDETSEE EQEATTLT~~
         **           *        **  ** *** *******
humtlr4  SVLGRHIFWR RLRKALLDGK SWNPEGTVGT GCNWQEATSI
```

FIG. 7A (CONT.)

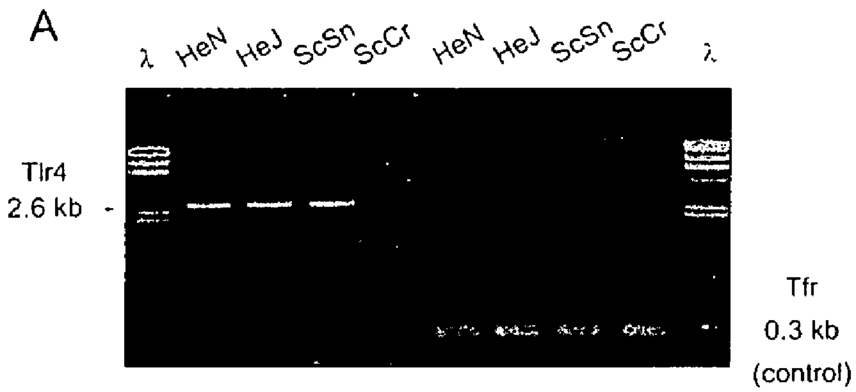
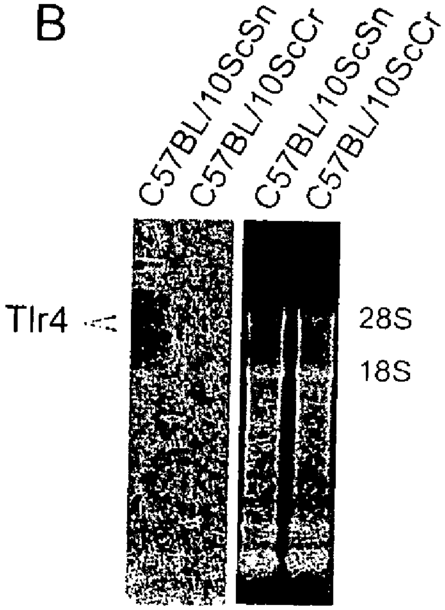
FIG. 8A-B

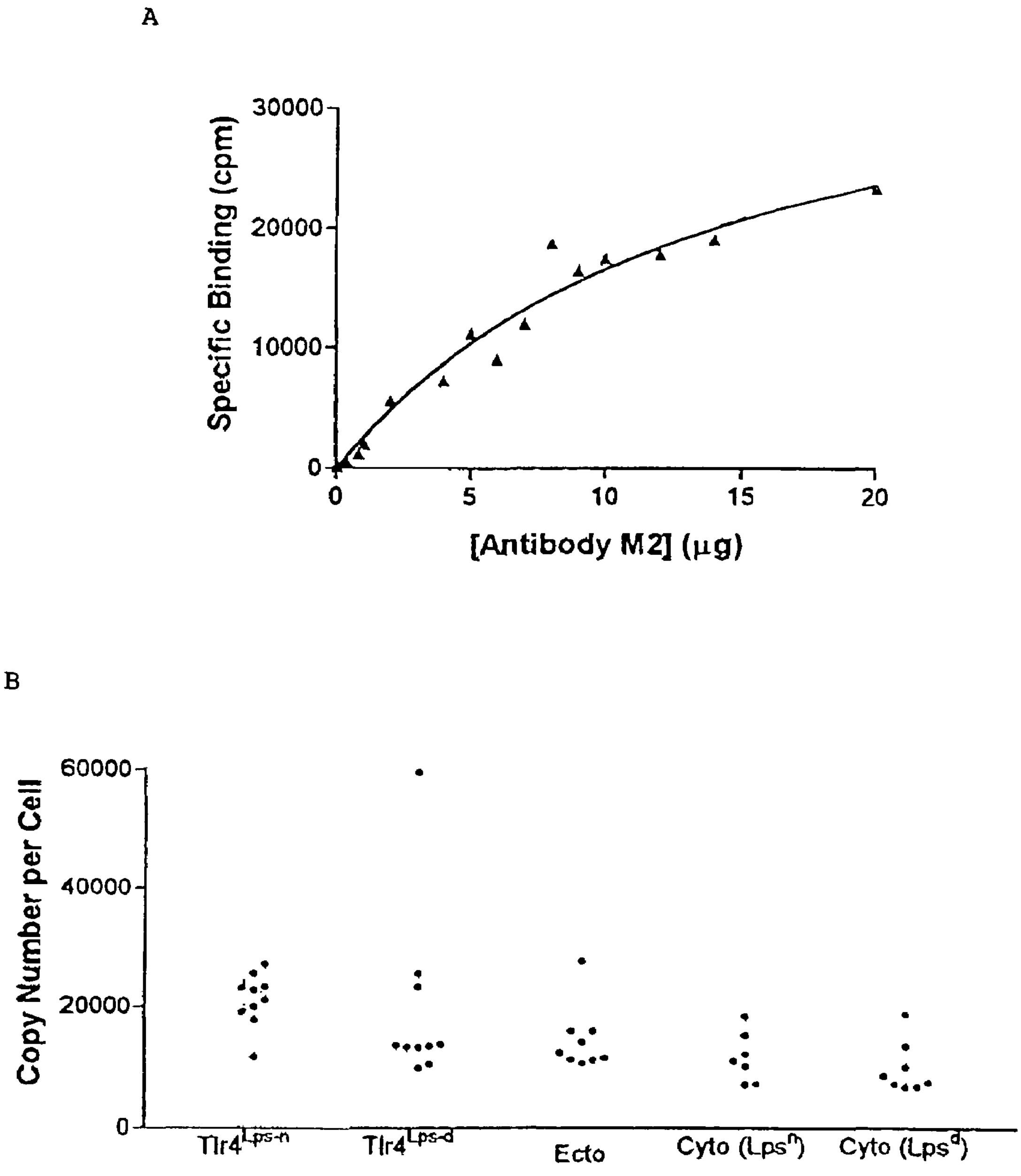
FIG. 15A-B

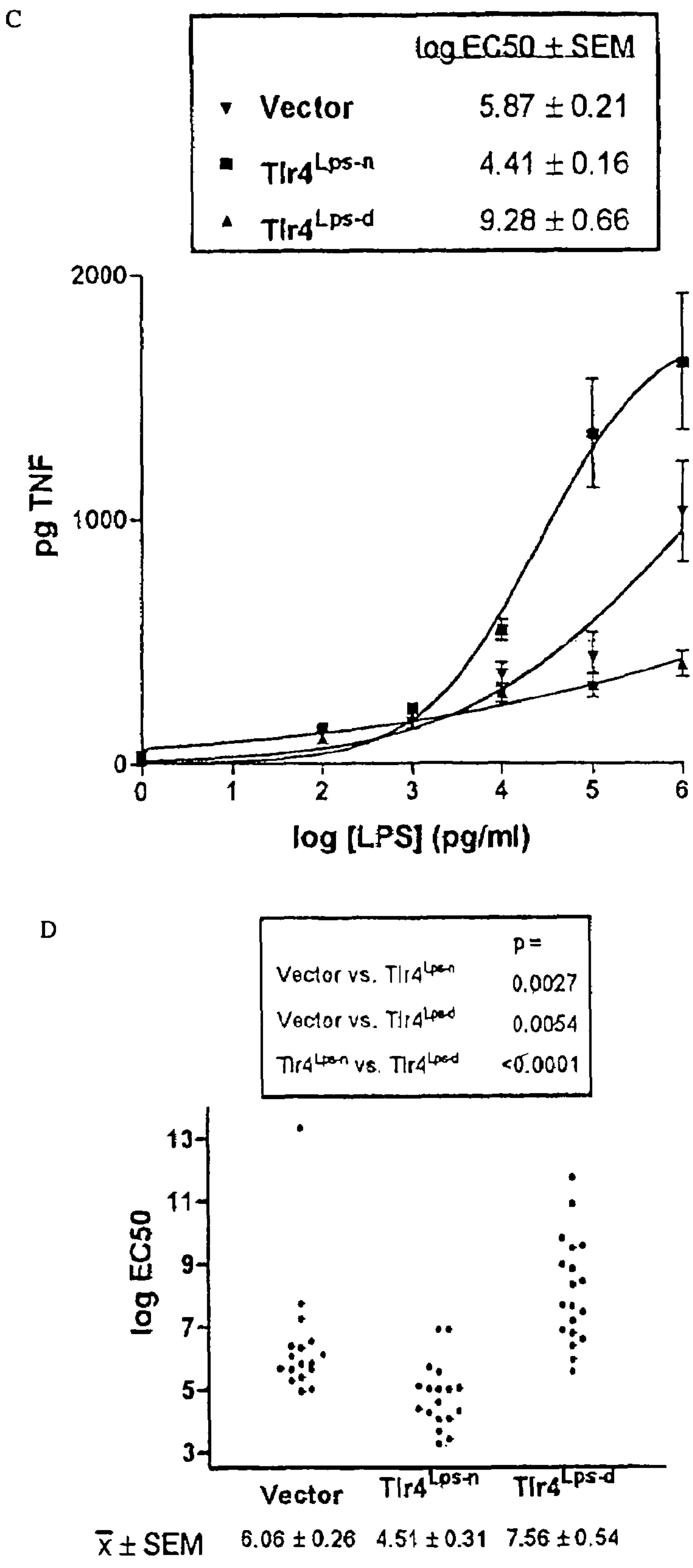
FIG. 15C-D

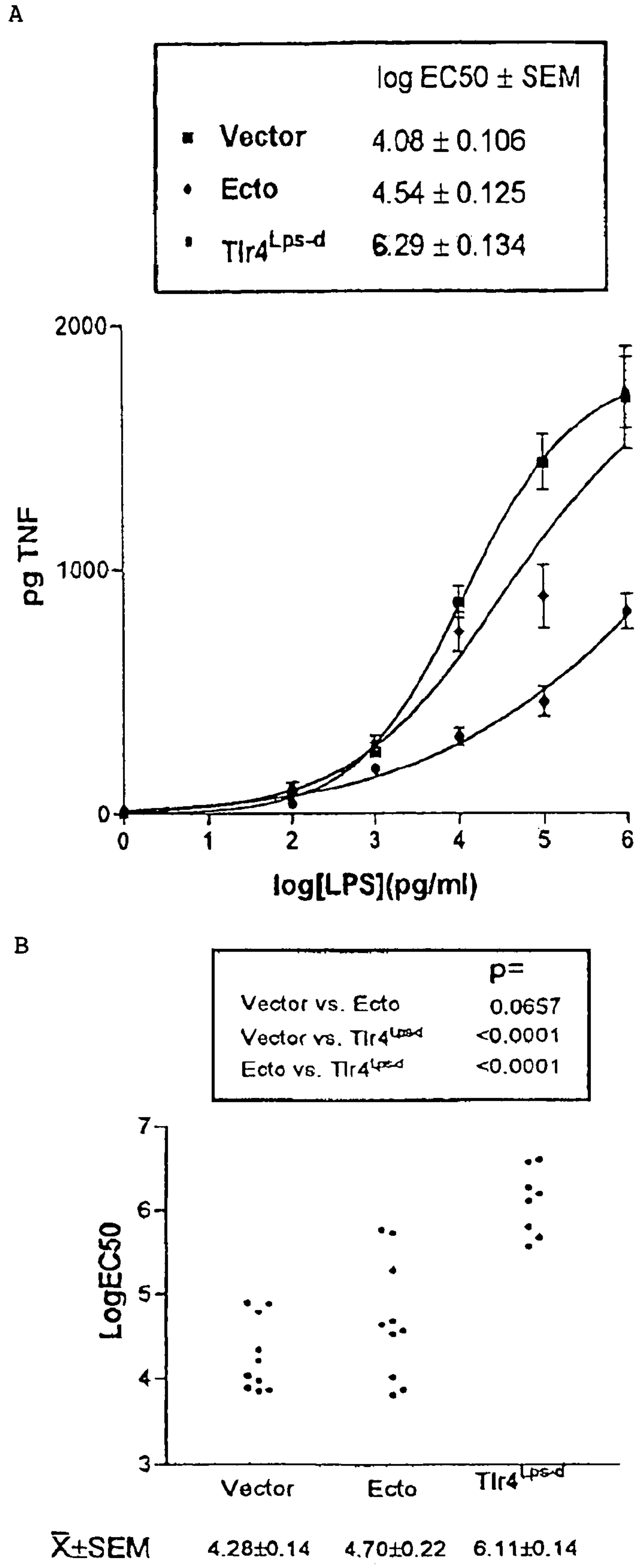
FIG. 16A-B

A
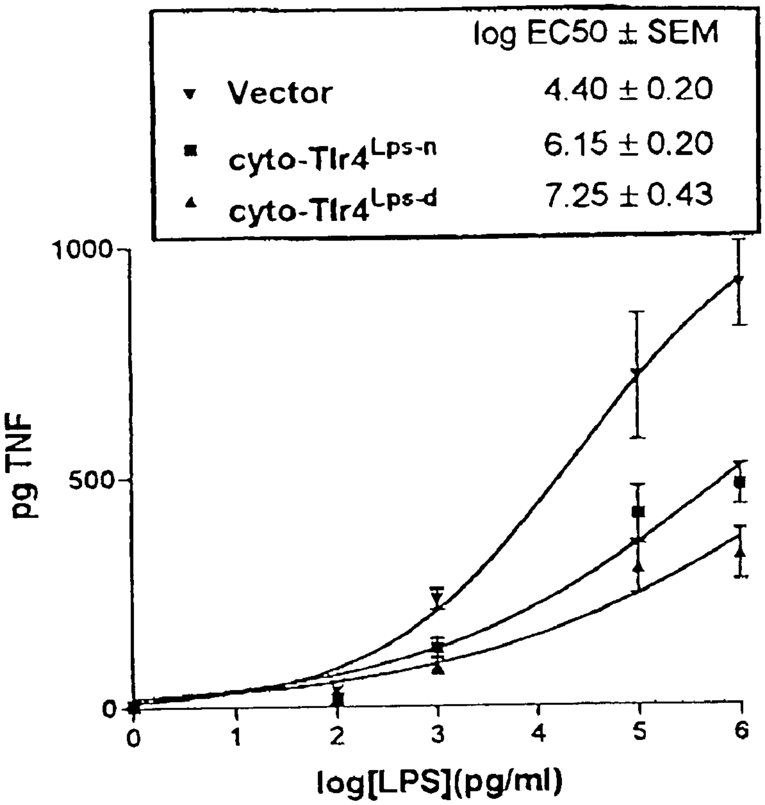
B
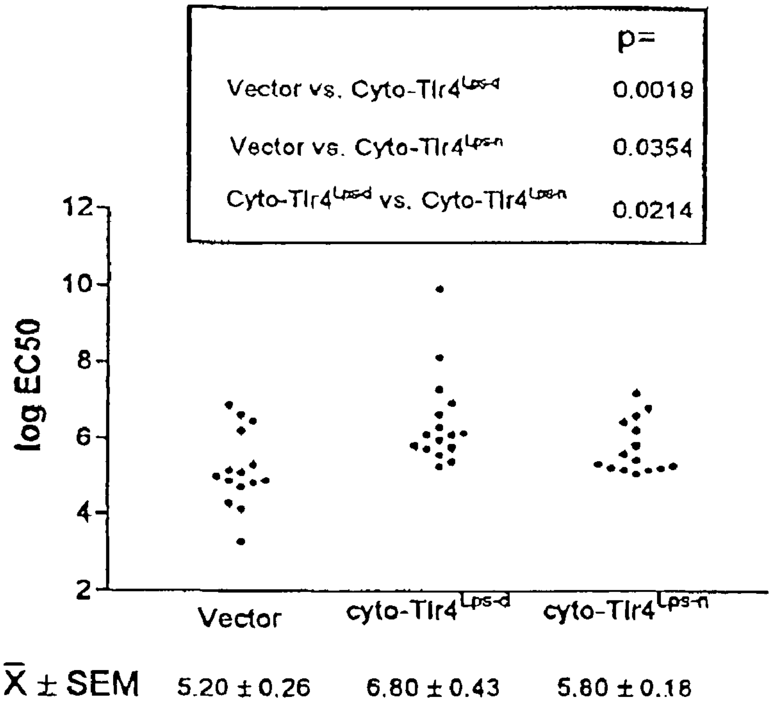
FIG. 17A-B

SEQUENCE LISTING

```
<160> NUMBER OF SEQ ID NOS: 104

<210> SEQ ID NO 1
<211> LENGTH: 4868
<212> TYPE: DNA
<213> ORGANISM: Homo sapiens

<400> SEQUENCE: 1

aaaatactcc cttgcctcaa aaactgctcg gtcaaacggt gatagcaaac cacgcattca      60

cagggccact gctgctcaca aaaccagtga ggatgatgcc aggatgatgt ctgcctcgcg     120

cctggctggg actctgatcc cagccatggc cttcctctcc tgcgtgagac cagaaagctg     180

ggagccctgc gtggaggtgg ttcctaatat tacttatcaa tgcatggagc tgaatttcta     240

caaaatcccc gacaacctcc ccttctcaac caagaacctg gacctgagct ttaatcccct     300

gaggcattta ggcagctata gcttcttcag tttcccagaa ctgcaggtgc tggatttatc     360

caggtgtgaa atccagacaa ttgaagatgg ggcatatcag agcctaagcc acctctctac     420

cttaatattg acaggaaacc ccatccagag tttagccctg ggagcctttt ctggactatc     480

aagtttacag aagctggtgg ctgtggagac aaatctagca tctctagaga acttccccat     540

tggacatctc aaaactttga aagaacttaa tgtggctcac aatcttatcc aatctttcaa     600

attacctgag tatttttcta atctgaccaa tctagagcac ttggaccttt ccagcaacaa     660
```

-continued

```
gattcaaagt atttattgca cagacttgcg ggttctacat caaatgcccc tactcaatct    720
ctctttagac ctgtccctga atcctatgaa ctttatccaa ccaggtgcat ttaaagaaat    780
taggcttcat aagctgactt taagaaataa ttttgatagt ttaaatgtaa tgaaaacttg    840
tattcaaggt ctggctggtt tagaagtcca tcgtttggtt ctgggagaat ttagaaatga    900
aggaaacttg gaaaagtttg acaaatctgc tctagagggc ctgtgcaatt tgaccattga    960
agaattccga ttagcatact tagactacta cctcgatgat attattgact tatttaattg   1020
tttgacaaat gtttcttcat tttccctggt gagtgtgact attgaaaggg taaaagactt   1080
ttcttataat ttcggatggc aacatttaga attagttaac tgtaaatttg gacagtttcc   1140
cacattgaaa ctcaaatctc tcaaaaggct tactttcact tccaacaaag gtgggaatgc   1200
tttttcagaa gttgatctac caagccttga gtttctagat ctcagtagaa atggcttgag   1260
tttcaaaggt tgctgttctc aaagtgattt tgggacaacc agcctaaagt atttagatct   1320
gagcttcaat ggtgttatta ccatgagttc aaacttcttg ggcttagaac aactagaaca   1380
tctggatttc cagcattcca atttgaaaca aatgagtgag ttttcagtat tcctatcact   1440
cagaaacctc atttaccttg acatttctca tactcacacc agagttgctt tcaatggcat   1500
cttcaatggc ttgtccagtc tcgaagtctt gaaaatggct ggcaattctt tccaggaaaa   1560
cttccttcca gatatcttca cagagctgag aaacttgacc ttcctggacc tctctcagtg   1620
tcaactggag cagttgtctc caacagcatt taactcactc tccagtcttc aggtactaaa   1680
tatgagccac aacaacttct tttcattgga tacgtttcct tataagtgtc tgaactccct   1740
ccaggttctt gattacagtc tcaatcacat aatgacttcc aaaaaacagg aactacagca   1800
ttttccaagt agtctagctt tcttaaatct tactcagaat gactttgctt gtacttgtga   1860
acaccagagt ttcctgcaat ggatcaagga ccagaggcag ctcttggtgg aagttgaacg   1920
aatggaatgt gcaacacctt cagataagca gggcatgcct gtgctgagtt tgaatatcac   1980
ctgtcagatg aataagacca tcattggtgt gtcggtcctc agtgtgcttg tagtatctgt   2040
tgtagcagtt ctggtctata agttctattt tcacctgatg cttcttgctg gctgcataaa   2100
gtatggtaga ggtgaaaaca tctatgatgc ctttgttatc tactcaagcc aggatgagga   2160
ctgggtaagg aatgagctag taaagaattt agaagaaggg gtgcctccat ttcagctctg   2220
ccttcactac agagacttta ttcccggtgt ggccattgct gccaacatca tccatgaagg   2280
tttccataaa agccgaaagg tgattgttgt ggtgtcccag cacttcatcc agagccgctg   2340
gtgtatcttt gaatatgaga ttgctcagac ctggcagttt ctgagcagtc gtgctggtat   2400
catcttcatt gtcctgcaga aggtggagaa gaccctgctc aggcagcagg tggagctgta   2460
ccgccttctc agcaggaaca cttacctgga gtgggaggac agtgtcctgg ggcggcacat   2520
cttctggaga cgactcagaa aagccctgct ggatggtaaa tcatggaatc cagaaggaac   2580
agtgggtaca ggatgcaatt ggcaggaagc aacatctatc tgaagaggaa aaataaaaac   2640
ctcctgaggc atttcttgcc cagctgggtc caacacttgt tcagttaata agtattaaat   2700
gctgccacat gtcaggcctt atgctaaggg tgagtaattc catggtgcac tagatatgca   2760
gggctgctaa tctcaaggag cttccagtgc agagggaata aatgctagac taaaatacag   2820
agtcttccag gtgggcattt caaccaactc agtcaaggaa cccatgacaa agaaagtcat   2880
ttcaactctt acctcatcaa gttgaataaa gacagagaaa acagaaagag acattgttct   2940
tttcctgagt cttttgaatg gaaattgtat tatgttatag ccatcataaa accattttgg   3000
tagttttgac tgaactgggt gttcactttt tcctttttga ttgaatacaa tttaaattct   3060
```

-continued

```
actttgatgac tgcagtcgtc aaggggctcc tgatgcaaga tgccccttcc attttaagtc   3120
tgtctcctta cagatgttaa agtctagtgg ctaattccta aggaaacctg attaacacat   3180
gctcacaacc atcctggtca ttctcgagca tgttctattt tttaactaat cacccctgat   3240
atatttttat ttttatatat ccagttttca tttttttacg tcttgcctat aagctaatat   3300
cataaataag gttgtttaag acgtgcttca aatatccata ttaaccacta tttttcaagg   3360
aagtatggaa aagtacactc tgtcactttg tcactcgatg tcattccaaa gttattgcct   3420
actaagtaat gactgtcatg aaagcagcat tgaaataatt tgtttaaagg gggcactctt   3480
ttaaacggga agaaaatttc cgcttcctgg tcttatcatg gacaatttgg gctagaggca   3540
ggaaggaagt gggatgacct caggaggtca ccttttcttg attccagaaa catatgggct   3600
gataaacccg gggtgacctc atgaaatgag ttgcagcaga agtttatttt tttcagaaca   3660
agtgatgttt gatggacctc tgaatctctt tagggagaca cagatggctg ggatccctcc   3720
cctgtaccct tctcactgcc aggagaacta cgtgtgaagg tattcaaggc agggagtata   3780
cattgctgtt tcctgttggg caatgctcct tgaccacatt ttgggaagag tggatgttat   3840
cattgagaaa acaatgtgtc tggaattaat ggggttctta taaagaaggt tcccagaaaa   3900
gaatgttcat tccagcttct tcaggaaaca ggaacattca aggaaaagga caatcaggat   3960
gtcatcaggg aaatgaaaat aaaaaccaca atgagatatc accttatacc aggtagatgg   4020
ctactataaa aaaatgaagt gtcatcaagg atatagagaa attggaaccc ttcttcactg   4080
ctggagggaa tggaaaatgg tgtagccgtt atgaaaaaca gtacggaggt ttctcaaaaa   4140
ttaaaaatag aactgctata tgatccagca atctcacttc tgtatatata cccaaaataa   4200
ttgaaatcag aatttcaaga aaatatttac actcccatgt tcattgtggc actcttcaca   4260
atcactgttt ccaaagttat ggaaacaacc caaatttcca ttggaaaata aatggacaaa   4320
ggaaatgtgc atataacgta caatggggat attattcagc ctaaaaaaag gggggatcct   4380
gttatttatg acaacatgaa taaacccgga ggccattatg ctatgtaaaa tgagcaagta   4440
acagaaagac aaatactgcc tgatttcatt tatatgaggt tctaaaatag tcaaactcat   4500
agaagcagag aatagaacag tggttcctag ggaaaaggag gaagggagaa atgaggaaat   4560
agggagttgt ctaattggta taaaattata gtatgcaaga tgaattagct ctaaagatca   4620
gctgtatagc agagttcgta taatgaacaa tactgtatta tgcacttaac attttgttaa   4680
gagggtacct ctcatgttaa gtgttcttac catatacata tacacaagga agcttttgga   4740
ggtgatggat atatttatta ccttgattgt ggtgatggtt tgacaggtat gtgactatgt   4800
ctaaactcat caaattgtat acattaaata tatgcagttt tataatatca aaaaaaaaaa   4860
aaaaaaaa                                                            4868
```

<210> SEQ ID NO 2
<211> LENGTH: 839
<212> TYPE: PRT
<213> ORGANISM: Homo sapiens

<400> SEQUENCE: 2

```
Met Met Ser Ala Ser Arg Leu Ala Gly Thr Leu Ile Pro Ala Met Ala
  1               5                  10                  15

Phe Leu Ser Cys Val Arg Pro Glu Ser Trp Glu Pro Cys Val Glu Val
             20                  25                  30

Val Pro Asn Ile Thr Tyr Gln Cys Met Glu Leu Asn Phe Tyr Lys Ile
         35                  40                  45
```

-continued

```
Pro Asp Asn Leu Pro Phe Ser Thr Lys Asn Leu Asp Leu Ser Phe Asn
     50                  55                  60

Pro Leu Arg His Leu Gly Ser Tyr Ser Phe Phe Ser Phe Pro Glu Leu
 65                  70                  75                  80

Gln Val Leu Asp Leu Ser Arg Cys Glu Ile Gln Thr Ile Glu Asp Gly
                 85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
        115                 120                 125

Gln Lys Leu Val Ala Val Glu Thr Asn Leu Ala Ser Leu Glu Asn Phe
    130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
                165                 170                 175

Leu Glu His Leu Asp Leu Ser Ser Asn Lys Ile Gln Ser Ile Tyr Cys
            180                 185                 190

Thr Asp Leu Arg Val Leu His Gln Met Pro Leu Leu Asn Leu Ser Leu
        195                 200                 205

Asp Leu Ser Leu Asn Pro Met Asn Phe Ile Gln Pro Gly Ala Phe Lys
    210                 215                 220

Glu Ile Arg Leu His Lys Leu Thr Leu Arg Asn Asn Phe Asp Ser Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Gly Asn Leu Glu Lys Phe
            260                 265                 270

Asp Lys Ser Ala Leu Glu Gly Leu Cys Asn Leu Thr Ile Glu Glu Phe
        275                 280                 285

Arg Leu Ala Tyr Leu Asp Tyr Tyr Leu Asp Asp Ile Ile Asp Leu Phe
    290                 295                 300

Asn Cys Leu Thr Asn Val Ser Ser Phe Ser Leu Val Ser Val Thr Ile
305                 310                 315                 320

Glu Arg Val Lys Asp Phe Ser Tyr Asn Phe Gly Trp Gln His Leu Glu
                325                 330                 335

Leu Val Asn Cys Lys Phe Gly Gln Phe Pro Thr Leu Lys Leu Lys Ser
            340                 345                 350

Leu Lys Arg Leu Thr Phe Thr Ser Asn Lys Gly Gly Asn Ala Phe Ser
        355                 360                 365

Glu Val Asp Leu Pro Ser Leu Glu Phe Leu Asp Leu Ser Arg Asn Gly
    370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
                405                 410                 415

Asn Phe Leu Gly Leu Glu Gln Leu Glu His Leu Asp Phe Gln His Ser
            420                 425                 430

Asn Leu Lys Gln Met Ser Glu Phe Ser Val Phe Leu Ser Leu Arg Asn
        435                 440                 445

Leu Ile Tyr Leu Asp Ile Ser His Thr His Thr Arg Val Ala Phe Asn
    450                 455                 460
```

-continued

```
Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
                485                 490                 495

Asn Leu Thr Phe Leu Asp Leu Ser Gln Cys Gln Leu Glu Gln Leu Ser
            500                 505                 510

Pro Thr Ala Phe Asn Ser Leu Ser Ser Leu Gln Val Leu Asn Met Ser
        515                 520                 525

His Asn Asn Phe Phe Ser Leu Asp Thr Phe Pro Tyr Lys Cys Leu Asn
    530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
        595                 600                 605

Cys Ala Thr Pro Ser Asp Lys Gln Gly Met Pro Val Leu Ser Leu Asn
    610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
        675                 680                 685

Arg Asn Glu Leu Val Lys Asn Leu Glu Glu Gly Val Pro Pro Phe Gln
    690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
            740                 745                 750

Ile Ala Gln Thr Trp Gln Phe Leu Ser Ser Arg Ala Gly Ile Ile Phe
        755                 760                 765

Ile Val Leu Gln Lys Val Glu Lys Thr Leu Leu Arg Gln Gln Val Glu
    770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
            820                 825                 830

Trp Gln Glu Ala Thr Ser Ile
        835
```

<210> SEQ ID NO 3
<211> LENGTH: 3811
<212> TYPE: DNA
<213> ORGANISM: Homo sapiens

<400> SEQUENCE: 3

-continued

```
acagggccac tgctgctcac agaagcagtg aggatgatgc caggatgatg tctgcctcgc     60
gcctggctgg gactctgatc ccagccatgg ccttcctctc ctgcgtgaga ccagaaagct    120
gggagccctg cgtggagact tggccctaaa ccacacagaa gagctggcat gaaacccaga    180
gctttcagac tccggagcct cagcccttca ccccgattcc attgcttctt gctaaatgct    240
gccgttttat cacggaggtg gttcctaata ttacttatca atgcatggag ctgaatttct    300
acaaaatccc cgacaacctc cccttctcaa ccaagaacct ggacctgagc tttaatcccc    360
tgaggcattt aggcagctat agcttcttca gtttcccaga actgcaggtg ctggatttat    420
ccaggtgtga aatccagaca attgaagatg gggcatatca gagcctaagc cacctctcta    480
ccttaatatt gacaggaaac cccatccaga gtttagccct gggagccttt tctggactat    540
caagtttaca gaagctggtg gctgtggaga caaatctagc atctctagag aacttcccca    600
ttggacatct caaaactttg aaagaactta atgtggctca caatcttatc caatctttca    660
aattacctga gtatttttct aatctgacca atctagagca cttggacctt tccagcaaca    720
agattcaaag tatttattgc acagacttgc gggttctaca tcaaatgccc ctactcaatc    780
tctctttaga cctgtccctg aaccctatga actttatcca accaggtgca tttaaagaaa    840
ttaggcttca taagctgact ttaagaaata attttgatag tttaaatgta atgaaaactt    900
gtattcaagg tctggctggt ttagaagtcc atcgtttggt tctgggagaa tttagaaatg    960
aaggaaactt ggaaaagttt gacaaatctg ctctagaggg cctgtgcaat ttgaccattg   1020
aagaattccg attagcatac ttagactact acctcgatga tattattgac ttatttaatt   1080
gtttgacaaa tgtttcttca ttttccctgg tgagtgtgac tattgaaagg gtaaaagact   1140
tttcttataa tttcggatgg caacatttag aattagttaa ctgtaaattt ggacagtttc   1200
ccacattgaa actcaaatct ctcaaaaggc ttactttcac ttccaacaaa ggtgggaatg   1260
ctttttcaga agttgatcta ccaagccttg agtttctaga tctcagtaga aatggcttga   1320
gtttcaaagg ttgctgttct caaagtgatt ttgggacaac cagcctaaag tatttagatc   1380
tgagcttcaa tggtgttatt accatgagtt caaacttctt gggcttagaa caactagaac   1440
atctggattt ccagcattcc aatttgaaac aaatgagtga gttttcagta ttcctatcac   1500
tcagaaacct catttacctt gacatttctc atactcacac cagagttgct ttcaatggca   1560
tcttcaatgg cttgtccagt ctcgaagtct tgaaaatggc tggcaattct ttccaggaaa   1620
acttccttcc agatatcttc acagagctga gaaacttgac cttcctggac ctctctcagt   1680
gtcaactgga gcagttgtct ccaacagcat ttaactcact ctccagtctt caggtactaa   1740
atatgagcca caacaacttc ttttcattgg atacgtttcc ttataagtgt ctgaactccc   1800
tccaggttct tgattacagt ctcaatcaca taatgacttc caaaaaacag gaactacagc   1860
attttccaag tagtctagct ttcttaaatc ttactcagaa tgactttgct tgtacttgtg   1920
aacaccagag tttcctgcaa tggatcaagg accagaggca gctcttggtg gaagttgaac   1980
gaatggaatg tgcaacacct tcagataagc agggcatgcc tgtgctgagt ttgaatatca   2040
cctgtcagat gaataagacc atcattggtg tgtcggtcct cagtgtgctt gtagtatctg   2100
ttgtagcagt tctggtctat aagttctatt ttcacctgat gcttcttgct ggctgcataa   2160
agtatggtag aggtgaaaac atctatgatg cctttgttat ctactcaagc caggatgagg   2220
actgggtaag gaatgagcta gtaaagaatt tagaagaagg ggtgcctcca tttcagctct   2280
gccttcacta cagagacttt attcccggtg tggccattgc tgccaacatc atccatgaag   2340
```

-continued

```
gtttccataa aagccgaaag gtgattgttg tggtgtccca gcacttcatc cagagccgct   2400

ggtgtatctt tgaatatgag attgctcaga cctggcagtt tctgagcagt cgtgctggta   2460

tcatcttcat tgtcctgcag aaggtggaga agaccctgct caggcagcag gtggagctgt   2520

accgccttct cagcaggaac acttacctgg agtgggagga cagtgtcctg gggcggcaca   2580

tcttctggag acgactcaga aaagccctgc tggatggtaa atcatggaat ccagaaggaa   2640

cagtgggtac aggatgcaat tggcaggaag caacatctat ctgaagagga aaaataaaaa   2700

cctcctgagg catttcttgc ccagctgggt ccaacacttg ttcagttaat aagtattaaa   2760

tgctgccaca tgtcaggcct tatgctaagg gtgagtaatt ccatggtgca ctagatatgc   2820

agggctgcta atctcaagga gcttccagtg cagagggaat aaatgctaga ctaaaataca   2880

gagtcttcca ggtgggcatt tcaaccaact cagtcaagga acccatgaca aagaaagtca   2940

tttcaactct tacctcatca agttgaataa agacagagaa aacagaaaga gacattgttc   3000

ttttcctgag tcttttgaat ggaaattgta ttatgttata gccatcataa aaccattttg   3060

gtagttttga ctgaactggg tgttcacttt ttccttttttg attgaataca atttaaattc   3120

tacttgatga ctgcagtcgt caaggggctc ctgatgcaag atgccccttc cattttaagt   3180

ctgtctcctt acagaggtta aagtctaatg gctaattcct aaggaaacct gattaacaca   3240

tgctcacaac catcctggtc attctcgaac atgttctatt ttttaactaa tcacccctga   3300

tatattttta tttttatata tccagttttc atttttttac gtcttgccta taagctaata   3360

tcataaataa ggttgtttaa gacgtgcttc aaatatccat attaaccact atttttcaag   3420

gaagtatgga aaagtacact ctgtcacttt gtcactcgat gtcattccaa agttattgcc   3480

tactaagtaa tgactgtcat gaaagcagca ttgaaataat ttgtttaaag gggcactct    3540

tttaaacggg aagaaaattt ccgcttcctg gtcttatcat ggacaatttg ggctataggc   3600

atgaaggaag tgggattacc tcaggaagtc accttttctt gattccagaa acatatgggc   3660

tgataaaccc ggggtgacct catgaaatga gttgcagcag atgtttattt ttttcagaac   3720

aagtgatgtt tgatggacct atgaatctat ttagggagac acagatggct gggatccctc   3780

ccctgtaccc ttctcactga caggagaact a                                 3811
```

<210> SEQ ID NO 4
<211> LENGTH: 799
<212> TYPE: PRT
<213> ORGANISM: Homo sapiens

<400> SEQUENCE: 4

```
Met Glu Leu Asn Phe Tyr Lys Ile Pro Asp Asn Leu Pro Phe Ser Thr
  1               5                  10                  15

Lys Asn Leu Asp Leu Ser Phe Asn Pro Leu Arg His Leu Gly Ser Tyr
             20                  25                  30

Ser Phe Phe Ser Phe Pro Glu Leu Gln Val Leu Asp Leu Ser Arg Cys
         35                  40                  45

Glu Ile Gln Thr Ile Glu Asp Gly Ala Tyr Gln Ser Leu Ser His Leu
     50                  55                  60

Ser Thr Leu Ile Leu Thr Gly Asn Pro Ile Gln Ser Leu Ala Leu Gly
 65                  70                  75                  80

Ala Phe Ser Gly Leu Ser Ser Leu Gln Lys Leu Val Ala Val Glu Thr
                 85                  90                  95

Asn Leu Ala Ser Leu Glu Asn Phe Pro Ile Gly His Leu Lys Thr Leu
            100                 105                 110
```

-continued

```
Lys Glu Leu Asn Val Ala His Asn Leu Ile Gln Ser Phe Lys Leu Pro
        115                 120                 125

Glu Tyr Phe Ser Asn Leu Thr Asn Leu Glu His Leu Asp Leu Ser Ser
    130                 135                 140

Asn Lys Ile Gln Ser Ile Tyr Cys Thr Asp Leu Arg Val Leu His Gln
145                 150                 155                 160

Met Pro Leu Leu Asn Leu Ser Leu Asp Leu Ser Leu Asn Pro Met Asn
                165                 170                 175

Phe Ile Gln Pro Gly Ala Phe Lys Glu Ile Arg Leu His Lys Leu Thr
            180                 185                 190

Leu Arg Asn Asn Phe Asp Ser Leu Asn Val Met Lys Thr Cys Ile Gln
        195                 200                 205

Gly Leu Ala Gly Leu Glu Val His Arg Leu Val Leu Gly Glu Phe Arg
    210                 215                 220

Asn Glu Gly Asn Leu Glu Lys Phe Asp Lys Ser Ala Leu Glu Gly Leu
225                 230                 235                 240

Cys Asn Leu Thr Ile Glu Glu Phe Arg Leu Ala Tyr Leu Asp Tyr Tyr
                245                 250                 255

Leu Asp Asp Ile Ile Asp Leu Phe Asn Cys Leu Thr Asn Val Ser Ser
            260                 265                 270

Phe Ser Leu Val Ser Val Thr Ile Glu Arg Val Lys Asp Phe Ser Tyr
        275                 280                 285

Asn Phe Gly Trp Gln His Leu Glu Leu Val Asn Cys Lys Phe Gly Gln
    290                 295                 300

Phe Pro Thr Leu Lys Leu Lys Ser Leu Lys Arg Leu Thr Phe Thr Ser
305                 310                 315                 320

Asn Lys Gly Gly Asn Ala Phe Ser Glu Val Asp Leu Pro Ser Leu Glu
                325                 330                 335

Phe Leu Asp Leu Ser Arg Asn Gly Leu Ser Phe Lys Gly Cys Cys Ser
            340                 345                 350

Gln Ser Asp Phe Gly Thr Thr Ser Leu Lys Tyr Leu Asp Leu Ser Phe
        355                 360                 365

Asn Gly Val Ile Thr Met Ser Ser Asn Phe Leu Gly Leu Glu Gln Leu
    370                 375                 380

Glu His Leu Asp Phe Gln His Ser Asn Leu Lys Gln Met Ser Glu Phe
385                 390                 395                 400

Ser Val Phe Leu Ser Leu Arg Asn Leu Ile Tyr Leu Asp Ile Ser His
                405                 410                 415

Thr His Thr Arg Val Ala Phe Asn Gly Ile Phe Asn Gly Leu Ser Ser
            420                 425                 430

Leu Glu Val Leu Lys Met Ala Gly Asn Ser Phe Gln Glu Asn Phe Leu
        435                 440                 445

Pro Asp Ile Phe Thr Glu Leu Arg Asn Leu Thr Phe Leu Asp Leu Ser
    450                 455                 460

Gln Cys Gln Leu Glu Gln Leu Ser Pro Thr Ala Phe Asn Ser Leu Ser
465                 470                 475                 480

Ser Leu Gln Val Leu Asn Met Ser His Asn Asn Phe Phe Ser Leu Asp
                485                 490                 495

Thr Phe Pro Tyr Lys Cys Leu Asn Ser Leu Gln Val Leu Asp Tyr Ser
            500                 505                 510

Leu Asn His Ile Met Thr Ser Lys Lys Gln Glu Leu Gln His Phe Pro
        515                 520                 525

Ser Ser Leu Ala Phe Leu Asn Leu Thr Gln Asn Asp Phe Ala Cys Thr
```

-continued

```
    530                 535                 540

Cys Glu His Gln Ser Phe Leu Gln Trp Ile Lys Asp Gln Arg Gln Leu
545                 550                 555                 560

Leu Val Glu Val Glu Arg Met Glu Cys Ala Thr Pro Ser Asp Lys Gln
                565                 570                 575

Gly Met Pro Val Leu Ser Leu Asn Ile Thr Cys Gln Met Asn Lys Thr
            580                 585                 590

Ile Ile Gly Val Ser Val Leu Ser Val Leu Val Val Ser Val Val Ala
        595                 600                 605

Val Leu Val Tyr Lys Phe Tyr Phe His Leu Met Leu Leu Ala Gly Cys
    610                 615                 620

Ile Lys Tyr Gly Arg Gly Glu Asn Ile Tyr Asp Ala Phe Val Ile Tyr
625                 630                 635                 640

Ser Ser Gln Asp Glu Asp Trp Val Arg Asn Glu Leu Val Lys Asn Leu
                645                 650                 655

Glu Glu Gly Val Pro Pro Phe Gln Leu Cys Leu His Tyr Arg Asp Phe
            660                 665                 670

Ile Pro Gly Val Ala Ile Ala Ala Asn Ile Ile His Glu Gly Phe His
        675                 680                 685

Lys Ser Arg Lys Val Ile Val Val Val Ser Gln His Phe Ile Gln Ser
    690                 695                 700

Arg Trp Cys Ile Phe Glu Tyr Glu Ile Ala Gln Thr Trp Gln Phe Leu
705                 710                 715                 720

Ser Ser Arg Ala Gly Ile Ile Phe Ile Val Leu Gln Lys Val Glu Lys
                725                 730                 735

Thr Leu Leu Arg Gln Gln Val Glu Leu Tyr Arg Leu Leu Ser Arg Asn
            740                 745                 750

Thr Tyr Leu Glu Trp Glu Asp Ser Val Leu Gly Arg His Ile Phe Trp
        755                 760                 765

Arg Arg Leu Arg Lys Ala Leu Leu Asp Gly Lys Ser Trp Asn Pro Glu
    770                 775                 780

Gly Thr Val Gly Thr Gly Cys Asn Trp Gln Glu Ala Thr Ser Ile
785                 790                 795
```

<210> SEQ ID NO 5
<211> LENGTH: 3395
<212> TYPE: DNA
<213> ORGANISM: Rattus norvegicus

<400> SEQUENCE: 5

```
tcgagcggcc gcccgggcag gtttctaact tccctcctga gatgggctta ttaattctag      60

aacaaaacca aaagtgagaa tgctaaggtt ggcactctca cttcctcttg ctctctagcc     120

agtatacctt tgaatacaat atttacagag gggcaaccgc tgggagagaa ggggcagggg     180

ccccagggac tctgccctgc caccatttac agttcgtcat gctttctcac ggcctccgct     240

ggttgcagaa aatgccagga tgatgcctct cttgcatctg gctgggactc tgatcatggc     300

attgttcctt tcctgcctga gaccaggaag cttgaatccc tgcatagagg tacttcctaa     360

tattacctac caatgcatgg atcagaatct cagcaaaatc cctcatgaca tcccttattc     420

aaccaagaac ctagatctga gcttcaaccc cctgaagatc ttaagaagct atagcttcac     480

caatttctca caacttcagt ggctggattt atccaggtgt gaaattgaga caattgaaga     540

caaggcatgg catggcttaa accagctctc aaccttggta ctgacaggaa accctatcaa     600

gagtttttcc ccaggaagtt tttctggact aacaaattta gagaatctgg tggctgtgga     660
```

-continued

```
gacaaaaatg acctctctag agggtttcca tattggacag cttatatcct taaagaaact    720
aaatgtggct cataatctta tacattcctt taagttgcct gaatattttt ctaatctgac    780
aaacctagaa catgtggatc tttcttataa ctatattcaa actatttctg tcaaagactt    840
acagtttcta cgtgaaaatc cccaagtcaa tctctcttta gacctgtctt taaacccaat    900
tgactccatt caagcccaag cctttcaggg aattaggctc catgaattga ctctaagaag    960
taattttaat agctcaaatg tactgaaaat gtgccttcaa aacatgactg gtttacatgt   1020
ccatcggttg atcttgggag aatttaaaaa tgaaaggaat ctggaaagtt ttgaccgttc   1080
tgtcatggaa ggactatgca atgtgagcat tgatgagttc aggttaacat atataaatca   1140
tttttcagat gatatttata atctcaattg cttggcaaat atttctgcaa tgtctttcac   1200
aggtgtacat ataaaacaca tagcagatgt tcctaggcat ttcaaatggc aatccttatc   1260
aatcattaga tgtcatctta agccttttcc aaagctgagt ctaccttttc ttaaaagttg   1320
gactttaact accaacagag aggatatcag ctttggtcag ttggctctgc caagtctcag   1380
atatctagat cttagtagaa atgccatgag ctttagaggt tgctgttctt attctgattt   1440
tggaacaaac aacctgaagt acttagacct cagcttcaat ggtgtcatcc tgatgagtgc   1500
caacttcatg ggtctagaag agctggaata cctggacttt cagcactcca ctttaaaaaa   1560
ggtcacagaa ttctcagtgt tcttatctct tgaaaaactt ctttaccttg acatctctta   1620
cactaatacc aaaattgact ttgatggcat atttcttggc ttgatcagtc tcaacacttt   1680
aaaaatggct ggcaattctt tcaaagacaa caccctttca aatgtcttta caaacacaac   1740
aaacttaaca ttcctggatc tttctaaatg ccaactggaa cagatatcta ggggggtatt   1800
tgacacactc tacagactcc agttattaaa catgagtcac aacaacctac tgtttctgga   1860
tccatcccat tataaacagc tgtactccct caggactctt gattgcagtt tcaatcgcat   1920
agagacatcc aaaggaatac tgcaacattt tccaaagagt ctagccgtct tcaatctgac   1980
taataattct gttgcttgta tatgtgaata tcagaatttc ttgcagtggg tcaaggacca   2040
gaaaatgttc ttggtgaatg ttgaacaaat gaaatgtgca tcacctatag acatgaaggc   2100
ctccctggtg ttggatttta cgaattccac ctgttatata tacaagacta tcatcagtgt   2160
atcggtggtc agtgtgcttg tggtagccac tgtagcattt ctgatatacc acttctattt   2220
tcacctgata cttattgctg gctgtaaaaa gtacagcaga ggagaaagca tctatgatgc   2280
atttgtgatc tactcgagcc agaatgagga ctgggtgaga aacgagctgg taaagaattt   2340
agaagaagga gtgccccgct ttcagctttg ccttcattac agggacttta ttcctggtgt   2400
agccattgct gccaacatca tccaggaagg cttccacaag agccggaaag ttattgtggt   2460
ggtgtctaga cactttatcc agagccgttg gtgtatcttt gaatatgaga ttgctcagac   2520
atggcagttt ctgagtagcc gctctggcat catcttcatt gtccttgaga aagtggagaa   2580
gtccttgctg aggcagcagg tcgaattgta tcgccttctt agcagaaaca cctacctcga   2640
gtgggaggac aatgctctgg ggaggcacat cttctggaga agactcaaaa aagccctgtt   2700
ggatggaaaa gccttgaatc cagatgaaac atcagaggaa gaacaagaag caacaacttt   2760
gacctgagga gtacaaaact ctgcgcctaa aacccattat gtttacaatt tccgaatgct   2820
acagttcatc tgggtttctg ctgtggacag ggaggccagg gagcacgagg cttctaacct   2880
caacgacctc acagggcaca aggaagtagc aatgtgatga aaccccatac tttccatgtg   2940
tatcaggtgt atgaattaag caactcaggc aaagaatcat aatcagcaaa gtttactctt   3000
```

-continued

```
ataaaaccta aggagaggag gctaaggccc agtgagaaca gaaaggaaca tcattcttct   3060

ctggatcttt gaatataagc acaacatgta gtgtgctgca gttaccttag aagagttttg   3120

atcatttaaa ctgaagtgaa tgtttccttc ctttcccttt ttctattgaa tataatttaa   3180

atggcactga ctctttttga gagaccctca ttcaaatttc ttcttccatt ttctgtcagt   3240

ttcttttttt ttaaatctag ttctacaaga aatatgactg atacatgctc aaagatatcc   3300

tggtcaatcc ttagaatgct atatttataa aataaaaatt tttagtgtac ttttattttt   3360

taaaacaaaa aaaaaaaaaa aaaaaaaaaa aaaaa                              3395


<210> SEQ ID NO 6
<211> LENGTH: 835
<212> TYPE: PRT
<213> ORGANISM: Rattus norvegicus

<400> SEQUENCE: 6

Met Met Pro Leu Leu His Leu Ala Gly Thr Leu Ile Met Ala Leu Phe
  1               5                  10                  15

Leu Ser Cys Leu Arg Pro Gly Ser Leu Asn Pro Cys Ile Glu Val Leu
             20                  25                  30

Pro Asn Ile Thr Tyr Gln Cys Met Asp Gln Asn Leu Ser Lys Ile Pro
         35                  40                  45

His Asp Ile Pro Tyr Ser Thr Lys Asn Leu Asp Leu Ser Phe Asn Pro
     50                  55                  60

Leu Lys Ile Leu Arg Ser Tyr Ser Phe Thr Asn Phe Ser Gln Leu Gln
 65                  70                  75                  80

Trp Leu Asp Leu Ser Arg Cys Glu Ile Glu Thr Ile Glu Asp Lys Ala
                 85                  90                  95

Trp His Gly Leu Asn Gln Leu Ser Thr Leu Val Leu Thr Gly Asn Pro
            100                 105                 110

Ile Lys Ser Phe Ser Pro Gly Ser Phe Ser Gly Leu Thr Asn Leu Glu
        115                 120                 125

Asn Leu Val Ala Val Glu Thr Lys Met Thr Ser Leu Glu Gly Phe His
    130                 135                 140

Ile Gly Gln Leu Ile Ser Leu Lys Lys Leu Asn Val Ala His Asn Leu
145                 150                 155                 160

Ile His Ser Phe Lys Leu Pro Glu Tyr Phe Ser Asn Leu Thr Asn Leu
                165                 170                 175

Glu His Val Asp Leu Ser Tyr Asn Tyr Ile Gln Thr Ile Ser Val Lys
            180                 185                 190

Asp Leu Gln Phe Leu Arg Glu Asn Pro Gln Val Asn Leu Ser Leu Asp
        195                 200                 205

Leu Ser Leu Asn Pro Ile Asp Ser Ile Gln Ala Gln Ala Phe Gln Gly
    210                 215                 220

Ile Arg Leu His Glu Leu Thr Leu Arg Ser Asn Phe Asn Ser Ser Asn
225                 230                 235                 240

Val Leu Lys Met Cys Leu Gln Asn Met Thr Gly Leu His Val His Arg
                245                 250                 255

Leu Ile Leu Gly Glu Phe Lys Asn Glu Arg Asn Leu Glu Ser Phe Asp
            260                 265                 270

Arg Ser Val Met Glu Gly Leu Cys Asn Val Ser Ile Asp Glu Phe Arg
        275                 280                 285

Leu Thr Tyr Ile Asn His Phe Ser Asp Asp Ile Tyr Asn Leu Asn Cys
    290                 295                 300
```

-continued

Leu Ala Asn Ile Ser Ala Met Ser Phe Thr Gly Val His Ile Lys His
305 310 315 320

Ile Ala Asp Val Pro Arg His Phe Lys Trp Gln Ser Leu Ser Ile Ile
325 330 335

Arg Cys His Leu Lys Pro Phe Pro Lys Leu Ser Leu Pro Phe Leu Lys
340 345 350

Ser Trp Thr Leu Thr Thr Asn Arg Glu Asp Ile Ser Phe Gly Gln Leu
355 360 365

Ala Leu Pro Ser Leu Arg Tyr Leu Asp Leu Ser Arg Asn Ala Met Ser
370 375 380

Phe Arg Gly Cys Cys Ser Tyr Ser Asp Phe Gly Thr Asn Asn Leu Lys
385 390 395 400

Tyr Leu Asp Leu Ser Phe Asn Gly Val Ile Leu Met Ser Ala Asn Phe
405 410 415

Met Gly Leu Glu Glu Leu Glu Tyr Leu Asp Phe Gln His Ser Thr Leu
420 425 430

Lys Lys Val Thr Glu Phe Ser Val Phe Leu Ser Leu Glu Lys Leu Leu
435 440 445

Tyr Leu Asp Ile Ser Tyr Thr Asn Thr Lys Ile Asp Phe Asp Gly Ile
450 455 460

Phe Leu Gly Leu Ile Ser Leu Asn Thr Leu Lys Met Ala Gly Asn Ser
465 470 475 480

Phe Lys Asp Asn Thr Leu Ser Asn Val Phe Thr Asn Thr Thr Asn Leu
485 490 495

Thr Phe Leu Asp Leu Ser Lys Cys Gln Leu Glu Gln Ile Ser Arg Gly
500 505 510

Val Phe Asp Thr Leu Tyr Arg Leu Gln Leu Leu Asn Met Ser His Asn
515 520 525

Asn Leu Leu Phe Leu Asp Pro Ser His Tyr Lys Gln Leu Tyr Ser Leu
530 535 540

Arg Thr Leu Asp Cys Ser Phe Asn Arg Ile Glu Thr Ser Lys Gly Ile
545 550 555 560

Leu Gln His Phe Pro Lys Ser Leu Ala Val Phe Asn Leu Thr Asn Asn
565 570 575

Ser Val Ala Cys Ile Cys Glu Tyr Gln Asn Phe Leu Gln Trp Val Lys
580 585 590

Asp Gln Lys Met Phe Leu Val Asn Val Glu Gln Met Lys Cys Ala Ser
595 600 605

Pro Ile Asp Met Lys Ala Ser Leu Val Leu Asp Phe Thr Asn Ser Thr
610 615 620

Cys Tyr Ile Tyr Lys Thr Ile Ile Ser Val Ser Val Val Ser Val Leu
625 630 635 640

Val Val Ala Thr Val Ala Phe Leu Ile Tyr His Phe Tyr Phe His Leu
645 650 655

Ile Leu Ile Ala Gly Cys Lys Lys Tyr Ser Arg Gly Glu Ser Ile Tyr
660 665 670

Asp Ala Phe Val Ile Tyr Ser Ser Gln Asn Glu Asp Trp Val Arg Asn
675 680 685

Glu Leu Val Lys Asn Leu Glu Glu Gly Val Pro Arg Phe Gln Leu Cys
690 695 700

Leu His Tyr Arg Asp Phe Ile Pro Gly Val Ala Ile Ala Ala Asn Ile
705 710 715 720

Ile Gln Glu Gly Phe His Lys Ser Arg Lys Val Ile Val Val Val Ser

-continued

```
                725                 730                 735

Arg His Phe Ile Gln Ser Arg Trp Cys Ile Phe Glu Tyr Glu Ile Ala
            740                 745                 750

Gln Thr Trp Gln Phe Leu Ser Ser Arg Ser Gly Ile Ile Phe Ile Val
        755                 760                 765

Leu Glu Lys Val Glu Lys Ser Leu Leu Arg Gln Gln Val Glu Leu Tyr
    770                 775                 780

Arg Leu Leu Ser Arg Asn Thr Tyr Leu Glu Trp Glu Asp Asn Ala Leu
785                 790                 795                 800

Gly Arg His Ile Phe Trp Arg Arg Leu Lys Lys Ala Leu Leu Asp Gly
                805                 810                 815

Lys Ala Leu Asn Pro Asp Glu Thr Ser Glu Glu Glu Gln Glu Ala Thr
            820                 825                 830

Thr Leu Thr
        835


<210> SEQ ID NO 7
<211> LENGTH: 24
<212> TYPE: DNA
<213> ORGANISM: Mus musculus

<400> SEQUENCE: 7

tgaacacata tataccaagg cagc                                              24


<210> SEQ ID NO 8
<211> LENGTH: 20
<212> TYPE: DNA
<213> ORGANISM: Mus musculus

<400> SEQUENCE: 8

accagagggt cattctccaa                                                   20


<210> SEQ ID NO 9
<211> LENGTH: 26
<212> TYPE: DNA
<213> ORGANISM: Mus musculus

<400> SEQUENCE: 9

caaaatatct gacaaaaaca agtgtg                                            26


<210> SEQ ID NO 10
<211> LENGTH: 20
<212> TYPE: DNA
<213> ORGANISM: Mus musculus

<400> SEQUENCE: 10

ggtgtcatca ccatgatgga                                                   20


<210> SEQ ID NO 11
<211> LENGTH: 23
<212> TYPE: DNA
<213> ORGANISM: Mus musculus

<400> SEQUENCE: 11

agtaagcaat gttcactcca acc                                               23


<210> SEQ ID NO 12
<211> LENGTH: 19
<212> TYPE: DNA
<213> ORGANISM: Mus musculus
```

-continued

<400> SEQUENCE: 12
tcccagcatt gatgctcac 19

<210> SEQ ID NO 13
<211> LENGTH: 20
<212> TYPE: DNA
<213> ORGANISM: Mus musculus

<400> SEQUENCE: 13
atgtgtgcca ttttgcatgt 20

<210> SEQ ID NO 14
<211> LENGTH: 24
<212> TYPE: DNA
<213> ORGANISM: Mus musculus

<400> SEQUENCE: 14
agtattgctt gataaatttg catg 24

<210> SEQ ID NO 15
<211> LENGTH: 25
<212> TYPE: DNA
<213> ORGANISM: Mus musculus

<400> SEQUENCE: 15
gttccgtttc tttttacaac tatgg 25

<210> SEQ ID NO 16
<211> LENGTH: 26
<212> TYPE: DNA
<213> ORGANISM: Mus musculus

<400> SEQUENCE: 16
atttgcctat tttattttca tttgtg 26

<210> SEQ ID NO 17
<211> LENGTH: 18
<212> TYPE: DNA
<213> ORGANISM: Mus musculus

<400> SEQUENCE: 17
ggaaggttga agcaagac 18

<210> SEQ ID NO 18
<211> LENGTH: 22
<212> TYPE: DNA
<213> ORGANISM: Mus musculus

<400> SEQUENCE: 18
gactcatgat ttgataactg ac 22

<210> SEQ ID NO 19
<211> LENGTH: 19
<212> TYPE: DNA
<213> ORGANISM: Mus musculus

<400> SEQUENCE: 19
gccaagaaag agcaaatag 19

<210> SEQ ID NO 20
<211> LENGTH: 19
<212> TYPE: DNA
<213> ORGANISM: Mus musculus -continued

<400> SEQUENCE: 20
cgattcctat ggctcagcc 19

<210> SEQ ID NO 21
<211> LENGTH: 20
<212> TYPE: DNA
<213> ORGANISM: Mus musculus

<400> SEQUENCE: 21
agtaattcag cttctcccaa 20

<210> SEQ ID NO 22
<211> LENGTH: 22
<212> TYPE: DNA
<213> ORGANISM: Mus musculus

<400> SEQUENCE: 22
cagatccatg atacagatat gc 22

<210> SEQ ID NO 23
<211> LENGTH: 21
<212> TYPE: DNA
<213> ORGANISM: Mus musculus

<400> SEQUENCE: 23
cctccagcac agtgtacaat g 21

<210> SEQ ID NO 24
<211> LENGTH: 21
<212> TYPE: DNA
<213> ORGANISM: Mus musculus

<400> SEQUENCE: 24
gtgtgtgtgt gtgtaagctt g 21

<210> SEQ ID NO 25
<211> LENGTH: 21
<212> TYPE: DNA
<213> ORGANISM: Mus musculus

<400> SEQUENCE: 25
tagaaagtgg aaacatctga c 21

<210> SEQ ID NO 26
<211> LENGTH: 22
<212> TYPE: DNA
<213> ORGANISM: Mus musculus

<400> SEQUENCE: 26
atgtaactca atcacagaac tc 22

<210> SEQ ID NO 27
<211> LENGTH: 20
<212> TYPE: DNA
<213> ORGANISM: Mus musculus

<400> SEQUENCE: 27
tcaagatcca taacctagac 20

<210> SEQ ID NO 28
<211> LENGTH: 22
<212> TYPE: DNA

-continued

<213> ORGANISM: Mus musculus

<400> SEQUENCE: 28
agacagacag atagacagaa ag 22

<210> SEQ ID NO 29
<211> LENGTH: 23
<212> TYPE: DNA
<213> ORGANISM: Mus musculus

<400> SEQUENCE: 29
gccctgaagg taaatcagta act 23

<210> SEQ ID NO 30
<211> LENGTH: 20
<212> TYPE: DNA
<213> ORGANISM: Mus musculus

<400> SEQUENCE: 30
gctcaggagg tacattgcct 20

<210> SEQ ID NO 31
<211> LENGTH: 19
<212> TYPE: DNA
<213> ORGANISM: Mus musculus

<400> SEQUENCE: 31
tcagtttgct tgcattctc 19

<210> SEQ ID NO 32
<211> LENGTH: 21
<212> TYPE: DNA
<213> ORGANISM: Mus musculus

<400> SEQUENCE: 32
aagtatggat gtgtgtgtaa g 21

<210> SEQ ID NO 33
<211> LENGTH: 20
<212> TYPE: DNA
<213> ORGANISM: Mus musculus

<400> SEQUENCE: 33
tgctaagatt gtgatgactg 20

<210> SEQ ID NO 34
<211> LENGTH: 21
<212> TYPE: DNA
<213> ORGANISM: Mus musculus

<400> SEQUENCE: 34
gactaggtga gagaaacaga c 21

<210> SEQ ID NO 35
<211> LENGTH: 22
<212> TYPE: DNA
<213> ORGANISM: Mus musculus

<400> SEQUENCE: 35
ttgggctgat agtacaatat ac 22

<210> SEQ ID NO 36
<211> LENGTH: 19

-continued

<212> TYPE: DNA
<213> ORGANISM: Mus musculus

<400> SEQUENCE: 36
ggagatttct aatgcttgg 19

<210> SEQ ID NO 37
<211> LENGTH: 20
<212> TYPE: DNA
<213> ORGANISM: Mus musculus

<400> SEQUENCE: 37
tggacaaaca ccacataaca 20

<210> SEQ ID NO 38
<211> LENGTH: 19
<212> TYPE: DNA
<213> ORGANISM: Mus musculus

<400> SEQUENCE: 38
cagactatca gatgactga 19

<210> SEQ ID NO 39
<211> LENGTH: 21
<212> TYPE: DNA
<213> ORGANISM: Mus musculus

<400> SEQUENCE: 39
acattagaat catttcctgc a 21

<210> SEQ ID NO 40
<211> LENGTH: 18
<212> TYPE: DNA
<213> ORGANISM: Mus musculus

<400> SEQUENCE: 40
gcaaagtctt gtgagtct 18

<210> SEQ ID NO 41
<211> LENGTH: 21
<212> TYPE: DNA
<213> ORGANISM: Mus musculus

<400> SEQUENCE: 41
cttaactgga gaggaaagat c 21

<210> SEQ ID NO 42
<211> LENGTH: 22
<212> TYPE: DNA
<213> ORGANISM: Mus musculus

<400> SEQUENCE: 42
cagttctgtc tttgtatctc tg 22

<210> SEQ ID NO 43
<211> LENGTH: 19
<212> TYPE: DNA
<213> ORGANISM: Mus musculus

<400> SEQUENCE: 43
agagagtgag cctcagtct 19

<210> SEQ ID NO 44

-continued

<211> LENGTH: 19
<212> TYPE: DNA
<213> ORGANISM: Mus musculus

<400> SEQUENCE: 44
ttgggtgatg attgtgaac 19

<210> SEQ ID NO 45
<211> LENGTH: 2951
<212> TYPE: DNA
<213> ORGANISM: Mus musculus

<400> SEQUENCE: 45
cctcctgcga cggggcagat cgattctaga acaaaaccaa aagtgagaat gctaaggttg 60
gcactctcac ttcctctttg aatatagtac ttgcagaggg gcacccactg ggagggaaga 120
ggcaggtgtc ccagggactc tgcgctgcca ccagttacag atcgtcatgt tctctcatgg 180
cctccactgg ttgcagaaaa tgccaggatg atgcctccct ggctcctggc taggactctg 240
atcatggcac tgttcttctc ctgcctgaca ccaggaagct tgaatccctg catagaggta 300
gttcctaata ttacctacca atgcatggat cagaaactca gcaaagtccc tgatgacatt 360
ccttcttcaa ccaagaacat agatctgagc ttcaacccct tgaagatctt aaaaagctat 420
agcttctcca atttttcaga acttcagtgg ctggatttat ccaggtgtga aattgaaaca 480
attgaagaca aggcatggca tggcttacac cacctctcaa acttgatact gacaggaaac 540
cctatccaga gtttttcccc aggaagtttc tctggactaa caagtttaga gaatctggtg 600
gctgtggaga caaaattggc ctctctagaa agcttcccta ttggacagct tataacctta 660
aagaaactca atgtggctca caattttata cattcctgta agttacctgc atatttttcc 720
aatctgacga acctagtaca tgtggatctt tcttataact atattcaaac tattactgtc 780
aacgacttac agtttctacg tgaaaatcca caagtcaatc tctctttaga catgtctttg 840
aacccaattg acttcattca agaccaagcc tttcagggaa ttaagctcca tgaactgact 900
ctaagaggta attttaatag ctcaaatata atgaaaactt gccttcaaaa cctggctggt 960
ttacacgtcc atcggttgat cttgggagaa tttaaagatg aaaggaatct ggaaattttt 1020
gaaccctcta tcatggaagg actatgtgat gtgaccattg atgagttcag gttaacatat 1080
acaaatgatt tttcagatga tattgttaag ttccattgct tggcgaatgt ttctgcaatg 1140
tctctggcag gtgtatctat aaaatatcta gaagatgttc ctaaacattt caaatggcaa 1200
tccttatcaa tcattagatg tcaacttaag cagtttccaa ctctggatct accctttctt 1260
aaaagtttga ctttaactat gaacaaaggg tctatcagtt ttaaaaaagt ggccctacca 1320
agtctcagct atctagatct tagtagaaat gcactgagct ttagtggttg ctgttcttat 1380
tctgatttgg gaacaaacag cctgagacac ttagacctca gcttcaatgg tgccatcatt 1440
atgagtgcca atttcatggg tctagaagag ctgcagcacc tggattttca gcactctact 1500
ttaaaaaggg tcacagaatt ctcagcgttc ttatcccttg aaaagctact ttaccttgac 1560
atctcttata ctaacaccaa aattgacttc gatggtatat ttcttggctt gaccagtctc 1620
aacacattaa aaatggctgg caattctttc aaagacaaca ccctttcaaa tgtctttgca 1680
aacacaacaa acttgacatt cctggatctt tctaaatgtc aattggaaca aatatcttgg 1740
ggggtatttg acaccctcca tagacttcaa ttattaaata tgagtcacaa caatctattg 1800
tttttggatt catcccatta taaccagctg tattccctca gcactcttga ttgcagtttc 1860
aatcgcatag agacatctaa aggaatactg caacattttc caaagagtct agccttcttc 1920

-continued

```
aatcttacta acaattctgt tgcttgtata tgtgaacatc agaaattcct gcagtgggtc   1980
aaggaacaga agcagttctt ggtgaatgtt gaacaaatga catgtgcaac acctgtagag   2040
atgaatacct ccttagtgtt ggattttaat aattctacct gttatatgta caagacaatc   2100
atcagtgtgt cagtggtcag tgtgattgtg gtatccactg tagcatttct gatataccac   2160
ttctattttc acctgatact tattgctggc tgtaaaaagt acagcagagg agaaagcatc   2220
tatgatgcat ttgtgatcta ctcgagtcag aatgaggact gggtgagaaa tgagctggta   2280
aagaatttag aagaaggagt gccccgcttt cacctctgcc ttcactacag agactttatt   2340
catggtgtag ccattgctgc caacatcatc caggaaggct tccacaagag ccggaaggtt   2400
attgtggtag tgtctagaca ctttattcag agccgttggt gtatctttga atatgagatt   2460
gctcaaacat ggcagtttct gagcagccgc tctggcatca tcttcattgt ccttgagaag   2520
gttgagaagt ccctgctgag gcagcaggtg gaattgtatc gccttcttag cagaaacacc   2580
tacctggaat gggaggacaa tcctctgggg aggcacatct tctggagaag acttaaaaat   2640
gccctattgg atggaaaagc ctcgaatcct gagcaaacag cagaggaaga acaagaaacg   2700
gcaacttgga cctgaggaga acaaaactct ggggcctaaa cccagtctgt ttgcaattaa   2760
taaatgctac agctcacctg gggctctgct atggaccgag agcccatgga acacatggct   2820
gctaagctat agcatggacc ttaccgggca gaaggaagta gcactgacac cttcctttcc   2880
aggggtatga attacctaac tcgggaaaag aaacataatc cagaatcttt acctttaatc   2940
tgaaggagaa g                                                         2951
```

<210> SEQ ID NO 46
<211> LENGTH: 2951
<212> TYPE: DNA
<213> ORGANISM: Mus musculus

<400> SEQUENCE: 46

```
cctcctgcga cggggcagat cgattctaga acaaaaccaa aagtgagaat gctaaggttg     60
gcactctcac ttcctctttg aatatagtac ttgcagaggg gcacccactg ggagggaaga    120
ggcaggtgtc ccagggactc tgcgctgcca ccagttacag atcgtcatgt tctctcatgg    180
cctccactgg ttgcagaaaa tgccaggatg atgcctccct ggctcctggc taggactctg    240
atcatggcac tgttcttctc ctgcctgaca ccaggaagct tgaatccctg catagaggta    300
gttcctaata ttacctacca atgcatggat cagaaactca gcaaagtccc tgatgacatt    360
ccttcttcaa ccaagaacat agatctgagc ttcaacccct tgaagatctt aaaaagctat    420
agcttctcca atttttcaga acttcagtgg ctggatttat ccaggtgtga aattgaaaca    480
attgaagaca aggcatggca tggcttacac cacctctcaa acttgatact gacaggaaac    540
cctatccaga gtttttcccc aggaagtttc tctggactaa caagtttaga caatctggtg    600
gctgtggaga caaaattggc ctctctagaa agcttcccta ttggacagct tataacctta    660
aagaaactca atgtggctca caattttata cattcctgta agttacctgc atatttttcc    720
aatctgacga acctagtaca tgtggatctt tcttataact atattcaaac tattactgtc    780
aacgacttac agtttctacg tgaaaatcca caagtcaatc tctctttaga catgtctttg    840
aacccaattg acttcattca agaccaagcc tttcagggaa ttaagctcca tgaactgact    900
ctaagaggta attttaatag ctcaaatata atgaaaactt gccttcaaaa cctggctggt    960
ttacacgtcc atcggttgat cttgggagaa tttaaagatg aaaggaatct ggaaattttt   1020
```

-continued

```
gaaccctcta tcatggaagg actatgtgat gtgaccattg atgagttcag gttaacatat   1080

acaaatgatt tttcagatga tattgttaag ttccattgct tggcgaatgt ttctgcaatg   1140

tctctggcag gtgtatctat aaaatatcta gaagatgttc ctaaacattt caaatggcaa   1200

tccttatcaa tcattagatg tcaactaagc agtttccaac tctggatcta ccctttctta   1260

aaagtttgac tttaactatg aacaaagggt ctatcagttt taaaaaagtg gccctaccaa   1320

gtctcagcta tctagatctt agtagaaatg cactgagctt tagtggtggc tgttcttatt   1380

ctgatttggg aacaaacagc ctgagacact tagacctcag cttcaatggt gccatcatta   1440

tgagtgccaa tttcatgggt ctagaagagc tgcagcacct ggatttttca gcactctact   1500

ttaaaaaggg tcacagaatt ctcagcgttc ttatcccttg aaaagctact ttaccttgac   1560

atctcttata ctaacaccaa aattgacttc gatggtatat ttcttggctt gaccagtctc   1620

aacacattaa aaatggctgg caattctttc aaagacaaca ccctttcaaa tgtctttgca   1680

aacacaacaa acttgacatt cctggatcct tctaaatgtc aattggaaca aatatcttgg   1740

ggggtatttg acaccctcca tagacttcaa ttattaaata tgagtcacaa caatctattg   1800

tttttggatt catcccatta taaccagctg tattccctca gcactcttga ttgcagtttc   1860

aatcgcatag agacatctaa aggaatactg caacattttc caaagagtct agccttcttc   1920

aatcttacta acaattctgt tgcttgtata tgtgaacatc agaaattcct gcagtgggtc   1980

aaggaacaga agcagttctt ggtgaatgtt gaacaaatga catgtgcaac acctgtagag   2040

atgaatacct ccttagtgtt ggattttaat aattctacct gttatatgta caagacaatc   2100

atcagtgtgt cagtggtcag tgtgattgtg gtatccactg tagcatttct gatataccac   2160

ttctattttc acctgatact tattgctggc tgtaaaaagt acagcagagg agaaagcatc   2220

tatgatgcat ttgtgatcta ctcgagtcag aatgaggact gggtgagaaa tgagctggta   2280

aagaatttag aagaaggagt gccccgcttt cacctctgcc ttcactacag agactttatt   2340

cctggtgtag ccattgctgc caacatcatc caggaaggct tccacaagag ccggaaggtt   2400

attgtggtag tgtctagaca ctttattcag agccgttggt gtatctttga atatgagatt   2460

gctcaaacat ggcagtttct gagcagccgc tctggcatca tcttcattgt ccttgagaag   2520

gttgagaagt ccctgctgag gcagcaggtg gaattgtatc gccttcttag cagaaacacc   2580

tacctggaat gggaggacaa tcctctgggg aggcacatct tctggagaag acttaaaaat   2640

gccctattgg atggaaaagc ctcgaatcct gagcaaacag cagaggaaga acaagaaacg   2700

gcaacttgga cctgaggaga acaaaactct ggggcctaaa cccagtctgt ttgcaattaa   2760

taaatgctac agctcacctg gggctctgct atggaccgag agcccatgga acacatggct   2820

gctaagctat agcatggacc ttaccgggca gaaggaagta gcactgacac cttcctttcc   2880

aggggtatga attacctaac tcgggaaaag aaacataatc cagaatcttt acctttaatc   2940

tgaaggagaa g                                                        2951
```

<210> SEQ ID NO 47
<211> LENGTH: 18989
<212> TYPE: DNA
<213> ORGANISM: Homo sapiens

<400> SEQUENCE: 47

```
tcccctactt tcttcacatt ctgcagtaaa cttggaggct gcatgttgaa tatgaaagta     60

taatgaaata aaagaagcct agaaccagga atcatacctg ggtaatccca atcagaaata    120

tcctcattga gtgtttcatg agccaggaaa acttttatta agtcacaata aaatctggaa    180
```

-continued

```
gtttatacag caattagctt agtctaacac ttgtcagttt tgtgcatatt tcttacagca    240
tatgcattac ctgccaaata aaagcaaaca cttctaggtc cctggcgaat atgggattcc    300
tccattgact gactgattat gggtcctgag ttgaacttgc tctgcatgaa ggatgtaggc    360
gatcaagtgg cttgttttgc ctctggccaa atctctacca ctatgcttaa gatgcgatta    420
attatgtaca acaaaccccc atgacacacg tttacctatg taacaaacct gctcatcctg    480
cacatgtact tctgaatgta aaaataaaag taaaaaaaaa gaaaacaaga ggtggttatt    540
attctactgt gggagaaatt ataggcccat aatggtaact aatcaccacg gtcttacctc    600
attataatac tgcatcggta agttcatcaa cataagcaag ttagatctga taaccaaggg    660
gcttacagtt tctaatttgt atttgacaca tggtctgcct tctggaagag cagcatagaa    720
cctagatgtc tttgattaag gtcagtaaat gattgagtgt taatcccatt catttcccag    780
gaaaaggaaa cctctttaca agtcaccacc agggattctc caatcacaca taggaaaaat    840
ttccaggaag acttctataa aacacatgta ttaacatctc cgaaaacata gttgaaagga    900
cttccctggg ccctttttcct tagttcctca tctagactat caagcggttt cctctccaaa    960
tgatgggaag aaagtgcatt tgtctattac acacttgtat tactctattc acttaagcac   1020
tgtgtcccag taatggggtc tagttatgtc tggcttgaaa tgacccacat atttgtttct   1080
cattcttagg aagtggagtg tttctgtatg tgtatatgtg atgggggtag gccaggagat   1140
tttttatcta ggcaataccc agcctgaaat cattattagc atgacatgag ttaaacgtat   1200
ttctatttta gaaagatgtt ttcaacagca ggatgaagaa tcaattggaa gagctggtac   1260
attgaaagag gtgaatctag actttgggag gcttcttaaa gtatattgaa ctagtctagg   1320
ccgtgggata tgttcaatag taatggtagt agaaatggcg actgacattt tggaattatt   1380
ttacagatac aatttctaca acttggtgga acatttttta aaatgtaggt tttattattc   1440
ggctatggtg aaaacaacag atcagaagat gatgccactg gaaatatagt ttgttgttta   1500
cagttcctaa gaagcggggg catgccacac catgcagggc cacattggta gcaccagagt   1560
ccgtcaggag gcagagggag caagaggaaa ttataggcac aagcttttat tgttgttact   1620
gcagaaaagg caaggcaagg cagggtaagc agggatagga ctggctagtt tgaataacct   1680
cagtgggctc tggggtagag ggtctgtctc tagttgtctg gtacctggac ctgtgatgat   1740
tagggctgaa taacagtgtc tacttgggtg taaaagccag gtagaggagg tggttcagag   1800
gaagggctct ggattgctta gtgtgcataa ggcatgctcc agagcaaatc ttttgctatt   1860
ttttagaact aactagccct ggtaagtgca gtctcttccc agatgccaga acatcaagaa   1920
cacagaaaag aagacaattg ggttaataca tgtttagcat gagaaatgag gaagtaaggg   1980
aaataaagtc aaagagattt ccaccttgga tgactatgtc aaagtgaaac accattaact   2040
ttccagggaa ctaaacttta ttgagcacct actctgtgtc aggcactgct ctaaaatctt   2100
tacatgaata atctcaatac tcagagcaaa gctttgacat ggaggttgtt tttatcttaa   2160
ctctactggt gtgttgatgg agtctacaag agtttgtgcc cagtccacca caaaatggtc   2220
cctcacagct tggtttttga cacgttggat tggaagtgct tggaggatat tacagtagaa   2280
ctatctagga cttagcatac ataatattcc tgttttaaat caggttctta tttaacagaa   2340
acttacattg cacttgctac tttccagaca ctgtcctaaa agctttacaa atgccagttc   2400
atttaatccc aatacaatac tttgagatac atattatcat cttcattcta tccacatttt   2460
caatcctcat catagctctc atttatggaa tgtaatgatg atgctctaga ctagacgttt   2520
```

-continued

```
tacgtaagtt agcttaattc agtaattcaa aacacatgcg attatcttcg ttttaaagac   2580
cagaaaacta aaggttggta ggtttgtata atttgactac cattgcgtat ctttatttta   2640
atacatttta taaatgcaag cttctgctat gattaaaagt gattaccaca ttttacagac   2700
cagaaagtaa taataagtgt tggtgaagat gtgaaaaaat gagaactcct gtacaccatt   2760
tgtgggaatg taaaatggta cagatgctgt ggagaatcat atggtgggtg ctcaaaaaat   2820
taaaaataga tttaccacat gatccagcaa tctcacttct gagtacgtat ccaaaagaat   2880
tgaaaacaga gactttaaga gatatttgta caaccatgtt tatggcagca ttattcacaa   2940
tagctaacgt gtggcaacaa tgcaagtgtc catgaacaga caaatggata agcaaaatgt   3000
ggtctataca tacaatggaa tattgttcag ctttaaaaag gaaggaggct ttgatctata   3060
ctacacagaa aagaaccttg aggacattat gcaaagtgaa ataagccagt gacaaaaaga   3120
tacatactgt atgattccac ttctaagagc tgcctagagt agtcaagatt atagagacaa   3180
aagtagtgca tagattcaag ggcctaggga aaggggaaat ggggagttat ttattaatga   3240
atagtggtga tgattgtaca aaaatatgaa cataattaat gccactaaat tgtacacata   3300
caaatggtca agataataaa ttttatgtta tgtcatgtta tgttatgtga ttttaccata   3360
atacagaaaa tgaaaaaaga aaagaaagaa agtaaagctt agcggtttac atgacttgac   3420
caatgcctca aagccatgag tcacccagct gagatctgaa cttcagtata ttccattctg   3480
aaatcccaga cttttcccaa tcttcttgta cttttcaaac tgtgtttcag ttgaggttta   3540
ttttcagttt tgtatgtgag tttcttcaca agaaggggcg ggccaaattg tgtcctgcaa   3600
aaacctacat atcgaagtcc taacccctct acctcagact atgactgtat atggagagag   3660
agccttgaaa gaggtatgta aggtagaatg aggtcattat ggtgggccct aatccaacat   3720
aactggtgtc cttataagaa ggggagatta gaattcagac acacttgctg acaccttgag   3780
ttcagactgg aagcctctag aattgtgaga aaatgaatgt ctgttgttta agccacccag   3840
tctgtggtat ttccttatgg cagccccagc aaactaatac aaatagtgtt tccacagctg   3900
aaacaaaatt ggaaaatcac cgtcatccta gagagttaca agggctattt taatagaacc   3960
tgattgtttt cctaaattca ccaagcccag gcagaggtca gatgactaat tgggataaaa   4020
gccaactagc ttcctcttgc tgtttcttta gccactggtc tgcaggcgtt ttcttcttct   4080
aacttcctct cctgtgacaa aagagataac tattagagaa acaaaagtcc agaatgctaa   4140
ggttgccgct ttcacttcct ctcacccttt agcccagaac tgctttgaat acaccaattg   4200
ctgtggggcg gctcgaggaa gagaagacac cagtgcctca gaaactgctc ggtcaaacgg   4260
tgatagcaaa ccacgcattc acagggccac tgctgctcac agaagcagtg aggatgatgc   4320
caggatgatg tctgcctcgc gcctggctgg gactctgatc ccagccatgg ccttcctctc   4380
ctgcgtgaga ccagaaagct gggagccctg cgtggaggta tgtggctgga gtcagctcct   4440
ctgaactttc cctcacttct gcccagaact tctcactgtg tgccctggtt tgtttatttt   4500
tgcaaaaaaa aaaagagtta aattacctta aagactcaag aagccacaga gatcaaataa   4560
ttcattgtta cagggcacta gaggcagcca ttgggggttt gttccatttg gaaattttga   4620
gtgctaacag gggcatgaga taacatagat ctgcttaagg tccctgctct gctaccttgt   4680
ggctctgtga agaaattatc aaacctgtct gagactagtt ttcgcatctg taagagaatt   4740
ataatacctt cttcactaga gagtaagcag actgcttcag tgtcatttct tcccactggt   4800
ggtctttaca ctcagcttca agcagtcacc ctgctccttt caatctcagg aaaaagatgg   4860
cttttgtgtg tgtgtctcta gagaaagaac tttctaagtg ggtgtcagac ttctgtatgc   4920
```

-continued

```
agtaatatag tttagtccag aggatgaaaa aaataagaga atgaaaaagg aaaagagaga   4980
gagagagaag aaaaaagcaa gagggaaata tgtataatgt cagctaatgc aacagtttct   5040
ttcttagtga aataccaatc agctggttgg taatcttatt catgatggat ctcttttgtt   5100
tttcccctgc gcagacttca cagttgcttt agaaacccat agtagagccg aacagctaag   5160
aaaatgattt acagtgaggc agggtcagaa actcaagaga gaaaaagcca gctgcagtcc   5220
tgaagttgag gatataggag aaaatcaagt aatatttagc aaagactaat tcattatctt   5280
gaagccatcc cttccctcaa ttccctgccc atagtcctcc tccttgtcct cttctctgta   5340
tccctctgct gttaggttaa tggagataga ttttctaatt aggctcactg cgagataaaa   5400
ccacagccaa acttgacttc ttttccccat gtaccttttc ctgtcagtcc ctgaagcctg   5460
tccatccctg cccatcccct tagttccact gtaaggcagg ccctcatttc ccctggcatt   5520
gactcttaca cactaactgc tttcctgatt ccagtcttct tcctttaact cattctgcac   5580
gttcttgttt gttatgtact tgcatttgtt gttattattt ttccttaggc ttcaatctaa   5640
caaattactc tccttaaaaa cttttaataa ctctccattg ccattagaac agctttctac   5700
cacagggcct ttgcactggc tatttcttct acctagaatg ctagatcagt gctatccatt   5760
ggcaatatta tgtgagccac atatgtactt ttaaagtttt tagtagcctc attaaaaaaa   5820
gaaacaagtg aatttaattt cgataatagt tttatttaac ttagcgtatt taaaataatg   5880
tttaaaattt taatatatat ttacctatta ttgatatttt tacattcctt gtttggtact   5940
aagtctggaa tttagtatat attttacatt taccacactt ctcaatttac actattcaca   6000
tttcttgtgt ttgataactg tgtatggcta gtgactaccg tattggtcag tgcagcccaa   6060
gtccttttca tgctttaatc actccattca gatctctgat taaatgtccc ctcctcaggg   6120
cagtcttcct tgattgcccc atgtagagct ctccagcctc acttatttgc ctcaaatccc   6180
cttatactgc ttaatatttt tttttctaga gcacaacatt ttatattttt gtttgtttat   6240
tttctctctc tccctttgta atggaatcgg taaggaggca ggatcattgc tggttttatt   6300
taccactata tttccagtgg ccagcacaca gtagccgcta gatgtgtaag tgataaatga   6360
ttgaaataat tgctgcagga caaagtctga ggccctcctg atctggcttg ccctcttact   6420
tagatttcac cactcccacc actcaccagc taatctgagt ttgttttcca ctctttacgt   6480
gctcacgttg tcctctcctt aggacatgtt tttcttcccc tttccacata tctaaacctt   6540
actcatcttc caagacccac tttaaaatct tccttttctg ggaagccttt cctgaatcca   6600
gacttgatct ctgctttctc tgaaccacag ggcatatttt ctaagcctat tttatggccc   6660
cttgagatag tgttagcttt gctcctatct aaactcttac tctagactgt gagtccattg   6720
aagtctggag ctgcatcata tttttctttg taatgcccac agcacttggc aggaaatgcc   6780
tacaatttgg acttaagtaa accttcattt aatcagttat tcaatcagtt agtgattcag   6840
caaatattta ttgagcacca accatttgcc agacaccatt ctgagtgctg gagacaaagc   6900
agtgggcaaa cccatcaaac ttgcaatgga atacaggaga tgaacaatac gatgagaaca   6960
atcagataga caacataatg ttagatggtt gtgcttcctg tgaaagggaa taaaagaggg   7020
caaagaaaga gtgcctggca ctgtttctat tagacaatat tgtctttgag gctccatggc   7080
ttgcaacatt taagcagaca tacgaatgaa gatctgcatg tttgaactct gactttgcgc   7140
atattacttc atttctttga atttccattt tcctcatctt taaatgctta tttgaagatt   7200
aagtgaaagt atataacaaa caagaactat gcaggcgtat ggtaaggat taatgataga   7260
```

-continued

```
tgataataat taatgttgac atctattgat cacttatact gtagcgggct tttaaataaa   7320
ctctttaaac accttatctc atttaatcct tcaaacattc tattggtttc aaacaacaga   7380
aaactacaat tagctggctt ctgcaaggaa ttttgttgga ggaaatgaga gcattcagaa   7440
attagatggg agcgttagag aattaggctt acaaagaatg tgggaaagta ggctagaaag   7500
cagtgtaaaa acaaagacag cataaagcac ttgaccttat ttactaggtt ccaccatggg   7560
aatccatgca ctctaaagat ttccccctat ttctacatca ctttgctcaa gggtcaatga   7620
gccaaggaaa agaatgcagt tgtcaaaatc tgggccatga ctaaggaagg tctggacatc   7680
ttgactgcca gacagtctcc ccaatgatat ggagtattta gaatgatact ggatatttta   7740
tttatttttt gtattttcaa cttttaagtt cagaggcaca tgtgcagagc atgcaggttt   7800
attacataag taaatgtgtg ccatggtgat ttgctgcata gatcatgaaa atatggaacg   7860
catcatggat ttgtgtgtca tccttgtgca ggggccatgc tcatcttctc tgtatccttc   7920
caattttagt atatgtgcta ctgcagcaag cacgatattg gatattttat tacctacatt   7980
ttacatatga taaaatgagg ctcactgagg tttttctttt gttcgtttta ttttgttttg   8040
tttttaaaga cttggcccta aaccacacag aagagctggc atgaaaccca gagctttcag   8100
actccggagc ctcagccctt caccccgatt ccattgcttc ttgctaaatg ctgccgtttt   8160
atcacggagg ttagaatgct gagcacgtag taggtgctct ttactttcta atctagagta   8220
agacaattta taagcatgaa ttgagtgaat ggatggatgg atatatggat ggaaggatgg   8280
acagatggat gaaaggttga ctgaattttg tgcttgcaca aaaagaggcc cctctccacc   8340
atctctggtc taggagaggg gagttgggag accatgcagt aaagatactt catgtcatgt   8400
gtaatcattg caggtggttc ctaatattac ttatcaatgc atggagctga atttctacaa   8460
aatccccgac aacctcccct tctcaaccaa gaacctggac ctgagcttta atcccctgag   8520
gcatttaggc agctatagct tcttcagttt cccagaactg caggtgctgg atttatccag   8580
gtaatgaatc cacttttaca tactgcacaa ggtgaggtgt tcattgtcct atcatttcat   8640
tattggactg gaaagcttgg tttgtggagt ctcatcttca ttcacttatt cattcataca   8700
acagatgtct tattaactat ataaccttga gcaagctacc tctattctcc aggtctcagt   8760
tttctaatct gtgaagtagg cagttggctg agacagcttc taagggcaat tctaatttta   8820
ggttttcttt taagacagga gagaaaatta gcttaaattc tttcataagc agctatttat   8880
tgactacttg ctatatgttg tacactctgc aagaagacag gcatatattg atatataaca   8940
cacagcccct gttgttaagg aggcatatct tcttgaaaga gttaatacct taaagtcctg   9000
ggtatggtcc tgggtacata gtatatagtc aacacatttt aattatgatt ttttggatct   9060
ggaaactgat ataaagatag cgacatataa cagtaggtga taaattatgt ttaaactaaa   9120
ggtaactaat tgtatttttc agaagagggg ccttctctgt ggtgggtagt caagaaagat   9180
ttcatgaact gcataagatt caaacaatgt ctagaatatt aaaactagtg tacaggatag   9240
ggaattagga aaagacaagt aacccaagga gaaagatgtc aagattaaag gaaaacatct   9300
gctgtgggca gggaataatg gctaagattt tcttttctga tgcagggaag tatatcgttt   9360
gttgtggcag gtgaaatgtc atcttgatat tttaggggaa ccaaattcta aaagggtttt   9420
catcatcggg gccttatttg caaatcgaac tagataatgg atcatgttct ctgcaatggt   9480
ttgtaaaaca tttcaaaaca ttttacatat tttttattat agaaattatt gataaagact   9540
aaggtcacag tataaaaatc ctttttagag cagacatttc tgtagaagag tgaacatatg   9600
acctattata ctctaatttg gatatagata ggatgtaaca aaggagtaat ggaacaattc   9660
```

-continued

```
aaaggcagtg gtatagtgca tagagtcctg ttggggtcag aagacctgag ccaagtttac   9720
ccccaacatt tataaccatg taaccttagg catattactt catctccctt aatcttagtt   9780
ttcatatctg atcaatggaa atgatgaaac ttattctgct ggattaaatg tgataataaa   9840
tattaatatg ctgtatatat ttaaattttt ataaaatata ttttataagc ataaagtatt   9900
cttacagaat ttcattaggt ttttaaaata atttcaactt ttatttttga ttcagggatt   9960
tacatggtta tattgcgtaa tgctgaggtg tagggtacaa tcgataccat cactcaggta  10020
gtgagcatag tacccaatag ttagtttttc aacccttgct gctttctctc tatcccctct  10080
ctagtaatcc ccagggtcta tttttgtcat ctttatgtcc atgtgtactc catgtttgga  10140
tcctacttat aaagtgagaa ctcatggtat ttggctttct gttcctttgt taatttgctt  10200
aggataatgg ctactagctg catctatgcc attatgttct aaatttcagt ttcctgcatg  10260
aaaattttgt caagtactct attaaggtag accacctctc cctttttttt ttttcaaaca  10320
agaagtagtt tttcaccaaa caatgtctct tatgtaattc atcttcaatc cactggatac  10380
ccaataaact tgccccagaa accttaaatc tgtgcttaca gagaggccag cttcccttct  10440
tgttaaccca taggagattc tgaattaggg caagcacaaa agatagcaca atagacatcc  10500
tttgcctttt cgtacagtgt tcacatacag taactcaact agtcttgtaa gaatgctttg  10560
tgatagacca ggcagccttc tttcccctat agaaatatat atatatttct ttttataggt  10620
gaggaaactg aagcttgaat aatttaaatg acttatatac attatcattg cttgttagcc  10680
acagaccaga gatttaagtt cacatctcca gaatccaact taaatgtttt ctttgtctta  10740
atactctact tctctaaagt gattatcacc aatgtaatga tatagagaca cagcaagacc  10800
ctttccttct cacctaatgt atagagcaat gcagagatag aatgatgggc tataacaatc  10860
atataattga aagaaagaac ttcaaaaata atcaagttca gctgtttgac ttataaatgt  10920
gataactaaa acctagagag gaaaagaggt actcaagatc acacagtagg agaggactgc  10980
agaaacacca aacccaagct cttttgtcca ctcttccagc gttctttcta ctatactgcc  11040
tatcctttat ctagttacca ataaataaca aaagcttgga ccacaatgct tttattgtct  11100
aggaaactcc tgaagaagct aaataaaatg ggtggggaat attgtaaatg taattcaggc  11160
tggattaaga aagaacttat ttgtacattg taactgacaa gcacctgcaa tgctgaaagg  11220
aatttttcat tggcttgctg tttgctggct gcatcaaagc cctgtctcta ggacatgtct  11280
ctgaacattg tgtgtagcat ggctttcatt tcttttagga taaaattcaa aaccctttat  11340
ctggttggta aacctctgcc taattgggaa ccttctttct ccacaactcc atattgtaca  11400
ctccaatttc atctctgttc tccaaccatg gaagctattt gtcatgattc ctccttgtgt  11460
catttttttt ctgtcaacct tggggctttt gtgtttgctg ttcacttcac ctccttttat  11520
tgttaacttc tactcatctt tcaattttca acttaagtgt tctcagagaa acctactttg  11580
attttcttgg tccacaacgg ttctctggat gtgaactctt atagcacata attttcactt  11640
ttttccacaa aactcgctcc tatcacctgt tacaagcatt tacctctgat aacaagaact  11700
ttcaaatatc tagctgtcat gtaagcactt ttcataaaca ttaagagtat ctgtgacact  11760
tatgtgtaat gtttcgtatc tctgaaattg atatttacca gtcatttatc ttggctacca  11820
actaacaact atccatatta tctgtaccaa tcagatgtat aatcacaatt ttgtgtgaca  11880
gaaaatggct aaacttgatc caaggctatt acatgcttta tcaactgcac aatctttata  11940
tatgtcaatt attgatcttt aactgatttc cttcttatgg attttctcct ctgcttatca  12000
```

-continued

```
tgtatgccta acatgacaaa aaagagccta tcattgcagc cagtatgata atactcagtc  12060
tgtggggctt cttatttgct tattccatca tcatctgtcc tgcttgatgt ctttgcctat  12120
gcacaatcat atgacccatc acatctgtat gaagagctgg atgactagga ttaatattct  12180
attttaggtt cttattcagc agaaatatta gataatcaat gtctttttat tcctgtaggt  12240
gtgaaatcca gacaattgaa gatggggcat atcagagcct aagccacctc tctaccttaa  12300
tattgacagg aaaccccatc cagagtttag ccctgggagc cttttctgga ctatcaagtt  12360
tacagaagct ggtggctgtg gagacaaatc tagcatctct agagaacttc cccattggac  12420
atctcaaaac tttgaaagaa cttaatgtgg ctcacaatct tatccaatct ttcaaattac  12480
ctgagtattt ttctaatctg accaatctag agcacttgga cctttccagc aacaagattc  12540
aaagtattta ttgcacagac ttgcgggttc tacatcaaat gcccctactc aatctctctt  12600
tagacctgtc cctgaaccct atgaacttta tccaaccagg tgcatttaaa gaaattaggc  12660
ttcataagct gactttaaga aataattttg atagtttaaa tgtaatgaaa acttgtattc  12720
aaggtctggc tggtttagaa gtccatcgtt tggttctggg agaatttaga aatgaaggaa  12780
acttggaaaa gtttgacaaa tctgctctag agggcctgtg caatttgacc attgaagaat  12840
tccgattagc atacttagac tactacctcg atgatattat tgacttattt aattgtttga  12900
caaatgtttc ttcattttcc ctggtgagtg tgactattga aagggtaaaa gacttttctt  12960
ataatttcgg atggcaacat ttagaattag ttaactgtaa atttggacag tttcccacat  13020
tgaaactcaa atctctcaaa aggcttactt tcacttccaa caaaggtggg aatgcttttt  13080
cagaagttga tctaccaagc cttgagtttc tagatctcag tagaaatggc ttgagtttca  13140
aaggttgctg ttctcaaagt gattttggga caaccagcct aaagtattta gatctgagct  13200
tcaatggtgt tattaccatg agttcaaact tcttgggctt agaacaacta gaacatctgg  13260
atttccagca ttccaatttg aaacaaatga gtgagttttc agtattccta tcactcagaa  13320
acctcattta ccttgacatt tctcatactc acaccagagt tgctttcaat ggcatcttca  13380
atggcttgtc cagtctcgaa gtcttgaaaa tggctggcaa ttctttccag gaaaacttcc  13440
ttccagatat cttcacagag ctgagaaact tgaccttcct ggacctctct cagtgtcaac  13500
tggagcagtt gtctccaaca gcatttaact cactctccag tcttcaggta ctaaatatga  13560
gccacaacaa cttcttttca ttggatacgt ttccttataa gtgtctgaac tccctccagg  13620
ttcttgatta cagtctcaat cacataatga cttccaaaaa acaggaacta cagcattttc  13680
caagtagtct agctttctta aatcttactc agaatgactt tgcttgtact tgtgaacacc  13740
agagtttcct gcaatggatc aaggaccaga ggcagctctt ggtggaagtt gaacgaatgg  13800
aatgtgcaac accttcagat aagcagggca tgcctgtgct gagtttgaat atcacctgtc  13860
agatgaataa gaccatcatt ggtgtgtcgg tcctcagtgt gcttgtagta tctgttgtag  13920
cagttctggt ctataagttc tattttcacc tgatgcttct tgctggctgc ataaagtatg  13980
gtagaggtga aaacatctat gatgcctttg ttatctactc aagccaggat gaggactggg  14040
taaggaatga gctagtaaag aatttagaag aaggggtgcc tccatttcag ctctgccttc  14100
actacagaga ctttattccc ggtgtggcca ttgctgccaa catcatccat gaaggtttcc  14160
ataaaagccg aaaggtgatt gttgtggtgt cccagcactt catccagagc cgctggtgta  14220
tctttgaata tgagattgct cagacctggc agtttctgag cagtcgtgct ggtatcatct  14280
tcattgtcct gcagaaggtg gagaagaccc tgctcaggca gcaggtggag ctgtaccgcc  14340
ttctcagcag gaacacttac ctggagtggg aggacagtgt cctggggcgg cacatcttct  14400
```

-continued

```
ggagacgact cagaaaagcc ctgctggatg gtaaatcatg gaatccagaa ggaacagtgg  14460
gtacaggatg caattggcag gaagcaacat ctatctgaag aggaaaaata aaaacctcct  14520
gaggcatttc ttgcccagct gggtccaaca cttgttcagt taataagtat taaatgctgc  14580
cacatgtcag gccttatgct aagggtgagt aattccatgg tgcactagat atgcagggct  14640
gctaatctca aggagcttcc agtgcagagg gaataaatgc tagactaaaa tacagagtct  14700
tccaggtggg catttcaacc aactcagtca aggaacccat gacaaagaaa gtcatttcaa  14760
ctcttacctc atcaagttga ataaagacag agaaaacaga aagagacatt gttcttttcc  14820
tgagtctttt gaatggaaat tgtattatgt tatagccatc ataaaaccat tttggtagtt  14880
ttgactgaac tgggtgttca ctttttcctt tttgattgaa tacaatttaa attctacttg  14940
atgactgcag tcgtcaaggg gctcctgatg caagatgccc cttccatttt aagtctgtct  15000
ccttacagag gttaaagtct agtggctaat tcctaaggaa acctgattaa cacatgctca  15060
caaccatcct ggtcattctc gagcatgttc tattttttaa ctaatcaccc ctgatatatt  15120
tttattttta tatatccagt tttcattttt ttacgtcttg cctataagct aatatcataa  15180
ataaggttgt ttaagacgtg cttcaaatat ccatattaac cactattttt caaggaagta  15240
tggaaaagta cactctgtca ctttgtcact cgatgtcatt ccaaagttat tgcctactaa  15300
gtaatgactg tcatgaaagc agcattgaaa taatttgttt aaagggggca ctcttttaaa  15360
cgggaagaaa atttccgctt cctggtctta tcatggacaa tttgggctag aggcaggaag  15420
gaagtgggat gacctcagga ggtcaccttt tcttgattcc agaaacatat gggctgataa  15480
acccggggtg acctcatgaa atgagttgca gcagaagttt atttttttca gaacaagtga  15540
tgtttgatgg acctctgaat ctctttaggg agacacagat ggctgggatc cctcccctgt  15600
acccttctca ctgccaggag aactacgtgt gaaggtattc aaggcaggga gtatacattg  15660
ctgtttcctg ttgggcaatg ctccttgacc acattttggg aagagtggat gttatcattg  15720
agaaaacaat gtgtctggaa ttaatggggt tcttataaag aaggttccca gaaaagaatg  15780
ttcatccagc ctcctcagaa acagaacatt caagaaaagg acaatcagga tgtcatcagg  15840
gaaatgaaaa taaaaaccac aatgagatat caccttatac caggtagaat ggctactata  15900
aaaaaatgaa gtgtcatcaa ggatatagag aaattggaac ccttcttcac tgctggaggg  15960
aatggaaaat ggtgtagccg ttatgaaaaa cagtacggag gtttctcaaa aattaaaaat  16020
agaactgcta tatgatccag caatctcact tctgtatata tacccaaaat aattgaaatc  16080
agaatttcaa gaaaatattt acactcccat gttcattgtg gcactcttca caatcactgt  16140
ttccaaagtt atggaaacaa cccaaatttc cattgaaaaa taaatggaca aagaaaatgt  16200
gcatatacgt acaatgggat attattcagc ctaaaaaaag ggggaatcct gttatttatg  16260
acaacatgaa taaacccgga ggccattatg ctatgtaaaa tgagcaagta acagaaagac  16320
aaatactgcc tgatttcatt tatatgaggt tctaaaatag tcaaactcat agaagcagag  16380
aatagaacag tggttcctag ggaaaaggag gaagggagaa atgaggaaat agggagttgt  16440
ctaattggta taaaattata gtatgcaaga tgaattagct ctaaagatca gctgtatagc  16500
agagttcgta taatgaacaa tactgtatta tgcacttaac attttgttaa gagggtacct  16560
ctcatgttaa gtgttcttac catatacata tacacaagga agcttttgga ggtgatggat  16620
atatttatta ccttgattgt ggtgatggtt tgacaggtat gtgactatgt ctaaactcat  16680
caaattgtat acattaaata tatgcagttt tataatatca attatgtctg aatgaagcta  16740
```

-continued taaaaaagaa aagacaacaa aattcagttg tcaaaactgg aaatatgacc acagtcagaa 16800
gtgtttgtta ctgagtgttt cagagtgtgt ttggtttgag caggtctagg gtgattgaac 16860
atccctgggt gtgtttccat gtctcatgta ctagtgaaag tagatgtgtg catttgtgca 16920
catatcccta tgtatcccta tcagggctgt gtgtatttga aagtgtgtgt gtccgcatga 16980
tcatatctgt atagaagaga gtgtgattat atttcttgaa gaatacatcc atttgaaatg 17040
gatgtctatg gctgtttgag atgagttctc tactcttgtg cttgtacagt agtctcccct 17100
tatcccttat gcttggtgga tacgttctta gaccccaagt ggatctctga gaccgcagat 17160
ggtaccaaac ctcatatatg caatattttt tcctatacat aaatacctaa gataaagttc 17220
atcttctgaa ttaggcacag taagagatta acaataacta acaataaaat tgaatagtta 17280
taataatata ttgtaataaa agttatgtga atgtgatctc tttctttctc tctctcaaaa 17340
tatcttactg tactgtactc acctattttc agaccataac tgaccatgaa acctgggaaa 17400
gtgaaactgt ggataagtga ggaactaaca tacatacatg attgtttatc tacagatgta 17460
tgcctcagtt tcttagtatg cttgaaaatg tatgattttg tgtatatccg tgctacatgt 17520
aagtgtggtt ctattcatat ttgaatatga attctgcata agtgtgttta ttcaagcaaa 17580
tgtacaaggc tctgagaagg aagatcaaca tacaacttgg aatatttcaa ggccgaaata 17640
ttcaaggctg acattggcct ccttcctatc agttccctct cccagatgga aattctagaa 17700
atggcaggtg aggtggacaa gcagggaaag aaattatatg catagaacag aaggagaaga 17760
aagagtaaag tcaggcctca gccagcctct ttttagctct ttaaatcctc tggatttaag 17820
agggataaag ggtggaataa ggataaatta atgccaattg taatgcctta aatttgtgtg 17880
ataccttaca acttgaaaca tattcacaaa actatatatt tgaatatctc attagctgag 17940
taaggtagca aatcataatt aactttttcc attttattga tgggaaagct gaagttcaat 18000
gaagtaaatt tttcaatagc ccacagagta ggaaagtgac aaaacctgag cctgggcctc 18060
caggtcactc aaggacactt tctttcttcc acacccaatt gcttcatgct taaagttggc 18120
aaaacaggaa gtgaaactcc tgcagttttc tgtgtggttg acactagcaa gggtttctca 18180
gttgaagcca tgaatcatta agccaataca tatgcatata tgttatacat accaaatgat 18240
ttatttataa ccctatcttt ccataaagga cttgaaggag cttcaaacaa aggatatgtg 18300
aacaataggg ttaatcaata ataagtagaa aatctggaca tagaataaaa agaggagaga 18360
aagacaccga gaatgagcgt taatacagtg ctttccattt ttctggtgtt ttgagtagcg 18420
tggcttttgg agaaagccaa aactcaaatt cactccttat caactgtgtg ccttgggctc 18480
catttctctg agagtctact tagctccaat gtaaaataag aatagaacta tgactttgta 18540
aggttgctct aaggattgaa aatcatgtat tatgttcaat acggggacac tgtccttatg 18600
ggtgagtact cccctaagac tttattaaga gggcactagg agaagcactg ggaggtcttc 18660
tcagtaacaa cactaaagta attgctattt ttccagcctg tggaaccaca gaagtgactg 18720
taactaaaat tagacatttc tttctgattc attctctact cacgggattg tcagacccca 18780
gtcttcttct ggactctata aactttttag aaatcatcag caggctcctg gagaagctta 18840
aatgaactca cacaatatgt gacagtgaac tccctgggag agtgaaaacc aaagtctaag 18900
ccagtgtctc catttacttg tgtgattgtg ggcaagtcat tcaagtgctt tgaggctcag 18960
gtcttaattc atgaabydca bydcabydc 18989

<210> SEQ ID NO 48
<211> LENGTH: 50000

-continued

<212> TYPE: DNA
<213> ORGANISM: Mus musculus

<400> SEQUENCE: 48

```
tttcacatcc atgataggtc aagaatgtaa tctaagttat aaggtttcac ctagtaacca     60
gatatatgga gatagaaaat aaacaataca cagtgggaag acctggcaca ttgtgaggta    120
agtgagtctg aattctgcat gccaatgtag gagactccag gcaaagctcg tggtgcagag    180
taagtctcaa ggtagcaggg gagaagaatc ttttcttttg gaggaattaa ccctttttag    240
tttatggcct tcaacctact gggtctggcc cactcacatt agagtgcttt gcttagtctt    300
agacatgaat ggaatgtaaa gtatctttat aagagtgaaa gactatctgt gtgtcatgac    360
ctatctatgt ttacatgtaa tattaaccat aacatgagca ctgacatttc tggattgtga    420
ccttcccgtc agaatatgta ttggaaggta aaactgaatc ttttttttctt tattgctttt    480
acttccctct ttgtgtatat attcacacaa aacttctttt agattattct gttttcttct    540
acaatgtcca tatttgcttc tctcctaggt tttggacaat tattttccta taaaatatta    600
gtgtgttccc tcgccctgtt cattataagt gaattaaact tgctgatact ttttaaaagt    660
ttgtattaac atagtttaag tatcttcctt tatgctaata aagattgcag attgaacaaa    720
atttgtagat tgtagtatgt gactcactgg cctaaaccct gctcctgtct cttacaatgc    780
aatcttgggt aaatgatttt acaatttatg cctcaatttt ttcttataat ttgaatgcat    840
taatacatat gaggtattaa aaagtactcg acaaataaaa ggttcttggg aaacacttgg    900
tgaatatagt cttatgactg acataagctt ctaccagttg aagtgaagaa tggggttcaa    960
cccgtcatga ttgtttagga agtatatcaa atatatgaaa ttaagcgaat cttcctctca   1020
gctccatcct aaaacccccct ggcgactctg attctgcata tttgcaatgt agttttctgt   1080
atgaaaaata gtgagccact agaaggtaag gggagtaagg aaagatgtta aggggttgat   1140
atttaggatc tggaaaataa catttacaca cttgtccccc acccctacaa cattgaaccc   1200
tgtataagat atagatatga ataaagcaca gattttcatc tctgaccact atcctcttca   1260
taaagtaaaa tttttgtgac ttacatctta gatttcctct gatggctttg atgaagctag   1320
gtatgcaagg gaagaaattt tatttacata aattccatgt aaaacatata aattcatgtg   1380
tttatataca catttataat tgtaatgtat ttgccacatt gggataacaa tactctcatc   1440
aacagctata aacctcatta ttaataatga gaaacattct tttgagtttt atcatggaag   1500
tataagagtt ccccaaaaca atatagccta gtgctgttgt tttgcagaga ttggaggtat   1560
gtccctattg ctgaaaacac tgacactatg aactttgaac aaaagaccat gagggtttcg   1620
gtagaatttg gtttgtatga ccacaaattg tcttttaacc agcaatgtca tactggagaa   1680
tgcatagttt ttcagatatg tattcatgct ttgtgctttt atttaatttc cttcttattg   1740
ggttttattc atttgtatgg tttgttgaaa tttcagtatt ttgagataag agctcactct   1800
ctagcccaag ctgatcaaaa attcactgtg tagcttcaac tgaccttaaa cttaagacaa   1860
tctttctgct ttatccttcc aagtgctggg attacaggca cagcccagct tgtggagttt   1920
aattttctaa aggacattgt gatgaatatc cttgtacact tatctttgga gcctgcccat   1980
gaatcaccac atgattaatt ttctagagaa aaactgcttt gtttctgttg ttcatcttta   2040
gaatctttaa tttttttcttt tgagagattc atacgtgtgc ccaatacact ttaatcctag   2100
ccatcttcca ttccctctgc aaatttcccc caaactgtcc caacttcatg acctctctgt   2160
tgttgatatg tattaaacac acttagtcta tttagtgcta tcagtatgtg cattggtgtg   2220
```

-continued

```
gggccaccta ttgaaatatg aacaaactgt tacaaaaggg cctcattctt gataaaagct   2280
tgtcaggaac cgcctaggaa aggttaaggc ttgtaggtgg ccttcctgga tgtggcctac   2340
tctttttgta tactctagaa tgtgtgagct ctgagaggca agatcccaag cttcatgcag   2400
ctgacagaca tttttcctat cactgttgca tagcctaaca attcatgggc atcagctcac   2460
ctcaattagc aaatttcctg cagatcaaca taaagataaa ctcttgtgaa ttagtgctgt   2520
ttagatgaat taatgatttt atagaattcc tcatttgatt catagaattt taagaagaaa   2580
gttttaagag aaagtttttg ttagaaaaat gttataaagt tagaatcaag aatagaatat   2640
gctcattcct cataatcata agataaagct gcataataag gaatacagtg agctttcaca   2700
attactaaaa taggcttggg tcaaatttgt attcaaggaa aaaacattca ggtccaagga   2760
gaaagccaca ggtatgcact atgataagac aaggtcaagc aaaactgttg ctttgaattt   2820
atgagcatat agaatgaaag actgctttga agttagtatc agcctcctcc tgtaaattcc   2880
attttgtgta acattttatc tatgaagtaa tttgctaata actgtttatg tataaaaagg   2940
ccgaagaaaa gaaataaagg tgtgatggtt tggcttggag gggctctgca agactcaccc   3000
atccctccct ccatccatcc atccacacat gtccatctat ccatccctcc ctccatccat   3060
ccatccacac atgtccatcc atccatccat ccatccatcc atccatccat ccatccagtt   3120
atagtggtgt agtcattttc tgcttcacct agtatatatg tattcctgtg agtgactttt   3180
acctctttgg tacacaagga gttaactagc caggcctgag aagggcccct ggcctgctgg   3240
ctagaaagaa gagcactagc aataaatcct ctactgaatt gctccctgct atacagcata   3300
tgttaattgc cagagaatta tatactaagt ttataaagta aataagaatt aagctttaca   3360
gcgcttaatg atgcacaaaa cagttagaga actaaaaggc cagagatcat caatcttttg   3420
acctgcatct gatgttgcgt cctacctcag cttgttcccc taagccagca gccccctgac   3480
ccccagtaaa aactgattct ttttaattgg ttattatatt tgtttacatt tcacatgtta   3540
ttccccttcc cggtttttcc tctgcatact ccccatcccc tccagctgcc ccctgcttct   3600
atgagggtgc tccccaaccc acttacccac tcttgcctca ctgccctagc attcacctat   3660
actgtggcat tgaaccttca tgggaccaag ggcctcctgt ccaattgatg ccccataagg   3720
ctcttcctat ggggttgcaa acccccttcag ctccttcagt cctttctcta actcctccac   3780
tggggtcccc gtgctcattt cgatggttgg cttcaagcat tctcctctgc atttttcagg   3840
aatcaattgc caatgagtct tcagttagga gtcgggcttc ataggtttca actccatcca   3900
tgctgggttt gtggctatct tgatttcgtc cagatgaact ctagatgaac tccttggatg   3960
tagtggtttg aatatgtttg gctcacggga tgacactatc aggaggtata accttattgg   4020
aataggtgtg gctttgttgg aggaagtatg ttaaagtatt ggagggcttt gaggtttctt   4080
agtgctcaag ctctacccag tgcagaagag agcttctttt ttcttgtctg actgcccaag   4140
acagaaacct tctgactgcc ttcagatcaa aatgcagaac tctagggtcc ttctccagca   4200
ccatgtctgc ctggatgctg ccatgctttt tgacattatg ataatggatt gaacctctga   4260
agctgtgagc aagcctcaat taaatgtttg tatttatgag aattgccttg gtcatggtgt   4320
ctcttcacag caataaaaac ctacaacaca tagcttctgt aaatttatgt gtgcaacata   4380
cctgtcatgc tctgaatgca ctgtttgctc agctttgcat agcttatcta caataacatt   4440
tccttataag gctcaggaac aattacagaa gagtgggtaa agatgttgta agagccattg   4500
acttgggaga actactgcaa aacagtgagt tccagacaca actctctctt caatgtggtg   4560
ctccttgtaa tttaatcccc atacctcaaa ccaagcacat ctttcacact ctgttcccca   4620
```

-continued

```
aattaacata tagcttgatt taatttagac ataatcagtt gctactggag gacttcctgc   4680
aattaaaatt gatgtttaca catttataag aaaattaaca aattatttgt agtgcaatta   4740
agtaaaagta atataagctt tttttacatt ttcctaaagt cagttcctta gatttttctt   4800
aagtacaaaa tttgatagat cttaacttgt ttcttttttc aaagcaattt agcaaatatt   4860
atttgaaact ggagaaagag atgccttgtt tactcaggtt aaaatgctga caatgaggtc   4920
ttaaattcat gtcatccact tgatctttga caaaggagct aaaaccatac agttgaaaaa   4980
aagacagcat ttttaacaaa tggtgctggc tcaactgtct gtcagcatgt acaaaaatgc   5040
aaattgaccc attcttatct ccttaggcaa agctcaagtc caagtggatc aagaacctct   5100
acataaaacc agataccctg aaatttataa aggagagagt ggagaagagg cttgaacaca   5160
tgggcaaagg ggaaaaattc ctgagcagaa caccagtggc ttaagatcaa gaatctacaa   5220
atggggcctc ataaaattgc aaagcttctg taatgcaaag gacactgtca ataggacaaa   5280
aaggcaaaca gattgggaaa agatctttac caatcctaca tccaatagag ggctaatatt   5340
caatatatac aaacaactca agaagttaga ctccagagaa ccaaataacc ctattaaaaa   5400
tggggtacaa gctaaacaaa gaattttcag ctgaggaata ttgaatggcc aagaatcacc   5460
taaagaaata ttgaacattg ttagtcatca gggaaatgca aatcaaaaca accctgagaa   5520
agtgtattcc tgaagtgtta taaaaatggt ccttaaacct aatgacctga ggagagtaat   5580
acagaaacat ctggggaaat aacaacatat ttactattta aaatactgaa gaaaatgtgg   5640
aatattttaa attaatttta aaatcaccat gtctatctta aaatgtcatt aaactatcac   5700
caaaggctaa tggataataa aaatgtgtta tatgtatacc atgagatttt agacagaaaa   5760
aaaaagtgaa ataatacaaa ttttaggaat gtgcatggat ttaaaaaatt atactcagac   5820
tggaattaca aaaatttcaa agactggacc aatagtcctt attcagaagg acaaatacta   5880
tataatatac ctcaaataaa gatgacaact ttgagggttt gatatgtgtt taatatggct   5940
gcagagggct gtttaagttt atggaacttg aaagtggtac atgagagaag gaaaaacttt   6000
taaagatgga ggaagaacta agacaatatc tgagacatga aagtggaaaa tgtgtgtatt   6060
attggtgggg aaaaggtaca gccatggcat ggggtgggaa gagattcaga gaaaagcatc   6120
aacaaactat atgtaaaagt gcatagtgga gccaaccatt tttaagccaa taaacaccaa   6180
ataaagcaat agtgaatact ctacaaaact aagtttctat ttagttttac tttcttcttc   6240
tcagtcaggt tttgctataa aaatattgaa atatgccaag tcctgtcaaa gattaagttt   6300
attcagagag cttaatgcta taattctttt caaaatttat aatcacacat atggccatat   6360
gtatacatct gaaaaaaatg ttcttgatta taattaccac tttcccaggc ctccgtttta   6420
gaatttactg tgtagctcac aaatggaaag agtaggtcac ctcatgtgaa aataaattac   6480
agagaacttt cataagcact gctactcaac caaggggctg gagacacgcc atccagctaa   6540
aagtagacct ggaaagggcc ctcatcagaa aacaacagag gaaatgtcat agagatagaa   6600
ataatttttg agttgttcaa agtcagacag atatattgac atgaagaact ggtcatgtgt   6660
ttgtatagga agaagtggaa aatgatctag cattcccaga agctcatagg gactataacc   6720
taatcacttt ttattccctt ttgttttttt ttttttttta atcaatcaat tttttgttga   6780
tttcccagct gtacttaaat tgtttagaat cagctcacaa gtaagctgtc cttccaaaag   6840
tcagtctatt gataaggctt ttctttctag cttgtctttg acaaaatagc tcatgacatt   6900
atagggtaaa tctcttaatc tcttctagcc ttaaaggttt ttgttgttgt tgatgatgat   6960
```

-continued

```
gttgttgtta attattaaaa tttaagtatc actcttgttt tttttttcct gtgccataga   7020
gatttcttct aaaaactttg ttatgaggtg attagtaaag cacatgtaag ctagatgttg   7080
ttttacatct agaaacaatg gcaagaggtt tctcttctca ttggtacaaa gtagcatttc   7140
cttcatttca agttgctaac taaaccgcaa tccaggctag tctcagtcta ctgacattga   7200
aatgtgtcag tgattaatgg caatatgatt atgttggtag ctaggttttc aaaccatcct   7260
agtcatttaa attcataaac tcactttact tatttggctt atgttacaga ataatgaatg   7320
taggaaccaa tgctcaataa tgcacaccaa tgtgaaactt caggttgtta tgtctaatta   7380
tattcacata tatttcattg gctaagtgaa tcatgaggta aaaccctaaa tgatcaaagt   7440
agagaagttt aagtgtgctt tagtgaataa tgacaaatat tgacaggaag aaaaaggtca   7500
ggacttaata atgcaatcaa agagatcctc tgacattgaa ataacttatt cctacttagt   7560
gaaatatcat atgctgtacc atacaggaac gcatttgaac cagttttaag gaacaagcat   7620
tggtagtaaa agttcattga gcccttgtct agcatacaag aatttctggc tttggtttcc   7680
caagctttca caaaaccaag atatactagt gcacacttaa aatgtaggaa atatgtcaaa   7740
agggtaagaa atagctgaac acattcagtt tctgacctcc aactcaaagt cggttagagg   7800
ctaggataga atgcatgaag ccctgtcata atgaaagaga gagagagaga gagagagaga   7860
gagagagaga gagagagaga gagagagaga gagagagaga gaaggaagga aggaaagaag   7920
gaaggaagga aggaaggaag gaaggaagga aggaaggaag gaaggaagga aggaaggaag   7980
gaaggaagga gggaaaagtt aataagtaca tcatatatca aaactggttg gtacctgtat   8040
acttgggtat ctccatgaag gataaatctg gactagaacc attaactgag gatattgccc   8100
agaggacatt tagagtagtt ttgtaattta ctctgcatgt tacattttat tttatattat   8160
gaatacatga aaagctatga aacagtgact aaacttagtt cattctatta atatagacgg   8220
aaattgtgga tgtcaaagtt atgagacatg ctttattttg tacttgtttt ggcgactatt   8280
tagtatttat ttttattttt aaaattaatt tgtttacatc acaagcacaa cttctcctcc   8340
ctcctctcct cccagtctct ttctcttacc tcctttctct acatcccccct cactttctcc   8400
tcagagaaag ggaagactcc catggacatt atcttgcctt ggcatatcaa cttgcagaag   8460
gactaagtac atctcctatt cagccttgag aaggcatccc agtcagggga gaggagccca   8520
aaggcaggca acagagttat agacagctgc tgctttattt gttgtaaagg acccacatga   8580
agaccaagct gcacatctat tacatatgtg cagagggttt agatccatcc catgcatgct   8640
ctctggttgg cagttcaatc tctatgagtc attttgtgcc taggctagtt gaccctgtag   8700
gttttcttgt agtgtctttg atgcctctag ctcctttaat ttttcctccc tatcttccac   8760
aatattcctc aagtccgcct gatgtttggt tgtggatctc tctatatgtt tactgggtaa   8820
agactctcag aggacagtta ttctaggttc ctgcttatca agaatagggt ctctcacatg   8880
gcatgagtct caaatagttg gtttagtcat ttataggcca tttccttaat ttctgctcca   8940
cctttaccct gtacatctta tagacaggat aatttgtggg tcaaaggttt tgtggttggg   9000
tttttgtcct catccctcca atggaagtct caaaggagat ggccatttca ggttccataa   9060
ctctgactac taggaatctt agctggagtc acctttatag gttcttggga attttacttt   9120
tcctgggttt ctagtttgtc taagagattc cccaattcta ccaattccag ttttatattc   9180
atctgtcagt ctcatatttt ctaccattta tttcttttga tttaacactg tatcaggttt   9240
tccaaaatac tgaagaatcc tcacatttcc ttgactaccc aagagtattc gtagacttaa   9300
agtctcataa ccaagaaata aaaattaatc acttcttatt gtgctggatg tttttttgca   9360
```

-continued

```
atgtagaatt ttataatgaa ttaaaactaa gttacaaatg ggctttacaa atttagtgat   9420
aagggtgcag taaatggtgg cttttctatg atacagccag tcttaactgc caacatatac   9480
attggataag aatgtcttgc tagttaaggg ggtagagctt agaagtaagg ttcattttta   9540
gagtgtccac caaagatatg accaagaatg atgaagcctg ggaagacttc tgtgagtgaa   9600
actacattgc agttttatct tgtcctattt gttcaagtag aaaattatct tatgagtctg   9660
tgagaatctt atcaacagcc aaattaatta ttcagtgtcc cagactatta aacaaaccat   9720
ttcttcccat gagagaggtt ccacaaaaaa agaaaacaga atcattttga acccccaaat   9780
tatatgtcag tgtcctcaaa catcagagga gagacctagg caaggtataa tattactgca   9840
ttattgacta gagtcaccat agataaccat gactgcaaaa aataaaataa aataaaataa   9900
aataaaataa aataaaataa aataaaacaa aacaaaataa aataaaataa aataaaagct   9960
acaaggggca agtaggatgg gtcagaaagt aaatgccctt tgctgccaag taccacaaac  10020
tgaattttga ccaatgaaac ctacaagatg gaaagacaaa ctgcctccta caaattgtct  10080
tctcattttc atatgaaaac tatcacacac acatacacac agagagagaa agagagagag  10140
agagagagag agagagagag agagagagag agagagagag agagagagag accacccttt  10200
aaaatccaaa agaaaagaat gttgaatatt tctcaaaagc aagatagcta tatatacctt  10260
aatgtgaaca ctagataaaa tacaaacacg ttgattgaaa tactactttg tatgctataa  10320
ttatatggag attgtatagg tcaatgatta aaataaattg tggggaaagt aaaaagggaa  10380
atgaataaat cgttaataaa caatttagga agacgaaaaa ttttctagtt ccctagcatc  10440
ctgtatttga gacttaagct tggaaccata tgaccccttg atctgctctt caatagtgtg  10500
tcaagctaga aaaaatagga acatgctaga atttctgtgt agcaagcccc tgattcaggg  10560
tcttaaagac gtctctaaaa aaaaaaaagc tgatttgatt tatttaggaa taagcatatt  10620
gtgtacattt ggtcttagtt ttcttaggtt ctgtttcatt ataattgatg aaattcattc  10680
attgtgttga gtgagagtaa ctgtagacaa agataaaggt gagacagcag tgtgcatatg  10740
gtcttttgaa ggagcccggg gagtggcaaa acagatgaga tccctctgat ccttcggttc  10800
taatccaggg cacattttag aatatcttac accgttccct gccctatgcc ttgacttctt  10860
atctttgcag agatattttc ctaaccagca aaatggagtg attgagctac ctgtgtgaaa  10920
cattcctcat aaaaagaagc ttatatttat ttttgttatt tgttgttttt aatctattca  10980
tttacttgta ttgatttgaa aactttaaca atcccaggga gcaaggaaag tattagatgc  11040
acaacattta aaaagttgta aatgtatatt gagtaatagt aagatttcct actgtctcgt  11100
tgaatttaag aataattact ttcctggaag aagcaattcc cccaccctcc ccaccccctg  11160
gaaactttca gtaaaatggg ctttggaagc atcatagtca tggacacaaa gatttattta  11220
atatgttcag tttaggtgag taccatagtc tttcaacaca atcttggaac caggaccatg  11280
accttgagct tgaattatag agaattacat atccatattt agcagatagt caacgttttt  11340
gtttttctat ttactagtat tatcatgtct tgaaacaacc tttgttctgt ctctcaccct  11400
cagtttttgt tgtctaacaa tcctcatagc tctctctgat aatgaaccta aactttatac  11460
agttaggaaa gatgtgaccc gatcatattg ttatatttct gatgtgactt tgaaaagagg  11520
tcctcaaata atgtattcag cactggatat gaatgatttg tcagtgtgca catttttttaa  11580
attgattttc ttattttttt atgtgtatga gtgcttggct gcatatatgt atgtaagtat  11640
aacacatgtg tacctgagga aaccagagag aatatcaaga cccctggaac tggagttgca  11700
```

-continued

```
gatggttgtg agcattcatg tgagctctgg gcactgagcc tgggtcctct tcaagtgaaa  11760
ggagtgctcc taacactgag ctatctcccc agctctctac tttgcaagtt attattttta  11820
aagtatctgt tttctggatg ccaaacagac cttttagtaa gagctatagg taaagacaaa  11880
ctccttaggt cctccctcct ctttccttca aggcccactg agaatttcat tattaatcat  11940
ctgtgcatta tctctatagt gtctgcctct ttattaatca cctccacgga atctatcgct  12000
attaatcata agtcttgagc ctgcatatta ccggtaatta tctcacaatt ttcgttacct  12060
cttggtttaa ttacttgttt tcccccagga atacaaacta ttttaagccc ttgactctga  12120
ggagtgtatg tgtgtgtgtc tgtctgtgtg tccgtgtatg tatgtgtgtg tatctgggac  12180
aggttttaag atatttccct taaaccctga ttatcagtgc atttagtaaa attatttaag  12240
ctaaagaatt acaatgtacc atcatttctg aaagcttaaa gatccttttt catatgaaga  12300
tataaagcca ggtataatct gtgatccttt cataatttac tgttatgtct tcttcaataa  12360
ttctttgaag gctttttaca aactggttga tttagtttct ccaggaataa gcacactggg  12420
tcccttcagg acgttatatt gtttggtttt ttattttttt tcttttactt taattcagtc  12480
gatacttggg gaaattagaa acaaatgaga ccaaaattca gaatcagtgt gatgaattct  12540
tattctcata agtgtaacca cacaacagag gccttgataa tctcagtttg atgcaaattt  12600
aatcacaaag caaatgcctc tccatcaatg ttattttatt tgcaaatgac agccactgta  12660
tatctagtac aaaatagaaa ataaaataaa tgtccagtct cctttgaaga agatatctta  12720
ctacagtgta tgtgtctatc atcatacttt cagaaatatc attttgagaa aaccaatagt  12780
ctcgaaagga agaaagctat ttttctaata tcacacaccc ctgattccat tttcctccat  12840
agtagcttat atgtgggtcc cactaattca ggaagcttca ctaaggattc taccgatgat  12900
ttacagttag aattctagtc taaatttgcc tgacatcaaa gcctgtctac tctactgggt  12960
tatattaaag caagcacata aattgtacca cttaatatac acatgtaaga aatgaaaggt  13020
agaacttaaa tgtcattgtc ctaaactagg gatgcttgag acacttgcag ttgagttatt  13080
aagatctatg gataccgtgg atgtgaacaa tatatagatt agtatattta tgccagcaaa  13140
tgtaaagccc tctttttttt caggtaccac caatgtgggc aggggtgggg gagtaaacac  13200
atggatgtgt tcttctgtcc acactcctta ttgacttctt accatgtgtc ttgagataac  13260
agtttctaaa tgtgcttaat gaagaaggaa gacattttac tgatggatgc ataagatcac  13320
ctagcatacc tctaagttgt ggaagatgct tctcagcatt attgaatcca ttttgtcagg  13380
gttgataagg tgagtgtaca cttccatata atcattttta tttatacagt ggcatttcag  13440
ggttgtactt taggagagag agaaagcatg atatgattca ttaaagacct tataacttat  13500
tttgagatat aataactata ctttagggtt acatgtaaca aacaattcta agcaagtttc  13560
tatatgcatt ctcttagttg actgcctacc agctctatga aatgacaact gttactactg  13620
ctatcctata aggaaaaata agtgagaggg agtttaattt gagcaaagac aatggtttgg  13680
ttaaatggaa aggtaaagtt acaagtatga aatgtgaaga tttaaataaa agtgattcaa  13740
tgctactaca caataatgga ggttatagaa attaattata gtattatgta ggtaaagaga  13800
aagttgaatc aatgcagagc ccaggataat tgaaagtttt tttttttttt tttttttttt  13860
ttgagacagg gtttctctgt ttagccctgg ctgtcctgga actcactttg ttgaccaggc  13920
tggcctcgaa ctcagaaatc cacctgtctc tgcctcctga gtgctgggat taaaggtgtg  13980
cgccatcacg cccagcagta attgaaagat ttaaaatttt cttttgtaca ggtatctaaa  14040
tgtagtattc atcaagataa gatataattt gtcaacctgg ggccaaatta agttgttctg  14100
```

-continued

```
tgaataatct tagatcaaag actacatttc atccatttcc tcagaaatgt gctttgagta  14160
tgtttaagga tagaagactc tatttctacc catggggtta taaaacacac caagaactac  14220
atgtgttaaa atttgtcttc caaagactca tgtcattaat tttaattaat ttacttttag  14280
cctggatcat aatgtctaca ttgtaatatt cattttcatt ggctctttag ttgatgtgta  14340
cctttcaaat ttctatgaaa acaatttcaa gaagattcag tgaggatcta ttatctgctc  14400
aatctattta aaactcacag tcaaatacaa cataagggaa caggactcca cttgggacag  14460
gtcaatggca gcatgcattg tgctatgtgc cttacatgag agctaacatc aaagctctgt  14520
cctgttattg ggcagtcttt tcttttcttt tcttttcttt tcttttcttt tcttttcttt  14580
tcttttttct tttcttttta atattgcctg gattgtttgt cttgtgttcc attccattgt  14640
tcctccatgt atttttgtag ggtgggggat gatagttaat ttgacaaata agccactatg  14700
ataaaaatgg acagggaata tccttccaaa gtaattttta cagtggagca gctatttaat  14760
tttcacatca cagttgagaa tgctgaatat tcattccttt gagttcataa atctgaaagc  14820
actttctcaa ttgtaaaaat gtatttatac aagagaagtg tcttagttag ggtttccatt  14880
tctgggaaga gacactatga ccacggcagg caactcttat aatggcaaat atgtaattgg  14940
ggctggtgta caggttcaga ggttcagtcc attatcatca agcaggaagc gtggccacat  15000
gcagtcagac atggtgctgg aaaaggaact gagatttcta tatctttttc caaaggcaat  15060
gagaagacag actttctagc agctagaagg atctcaaagg tcaccccaaa gtgacatatt  15120
tcctccacca aggccacacc tacttctaca aggccacacc tgctaatagt accactccct  15180
gggacaagta ttctcaaact accactagaa gtattgagaa ttacatgtat attgtaagta  15240
gttaatttgg taaggagatg aaaataaatg aaactttaaa aaaaaaaaaa aagagttcct  15300
ctaaatgcat gctgttcaaa tgactcagca aattttggta cttgctgcca agactgaaga  15360
tgagaactca gtccctaaag cagatctctg aatcccgtat gtgtatacag caaggtatgc  15420
atgtgcataa cctcctaaat atgtaaatag atgacactga tattatcaaa taccaatagc  15480
caaatggaca aatagcttgg atcatgtgat gctgataaat gagataatta gaaggactgt  15540
gaagaacttg tattacaagt gagacaggga accattcaag actcttgata atggggctag  15600
tatcttgctt ctactatttt tggtatcttc tagataccag tggctagaat gcatccacca  15660
tatgaaatgg caaacaatgt ctaggaggga gatttataca gtgtcagtta ctggtcaata  15720
ttattattta cactacctac atccatcagt ggtttctata tagaaacaga aattacattt  15780
acagtccact catctataac ttgaaggaaa gaaaaaggga taatatgaaa atgatagtac  15840
tttcatatct aataaacttc ctatgtgtta gcctctagtc taggtgattt gtgtattctg  15900
ttctggacaa tctgataaag aaaatacttg ttatccttga ttatagatga catatataat  15960
tagcctaagt taattccttt ggcaaataat atagaagaaa taaaaaaatc tcaagtattc  16020
taatttctga aacttatttt tggggggttg gcatttctcc tccatcattt tttcattctt  16080
ttctatattt ttcaagtgga ataaaaattt tcatatgaat tttataggtc tcaccataat  16140
atttacttct acattcaacc aaaaattcat ttctcaagaa ttaaataata tgttttaact  16200
agattccaga ggaaaacatt gtctcgagca tatgtggttg tcttcttctt cttcttcttc  16260
ttcttcttct tcttcttctt cttcttcttc ttcttcttct tcttcttctt cttcttcttc  16320
ttcttcttct tctcctcctt ctcccccttc tccctctccc cctccccctc ttcctcctcc  16380
tccccctcct cctcatcttc ctcctcctcc tctttcttct ccttctcttc ctggtcctta  16440
```

-continued

```
gaaatatatt cttacttcta aacaagaaaa aaaatgatga acaactctag attaattttt  16500
tctcagaagg ccaggtttca ggtgtaatga gtatacattc ctagttctcc ccctcctaag  16560
aggtatcttc tcttcaggat gctaaggatt aatatatatt attggcattt ggcaaagatg  16620
gctgctggca aattgtttag aaatctggcc tattttagag ttacttcata taaaatcagg  16680
agtgatgcat tctgtgatct gggcaaggtc cacagggtcc aagatttaca ttgtataatt  16740
agatattgaa ttttcaatcg ccttgtaaaa cttggaatgt tttttgttgt tgagtcattt  16800
gttattgtaa ttttatgtgt ttgcacttga gctgatggct tctgagaacc tcttcttaaa  16860
tgaagatttt gttttgtgca agcaagcaat tgaattacct ctttcctaaa attattcagt  16920
caccttatta gtgtcttgtg cttttgactt acattgtcta tttaattgaa atgttaggtt  16980
ctcttatgga tttacaccag gctttcccac aaacctgcag agcagcagca tctttttgag  17040
gtgaggctaa tctaattatc taggcttaac aatctggagg cagagaattt ctgaatgaga  17100
tgttatgtcc agcattctct acttcttaaa aataaacatt tctaagtaat ggaaaatttg  17160
ttcaagttga tagtgtaatt gaagaaagaa aagaaaattt tctgtttgga agctacagtg  17220
gttgtgttac tttatagaag cagtcatttt ctctttgtac aatattttta attaattaaa  17280
atggttttgt tcttaaatgt aaaatttctg ggaatttgtg attttacatt tatcacaaca  17340
tcccttgttc agcatgctag aagctttgaa cattccatta tggatgtttt tatttttat  17400
tttttaatga ggagctttta tatctcaagt tcagtatgta tctgaaaatg gccttgaact  17460
tctcatccta ttgcctacac tttctgaata atggggtgac aaaggttgcc aaacctgctt  17520
tttgtagcat tcagaataga aaccaagtct ttgtgcaggc caattctcta caatctgagc  17580
tataccctta gattacaggt gaaataatta aagtagaaat aatggtatta tgcttgagat  17640
ctacacaagc caagaaacta gatttagctt tctggttctt attcctttct tctccaagtt  17700
taaggtcctg cttttctttg tttctaattt gatggtctag ttgttgttct aattttcttt  17760
atctcatggt tacaatgatt cattcaatag cactcattcc tatgaaaaaa caagactgtg  17820
agtacaatat tgtgccagtt ggcttttggg taagaaaata tttaaattta tatatgctta  17880
tttggattat agattgtaac tttattatga caaagagaag agaaatgcct tggactggta  17940
ttctagaata tcaattgaaa ttagagatca gaaaggtaag aatgtctgca tgaaataaat  18000
aaatgataaa ctcactaaaa gacacagatg aattaatgga ggaaatgaaa aagagagaga  18060
atagaaaacg gaaacaagtc tttttaagta tatatgactt ttacagaaga gtgaatgtga  18120
gctaatcctt taaggagaga aagggaaaat taattgtttg tctgtctctc taatccttag  18180
tatcaccttt tgaatacaca gaataagaac aaagaaacaa attatgtcag aaaacaagtg  18240
actatttgat gaagtgactc catgagaagg tcaatatttt acgttcaagg tctttttgac  18300
atagctcaag ttactgttat attgagttat tgttatattg agttatagtc attttgaaat  18360
ttatttccca tatttttgtg tgttttctaa ctttgtgctc aattttcttc tcaatttata  18420
tacctcctct ctttcactca ctatatatat gtaaatatat atgcatatat gtaaatatat  18480
atgcatatac gtatttttat atatgcatat ataggtacgt atgtgagcat ttaatagtac  18540
tctcttgaac ttgtattctc atttacaata ttgtgagtac tagtttcaca atttgatatt  18600
aacctactgg taaaaacgat ttgtatctga gttcaactat tctgctatgg tgatgtttgt  18660
tgatccacag ataaatttct cagagaaaat aatgaaaagt gctttatatt cacaaataga  18720
tatttatgtt atctagacag cccagagggc acatggctaa tgatgaaaat ataatcaaga  18780
caatccactg aaactcagtg ataatcatag gagtttatag cacctgacac aagatagtca  18840
```

-continued tgtagtcacc cagttctccc acattggtga gacatacgga aacactggat aggtgaggtt 18900
aagaacatag gtttctgcct agccctactc tttaatttca ataatgatgt tgatagtgag 18960
tgattttcag agatgcctcc tggaatacgt tctatgtaca ctatttttct ctttgattat 19020
taatatttga tttcttgatg attttacttt gtacaccctc atcatctttt tgtttgtttg 19080
tttgttttgt ttgtttgttt gttttgtttt tgttttttcg agacagggtt tctctgtata 19140
gccctggctg tcctggaact cactttgtag accaggctgg cctcgaactc agaaatccac 19200
ctgcctctgc ctctcaagtg ctgggattaa aggcatgtac caccatgcct ggcaatacag 19260
cctcgtcttt aaatagttca gttcagtaaa aaaaaaaaaa aacaacatag cattctgtct 19320
ttgacccaaa accctctctt tctcatctct ctacttgtaa tctatttgta ttactgtgta 19380
gaagtatgct ctaggtttgt gcaggatgga tttgtgtcag ctgcagtttt catgactatc 19440
ccctaaatat gtaagtaaag tcttctcaga taaagtcact tttttagtgg gaaaaatcat 19500
actttaatta atctcaagca gtttgcttcc cacggatcac aaagaaatag tatagatatt 19560
tctctccctc cacaccttat aattgctcaa aaatgaaggc aagtttgttc tggatgctaa 19620
atatgagtct cttgtttcca caagaatgaa agaatgatcc agtgtgcaga attccaatac 19680
tatccctgcc tcccgtgtaa agagtgatgg aaggtgagcc taaagaaact gtagatcagc 19740
actgagcaat ctgtggccat atgctgcccc ttggttttgc catatggctc tgagtctaat 19800
ttcaaactcc tctgtcagca cattcaaagg tgaagaatgt agagacgaaa gaaacaccac 19860
catagggttt gtaagtggac agtcctctag caggtgctct ccagctgggc tggggcagca 19920
gcagaattaa gggtttgtga ctgataaaag taaaacaaat gcctgagggg agaggagagg 19980
ctctggagca gctgggccca cagtgtcatg tcctagtttc agagccccaa agtacccaag 20040
gggtgtgggg gtgtgtgtgg agaaaaacat cgagaatatt ctattgagtg atcacaaaat 20100
gagcattgtt tttattttct cttagctatg tcacttttga acttagcaat gtagctttat 20160
taaatacttt ccagtgtttt gtgtatattt ttgaaatttg aacatctgtg catcattttt 20220
cccagtcttt tcttttagag attcccatat tcttctagtg tgtatggagg gaaagcagag 20280
actcattcat ggaatttagc agaatttgat aaataagaca atttactaat gccctcatta 20340
atttccttga aaaattcatg tcattacaca gtgaattatc tggttgtgtg ctattcacaa 20400
tgatgtgtaa cagtatgacg tgcaagtcta gcacagtgtt gcatcagact atttctaaga 20460
atatgccctc agtcactttc ttaaaaaggg gatgcgtagg tcatgcaaaa ttgagaaaaa 20520
caggagaaat ataatgggca gtattcacgg caaggaacag ttgtaaagag caccccccctt 20580
gtttaataca aagtgtctta agcacttatg ctgggcagac acaactgaac attctgtctg 20640
gaactaagga gtagcagaca caagctgtgc taacttatat attactgacc aatgtataaa 20700
atgagacatc aaccaattac tattgtttta taaagttatt gccataaacg ttgctactga 20760
attcctccaa ggtatcaagc actgtaatgg gcatgcagta tgaagaggca gtgcagattc 20820
agctgttatc ttggaggatc tgaaagtcta gtgggtagag aaaagttttc ctaaaacagg 20880
acagatattt gttgtgtaaa tgttaaggta aagtggatag tacctaactg gggaggctgc 20940
acagtgttag tgaattcaaa ttaagtgtta gtgaattcaa attcttagtg tagggacttc 21000
cacagcatac aaatattgaa tcacggcata gtaagtgata ggagattgga aatgagagca 21060
taaggacaca agataatatc atgctttaaa attgtaggag aaacactgag gccggtgctt 21120
acttcaagag accgaaatac gtatcaggaa gtgatttcca cataggccag tgaattatgt 21180

-continued

```
agaactgaga acaacacttt gaatggaatg aacgttttct tcattcacac cagggattca  21240
gttttgctct tgccatagtg atatgctctt aatcttctac ttcagacctt ctttgccttt  21300
ccctttctct attctctatg accacaatac cacaggcaag gtgaggaagg agactagctt  21360
atggcagtgg cccccaggaa agcacatttt tctgtctgtt tagccagtgt tttcactttt  21420
taaaaaacaa cttattgttc tctatagaca aataattctc aattgaatac agcatgttac  21480
tgattgtaag tcatactttt atttaccaca aagaaaaaac taaaacccct gtcacttata  21540
actgcaatgc gtcatcagtc agaaagccca ttgtgaactg atgtatgtta gtagattgga  21600
aggaatcagt taaagttcta atatatgaca agctgcagga aacattctgt accagactgt  21660
actgtggtta tttattctca cagtctctta atcaccatga aatgggcaaa tacaggctgt  21720
aaaattgtgt tatttacact tcagtgatgg aaataaatgt tatgttactc atttatagta  21780
tatcattggc attgggtagt ggattctgca gtttatgaca atctctctct cgctcgctct  21840
gtcgctctgt cgctctctct ctctctttct ttcatatgtg tgcacaccct ctgtgtgtgt  21900
gtgtgtgtgt gtgtgtgtgt gtgtgtgtgt gtgtgtgtgt gtgtgtgtgt acttcaagtg  21960
agatgggagg taaaaaggtt aggaaatacc catttataac taatgaagtc ttaggacagc  22020
ctagagccac agagggagag atgcacatca gtggtgacag agtaaaccta gttacaaata  22080
tgggtgtgtt tccctcctcc tttcagatat tgcagaaaac cccaaggcta tgtatcaaat  22140
gtagtaacac aattaaataa aaagactctg atcatgaatg actcctaact tgtttgcaac  22200
caataatgat cttactgacc acttattgag caagaaatat gtatcgtgtt atgtgtgtta  22260
tgtcaccata gaaattacat taatttaaca ctggtcttat gtggtgtact taacttttta  22320
ctaaatggtc agtatctgac aactttgacg agatggtcat ttgtttctgg ctaagatggg  22380
actcttcctt tgactaagtg attgtaggtc ttctgttgaa cctgctgcac aataataatg  22440
tagaaaacta aatggcttcc tattcagtct actctccatt gtaggataaa aactgacatc  22500
atgatggtag ctaagtatca attttttact cattgcaaaa ccacatttgc atgtttattg  22560
aggtttagca aataaaacat tactgcttac ggcttctctc ttctactttg tacttggttt  22620
gtcttctaga agaggctgac agaactttaa tggtctggtt aaggtcacca catgctagtg  22680
tattgttatc atttggtttt cagaaaaaga aatacccaca caaagcactc tcctgaatat  22740
tcctatcata ggtatgaaag ctctcaatga agatgtatat aaaatgtgtg catcaatacc  22800
tcctgagaca caatttagaa gagattattt gattcttttct ctgaggcttc tttttacctg  22860
ttcttccctt tggtagcaag aaaggacatg tgcatcttgg gcgtggatgt acttctcagt  22920
attctgtcct taattatcac actagattat ttttcttttc ttttttttta tttttctttt  22980
taaaaatttt ttattaggta ttttcctcgt ttacatttcc aatgctagcc caaaagtccc  23040
ccatacccac ccaccccccac tcccctaccc actcattccc cctttttggc cctggtgttc  23100
ccttgtactg gggcatataa tgtttgcaag tccaatgggc ctctctttcc agtgatggcc  23160
gactgggcca tcttttgata catatgcagc tagagacaag agctctgggg tactggttag  23220
ttcataatgt tgttctacct atagggttgt agatcccttt agctccttgg gtactttctc  23280
tagctcctcc attggggacc ctgtgatcca tccaatagct gactgtgagc atccacttct  23340
gtgtttgcta ggccccggaa tagtctcaca agagacagct atatctggtc cttctcaggg  23400
aaggctggcg atctaagcac tattactatt gcagcaaaga catactctac ttggtatgca  23460
ttacagacat tgattggagg atgagggggg ttaggaaagt taagatttca gaagatgaca  23520
gtctagattc tttaagtcta ttttacaatg tttttctcta gcctaggcca agagacatag  23580
```

-continued

```
tcagtgagga atttcatttt agaattattt tacatttgaa gtttctagaa tttggcacaa  23640
tttctaaatg tgtagtgaga taaatggatg aggaagggat taactttaaa aagctagatt  23700
ttgattttgt cctttaattc attgattgct tgtttgtgtc tgtcatatcc ccatgtatgt  23760
acttagattt atgtatctgc atgtgaagga taggaggatt tcggtgtctt actgtgactt  23820
tgtactttat tccctaggaa gagggtctct tactgaactt gtatgtagac ttgtggccaa  23880
gaagctccac agagcccctg gaaaggagta gctgagagaa ttctaacctg attgatggtg  23940
atctagactt ttgcagcttt gttgtagcta aaatacattt gaggttctta tgacacacct  24000
tgggggtatc gactggacta gtgatgttta tccttctatt catcagaaac ttatatgaac  24060
ttgcttttcc tcaggcatgg ctctaacagc tttacaacta ctctttgagg aagtatgatt  24120
atccttatat tgcccacatt ttatttttat aattgccata gttgtctttt atgggatata  24180
atgaggatct gtgctatgat taatttaatt caaccacaca agatagataa tcttctattt  24240
atttaaagat ttttcttttt attttcattc atgtatgagt gtttacctac atatttgtat  24300
gactatcaca tgcagtgtcc atgcgagtca gaggagagaa atagattccc tggaattaga  24360
gttacagatg gttgtgggat agcatatggg tgctgggaag caaacccctt tctttcagaa  24420
gagcagaaat gactcttaat tgatgagcta tcttcccaac tctatacctt cattctcata  24480
gtagcaaatg gagaactggc ttgtatagct tgactgctgt catgcatctt tttttttttt  24540
tttctcttca gaggcagatg gatctttgaa tcagaacaat gaagggaccc agtctctcca  24600
tggaagtgga gactgtacat aattttgcag gggcttgggg ttttatatgg tgaaaagggg  24660
gatttgggga tagaagtttc ataatgcagg tcagttctcc tgaagtctca gtggaggttg  24720
gaggttgctg gtattttcat cttcttatca gaagcttccc tgggaagcta ccacatgcca  24780
gcagtccaca gatgatccaa gcagaatcac atagccttct aagtgtatgt attctaaata  24840
ttagtattta gatatgtcaa ataatgtaaa tatgtaaaga aggagggagg taaaaactgt  24900
tctcaggttt acagggctga aaatgaggct caggaaataa aatcatttgg acaaggtgat  24960
ctggtgttta gtcatctgac ctgaccttta cttcagcaac ttctgattcc cttcactact  25020
tcttcactag cagtgtcaca tgtagaatta tgtactgttc cctaaaattc ataggctgtg  25080
cctgtttctg tgactgcaat ttaaaaattc atctcccagt gccatgtcct atgacttgaa  25140
tttaatgaga taattaaagt aaactaatgt cttatgggtc tgccttaata caatataact  25200
gattatttta aaaaaagagg tcaggggcca gggagatatc tcagttgata aaatgtttca  25260
aattcatgaa gacctgcaga tcctcagtaa cagcatttaa aaaaatgaaa ttaataaacc  25320
aataaaaagc aaacatcgta aaaaaacaac atcacaaaca acaaaaaccc gaatgctgat  25380
atctataatt ccagcactgg gaaaaggcta gctacaggtg ggagatctca aaacttaact  25440
gatcagtcag tatagccaag gaatcagtac caggttcagt tagagacctc ggctccaaaa  25500
caatggtgga gcctcttgag tttctcccac agctcacgag cctgctccta tctttcctga  25560
acgttctcct tttaataata aacactatga tcctgtttcc aataataaat agtaattaat  25620
aataaaagaa gattgagaac tgagaactgc agaaggcact caatagtgaa ctctggcttt  25680
tacacacaca cacacacaca cacacacaca cacacacaca cacacacaca cacacacaca  25740
cacacacgaa atatacatcc cccccgtgaa cgaatgaaca cgtacacaca taggtaaaag  25800
aaagcatcat gacacaagac acggcaactg atgatatctt catcctgggt tttaatctct  25860
agcattgtga gaaaatatgt tcctctagtc tgaaacatcc agtccctaat actgtgctct  25920
```

-continued gggagacttg ggagtctaac tgaagcagta agcatcctct gttgaaaata aagaaggaat 25980
gaggatgttg ctccacgcca gttccctgcc ttcaccaagc ccagaggtca gatgacttcc 26040
tgggatgaaa gccagcttcc tcttgctgtt cctccagtcg gtcagcaaac gccttcttcc 26100
tgttctagtc ttcagtcttc taacttccct cctgcgacgg ggcagatcga ttctagaaca 26160
aaaccaaaag tgagaatgct aaggttggca ctctcacttc ctctttgaat atagtacttg 26220
cagaggggca cccactggga gggaagaggc aggtgtccca gggactctgc gctgccacca 26280
gttacagatc gtcatgttct ctcatggcct ccactggttg cagaaaatgc caggatgatg 26340
cctccctggc tcctggctag gactctgatc atggcactgt tcttctcctg cctgacacca 26400
ggaagcttga atccctgcat agaggtatgt gtcttgatcg catgtgatca caccctttcc 26460
tgctagcctg ccttgtttct caaaactatc cacagctcag agctccctgt gtgtgctctg 26520
cttagtttat tttgcacgaa ggagttaaac taaccaaaaa cttgagaagc cttggcaaca 26580
aaaagcctca gtgttaacac agggcaggaa caggcagcca ggggtgtctt gtttcattta 26640
aggcgtctga gtcatgattt agggacttga aattagtaaa actagtttat agtcattgtt 26700
ctgtgacata cctgagagtc gttaaagaac ttactgaacg tctctgaggc cagtattcac 26760
gggacgaaag catgactgta atcactgaaa aatgtaagta ggctgtaatt tcagggcttt 26820
ctgtgggaac tctggccact cagcttttag cggtcattcc ttccctttcc aaatcaagtg 26880
aaggtagctg tgtcttttct gctgctttcg aagcatcttt gagatgcttt gagtggtagc 26940
tcagcaggta aggtcagtgg ctgccaagcc tgatgaaaat ctgagttcaa gcctcaagcc 27000
tcacaagtta gaggcaggga atctcctcct ttaagatgtc ttctcacttg caagtgtctg 27060
ccttggcagg tgtgtatatg catgagcaca cacacaaatg aataaaggga acaattgtct 27120
taaatgaaag aatttctatt aaaaaataaa acaacaaaac acacaaaaac acaaagactt 27180
ttctaagtga ttttagtatt ctgcaactaa ttctaggaga taaagaaatg ggaggggtga 27240
gggaaggaga gggacagagc aacttaaaac atcaattagt tactgctaag gcagtaactc 27300
ccgttttggt cgaatactga gtcgtgagta atctgaccca tgactcattc ttgttttcct 27360
cctgcacaga ccacgcaatt atcttagaag ctcacaatag aactgagcaa acaaggaagg 27420
aattcggggt gaggtaggct cagaagctca aaactggttc aatgagttaa gatacatgac 27480
attcacatgg ggaaaaatac tgttaatttt aaaaagttat aatcacagta tcttgctttc 27540
tgattcctca gttatgttgg cagagatgga atttccaatc agtgctacac tgagataaaa 27600
tcccgttgct cttggtgtct ggtgtgcttt gtcaactctc aaagcttgct tgttccttct 27660
gtaagccagg tctcagggcc cttggccttg tcttcaggag tgattcctga ctggtttcct 27720
agttcatatt cctttctata cccacacaca gtttcttctt tatttgttgt tattggtcca 27780
ggggcttaga tttatcaaac tactccttta tactcttaat aactctttgg aaccatgatg 27840
gttgcttcat cctacagggc cttagcactg cctaagctaa ctacacacac catcatccct 27900
cacctaggtc aaggctcacc atgctaaaat tatggaatcc ctgtatatag tttaaaactt 27960
cactgttgat caaattgaaa aattaagaat aaatgcatca aattagtttc aatgattttt 28020
atgcaattaa atatagttat gatgcgtgaa atataataaa agcatcccac actaacactg 28080
gctaagcact agcctcaggt ctgtctccag ccctatggac aggccgagga gaacatgttc 28140
tttcctttag ccagggtctg tctcacccat gcctgctctg tgtctccaga gctctgaaat 28200
tgctcttttc accaggctcc ataagttacc atggctggct gatgccaagc acgccccaca 28260
tttccaaatt cctgcagctg gctggggtgt actttttttt tattagatat tttctttata 28320

-continued

```
tacatttcaa atgccaccct gaaagttccc tataccctcc ccccaccctg ctcccctatc  28380
cacccagtcc cacttcttgg ccctggcgtt tccctgtact ggagcataaa aagtttgggc  28440
ctctcttccc agtgatggct gattaggcca tcttctgcta catatgcagc tagagatacg  28500
agctctgggg gtactggtta gttcattttg gctggggtgt actcttgcac accacactct  28560
accaccatac ttttctctgg agcccagttg agttgccatg tgaaggaaaa cacaacacac  28620
acttggtcta caatcaacag gtaacacaat gttgggtgca gaacctagca tcctaatttt  28680
tttttattag atattttctt aatttacatt tcaaatgcta tcctcacagc cccctatacc  28740
ctcccctctg ccctgctccc caacctaccc actcctgctt cctggctctg ccattcccct  28800
gtactgtttt tgtaaactaa tctatgttaa aaatcctccg actcaggagc ctcttgttct  28860
tgtggagact tgaggaccca ggatagggga acactaggct gttaaggcag gagtgggtgt  28920
gagggtgagg gagcaccctc atagaggtag gggggtgggg gacggcgagg gggtaggggg  28980
cttgtggagg gaaaaccggg aagggggata acatttgaaa tgtaaatgag taaaataacc  29040
aaaaaacaaa caaacaaaat cctcaggtgg cagatcttgg aggatccacc acttgaattg  29100
acagcctccg actatctgca atgtgcctct aatgctctca gccatccaca aagagacctt  29160
ccttactcct gcctccctct tcctcttcct cttcccgact cggaagtccc acctactcat  29220
ctagtgattg gtttcctgta atgtttatta gggggaaatc ctaccacata gttaagcaat  29280
tacgaagata ccttatgttc aatttttgat acaggaaatt agacattcag caacattttt  29340
gttttactgg acattttgat ttctcctatg cgtgtttcat atttcatagc tatgtgtggc  29400
ttatagctgc agtactctaa tgtggagctt tgatttcagg attatctttt tcattttatg  29460
tagatttctc tgtgaatgtc tcctcaggtt gatttttctt gattgcctca tgtacatttt  29520
ccccttacc ctctccatat gctctttcat tgatcatatc attttgtatg tttgtctttt  29580
atttttccac catttattct cccctttgtg tagaataaac aagaagggag tattactgct  29640
gggtttgtta gcatgtcacc aatgcctctc agtggttaac gctaagaccc tttagtacag  29700
ttcctcaggt tgtggtgacc ttcacccata aaattccttt tgttgctact tcttaactat  29760
aattttgtta tggtgttgaa cgataatgta actatcccct atgcaggata tgtgatatgt  29820
gatcctgtaa atggattgtt tgacccttaa atgggtcaaa gtccacaggt taagaaccac  29880
tggcctagat catgataggt cttcagttgt atgtgtagta tgtgtgaaac cagtgaaaga  29940
atgacttctg aacaccatct gatgtcctcg tgttctgcct gtggcttctc catgacagaa  30000
ggctctgcca gtttgtctac atttgttccc acttgttatt atttgcttat gttcttttct  30060
ccttttgaca tacatatttt ttcctttacc acacatttcc ttgatcagct ttccttctga  30120
atctagaatc tgtgtctttg caactttcgt agttcttatt catgttcttc tctgttagct  30180
ggttctatga gtgcagtgcc atcagaaatc atgtaacatg tattcttgta ccacccatgg  30240
cctttagcag aaaaagccta ctatttaact tatacgggct ggtgtcccac caattacaca  30300
atatttatca ttcattcatc caacaaatgt ctattgagca ttgagaggtc accatgtacc  30360
tttctgagcc ttgaagataa atagcaaaca aaaatcatca gagcatcaat gctcatggtt  30420
caattgataa atgaaaagca tctggaaaat aactatatag gcaagagatt taccttgtca  30480
tcaaaatctg taaaggaaac aaaagagggt gagagaagaa tttctgtctg atgccttact  30540
ctcttagata cattgccttc aaggatccga tgatgagtac catttaggga gatgtgtgtg  30600
aagaagcctg tttatgtatg aatcttctga ctatatgtgt attaccccac ctcttttatt  30660
```

-continued

```
ttctttgtct ttagaggatt ttttgaagat tagtataaaa tacataagtt gtaagtaaat  30720
gctaatatgt agcaaggaat gaatagtaac caatgataat taacattaat atttatcact  30780
ttaattaatg caagctttga gataagctct gatctcattt agccctttga gaattctatt  30840
gcttttaaat aagagaaaac aaaactcact gggttaagca aagcattttg ccagatgaaa  30900
tcatataatt atgatattac atgaaatgtt atggtatagg gttcacaata aatgtgagaa  30960
aacagataaa actagtggag attatgatag agaaaacact caaccctgag tacaattttc  31020
taccactgga atccatgcac tataagacag cctctgatcc caggaccaaa ctgagaaagt  31080
caatgaatct aagaacaaaa ataattgtca aaaaataagg cagaatctag gaaatgtctg  31140
tatattttta ttggtactct ccatgtagct gtatataatg aaaatgatga attagaacaa  31200
caataatttt acataaaagt atatacaagc atacattaac atggctttta catacaacta  31260
gcgaggttca cagaagatat tataaagtca aaccagcaca caagcaaaac tttgtcccac  31320
actcagtatt ctttagttct ttgtgtagtg ttgaagactc ctgcacatgt gtagctgttg  31380
gccttttaca tctcatgtgc aggcagccat gtcagtgaaa ctttatgggt gtagcttttg  31440
acattaagaa tcacagtatc acagtaaagt tcgtaacctt tggactcata atctttcgtc  31500
ctcctctcag tgatccctga cctgtaggtg ttggagttgt attgtaagtg cttccattgg  31560
cactggactc cagaattctg cattttggtt ggttgtgatt tttttgtcgt gatctctgtt  31620
tataaagtgg gagaaatagt ctttcccaag caatagcaca gcaattagtt accaaatgcc  31680
aaatggccaa ccctgaaaac atatacataa gtaatattat acaaactgaa caggttctac  31740
ttatatatgt gggattttat ttatacaata tacaatatat atatatcaac aattaatgaa  31800
gcgggcaaca cggacttgaa aaacagcaaa gacaagggag taagaaaaaa actttaagag  31860
tggaaaagga aaagtgaagt gatataatta taatttcaaa taatagtaat aaaaaagatc  31920
tactctgtac caagtggcac acaacacttg ttatgaaatt aaggttttca gacttgagag  31980
ttatgtaaca cctgattcta ttgtttctca tttaatcata attttgttgt agcagaatgt  32040
taacatattg agaattcagg ggatattttt tcttcctgat atgtggaata agatgtcttg  32100
caaatatgaa gaggcagata aataaatgga gaaggatggg tgtgatacca tatccccaga  32160
atggcaggta ttttgggagt ccaatgttat ctttgactgt atagctaatt taaggccaga  32220
ctggtctata ggaaagcttg tttcaaccaa aataaatcat gaacgaatga atgaataggt  32280
ggacaatatg ttgagtggca tgtacatgtg agagttttat caccccatta ttcatctttg  32340
gagaggagtg ggaacacacg gttggaaaca taacaattgt tgtgtggtat ttacaggtag  32400
ttcctaatat tacctaccaa tgcatggatc agaaactcag caaagtccct gatgacattc  32460
cttcttcaac caagaacata gatctgagct tcaacccctt gaagatctta aaaagctata  32520
gcttctccaa tttttcagaa cttcagtggc tggatttatc caggtaatga atgagctttt  32580
atgtgatgca gaatgtgaag tagttatttt ttatatcatt gcattcttgg cttagaaaac  32640
caaggtggtt ctaactaaac ttccttctgt catctattca gtagtgctac aacttgctgt  32700
aaatccttgg aaaagctact tttatttaac tggtttcagt tggatgggcc actagataag  32760
aatatctaag ggcaattcta acctctacat tatttaaaac aatttcatta gatatttatg  32820
aaccatgtct tatatgttgt atgtctaaac tacagaagaa gaatttatag atacaaaacc  32880
catactccta attattaagc aggataaaat cctctttaac aaataagtaa gttaaagtct  32940
tgtccttatt attgaacata cagcacaaat aaaataaatg ttaactaatg ctaatactgt  33000
tgtttataac agtaagtaat aaaatatgtg aaaataaggg caacacactg tgtcctatag  33060
```

-continued

```
aagagtgaat gttttgttat gtgtgtgaga ggatcaggaa agattttgag acatgagtac  33120
atatgtaaga tacctgaaat attgaaagta gaaaagagag tagagattga aaaaaaaact  33180
aacttaggag ggagatgtaa atgtccaagt aaaacatcaa ctatgggcaa gaaacagtta  33240
ctaagattgt cctttctgat tcagggcatc ttaccatttg ttggaacata aaaactttta  33300
gccagtattt caggcgggaa gctcaatata ttttattggt taaaattgct ctttgacaat  33360
ttcatacatc tatgtaatgc atacagctac tcttaccttc acccacactg agttttctct  33420
gatcactgtt agctctgacc ccttccaaaa tgtctccaac ctatattcat accttcttat  33480
ttattgtttg acccactgat tttaaccagg ttctctgtgt gaccatagat ttagaaaaac  33540
ctatctgaga ctagtgaggt taaccatttg ataagcaact aaaaccagtg acggtttctc  33600
cccaaaaatc taaactttgg cagagaagaa atgattccat ggtcccctcc atgatcagta  33660
aatatctatt ggcatgatca gtgcagggaa ccacagcttc tatgacatca gatttgcaaa  33720
gtctttgtca tgtcccacat gtccctcatg tcccacaaat ccctcctctc tctgtctctt  33780
ggctcttaca tttctatcag attcctcgtc ctttataatc cctgactctt ggagagggat  33840
ttgtgaatgt tcattacagg ggtgatcaca gaactatgtt ttgcttcttc tagcatcttg  33900
tacatctaag aatatcctca ttcactactg tttactataa agggaagtga catttgttaa  33960
ggggtataaa tgtaaatatt tagacagaag tctggtacta tgctaattta actaaaccac  34020
aataaccaat gccctctctg caccccaaac atcagggtca taggcctctc taagcaacat  34080
tttttgaaca ggttaacagt actagccttg gacaaaaatc taatccaaga aagctttgtt  34140
actcctaaaa tagttatgcc agaatttcag cactggacac atcttgcctg gcaggttcat  34200
gtaatagttc atctgggcca tagctggaag agaccagtaa tgatttttcc ccaccagcct  34260
tcatgacacc tttctgctga aagcaaatca gcagagagaa cattggttgt gcttcagctt  34320
catgtcagtg ggttgtactg atcaaggaga tccttaggtg ttgaagttga acgatgaacc  34380
tcttctctac catattccta aagctactgg aatgtttcac acatgtgttt ttgttctaaa  34440
atttagagta tggtattaaa agtcttctgc agagcagaca atactgtaaa tcattagtga  34500
actagaaaat gtattatact ctttacagga gcatgataga tggagaattc caaaggaaga  34560
ggaccacagc tctgttggtg gagcctgtgc tttctccaac gtttagcacc atgtgccctg  34620
ttgcttgtaa cttttcctga gtctctgtct tctctcctag taaaggaaaa tggtaaatct  34680
ccctccatgg tgaaaagtta ataaatgaga gattattaaa attatttagt gagtttatga  34740
gtttgaaaac atgctatcat aatcacttta ttaaattgta cattctactt atcccaggga  34800
gatagatttg aagagaactg aggtaagcag gtaaaaaact ctaaacagaa taatctcttt  34860
ttaatataga gaacatagtt tttcacccag tataattgag aattgatcta aagtataatg  34920
taagataatt ccttaaaggt ttggagtttg tattcaggaa aaaggtaagt tcctcttccc  34980
ttagctcaca ggatattttg cattagagca aagcagacaa tctactcctg tgcctttctt  35040
taaaaaaaaa gataattttc attatgtaat ttcaaatgtt gtcccttttc ctggtttccc  35100
cccctgaaaa cccactatct tcaccccctc cccctgctca ccaacacacc cacatccact  35160
tactggccct ggcattctct tatgttgggg catagaactt tcacagcacc aagggcctct  35220
cctcccattg atgaccaact aggccattct ctgttacata tgcagctaga gccatgaatc  35280
acaccatatg ttttctttgg ttagtggttt agtcccaggg agctctgggg gtactggtta  35340
gttcatattg ttgttcttcc tagcactgca aacccccttca gctccttggg tactttctgt  35400
```

-continued

```
attttattca ctggggaccc tgtgctccgt ccaatggatg gctgtgagca tccacttctg  35460
tatttgtcag gcactggcag accctctcag gagacagcta tatcaggctt ctgtcagaaa  35520
gctcttgttg atatacacaa tagtgcctca atttgatggt tgtttatggg atggatcccc  35580
aggtggcagt ctctggatgg tcatgccttc agtctcttct ccacactttg tctcggtaac  35640
tcttttcatg ggtattttgt tcccacttct aaaaaggatt gaagtatgca cactttggcc  35700
ttccttcttc ttgagtttca tgtgtttttt gaattgtatc ttgggtattc tgagcttctg  35760
ggctaatatc cagaattaag tgcatatcat gtgtcttctt ttatgactgg gttacctcac  35820
tcaggatgat gccctccagg tccattcatt tgcctaagaa tgtcatagat tcactgtttt  35880
taatagctgc atagtactcc actgtgcaaa tgtaccatat tttttgtatc catttctctg  35940
ttgagggaca tctaggttct ttcaagcatc tggctattat aaataaaact gctatgaaca  36000
tagtagagca tgtgtcctta ttacaaggtg aagcatcatc tggatatttg ccttggagtg  36060
gtattgctgg atcctcaggt agtaccatgt ccaattttct gaggaaccac caaactgatt  36120
tccagagtgg ttatatcagt ttacagttct gccagcaatg gaagagtgtt cctccttctc  36180
tacatcttgc gagcatctgc tgtcacttga gtttttgatc ttagtcattc tgactggtgt  36240
gaagtggaat atcagggttg ttttgatttg catttccctg atgactaagg atgttaaaca  36300
ttttttttagg tacttttcag tcattcagta ttcctcagtt gagaattcct tctttagttc  36360
tgtaccccat ttttcaatat acacaatcat aatcatatat gtatgtatat gatttggcaa  36420
tagaatccta acagaaagtg gaaacttgag aaagaatcaa acttagttgc ctcatttaga  36480
agtggaatga tagaaactca cagaaattaa tgggttccca agatcatgca ggaagaatgg  36540
agagttaaca tggctccatg gattcctctt gcgatattct ttttaacata cctctacctt  36600
ttgttaaatt actaaggaat aaccaaatca cagaccaaaa ctcttttatt acctatgaat  36660
actccaaaga aaataggaaa agtgagggaa ggtaattggg ttagatttgg aagtgactct  36720
tttgctaaat gtatctggca tgcatctatg acaacatctg tcatgaatca ctgttggctg  36780
cgtctgagtt ctgtggctag cttgtctctg tggaagcttt acgtagtaca gcttacattt  36840
atcttggaat aaaatttaga atatttcatt gagcttgtga gtctacacta ttcccactct  36900
tgccatacct ttatattatt cttcctcagt ttccttgttg cccttcagtc acagagactc  36960
tgttgtggct cctccgtctg gcatgcctgc taactactac aacttttgga tcgctgtttt  37020
cttcatatat tcttcacatt cgctcatatt gatcattgaa atttccactt acttattctc  37080
aagtgtaatc tgcttttatc tggtgagaga gggtcaattc ttttgatgtg aatattctta  37140
acccatttc ttcttcttct ataaagctta ctcatgtccc taataattaa catttacctg  37200
tgataatgac agactcaaaa taactagcca tcatatatca gtaaagtttt gtaaacattt  37260
atgccattct tgactcttga cacctatgtg tcattatata tgcctttaaa attaactttc  37320
accagtaatt tatcatgact agcaaataat gaccacccat attgcctata ctcattagtt  37380
gtaaaattat atctatgtct ggaaaaaatg cataaattaa tctaagacta ctacatatca  37440
actgtcttta tgtaccccag ttatgatctt gaattgattt tttctaatgg atttgctgcc  37500
tgacatagtg tgatagttta tcatcactgt agcaagtgtg aaaatgacaa atctgcagag  37560
ttcctctcct gctcacacca tcatcacctg ttttgctctg tacagttttc tctttacaat  37620
aacatggtat atcatatctg tttgtatcat agtatggtag ggactgttat gtcattagaa  37680
agggtttttt tttcagcaaa aatacataat tggtatctct tttgcccata ggtgtgaaat  37740
tgaaacaatt gaagacaagg catggcatgg cttacaccac ctctcaaact tgatactgac  37800
```

-continued

```
aggaaaccct atccagagtt tttccccagg aagtttctct ggactaacaa gtttagagaa  37860
tctggtggct gtggagacaa aattggcctc tctagaaagc ttccctattg gacagcttat  37920
aaccttaaag aaactcaatg tggctcacaa ttttatacat tcctgtaagt tacctgcata  37980
tttttccaat ctgacgaacc tagtacatgt ggatctttct tataactata ttcaaactat  38040
tactgtcaac gacttacagt ttctacgtga aaatccacaa gtcaatctct ctttagacat  38100
gtctttgaac ccaattgact tcattcaaga ccaagccttt cagggaatta agctccatga  38160
actgactcta agaggtaatt ttaatagctc aaatataatg aaaacttgcc ttcaaaacct  38220
ggctggttta cacgtccatc ggttgatctt gggagaattt aaagatgaaa ggaatctgga  38280
aatttttgaa ccctctatca tggaaggact atgtgatgtg accattgatg agttcaggtt  38340
aacatataca aatgattttt cagatgatat tgttaagttc cattgcttgg cgaatgtttc  38400
tgcaatgtct ctggcaggtg tatctataaa atatctagaa gatgttccta aacatttcaa  38460
atggcaatcc ttatcaatca ttagatgtca acttaagcag tttccaactc tggatctacc  38520
ctttcttaaa agtttgactt taactatgaa caaagggtct atcagtttta aaaaagtggc  38580
cctaccaagt ctcagctatc tagatcttag tagaaatgca ctgagcttta gtggttgctg  38640
ttcttattct gatttgggaa caaacagcct gagacactta gacctcagct tcaatggtgc  38700
catcattatg agtgccaatt tcatgggtct agaagagctg cagcacctgg attttcagca  38760
ctctacttta aaaagggtca cagaattctc agcgttctta tcccttgaaa agctacttta  38820
ccttgacatc tcttatacta acaccaaaat tgacttcgat ggtatatttc ttggcttgac  38880
cagtctcaac acattaaaaa tggctggcaa ttctttcaaa gacaacaccc tttcaaatgt  38940
ctttgcaaac acaacaaact tgacattcct ggatctttct aaatgtcaat tggaacaaat  39000
atcttggggg gtatttgaca ccctccatag acttcaatta ttaaatatga gtcacaacaa  39060
tctattgttt ttggattcat cccattataa ccagctgtat tccctcagca ctcttgattg  39120
cagtttcaat cgcatagaga catctaaagg aatactgcaa cattttccaa agagtctagc  39180
cttcttcaat cttactaaca attctgttgc ttgtatatgt gaacatcaga aattcctgca  39240
gtgggtcaag gaacagaagc agttcttggt gaatgttgaa caaatgacat gtgcaacacc  39300
tgtagagatg aatacctcct tagtgttgga ttttaataat tctacctgtt atatgtacaa  39360
gacaatcatc agtgtgtcag tggtcagtgt gattgtggta tccactgtag catttctgat  39420
ataccacttc tattttcacc tgatacttat tgctggctgt aaaaagtaca gcagaggaga  39480
aagcatctat gatgcatttg tgatctactc gagtcagaat gaggactggg tgagaaatga  39540
gctggtaaag aatttagaag aaggagtgcc ccgctttcac ctctgccttc actacagaga  39600
ctttattcct ggtgtagcca ttgctgccaa catcatccag gaaggcttcc acaagagccg  39660
gaaggttatt gtggtagtgt ctagacactt tattcagagc cgttggtgta tctttgaata  39720
tgagattgct caaacatggc agtttctgag cagccgctct ggcatcatct tcattgtcct  39780
tgagaaggtt gagaagtccc tgctgaggca gcaggtggaa ttgtatcgcc ttcttagcag  39840
aaacacctac ctggaatggg aggacaatcc tctggggagg cacatcttct ggagaagact  39900
taaaaatgcc ctattggatg gaaaagcctc gaatcctgag caaacagcag aggaagaaca  39960
agaaacggca acttggacct gaggagaaca aaactctggg gcctaaaccc agtctgtttg  40020
caattaataa atgctacagc tcacctgggg ctctgctatg gaccgagagc ccatggaaca  40080
catggctgct aagctatagc atggacctta ccgggcagaa ggaagtagca ctgacacctt  40140
```

-continued cctttccagg ggtatgaatt acctaactcg ggaaaagaaa cataatccag aatctttacc 40200
tttaatctga aggagaagag gctaaggcct agtgagaaca gaaaggagaa ccagtcttca 40260
ctgggccttt tgaatacaag ccatgtcatg ttctgtgttt cagttgcttt agaagagtat 40320
tgatagtttc aactgaactg aacggtttct tactttccct tttttctact gaatgcaata 40380
ttaaatagct ctttttgaga ggtcttcatt ccaatttcat cttccatttt atgtcatttt 40440
cttttctttt ttttttttat ctaattctat aagaaatatg attgatacac gctcacagat 40500
agcctggcca atcctaagaa tgctatattt attaaataca attcctagta tacttttact 40560
tttataaatt cagttatcgt ttttcatgcc ttgactataa actaatatca taaataagat 40620
tgttacaggt atgctaagaa ggcccatatt tgactataat tttttaagaa agtatgtaaa 40680
atatactttg tcatattgtc actgaatgtc attcttaagt tattacctaa gttatggatg 40740
tcacagagtc agtgttaaaa ataatttggt tgatagaaat atttttaatc aggagggaaa 40800
agtggagagg ggtgcaggaa cagaaatcat gatttcatca tttattcttg atttttccgg 40860
aagttcacat agctgaatga caagactaca tatgctgcaa ctgatgttcc ttctcatcaa 40920
ggatactctc tgaaggactt gagaacattt tggggaggaa gaaaggtcta acatcctttt 40980
ccttcatcat tctcatttct ggacatgcct tgtgagatgg atgaatgttg ggagtacaca 41040
tttctgcttt caccttattt cagtcagcat gaacactgaa tatataatgt catttcacag 41100
tgtgtgtgtg tgtgtgttgt gtatgtacat atatgaacct gtacatgtgt ttaagtttaa 41160
agagaaaata gtgtacagag cagctctata tttgtgatag ggctttaaat agttgagcta 41220
attcagaaaa gtatggagat ttcttggtaa aggaaaccaa agtagaatca ttacaagatc 41280
taacaataaa aattttgaaa caatcctaca agtaaatata ttggattttc ttgtccatta 41340
agacaatatt catactattg aaattatgga aacaaccctt ggaaggttaa tgcatagaga 41400
cagaatgcta tctacttgca gtggaatgtg atttgacctt ggagaagaag caaaccttgc 41460
tacttgtgag cagatgcata aaggtggagg ttttttattg taagtgaaat atgccaggca 41520
cagaaggaac tggcctttca ggaacttttg atgacatgag caaagttaga aaaaataata 41580
tgcagaacaa tagaagagga agacaaaaga aagacagccc taggatgtat tcttcacaac 41640
gattttaaac aatatgcttg aaagagaatg aagttattag tatcaattaa gatgtctaca 41700
attttcataa ttccattcaa actggaacat agccacctaa ttatttgtct cttgttagcc 41760
aagtgaaata gcagatcaag aatctcccca tttttctgat ataaaaaccc aaattctaat 41820
gcagtaaatg tcttgtcaat cagccagata gcacagaaga ggcaaggcga cagtctgtgc 41880
cccttccctc tcacagaaac tcctgtgcac tctagcccac tgcttcaggc tacaagctag 41940
aaaagcaaga agtgaaagtg ccacagttct ctatgtggtt agtgccagtc agggtcattc 42000
aacttaaacc atgagtcatt aagaaaatac atatgcatgc atgcattaat gcacagagta 42060
gtttatttat aacaactctt tccataaagg gctggggagt tttcaacaaa atataaagga 42120
acaattagtt taatcaaaag aaagaaatat aggcagaaga aagaaatgaa agaaagaaag 42180
gaaagtttta actgtgtatt ccaggtttaa ttctagagat cttctggaat tttagagagt 42240
gtgacttttg gagaattcct aaactcattt tcagattata ttacgtatgt gacttggcct 42300
tcatctgtct gagagctaag aaagaaatga agatcatgca tttattatta ggccattaca 42360
aactaataaa tataaagata aaagggagac tctgtggatg agtctccctc ttggctttct 42420
tatgggtagt cagagagaag cactcagtag ccttatcctt gacaacattt ttgtcacatt 42480
tgttttccca gtctgtagga caacagcagt ccttatgact aaagtagatt gtatcttttt 42540

-continued

```
tacctagctt ctattcatct gtgttgtcct agcttccttt ttgagtctac agcctttgag  42600
aaatcactag aagtcactgg aacctcatgc tttgacttga ggcagtcctc atatgtgttc  42660
ctaggtactc gaggggtcag ttgggagact ggggagccat atcttaacca tcagctttgc  42720
ttccttggtg ttgagcatca tgcctgacaa agtaagcaga caatgcctgt atacgtgaag  42780
aagaggagaa tcattaatgc atgttttctt ggtgtgctgt tgtccttgat acattccagt  42840
tcagaatcta aagtcctagg gatcttagct gtcaacttag ttttccctgt ctgtcacttt  42900
gtatggatga tttaaattgc ttcttcactt ggttgcttga caccatgtat tctaaaattt  42960
tgtggaaggt gtgtgttggg ggggggcgta gttctaacaa tagtgttctc tagtggatac  43020
attaaaatca tattcagcta attaatattt gattaagttt tgcatgctat accgatttga  43080
taaacattca caaaatcaca ggcttcaaga tttttcttaa cacatccaaa gtacacaggc  43140
attaaatggg caaaactaaa tatcaaactg actttattta atagtttctc tactgttctc  43200
ttttgtttta tgtcaagagt tgaatgccac tgttctgtat ttttaattat ttattgtttg  43260
ctattgtgag aattcaaagc cagaactttg aggagctgac agaggcactg tggcctatga  43320
agacagtttt tggagttaac aatttccttg gtaactatgg actatgtctc cacacttcag  43380
ctctcatatc tgatggaata aactcctttc caggaggctt ctacttatgc taatgcaccc  43440
aagcaaacaa ggaggctaat agaaccagct gtttctgtct ttatagcaat ttcccaacat  43500
tctacacttg aggatttctt ctgtcacatg atttttttca ttgggcattc tttcaatcct  43560
tcattaaatg gccgagactt ctcactagac cccaactcaa tgaaattctt aagctgctag  43620
cattgaacaa cactgacttt ttcaaagcac cttgataggg aatttaagct ggaccatctg  43680
aagcaggaaa gtctgttgtt ttgatggaat ttcctaatgg taccattgtg gctttatttt  43740
gccttgttaa tgtaagggat tcaaagcatt tcaacttact actcatagtt caagcatcta  43800
ttttgcagat gcactgaaaa ttaagagatt ggagagtttg tcatatatat ttccatcatc  43860
aactattcta gttcttacta aagaaggagg gtgcaaaaat ttgaaggata tgttaaagtg  43920
ccttctatac ttaatgattc ttctagaaaa ggcaaagtgt tgatcttgtt ctttgttatg  43980
gtattatatc ttctcatggt aatttgaaag aagtttacat accaatttca gtttgtttac  44040
ctaggccttg agagtcattc tacagtacac gattaggcta ctatgaagac aaaagaaatc  44100
attgtgggga aactcagtac agctctagat ttacctttta taatagatga atcccagaat  44160
gataaagatc aagcctggca tgatgttaat ttagtgggct aggatcctgg aaacctccta  44220
aaataggaca tcccatgcat ttggccttag ccagtgaggc atctctgaga aagtgtagaa  44280
aaacttgcaa ggaggttcag tgctctgaaa gacacagagt caaatgtaca tgtaattcca  44340
gttcttcttt tatatatgtg tactttacat agtccctgaa gtatcgagag gctcaggtat  44400
aggtgctacc accttgatag agttcactta gccaaaatgc agaaatggat gcccagagag  44460
aatagattac ttgtcctgca tcctgtaact taaaatgtgt taataatcat cataataaat  44520
tctatctgcc aaatatttca tatgtgcatg agactgtttt agtttaatta ttaaaattgc  44580
tttctgatgc agctcttagc cacattgtca tttcccatac aatgaaactg agaccaaaaa  44640
gcaaattctc caattccaag ggtagaattc aagtaatcct gatatccaga gctgctaatt  44700
ttttgccaca cagtagactg ctgcagtgtc tgggcttttt tgctggggct cattcactca  44760
ctaacgggag aatcctgtgg acaaggtcag caactccctt accatctaga aattgaaggt  44820
ttcaaaggca ctgcatgtga ctttccttga tttctatgga aatgaagatg gtccctcctg  44880
```

-continued

```
tgacagtgct aagtgccgag tctgagtgta aatgtgcttt ttggcacaaa ttgttctgtt  44940
ctaatagtgt tgattataat tataaaataa tgtgtttctg aaaggctgca agcaattctg  45000
ggaatgacaa taagggtttc gaaacaacat ggtatttatg tgagaagtgt tttgttgaaa  45060
attaaacctg tgtttaggag aaaggatcct gttgtttgct cctaagaaac tatcacacca  45120
tgtaattaaa tcagagccag ttggttgcca attggagttc ttgtctcaca tgaacaatat  45180
tgtatcacct acaacaaaca agatatgact gaccagaggt agccaagact ctttacccaa  45240
atcctgtttc tctatcttct cagggcccag aaaaaagatg gaaatgcatg gtcagttttt  45300
ttccaaggct gggaattaac cttgtagggt gaagccttcc tcaagttcat ctcagattgt  45360
ccgtaaggaa taggtttttc attcaagggc cttttatagg aggctgtatc tgtaaataag  45420
tgaggaattc aatgtttgag aggctgtctt gacttccttt cttgggagga aaaacaaaat  45480
ccttctatga agattaggaa tgtcttcgat gttctcagac ctcaaaggca gaaaaaagta  45540
tgcagtgtaa tttgtttgta tgtatctctc ttaaaataat atctaccata acattgtctc  45600
ccaacccgga tttgtgtttt attttcacca aggacatcat aaggtttaaa gcagatcttg  45660
caagggacgt cataaaaata gatatatgac aggatggtaa agtttaccag gctgaagaac  45720
cacttgatga ttttggctat atttaattat ataaatttct gcttttatta tctctcttgc  45780
tagaaatttt atttgataac tagagtttaa taatctgtat ttttaaaaat attctatgtg  45840
caattttaag tataaacaga tctggaaatt actatttaag aggcaacagc ctataatgta  45900
ccatgtttaa tatggccatg tgctctgtcc ttgagattta ctgctgagag ccaaagaaag  45960
atcaacaaaa tggaacggga aacttattta tttatttatt tatttattta tttatttatt  46020
tatttattta tttatttatt ttaaagaaaa aggtgcttca tttatctgat gattttattc  46080
ttttacactg tgtaattgat tcttctcaat tctatctgat cagactcatg tggaagaatc  46140
tgtccagttt gatgtaatct tcaaacatcc acatagaagt tataatctga cagtcatgtg  46200
tttctcctgg tttctacatt atatgttgcc ttcttcatcc ccttttggaa tttgagatac  46260
ataagcttaa atcagaataa tatcatggtc tgtcatgaac tctctgaggc atctgttgac  46320
agctttaatt tattggttta tcaaccccaa acataccaag tctaacttac ctcccatttg  46380
taaactgaat attcacttgt cactgacata cacagctgca acaaatggcc ttctctgtaa  46440
agcaccaggc tctcctgcac agacttacca cataattgtc agtcttccca ggaaaccctt  46500
ttcattcctg ttgaggggag gtaaggcagt gagcactaat agcttaaatt cagtcatttt  46560
gacctttaaa ctaccaaccc tgaatcttct ggaggagtct atggctcccc agtgggaaac  46620
gcatgctgga gaaacttact acttgcaaaa agcacttttg aaataagctg tggggatgaa  46680
tctctgctta atgctgtgct cagctcactg cagggtcctg cggagtcttt actcttcatc  46740
ttctgcagca tgggctgtgg cctgagagct gcactgctaa gtgtagggag cctcctttct  46800
gccactcact gaattagggt ctgaccaatt gtgtcattca gggtgcagac tagccactag  46860
aaaacttcct ctgagctcaa gtatcatacc ccgagaacgg cacagagagg taggaccatt  46920
atttttgcag ggcatgagtt gcctgcaaat tagatgggtg tattttttta tggttaatgt  46980
gctggttatt tttacttatc atgattgatg agtggtaaac aatgacctct ataaaaatac  47040
atgtgtgttt agaatatgag tttattagag ggaaaaaaca aaatttagca gagagatgca  47100
gatgtggaga gagacaggag aaagggctag agatggatat cagcagttgg gggcagaggt  47160
gtgcatctct ataatgtgcc agagacctgg tgtggagatg cttccaggag tctatggggg  47220
tgtctttaac ttcagctaag agatcctagc actggcagat acagagcttg aagtggcaac  47280
```

-continued

```
ctcctttata gccaactaag atccctcagt ggagggataa ggacaacaac ccactcacaa  47340
aacttttgac ccaaaatctg tcctgtctgc aagaagggac agaaatggaa ccgagattga  47400
gggcatggcc aatcaatgac tatcccaact tgagactcat ccctctagac tgaaacacaa  47460
agaaaagggc aaacatgggc agaaatttgg accctgaact tatgtagcat atgtacagct  47520
tggtattcat gtgtggattc ctcaacaact gcagcagggg ctgtccctga atctgttgcc  47580
tgcttgtgga tcctgttccc ctaactaagt tgccttgtct ggtctcagtg agagagggat  47640
gaaactcttc ctgcagtgac ttgatatgtc aaggtcaagt gatacccagg ggctgggagt  47700
cttcccattc tcagaggaaa aggggaagag gcgtggggaa gggactgtgt gagggggcac  47760
tgggaagagg gatgctgaga ttggggtgta aggtgaacaa gtaagtaaat taatggaaaa  47820
aaggaagtta tcaccagtgc aattcccaaa gggaaagaag caaacccctg tcagatgatg  47880
ggctgaagtt ccggttatcc ttcttgcatg cttacctctg caaaacagtc tccacatctg  47940
taaaactcca aagatgaagt aaatgtccat ctccacaatt ctattctgta attagaacag  48000
taaccctacc atgcaactct tttgctctcc tggactgtgg ttctaacatt tgtgacctca  48060
ttatagcata caaagactag aagcatcttt catcaattaa taagcactca agcattagta  48120
atttttcact ttttcctcag ttccagaaaa ggattgagct aagatcagtt gagtggttaa  48180
acaaagtact attgaaggca ggaaggatgg ctggttaact gctgcaacca gtgatatcat  48240
aatataaagg ccagttcctg gatgtttgga ttcactgttt acaatgtaaa agtatatgta  48300
cagctatagg tatgatagct ttgagagtca agtaagactg gggattcaag aaaattcaac  48360
agagtgcaat tgaaatacca taaatgatat gtatctcttt tgccaaatca tataaccccc  48420
aaaacacctt ccatcatgca tatgcattaa gaagcttgta aattaatcat ctgcaccatt  48480
ttcacaagat tatcttggag tttagcagtg tttttttttt atacttggcc actttgaata  48540
atcttaagga gagaaataca gtttgtctaa atccaagcac gtcttgaact aatgcttaca  48600
attatccttg tttcccacat ttgacattta aagtgatata tcataggttc ctacattgct  48660
agctgtggaa gcgccatctg accccttgtg cctctcacca tctgtgaatt cttgtcagct  48720
cagagtaaac tctgcataaa tttcaccatt gaagattagt gatagaagag aactctattc  48780
gctctttctt ctggctttat tttttatttt taatgctgtc tgattgccca aggtatgtat  48840
ggagggtgta cacagacggt acacagacct aagtcaggtg tctaagcatc ccaggaactt  48900
cccttccaat attcttttct gagcatatgc cctcagttag ttttcctctt catatgatct  48960
gtgctcctgt ttataccaaa ctctcggctc tggcagcatc ctcgtccaaa aagcacaagt  49020
tcagttaagt tcactggtca cataccacca ccattttcta ctctttatac tttctttccc  49080
tgattacatt ccaatagtgt gtaggcatga acacatgtgc acacatacac acatgtgcag  49140
attatagtcc acttgtagca ataagaggat tctcagtaca attcgtggga gttggatttc  49200
tcctgccccc acataggtac aattaatccc agtactcggg aggcaaaggc aggcagattc  49260
ctgagttcaa ggccagcctg gtttaaaaag tgagttccag gacagccaaa gctacccaga  49320
aaaaccccgt ttcaaaaaac caaataaaaa aaaaaaaaaa aaaaaaaaaa aaaaaaaaaa  49380
aaaaaaaaaa ggatcgaatt ctaattatca gccaaggtag ggaatacctt tatcttttgt  49440
gacatatgtg gaccatactt taagtttttg tgggtactaa cttcattctt gttttatttt  49500
tctctgtctc tctgaattct ctttctcttt cctattaccc ttatgcccaa agcatgagaa  49560
ttccaacttc catatttgtg tttattcttt ctttgcactt ttcctctctt tctgttttgt  49620
```

-continued

```
aactctataa cccttttttgt ttgcttgttt ttgcatggga tagttattat gcattctatc  49680

tcactatgtt agaaaaaata gtttcagctc tgggaattga gcagttctgt gctgatttca  49740

tgtctaacac tatatgcttt tttttcctct ccttcaaata gaggtaatag ataccttttca  49800

gtatctatta gcagaggagt ttgcagacat atacaaagtt catttttctc ctaggaagtt  49860

ttcttttctt tgcttttcat gccatctaac atttgtagga aagctgcttt ctgctaccac  49920

aatacaagat gcatgaaggg gcggagctaa gtgtcaaaat catgctccca aagttttata  49980

cattttaggt tattttcaga                                              50000
```

<210> SEQ ID NO 49
<211> LENGTH: 25
<212> TYPE: DNA
<213> ORGANISM: Mus musculus

<400> SEQUENCE: 49

```
cagtcggtca gcaaacgcct tcttc                                           25
```

<210> SEQ ID NO 50
<211> LENGTH: 25
<212> TYPE: DNA
<213> ORGANISM: Mus musculus

<400> SEQUENCE: 50

```
caaggcaggc tagcaggaaa gggtg                                           25
```

<210> SEQ ID NO 51
<211> LENGTH: 24
<212> TYPE: DNA
<213> ORGANISM: Mus musculus

<400> SEQUENCE: 51

```
ttattcatct ttggagagga gtgg                                            24
```

<210> SEQ ID NO 52
<211> LENGTH: 26
<212> TYPE: DNA
<213> ORGANISM: Mus musculus

<400> SEQUENCE: 52

```
aaggaagttt agttagaacc accttg                                          26
```

<210> SEQ ID NO 53
<211> LENGTH: 26
<212> TYPE: DNA
<213> ORGANISM: Mus musculus

<400> SEQUENCE: 53

```
tctcctgctc acaccatcat cacctg                                          26
```

<210> SEQ ID NO 54
<211> LENGTH: 24
<212> TYPE: DNA
<213> ORGANISM: Mus musculus

<400> SEQUENCE: 54

```
catctgttcc atgggctctc ggtc                                            24
```

<210> SEQ ID NO 55
<211> LENGTH: 19
<212> TYPE: DNA
<213> ORGANISM: Homo sapiens

<400> SEQUENCE: 55
gctcggtaaa cggtgatag 19

<210> SEQ ID NO 56
<211> LENGTH: 20
<212> TYPE: DNA
<213> ORGANISM: Homo sapiens

<400> SEQUENCE: 56
tgagaagttc tgggcagaag 20

<210> SEQ ID NO 57
<211> LENGTH: 18
<212> TYPE: DNA
<213> ORGANISM: Homo sapiens

<400> SEQUENCE: 57
tctctggtct aggagagg 18

<210> SEQ ID NO 58
<211> LENGTH: 19
<212> TYPE: DNA
<213> ORGANISM: Homo sapiens

<400> SEQUENCE: 58
ccagtccaat aatgaaatg 19

<210> SEQ ID NO 59
<211> LENGTH: 30
<212> TYPE: DNA
<213> ORGANISM: Homo sapiens

<400> SEQUENCE: 59
ccatcacatc tgtatgaaga gctggatgac 30

<210> SEQ ID NO 60
<211> LENGTH: 30
<212> TYPE: DNA
<213> ORGANISM: Homo sapiens

<400> SEQUENCE: 60
tgactttctt tgtcatgggt tccttgactg 30

<210> SEQ ID NO 61
<211> LENGTH: 18
<212> TYPE: DNA
<213> ORGANISM: Mus musculus

<400> SEQUENCE: 61
atgccatgcc ttgtcttc 18

<210> SEQ ID NO 62
<211> LENGTH: 16
<212> TYPE: DNA
<213> ORGANISM: Mus musculus

<400> SEQUENCE: 62
tttaaattct cccaag 16

<210> SEQ ID NO 63
<211> LENGTH: 15
<212> TYPE: DNA

-continued

<213> ORGANISM: Mus musculus

<400> SEQUENCE: 63
cagctcttct agacc 15

<210> SEQ ID NO 64
<211> LENGTH: 20
<212> TYPE: DNA
<213> ORGANISM: Mus musculus

<400> SEQUENCE: 64
tgtgaacatc agaaattcct 20

<210> SEQ ID NO 65
<211> LENGTH: 19
<212> TYPE: DNA
<213> ORGANISM: Mus musculus

<400> SEQUENCE: 65
tgagattgct caaacatgg 19

<210> SEQ ID NO 66
<211> LENGTH: 22
<212> TYPE: DNA
<213> ORGANISM: Mus musculus

<400> SEQUENCE: 66
ttgaaacaat tgaagacaag gc 22

<210> SEQ ID NO 67
<211> LENGTH: 19
<212> TYPE: DNA
<213> ORGANISM: Mus musculus

<400> SEQUENCE: 67
cctggctggt ttacacgtc 19

<210> SEQ ID NO 68
<211> LENGTH: 22
<212> TYPE: DNA
<213> ORGANISM: Mus musculus

<400> SEQUENCE: 68
tttcatgggt ctagaagagc tg 22

<210> SEQ ID NO 69
<211> LENGTH: 18
<212> TYPE: DNA
<213> ORGANISM: Mus musculus

<400> SEQUENCE: 69
aagaactgct tctgttcc 18

<210> SEQ ID NO 70
<211> LENGTH: 19
<212> TYPE: DNA
<213> ORGANISM: Mus musculus

<400> SEQUENCE: 70
tcagaaactg ccatgtttg 19

<210> SEQ ID NO 71
<211> LENGTH: 20

-continued

<212> TYPE: DNA
<213> ORGANISM: Mus musculus

<400> SEQUENCE: 71
tgagctggta aagaatttag 20

<210> SEQ ID NO 72
<211> LENGTH: 21
<212> TYPE: DNA
<213> ORGANISM: Mus musculus

<400> SEQUENCE: 72
ctgacgaacc tagtacatgt g 21

<210> SEQ ID NO 73
<211> LENGTH: 19
<212> TYPE: DNA
<213> ORGANISM: Mus musculus

<400> SEQUENCE: 73
atgtcaagtt tgttgtgtt 19

<210> SEQ ID NO 74
<211> LENGTH: 26
<212> TYPE: DNA
<213> ORGANISM: Homo sapiens

<400> SEQUENCE: 74
gagctggatg actaggatta atattc 26

<210> SEQ ID NO 75
<211> LENGTH: 22
<212> TYPE: DNA
<213> ORGANISM: Homo sapiens

<400> SEQUENCE: 75
tcaaattgca caggccctct ag 22

<210> SEQ ID NO 76
<211> LENGTH: 22
<212> TYPE: DNA
<213> ORGANISM: Homo sapiens

<400> SEQUENCE: 76
caatctctct ttagacctgt cc 22

<210> SEQ ID NO 77
<211> LENGTH: 22
<212> TYPE: DNA
<213> ORGANISM: Homo sapiens

<400> SEQUENCE: 77
aatactttag gctggttgtc cc 22

<210> SEQ ID NO 78
<211> LENGTH: 22
<212> TYPE: DNA
<213> ORGANISM: Homo sapiens

<400> SEQUENCE: 78
gaagttgatc taccaagcct tg 22

<210> SEQ ID NO 79

-continued

<211> LENGTH: 23
<212> TYPE: DNA
<213> ORGANISM: Homo sapiens

<400> SEQUENCE: 79
ggaagtcatt atgtgattga gac 23

<210> SEQ ID NO 80
<211> LENGTH: 26
<212> TYPE: DNA
<213> ORGANISM: Homo sapiens

<400> SEQUENCE: 80
cttcctggac ctctctcagt gtcaac 26

<210> SEQ ID NO 81
<211> LENGTH: 22
<212> TYPE: DNA
<213> ORGANISM: Homo sapiens

<400> SEQUENCE: 81
gaaggcagag ctgaaatgga gg 22

<210> SEQ ID NO 82
<211> LENGTH: 26
<212> TYPE: DNA
<213> ORGANISM: Homo sapiens

<400> SEQUENCE: 82
tcagatgaat aagaccatca ttggtg 26

<210> SEQ ID NO 83
<211> LENGTH: 18
<212> TYPE: DNA
<213> ORGANISM: Homo sapiens

<400> SEQUENCE: 83
aacaagtgtt ggacccag 18

<210> SEQ ID NO 84
<211> LENGTH: 19
<212> TYPE: DNA
<213> ORGANISM: Homo sapiens

<400> SEQUENCE: 84
gtaaatttgg acagtttcc 19

<210> SEQ ID NO 85
<211> LENGTH: 21
<212> TYPE: DNA
<213> ORGANISM: Homo sapiens

<400> SEQUENCE: 85
ttcagtattc ctatcactca g 21

<210> SEQ ID NO 86
<211> LENGTH: 20
<212> TYPE: DNA
<213> ORGANISM: Homo sapiens

<400> SEQUENCE: 86
ttataagtgt ctgaactccc 20

-continued

<210> SEQ ID NO 87
<211> LENGTH: 19
<212> TYPE: DNA
<213> ORGANISM: Homo sapiens

<400> SEQUENCE: 87
tcggtcctca gtgtgcttg 19

<210> SEQ ID NO 88
<211> LENGTH: 18
<212> TYPE: DNA
<213> ORGANISM: Homo sapiens

<400> SEQUENCE: 88
gtgtcccagc acttcatc 18

<210> SEQ ID NO 89
<211> LENGTH: 18
<212> TYPE: DNA
<213> ORGANISM: Homo sapiens

<400> SEQUENCE: 89
aacctcctga ggcatttc 18

<210> SEQ ID NO 90
<211> LENGTH: 19
<212> TYPE: DNA
<213> ORGANISM: Homo sapiens

<400> SEQUENCE: 90
gtttcaaatt ggaatgctg 19

<210> SEQ ID NO 91
<211> LENGTH: 18
<212> TYPE: DNA
<213> ORGANISM: Homo sapiens

<400> SEQUENCE: 91
aaggaaacgt atccaatg 18

<210> SEQ ID NO 92
<211> LENGTH: 19
<212> TYPE: DNA
<213> ORGANISM: Homo sapiens

<400> SEQUENCE: 92
aagcacactg aggaccgac 19

<210> SEQ ID NO 93
<211> LENGTH: 18
<212> TYPE: DNA
<213> ORGANISM: Homo sapiens

<400> SEQUENCE: 93
gatgaagtgc tgggacac 18

<210> SEQ ID NO 94
<211> LENGTH: 20
<212> TYPE: DNA
<213> ORGANISM: Homo sapiens

<400> SEQUENCE: 94
tcctcttcag atagatgttg 20

-continued

<210> SEQ ID NO 95
<211> LENGTH: 18
<212> TYPE: DNA
<213> ORGANISM: Homo sapiens

<400> SEQUENCE: 95
tttctttgtc atgggttc 18

<210> SEQ ID NO 96
<211> LENGTH: 20
<212> TYPE: DNA
<213> ORGANISM: Homo sapiens

<400> SEQUENCE: 96
tttaggttct tattcagcag 20

<210> SEQ ID NO 97
<211> LENGTH: 21
<212> TYPE: DNA
<213> ORGANISM: Homo sapiens

<400> SEQUENCE: 97
gctctagatt ggtcagatta g 21

<210> SEQ ID NO 98
<211> LENGTH: 839
<212> TYPE: PRT
<213> ORGANISM: Homo sapiens

<400> SEQUENCE: 98

```
Met Met Ser Ala Ser Arg Leu Ala Gly Thr Leu Ile Pro Ala Met Ala
  1               5                  10                  15

Phe Leu Ser Cys Val Arg Pro Glu Ser Trp Glu Pro Cys Val Glu Val
             20                  25                  30

Val Pro Asn Ile Thr Tyr Gln Cys Met Glu Leu Asn Phe Tyr Lys Ile
         35                  40                  45

Pro Asp Asn Leu Pro Phe Ser Thr Lys Asn Leu Asp Leu Ser Phe Asn
     50                  55                  60

Pro Leu Arg His Leu Gly Ser Tyr Ser Phe Phe Ser Phe Pro Glu Leu
 65                  70                  75                  80

Gln Val Leu Asp Leu Ser Arg Cys Glu Ile Gln Thr Ile Glu Asp Gly
                 85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
        115                 120                 125

Gln Lys Leu Val Ala Val Glu Thr Asn Leu Ala Ser Leu Glu Asn Phe
    130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
                165                 170                 175

Leu Glu His Leu Asp Leu Ser Ser Asn Lys Ile Gln Ser Ile Tyr Cys
            180                 185                 190

Thr Asp Leu Arg Val Leu His Gln Met Pro Leu Leu Asn Leu Ser Leu
        195                 200                 205

Asp Leu Ser Leu Asn Pro Met Asn Phe Ile Gln Pro Gly Ala Phe Lys
    210                 215                 220
```

-continued

```
Glu Ile Arg Leu His Lys Leu Thr Leu Arg Asn Asn Phe Asp Ser Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Gly Asn Leu Glu Lys Phe
            260                 265                 270

Asp Lys Ser Ala Leu Glu Gly Leu Cys Asn Leu Thr Ile Glu Glu Phe
        275                 280                 285

Arg Leu Ala Tyr Leu Asp Tyr Tyr Leu Asp Asp Ile Ile Asp Leu Phe
    290                 295                 300

Asn Cys Leu Thr Asn Val Ser Ser Phe Ser Leu Val Ser Val Thr Ile
305                 310                 315                 320

Glu Arg Val Lys Asp Phe Ser Tyr Asn Phe Gly Trp Gln His Leu Glu
                325                 330                 335

Leu Val Asn Cys Lys Phe Gly Gln Phe Pro Thr Leu Lys Leu Lys Ser
            340                 345                 350

Leu Lys Arg Leu Thr Phe Thr Ser Asn Lys Gly Gly Asn Ala Phe Ser
        355                 360                 365

Glu Val Asp Leu Pro Ser Leu Glu Phe Leu Asp Leu Ser Arg Asn Gly
    370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
                405                 410                 415

Asn Phe Leu Gly Leu Glu Gln Leu Glu His Leu Asp Phe Gln His Ser
            420                 425                 430

Asn Leu Lys Gln Met Ser Glu Phe Ser Val Phe Leu Ser Leu Arg Asn
        435                 440                 445

Leu Ile Tyr Leu Asp Ile Ser His Thr His Thr Arg Val Ala Phe Asn
    450                 455                 460

Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
                485                 490                 495

Asn Leu Thr Phe Leu Asp Leu Ser Gln Cys Gln Leu Glu Gln Leu Ser
            500                 505                 510

Pro Thr Ala Phe Asn Ser Leu Ser Ser Leu Gln Val Leu Asn Met Ser
        515                 520                 525

His Asn Asn Phe Phe Ser Leu Asp Thr Phe Pro Tyr Lys Cys Leu Asn
    530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
        595                 600                 605

Cys Ala Thr Pro Ser Asp Lys Gln Gly Met Pro Val Leu Ser Leu Asn
    610                 615                 620

Ile Thr Cys Gln Met Asn Lys Thr Ile Ile Gly Val Ser Val Leu Ser
625                 630                 635                 640
```

-continued

```
Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
        675                 680                 685

Arg Asn Glu Leu Val Lys Asn Leu Glu Glu Gly Val Pro Pro Phe Gln
    690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
            740                 745                 750

Ile Ala Gln Thr Trp Gln Phe Leu Ser Ser Arg Ala Gly Ile Ile Phe
        755                 760                 765

Ile Val Leu Gln Lys Val Glu Lys Thr Leu Leu Arg Gln Gln Val Glu
    770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
            820                 825                 830

Trp Gln Glu Ala Thr Ser Ile
        835


<210> SEQ ID NO 99
<211> LENGTH: 835
<212> TYPE: PRT
<213> ORGANISM: Mus musculus

<400> SEQUENCE: 99

Met Met Pro Pro Trp Leu Leu Ala Arg Thr Leu Ile Met Ala Leu Phe
  1               5                  10                  15

Phe Ser Cys Leu Thr Pro Gly Ser Leu Asn Pro Cys Ile Glu Val Val
            20                  25                  30

Pro Asn Ile Thr Tyr Gln Cys Met Asp Gln Lys Leu Ser Lys Val Pro
        35                  40                  45

Asp Asp Ile Pro Ser Ser Thr Lys Asn Ile Asp Leu Ser Phe Asn Pro
     50                  55                  60

Leu Lys Ile Leu Lys Ser Tyr Ser Phe Ser Asn Phe Ser Glu Leu Gln
 65                  70                  75                  80

Trp Leu Asp Leu Ser Arg Cys Glu Ile Glu Thr Ile Glu Asp Lys Ala
                85                  90                  95

Trp His Gly Leu His His Leu Ser Asn Leu Ile Leu Thr Gly Asn Pro
            100                 105                 110

Ile Gln Ser Phe Ser Pro Gly Ser Phe Ser Gly Leu Thr Ser Leu Glu
        115                 120                 125

Asn Leu Val Ala Val Glu Thr Lys Leu Ala Ser Leu Glu Ser Phe Pro
    130                 135                 140

Ile Gly Gln Leu Ile Thr Leu Lys Lys Leu Asn Val Ala His Asn Phe
145                 150                 155                 160

Ile His Ser Cys Lys Leu Pro Ala Tyr Phe Ser Asn Leu Thr Asn Leu
                165                 170                 175
```

-continued

```
Val His Val Asp Leu Ser Tyr Asn Tyr Ile Gln Thr Ile Thr Val Asn
            180                 185                 190

Asp Leu Gln Phe Leu Arg Glu Asn Pro Gln Val Asn Leu Ser Leu Asp
        195                 200                 205

Met Ser Leu Asn Pro Ile Asp Phe Ile Gln Asp Gln Ala Phe Gln Gly
    210                 215                 220

Ile Lys Leu His Glu Leu Thr Leu Arg Gly Asn Phe Asn Ser Ser Asn
225                 230                 235                 240

Ile Met Lys Thr Cys Leu Gln Asn Leu Ala Gly Leu His Val His Arg
                245                 250                 255

Leu Ile Leu Gly Glu Phe Lys Asp Glu Arg Asn Leu Glu Ile Phe Glu
            260                 265                 270

Pro Ser Ile Met Glu Gly Leu Cys Asp Val Thr Ile Asp Glu Phe Arg
        275                 280                 285

Leu Thr Tyr Thr Asn Asp Phe Ser Asp Asp Ile Val Lys Phe His Cys
    290                 295                 300

Leu Ala Asn Val Ser Ala Met Ser Leu Ala Gly Val Ser Ile Lys Tyr
305                 310                 315                 320

Leu Glu Asp Val Pro Lys His Phe Lys Trp Gln Ser Leu Ser Ile Ile
                325                 330                 335

Arg Cys Gln Leu Lys Gln Phe Pro Thr Leu Asp Leu Pro Phe Leu Lys
            340                 345                 350

Ser Leu Thr Leu Thr Met Asn Lys Gly Ser Ile Ser Phe Lys Lys Val
        355                 360                 365

Ala Leu Pro Ser Leu Ser Tyr Leu Asp Leu Ser Arg Asn Ala Leu Ser
    370                 375                 380

Phe Ser Gly Cys Cys Ser Tyr Ser Asp Leu Gly Thr Asn Ser Leu Arg
385                 390                 395                 400

His Leu Asp Leu Ser Phe Asn Gly Ala Ile Ile Met Ser Ala Asn Phe
                405                 410                 415

Met Gly Leu Glu Glu Leu Gln His Leu Asp Phe Gln His Ser Thr Leu
            420                 425                 430

Lys Arg Val Thr Glu Phe Ser Ala Phe Leu Ser Leu Glu Lys Leu Leu
        435                 440                 445

Tyr Leu Asp Ile Ser Tyr Thr Asn Thr Lys Ile Asp Phe Asp Gly Ile
    450                 455                 460

Phe Leu Gly Leu Thr Ser Leu Asn Thr Leu Lys Met Ala Gly Asn Ser
465                 470                 475                 480

Phe Lys Asp Asn Thr Leu Ser Asn Val Phe Ala Asn Thr Thr Asn Leu
                485                 490                 495

Thr Phe Leu Asp Leu Ser Lys Cys Gln Leu Glu Gln Ile Ser Trp Gly
            500                 505                 510

Val Phe Asp Thr Leu His Arg Leu Gln Leu Leu Asn Met Ser His Asn
        515                 520                 525

Asn Leu Leu Phe Leu Asp Ser Ser His Tyr Asn Gln Leu Tyr Ser Leu
    530                 535                 540

Ser Thr Leu Asp Cys Ser Phe Asn Arg Ile Glu Thr Ser Lys Gly Ile
545                 550                 555                 560

Leu Gln His Phe Pro Lys Ser Leu Ala Phe Phe Asn Leu Thr Asn Asn
                565                 570                 575

Ser Val Ala Cys Ile Cys Glu His Gln Lys Phe Leu Gln Trp Val Lys
            580                 585                 590
```

-continued

```
Glu Gln Lys Gln Phe Leu Val Asn Val Glu Gln Met Thr Cys Ala Thr
        595                 600                 605

Pro Val Glu Met Asn Thr Ser Leu Val Leu Asp Phe Asn Asn Ser Thr
    610                 615                 620

Cys Tyr Met Tyr Lys Thr Ile Ile Ser Val Ser Val Val Ser Val Ile
625                 630                 635                 640

Val Val Ser Thr Val Ala Phe Leu Ile Tyr His Phe Tyr Phe His Leu
                645                 650                 655

Ile Leu Ile Ala Gly Cys Lys Lys Tyr Ser Arg Gly Glu Ser Ile Tyr
            660                 665                 670

Asp Ala Phe Val Ile Tyr Ser Ser Gln Asn Glu Asp Trp Val Arg Asn
        675                 680                 685

Glu Leu Val Lys Asn Leu Glu Glu Gly Val Pro Arg Phe His Leu Cys
    690                 695                 700

Leu His Tyr Arg Asp Phe Ile Pro Gly Val Ala Ile Ala Ala Asn Ile
705                 710                 715                 720

Ile Gln Glu Gly Phe His Lys Ser Arg Lys Val Ile Val Val Val Ser
                725                 730                 735

Arg His Phe Ile Gln Ser Arg Trp Cys Ile Phe Glu Tyr Glu Ile Ala
            740                 745                 750

Gln Thr Trp Gln Phe Leu Ser Ser Arg Ser Gly Ile Ile Phe Ile Val
        755                 760                 765

Leu Glu Lys Val Glu Lys Ser Leu Leu Arg Gln Gln Val Glu Leu Tyr
    770                 775                 780

Arg Leu Leu Ser Arg Asn Thr Tyr Leu Glu Trp Glu Asp Asn Pro Leu
785                 790                 795                 800

Gly Arg His Ile Phe Trp Arg Arg Leu Lys Asn Ala Leu Leu Asp Gly
                805                 810                 815

Lys Ala Ser Asn Pro Glu Gln Thr Ala Glu Glu Glu Gln Glu Thr Ala
            820                 825                 830

Thr Trp Thr
        835
```

<210> SEQ ID NO 100
<211> LENGTH: 25
<212> TYPE: DNA
<213> ORGANISM: Mus musculus

<400> SEQUENCE: 100
atcgatacca ggaggcttga atccc 25

<210> SEQ ID NO 101
<211> LENGTH: 26
<212> TYPE: DNA
<213> ORGANISM: Mus musculus

<400> SEQUENCE: 101
tatcgatacc aggaagcttg aatccc 26

<210> SEQ ID NO 102
<211> LENGTH: 34
<212> TYPE: DNA
<213> ORGANISM: Mus musculus

<400> SEQUENCE: 102
cagggtacct cacaggtgaa aatagaagtg gtat 34

-continued

<210> SEQ ID NO 103
<211> LENGTH: 31
<212> TYPE: DNA
<213> ORGANISM: Mus musculus

<400> SEQUENCE: 103
gccgaattca atgtacaaga caatcatcag t 31

<210> SEQ ID NO 104
<211> LENGTH: 835
<212> TYPE: PRT
<213> ORGANISM: Mus musculus

<400> SEQUENCE: 104

Met Met Pro Pro Trp Leu Leu Ala Arg Thr Leu Ile Met Ala Leu Phe
1 5 10 15

Phe Ser Cys Leu Thr Pro Gly Ser Leu Asn Pro Cys Ile Glu Val Val
20 25 30

Pro Asn Ile Thr Tyr Gln Cys Met Asp Gln Lys Leu Ser Lys Val Pro
35 40 45

Asp Asp Ile Pro Ser Ser Thr Lys Asn Ile Asp Leu Ser Phe Asn Pro
50 55 60

Leu Lys Ile Leu Lys Ser Tyr Ser Phe Ser Asn Phe Ser Glu Leu Gln
65 70 75 80

Trp Leu Asp Leu Ser Arg Cys Glu Ile Glu Thr Ile Glu Asp Lys Ala
85 90 95

Trp His Gly Leu His His Leu Ser Asn Leu Ile Leu Thr Gly Asn Pro
100 105 110

Ile Gln Ser Phe Ser Pro Gly Ser Phe Ser Gly Leu Thr Ser Leu Glu
115 120 125

Asn Leu Val Ala Val Glu Thr Lys Leu Ala Ser Leu Glu Ser Phe Pro
130 135 140

Ile Gly Gln Leu Ile Thr Leu Lys Lys Leu Asn Val Ala His Asn Phe
145 150 155 160

Ile His Ser Cys Lys Leu Pro Ala Tyr Phe Ser Asn Leu Thr Asn Leu
165 170 175

Val His Val Asp Leu Ser Tyr Asn Tyr Ile Gln Thr Ile Thr Val Asn
180 185 190

Asp Leu Gln Phe Leu Arg Glu Asn Pro Gln Val Asn Leu Ser Leu Asp
195 200 205

Met Ser Leu Asn Pro Ile Asp Phe Ile Gln Asp Gln Ala Phe Gln Gly
210 215 220

Ile Lys Leu His Glu Leu Thr Leu Arg Gly Asn Phe Asn Ser Ser Asn
225 230 235 240

Ile Met Lys Thr Cys Leu Gln Asn Leu Ala Gly Leu His Val His Arg
245 250 255

Leu Ile Leu Gly Glu Phe Lys Asp Glu Arg Asn Leu Glu Ile Phe Glu
260 265 270

Pro Ser Ile Met Glu Gly Leu Cys Asp Val Thr Ile Asp Glu Phe Arg
275 280 285

Leu Thr Tyr Thr Asn Asp Phe Ser Asp Asp Ile Val Lys Phe His Cys
290 295 300

Leu Ala Asn Val Ser Ala Met Ser Leu Ala Gly Val Ser Ile Lys Tyr
305 310 315 320

Leu Glu Asp Val Pro Lys His Phe Lys Trp Gln Ser Leu Ser Ile Ile
325 330 335

-continued

```
Arg Cys Gln Leu Lys Gln Phe Pro Thr Leu Asp Leu Pro Phe Leu Lys
            340                 345                 350

Ser Leu Thr Leu Thr Met Asn Lys Gly Ser Ile Ser Phe Lys Lys Val
        355                 360                 365

Ala Leu Pro Ser Leu Ser Tyr Leu Asp Leu Ser Arg Asn Ala Leu Ser
    370                 375                 380

Phe Ser Gly Cys Cys Ser Tyr Ser Asp Leu Gly Thr Asn Ser Leu Arg
385                 390                 395                 400

His Leu Asp Leu Ser Phe Asn Gly Ala Ile Ile Met Ser Ala Asn Phe
                405                 410                 415

Met Gly Leu Glu Glu Leu Gln His Leu Asp Phe Gln His Ser Thr Leu
            420                 425                 430

Lys Arg Val Thr Glu Phe Ser Ala Phe Leu Ser Leu Glu Lys Leu Leu
        435                 440                 445

Tyr Leu Asp Ile Ser Tyr Thr Asn Thr Lys Ile Asp Phe Asp Gly Ile
    450                 455                 460

Phe Leu Gly Leu Thr Ser Leu Asn Thr Leu Lys Met Ala Gly Asn Ser
465                 470                 475                 480

Phe Lys Asp Asn Thr Leu Ser Asn Val Phe Ala Asn Thr Thr Asn Leu
                485                 490                 495

Thr Phe Leu Asp Leu Ser Lys Cys Gln Leu Glu Gln Ile Ser Trp Gly
            500                 505                 510

Val Phe Asp Thr Leu His Arg Leu Gln Leu Leu Asn Met Ser His Asn
        515                 520                 525

Asn Leu Leu Phe Leu Asp Ser Ser His Tyr Asn Gln Leu Tyr Ser Leu
    530                 535                 540

Ser Thr Leu Asp Cys Ser Phe Asn Arg Ile Glu Thr Ser Lys Gly Ile
545                 550                 555                 560

Leu Gln His Phe Pro Lys Ser Leu Ala Phe Phe Asn Leu Thr Asn Asn
                565                 570                 575

Ser Val Ala Cys Ile Cys Glu His Gln Lys Phe Leu Gln Trp Val Lys
            580                 585                 590

Glu Gln Lys Gln Phe Leu Val Asn Val Glu Gln Met Thr Cys Ala Thr
        595                 600                 605

Pro Val Glu Met Asn Thr Ser Leu Val Leu Asp Phe Asn Asn Ser Thr
    610                 615                 620

Cys Tyr Met Tyr Lys Thr Ile Ile Ser Val Ser Val Val Ser Val Ile
625                 630                 635                 640

Val Val Ser Thr Val Ala Phe Leu Ile Tyr His Phe Tyr Phe His Leu
                645                 650                 655

Ile Leu Ile Ala Gly Cys Lys Lys Tyr Ser Arg Gly Glu Ser Ile Tyr
            660                 665                 670

Asp Ala Phe Val Ile Tyr Ser Ser Gln Asn Glu Asp Trp Val Arg Asn
        675                 680                 685

Glu Leu Val Lys Asn Leu Glu Glu Gly Val Pro Arg Phe His Leu Cys
    690                 695                 700

Leu His Tyr Arg Asp Phe Ile His Gly Val Ala Ile Ala Ala Asn Ile
705                 710                 715                 720

Ile Gln Glu Gly Phe His Lys Ser Arg Lys Val Ile Val Val Val Ser
                725                 730                 735

Arg His Phe Ile Gln Ser Arg Trp Cys Ile Phe Glu Tyr Glu Ile Ala
            740                 745                 750
```

-continued

```
Gln Thr Trp Gln Phe Leu Ser Ser Arg Ser Gly Ile Ile Phe Ile Val
        755                 760                 765

Leu Glu Lys Val Glu Lys Ser Leu Leu Arg Gln Gln Val Glu Leu Tyr
    770                 775                 780

Arg Leu Leu Ser Arg Asn Thr Tyr Leu Glu Trp Glu Asp Asn Pro Leu
785                 790                 795                 800

Gly Arg His Ile Phe Trp Arg Arg Leu Lys Asn Ala Leu Leu Asp Gly
                805                 810                 815

Lys Ala Ser Asn Pro Glu Gln Thr Ala Glu Glu Glu Gln Glu Thr Ala
            820                 825                 830

Thr Trp Thr
        835
```

LPS-RESPONSE GENE COMPOSITIONS AND METHODS

This application claims priority to and specifically incorporates by reference, the content of U.S. Provisional Application Ser. No. 60/100,403 filed Sep. 15, 1998 and U.S. Provisional Application Ser. No. 60/102,392 filed Sep. 29, 1998. The entire text of each of the above-referenced disclosures is specifically incorporated by reference herein without disclaimer.

BACKGROUND OF THE INVENTION

1. Field of the Invention

The present invention relates generally to the fields of microbiology and immunology. More particularly, it concerns the response of macrophages to endotoxin exposure from Gram-negative bacteria and methods of detecting and treating individuals at high risk for infection by Gram-negative bacteria and inhibiting sepsis and septic shock.

2. Description of Related Art

"Innate" or "natural" immunity is largely subserved by macrophages and NK cells. These cells lack the huge repertoire of pathogen receptors that comprise the afferent limb of "specific" immunity, e.g., the receptors found on T-cells and B-cells. Rather, they rely upon very broadly effective mechanisms for the recognition of invasive organisms. An important case in point concerns Gram-negative bacteria, all of which bear endotoxin (lipopolysaccharide, LPS) molecules in their outer membrane, which trigger a strong immune response on the part of the host which produces a shock-like syndrome, characterized by low blood pressure and hyporeactivity to vasoconstricter agents.

When macrophages are exposed to pure preparations of endotoxin, they secrete numerous cytokine mediators, including tumor necrosis factor (TNF, TNFα), interleukin-1 (IL-1), interferon-α/β, GM/CSF, IL-8 and ultimately smaller "autocoid" molecules, all of which mediate an intense inflammatory reaction. Endotoxin recognition acts as an early warning signal through which a host may mount a timely defense against invasion by Gram-negative organisms. However, widespread activation of macrophages by endotoxin results in the development of septic shock. By most estimates, Gram-negative septic shock is responsible for 100,000 deaths per year in the United States alone. The entire syndrome of hypotension, coagulopathy, pulmonary edema and acute renal failure results, in large part, from the release TNF and other cytokines in response to exposure to endotoxin.

TNF is probably the most important mediator of local inflammatory processes as well as septic endotoxin shock. It is produced quickly and in large amounts by macrophages that encounter endotoxin (Beutler et al., 1985a). TNF causes shock when administered to animals (Tracey et al., 1986), and blockade of TNF synthesis or activity markedly attenuates the lethal effect of endotoxin (Beutler et al., 1985b). The relationship between endotoxin and TNF is therefore directly correlated. Surprisingly, however, little is known about the mechanism by which endotoxin triggers host cells to release TNF.

The cognate receptor for endotoxin, complexed with lipopolysaccharide binding protein (LBP) in plasma, is the GPI-linked cell surface membrane protein CD14. CD14 effectively concentrates endotoxin onto the surface of macrophages and other defensive cells of the host (Wright et al., 1990). However, it does not actually signal the presence of endotoxin, as CD14 has no cytoplasmic component with which to do so.

Endotoxin is known to trigger both tyrosine and serine phosphorylation events within the macrophage cell, and at least in part, ras, raf, MEK, and members of the MAP kinase family are also involved in signal transduction (Geppert et al., 1994). The endpoints of endotoxin signaling include activation of the transcription of TNF and various genes, and activation of the translation of TNF mRNA (Beutler et al., 1986; Han et al., 1990). At the protein level, this stimulation by endotoxin leads to a several thousand-fold augmentation of cytokine biosynthesis by a macrophage cell. But the initial controlling element and event in the signaling pathway of macrophage response to endotoxin has not been identified. Thus, in spite of its importance, most of the endotoxin signaling pathway remains relatively unknown. Recently however, the Toll-like receptor 2 (TLR2) has been suggested to partially mediate lipopolysaccharide-induced cellular signaling (Gerard, 1998; Yang et al., 1998).

Thirty years ago, mice of the C3H/HeJ strain were noted to be specifically and globally unresponsive to endotoxin, while closely related animals of the C3H/HeN or C3H/OuJ substrains exhibited normal responses (Sultzer, 1968). The median lethal dose of endotoxin is more than 100-fold higher in C3H/HeJ mice than in either of these other strains. Macrophages of C3H/HeJ mice fail to produce cytokines in response to endotoxin, and B-lymphocytes of C3H/HeJ mice are not driven to proliferate by endotoxin. While C3H/HeJ mice are highly resistant to the lethal effect of endotoxin, they are unusually sensitive to infection by gram-negative organisms. The mean lethal inoculum with *Salmonella typhimurium*, for example, is two organisms in C3H/HeJ mice, whereas several thousand organisms are required to kill mice of the C3H/HeN strain. Hence, the ability to sense the presence of endotoxin is required for defense against gram-negative organisms and it is speculated that individuals that suffer from sepsis and septic shock have a similar genetic mutation which causes them to be more susceptible to infection.

These defective responses by the C3H/HeJ mice are the result of a single, codominant mutation, which maps to a position between the widely separated Mup-1 (Major urinary protein) and Ps (polysyndactyly) loci on mouse chromosome IV (Watson et al., 1978). Mice homozygous for the mutant allele of the "Lps gene" are unresponsive to endotoxin, whereas homozygotes for the common allele are normally responsive, whether lethality or cell-based assays are employed as an index. Heterozygotes exhibit intermediate levels of response. The protein encoded by this mutant gene is the most important known determinant of endotoxin-induced TNF biosynthesis, and indeed, of all reactions to endotoxin.

Many attempts to identify the product of the Lps gene, or to clone it have been made. With the recognition that CD14 serves as the principle cell-surface receptor for endotoxin, it was proposed that the Lps gene might encode an associated polypeptide chain with signal transducing potential, or more broadly, an early component of the signal transduction apparatus. Attempts to identify a CD14 binding molecule, which might be the product of the Lps gene, have been pursued by several investigators. Two-hybrid screening, affinity chromatography, and cross linking approaches have thus far each failed to pinpoint a protein that specifically engages CD14. Expression cloning strategies have also been applied in the search for the Lps gene product without success.

Given the occurrence of gram-negative bacteremia and the high and rising incidence of gram-negative nosocomial infections, a certain subset of the population appears to be at high risk to develop endotoxic shock even if adequate antimicrobial therapy is instituted. It would be useful to know which patients are at high risk for gram-negative bacterial infections and sepsis in advance of its onset. Diagnostic methods that predict the risk of infection as well as the clinical course of sepsis could be reasonably applied to most hospitalized patients. In addition, it is clear that there is an immediate and increasing need for new drugs and treatment methods that regulate macrophage response to gram-negative bacterial infections. Unfortunately, given the current lack of understanding of the regulation of the macrophage response to endotoxin, these drugs and methods have not been developed, and patients continue to be at risk for these life-threatening infections.

SUMMARY OF THE INVENTION

The present invention relates in part to methods for screening for susceptibility to infection. These methods are based on the Inventors' discovery that the Toll-4 or TLR-4 polypeptide plays a role as the LPS receptor and is, therefore, involved in the pathway leading to immune responses in response to certain infections, including especially, certain infection involving Gram negative bacteria. In particular embodiments, the invention provides screening methods for identifying individuals at risk for certain infections. Testing positive for such screens would permit proactive counseling and/or treatment of susceptible individuals. For example, in particular circumstances an individual may be taking immunosuppressive drugs or be immunodeficient. It would be advantageous in this, and in other instances, for the individual susceptible to infection, to be apprised of the risk to Gram negative bacterial infection. Recently the nomenclature for the Toll-4 protein has been changed to TLR-4 (Toll-like receptor 4). Thus, in the context of the present invention it is important to note that Toll-4 and TLR-4 are used interchangeably. The new nomenclature will be used herein, unless such designation leads to ambiguity in certain textual embodiments.

Such methods for screening for the susceptibility to infection generally comprise: obtaining sample nucleic acid from an animal; and analyzing the sample nucleic acid to detect a mutation in a gene encoding a TLR-4 polypeptide relative to a sequence of a gene encoding a native TLR-4 polypeptide; wherein a mutation in the gene encoding the TLR-4 polypeptide is indicative of susceptibility to infection. In most cases, the nucleic acid analyzed is DNA, and the step of analyzing the TLR-4-encoding nucleic acid comprises sequencing the TLR-4-encoding nucleic acid to obtain a sequence. In order to determine whether a mutation exists in the obtained sequence of the TLR-4-encoding nucleic acid, the sequence may be compared to a native nucleic acid sequence of TLR-4. For example, the native nucleic acid sequence of TLR-4 may have a sequence set forth in SEQ ID NO:1, SEQ ID NO:3, SEQ ID NO:5, SEQ ID NO:46, SEQ ID NO:47 or SEQ ID NO:48. In another example, the native TLR-4 polypeptide may have an amino acid sequence set forth in SEQ ID NO:2, SEQ ID NO:4, SEQ ID NO:6, SEQ ID NO: 98 or SEQ ID NO:99. Of course, nay methods of determining whether a mutation is present in the gene encoding the TLR-4 polypeptide is within the scope of the invention.

In cases where the TLR-4-encoding nucleic acid comprises a mutation, that mutation may be a point mutation, or any other type of mutation. The step of analyzing the TLR-4-encoding nucleic acid may comprise PCR, an RNase protection assay, or an RFLP procedure. Alternatively, an antibody that discriminates wild-type TLR-4 from mutant TLR-4 nucleic acid or TLR-4 polypeptide may be used in an immunodetection format or the TLR-4 polypeptide may be directly sequenced.

It is contemplated that the mutation in the TLR-4 encoding nucleic acid may arise through deletion mutations, insertion mutations, frameshift mutations, nonsense mutations, missense mutations or splice mutations. In particularly preferred embodiments, the sample nucleic aid comprises a mutation that results in a change from PRO to HIS at residue 712 of a TLR-4 protein of SEQ ID NO:99. In other preferred embodiments, the sample nucleic acid comprises a mutation that results in a change from GLU to LYS at residue 178, a change from ARG to HIS at residue 763, a change from GLN to ARG at residue 188, a change from ASP to GLY at residue 299, a change from ASN to SER at residue 329, a change from GLU to LYS at residue 474, a change from ARG to HIS at residue 763, a change from TYR to CYS at residue 46, a change from PRO to HIS at residue 145, a change from CYS to TYR at residue 281, a change from ASN to HIS at residue 624, or a change from THR to ILE at residue 399 of the native TLR-4 polypeptide amino acid sequence of SEQ ID NO:98. In yet other embodiments, the sample nucleic acid comprises at least a second mutation, wherein the second mutation results in a deletion of VAL-GLY-THR at residues 827–829 of the native TLR-4 polypeptide amino acid sequence of SEQ ID NO:98.

In particular embodiments of the invention, the sample nucleic acid comprises at least one point mutation relative to a nucleic acid sequence from a gene encoding a native TLR-4 polypeptide, wherein the mutation is in nucleotide 2342 of the nucleic acid sequence of SEQ ID NO:46. In further embodiments, the sample nucleic acid comprises at least two point mutations relative to a nucleic acid sequence from a gene encoding a native TLR-4 polypeptide, wherein at least one mutation is a change from nucleotide C to nucleotide A at position 2342 of the nucleic acid sequence of SEQ ID NO:46.

In other cases, at least one mutation is in Exon 2, Exon 3 or Intron 2 of the sequence of SEQ ID NO:47, wherein said at least one mutation is a change from nucleotide A to nucleotide G at position 8457, a change from nucleotide G to nucleotide A at position 8612, a change from nucleotide A to nucleotide G at position 8631, a change from nucleotide A to nucleotide G at position 12245, a change from nucleotide T to nucleotide C at position 12293, a change from nucleotide C to nucleotide A at position 12412, a change from nucleotide C to nucleotide A at position 12413, a change from nucleotide A to nucleotide G at position 12541, a change from nucleotide G to nucleotide A at position 12820, a change from nucleotide A to nucleotide G at position 12874, a change from nucleotide A to nucleotide G at position 12964, a change from nucleotide C to nucleotide T at position 13174, a change from nucleotide G to nucleotide A at position 13398, a change from nucleotide G to nucleotide A at position 13769, a change from nucleotide A to nucleotide C at position 13848, a change from nucleotide G to nucleotide A at position 13937, or a change from nucleotide G to nucleotide A at position 114266 of the sequence of SEQ ID NO:47. In another embodiment, at least one mutation is a deletion of nucleotide T at position 12228 of the sequence of SEQ ID NO:47. In a preferred embodiment, at least one mutation is a change from nucleotide A to nucleotide G at position 12245 of the gene sequence and a deletion of nucleotides 14453 to 14461 of the sequence of SEQ ID NO:47. In other embodiments, the sample nucleic acid sequence comprises at least two mutations relative to the sequence of SEQ ID NO:47, wherein at least two mutations comprise a change from nucleotide C to nucleotide T at position 12399 and a change from nucleotide G to nucleotide A at position 12510, a change from nucleotide C to nucleotide A at position 12413 and a change from nucleotide G to nucleotide A at position 14266, or a change from nucleotide A to nucleotide G at position 12874 and a change from nucleotide C to nucleotide T at position 13174 of the sequence of SEQ ID NO:47.

In other embodiments, the present invention relates to methods of reducing susceptibility of an animal to infection comprising the step of modulating an LPS mediated response in the animal. In most animals, a mutation or other defect can cause the animal to be unable to mount an appropriate response in the presence of an infectious agent, for example, a gram negative bacteria. These methods often comprise diagnosing an animal with an infection or one susceptible to infection via analysis of a TLR-4-encoding nucleic acid sequence for a mutation relative to a sequence of a gene encoding a native TLR-4 polypeptide, wherein the native TLR-4 polypeptide is a TLR-4 polypeptide that has the sequence of SEQ ID NO:2, SEQ ID NO:4, SEQ ID NO:6, SEQ ID NO:98 or SEQ ID NO:99. In some cases, modulating LPS receptor function comprises providing a TLR-4 polypeptide to the animal. The TLR-4 polypeptide is a native TLR-4 polypeptide, for example, one have the sequence of SEQ ID NO:2, SEQ ID NO:4, SEQ ID NO:6, SEQ ID NO:98 or SEQ ID NO:99. Alternatively, the TLR-4 polypeptide may be a modified TLR-4 polypeptide created by molecular biological methods. In some cases, the provision of a TLR-4 polypeptide is accomplished by inducing expression of a TLR-4 polypeptide. For example, the expression of a TLR-4 polypeptide encoded in the animal's genome may be induced. Alternatively, the expression of a TLR-4 polypeptide encoded by a nucleic acid provided to the animal is induced. In other cases, the provision of a TLR-4 polypeptide is accomplished by a method comprising introduction of a TLR-4-encoding nucleic acid to the animal. In some embodiments, the provision of a TLR-4 polypeptide is accomplished by injecting a TLR-4 polypeptide into the animal. In yet other embodiments, a TLR-4 polypeptide is provided as a single chain antibody construct and delivered via adenovirus. The invention also relates to the inventor's discovery that certain mutants of TLR-4 fail to bind LPS, and as a result, the host having such mutations are rendered more susceptible to the bacterial infection.

The invention further contemplates methods of modulating an LPS mediated response comprising modulating TLR-4 function in an animal. Such methods often comprise the step of diagnosing the animal via analysis of a TLR-4-encoding nucleic acid sequence for a mutation. This modulation can be accomplished by providing a TLR-4 polypeptide to the animal in any manner discussed above. Alternatively, the modulating TLR-4 function in the animal comprises providing a modulator of TLR-4 to the animal.

The process of modulating an LPS mediated response in the animal may comprise providing a modulator of TLR-4 to the animal. As used herein, a "modulator of TLR-4" is any substance that affects the functioning of TLR-4 in the LPS pathway. For example, the modulator of TLR-4 may be an agonist or antagonist of TLR-4. The modulator of may TLR-4 modulate the transcription and/or translation of a TLR-4-encoding nucleic acid.

In some cases, the methods of reducing susceptibility to an infection involve diagnosing an animal with susceptibility to infection via analysis of an TLR-4-encoding nucleic acid sequence for a mutation, in any of the manners discussed above.

Additional aspects of the invention relate to methods of screening for modulators of an LPS mediated response comprising the steps of: a) obtaining a TLR-4 polypeptide; b) determining a standard activity profile of the TLR-4 polypeptide; c) contacting the TLR-4 polypeptide with a putative modulator; and d) assaying for a change in the standard activity profile. In these cases, the TLR-4 polypeptide may have the amino acid sequence of SEQ ID NO:2, SEQ ID NO:4, SEQ ID NO:6, SEQ ID NO:98 or SEQ ID NO:99. The standard activity profile of the TLR-4 polypeptide is determined by determining the ability of the TLR-4 polypeptide to stimulate transcription of a reporter gene, the reporter gene operatively positioned under control of a nucleic acid segment comprising a promoter from a TLR-4 gene.

In other embodiments, a method of modulating an LPS mediated response comprising modulating TLR-4 function in an animal is provided, often further comprising the step of diagnosing the animal for susceptibility to infection via analysis of a TLR-4-encoding nucleic acid sequence for a mutation relative to a sequence of a gene encoding a native TLR-4 polypeptide. In certain embodiments, the animal susceptible to infection is provided a TLR-4 polypeptide, wherein the TLR-4 polypeptide is a TLR-4 polypeptide that has the sequence of SEQ ID NO:2, SEQ ID NO:4, SEQ ID NO:6, SEQ ID NO:98 or SEQ ID NO:99. In specific embodiments, the provision of a TLR-4 polypeptide is accomplished by inducing expression of a TLR-4 polypeptide in the animal, introduction of a TLR-4-encoding nucleic acid to the animal or by injecting a TLR-4 polypeptide into the animal. In other embodiments, the step of modulating TLR-4 function in the animal comprises providing a modulator of TLR-4 to the animal, wherein the modulator of TLR-4 may be an agonist of TLR-4 or antagonist of TLR-4, wherein the agonist of TLR-4 or antagonist of TLR-4 modulates transcription or translation of a TLR-4-encoding nucleic acid.

In some preferred embodiments, the invention contemplates methods of screening for modulators of an LPS mediated response comprising: a) obtaining a TLR-4-encoding nucleic acid segment; b) determining a standard transcription and translation activity of the TLR-4-encoding nucleic acid sequence; c) contacting the TLR-4-encoding nucleic acid segment with a putative modulator; d) maintaining the nucleic acid segment and putative modulator under conditions that normally allow for TLR-4 transcription and translation; and e) assaying for a change in the transcription and translation activity of TLR-4.

Yet other embodiments relate to modulators of an LPS mediated response prepared by a process comprising screening for modulators of an LPS mediated response comprising: a) obtaining a TLR-4 polypeptide; b) determining a standard activity profile of the TLR-4 polypeptide; c) contacting the TLR-4 polypeptide with a putative modulator; and d) assaying for a change in the standard activity profile. Such modulators may be prepared by a process comprising screening for modulators of an LPS mediated response comprising: a) obtaining a TLR-4-encoding nucleic acid segment; b) determining a standard transcription and translation activity of the TLR-4 nucleic acid sequence; c) contacting the TLR-4-encoding nucleic acid segment with a putative modulator; d) maintaining the nucleic acid segment and putative modulator under conditions that normally allow for TLR-4 transcription and translation; and e) assaying for a change in the transcription and translation activity.

The invention further relates to methods of treating Gram-negative bacterial infections comprising administration of an agent that modulates the recognition of endotoxin through an LPS mediated response. For example, the agent may simulate or inhibit the activity of a TLR-4 polypeptide.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A, Map based on 493 meioses analyzed in the SWR backcross. FIG. 2B, Map based on 1600 meioses analyzed in the C57BL/6 backcross. Scale refers to physical distances (note 1 Mb bar), determined on the basis of fluorescence in situ hybridization data and pulse-field gel electrophoresis, performed using YACs and BACs that span the critical region (FIG. 4 and FIG. 5). Though only one of the markers (7.3) could be used in both analyses, the maps shown in FIG. 2A and FIG. 2B are perfectly aligned and drawn to the same scale. Interruptions in map FIG. 2B indicate that D4MIT164 and D4MIT27 are quite remote from the region of interest. Numerals above brackets refer to the number of crossovers within each mapping panel that separate individual polymorphic markers from the $Lps^d$ mutation. D4MIT markers are shown in shaded circles; novel markers defined in Table I are placed in the correct physical order (centromere is on the left), and indicated by non-shaded circles. The heavily shaded bar coinciding with the zero region of each map refers to an area in which no crossover events were observed, between any of the markers themselves, or between the markers and $Lps^d$. The location of the $Lps^d$ mutation is necessarily bounded by markers B and 83.3, as indicated by the heavy bar at the bottom of the Figure.

FIG. 4A: Centromere is to the left. Sixty-three BACs are included in this contig. A gap of small size (probably less than 100 kb) separates BACs 24 and 25. The remainder of the contig is seamless. The apparent gap between BACs 58 and 59 is covered by YAC clone 100E4. Vertical lines indicate the ends of selected BACs contacting SP6 or T7 primer sites within the BAC cloning vector. Tic marks indicate specific unique markers listed above the contig. Microsatellite markers are given alphabetical or numerical designations. D4MIT markers (325, 25, 178, 7, 132, and 83) are shown in large type. Circled microsatellite markers were polymorphic with respect to C3H/HeJ and SWR (magenta) or C3H/HeJ and C57BL/6 (orange). Double arrows at the top of the Figure indicate physical distances estimated by interphase FISH analysis (numbers indicate megabases; margin of error=±10%). Vertical lines separating arrows point to the center of the BACs used for FISH distance measurements (L22, 297O12, 259N13 346B6, 217B22, 215K4, and 293L15). All BACs are drawn to scale, based on sizes obtained through pulsed-field gel electrophoresis.

FIG. 4B: Bars indicate genetic distances assigned by means of two independent back-crosses[1]. A backcross involving SWR mice yielded 493 meaningful meioses. Three crossovers were observed between marker 83.3 and marker 7.11, corresponding to a genetic distance of 0.6 cM, and one crossover was observed between marker D4MIT325 and marker 25.5, corresponding to a genetic distance of 0.2 cM (magenta bars). A backcross involving C57BL/6 mice yielded 1600 meaningful meioses. Four crossovers were observed between marker B and marker A, corresponding to a genetic distance of 0.25 cM and 13 crossovers were observed between marker C and marker B, corresponding to a genetic distance to 0.8 cM (orange bar). On 2093 meioses, the mutation is therefore confined to an interval between markers B and 83.3. This corresponds to a physical distance of 2.6 Mb (denoted by the blue bar). Complete absence of crossovers (the zero region) was observed in the composite of the two crosses over a 1.2 Mb interval extending from marker A though marker 7.11 (denoted by the black bar). No polymorphic markers capable of distinguishing C57BL/6 from C3H/HeJ were identified distal to marker 7.11 in the critical region. The BACs represented in this Figure are as follows:

(1. 4L22 2. 329E1 3. 331E22 4. 18J9 5. 259B3 6. 147P7 7. 179M4 8. 297012 9. 363L11 10. 353J12 11. 151O8 12. 312J8 13. 358P4 14. 327O21 15. 297N10 16. 92G10 17. 259N13 18. 243O20 19. 216C14 20. 131M6 21. 49K20 22. 135O17 23. 274K20 24. 336A11 25. 309I17 26. 152C16 27. 352P10 28. 58H7 29. 84C8 30. 346B6 31.373I18 32. 288K23 33. 291G16 34. 276O8 35.340I16 36. 269E13 37. 62A9 38. 389F15 39. 353O21 40. 197M3 41. 293J8 42. 220E13 43. 181N19 44. 369F7 45. 430N20 46. 370J14 47. 213O15 48. 265H22 49. 20B5 50. 175I18 51. 247P7 52. 264N15 53. 204O1 54. 217B22 55. 178D24 56. 300H9 57. 188A22 58. 289J11 59. 152B3 60. 288O20 61. 216K4 62. 293L15 63. 147M3)

All BAC designations refer to the Research Genetics mouse BAC library, with the exception of BACs 84C8 and 389F15, which were obtained from Genome Systems (mouse C57BL/6 BAC library).

Figure 5:
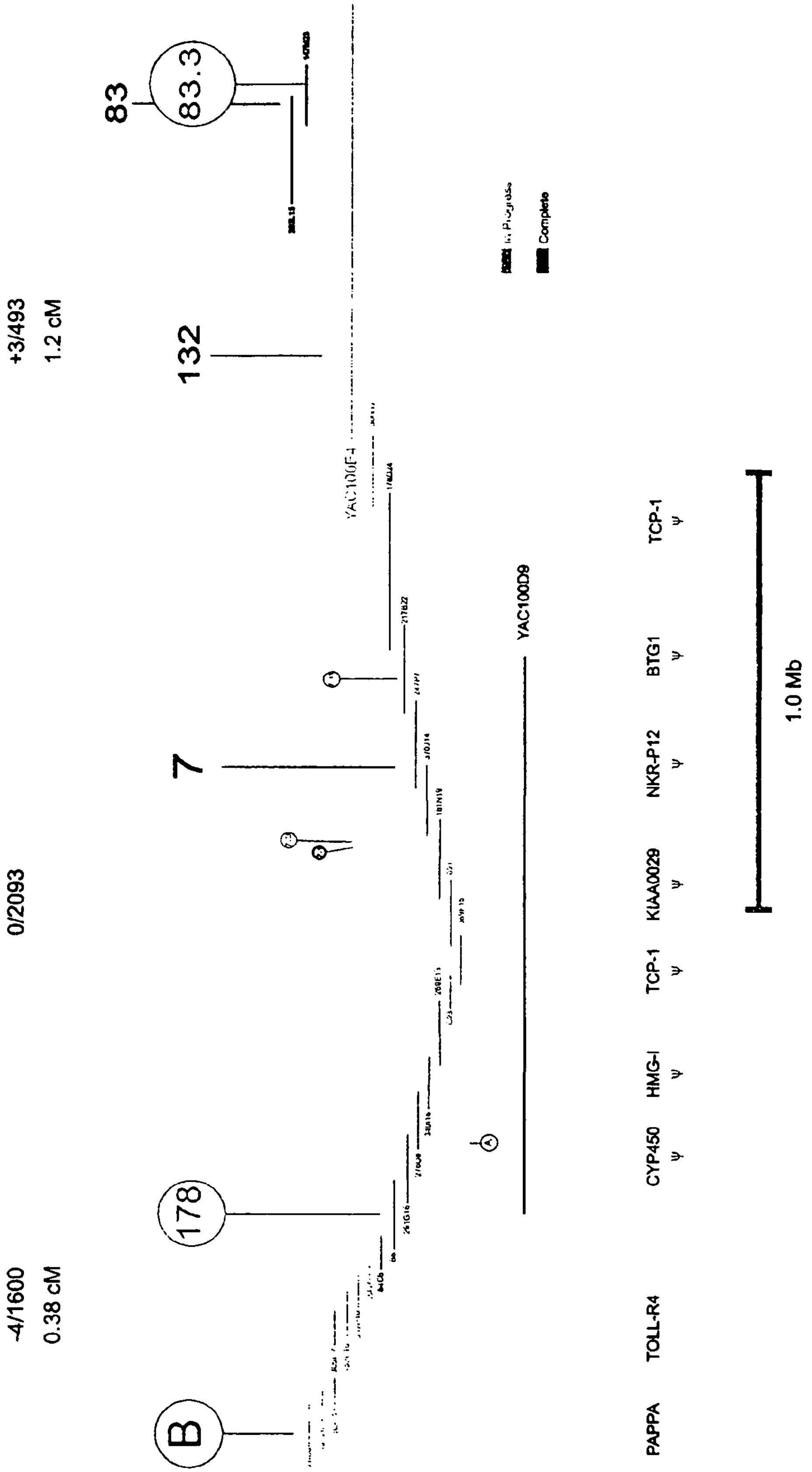

FIG. 5. Minimal contig of BACs and a single YAC, sequenced in the search for Lps. BACs sequenced to completion or to the point of finishing are shown in blue ("complete"). BACs sequenced to a high density, but not yet at the point of finishing, are shown in red ("in progress"). YAC clone 100E4 has also been partially sequenced. BACs 293L15 and 147M3 have not been sequenced. Bar at the top of the figure refers to genetic distances from limiting markers B and 83.3 to $Lps^{d}$. The zero recombination area is shown in black. Several of the polymorphic markers used in mapping (circled) are included as landmarks. The positions of the pseudogenes detected are shown at BAC-level resolution; sequences from TLR-4, considered the prime candidate gene, were detected in BAC 309I17 and in BAC 152C16.

Figure 6:
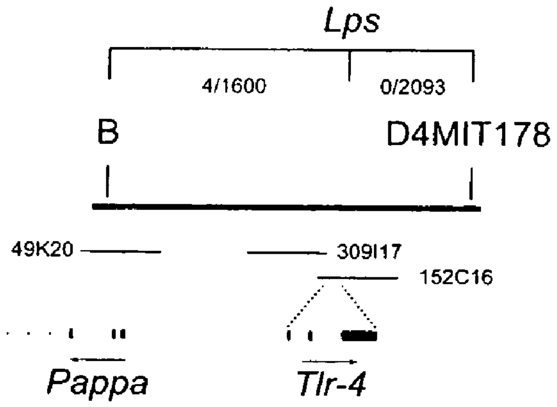

FIG. 6. TLR-4 receptor locus and a portion of the Pappa locus. The two genes were identified by GRAIL and BLAST analysis. The orientation and location of TLR-4 and Pappa are shown with respect to the nearest genetic markers.

FIG. 7A. Amino acid sequence of mouse mutant J-Toll-4 (SEQ ID NO: 104), mouse N-Toll-4 (SEQ ID NO: 99), rat TLR-4 (SEQ ID NO: 6) and human TLR-4 (SEQ ID NO: 2). The mutant mouse J-toll TLR-4 amino acid sequence contains a point mutation at residue 712 (proline to histidine), not found in the amino acid sequences of N-Toll-4, rat TLR-4 or human TLR-4. The numbering system in this figure does not take into account the spacing to maximize the sequence alignment.

Figure 7B:
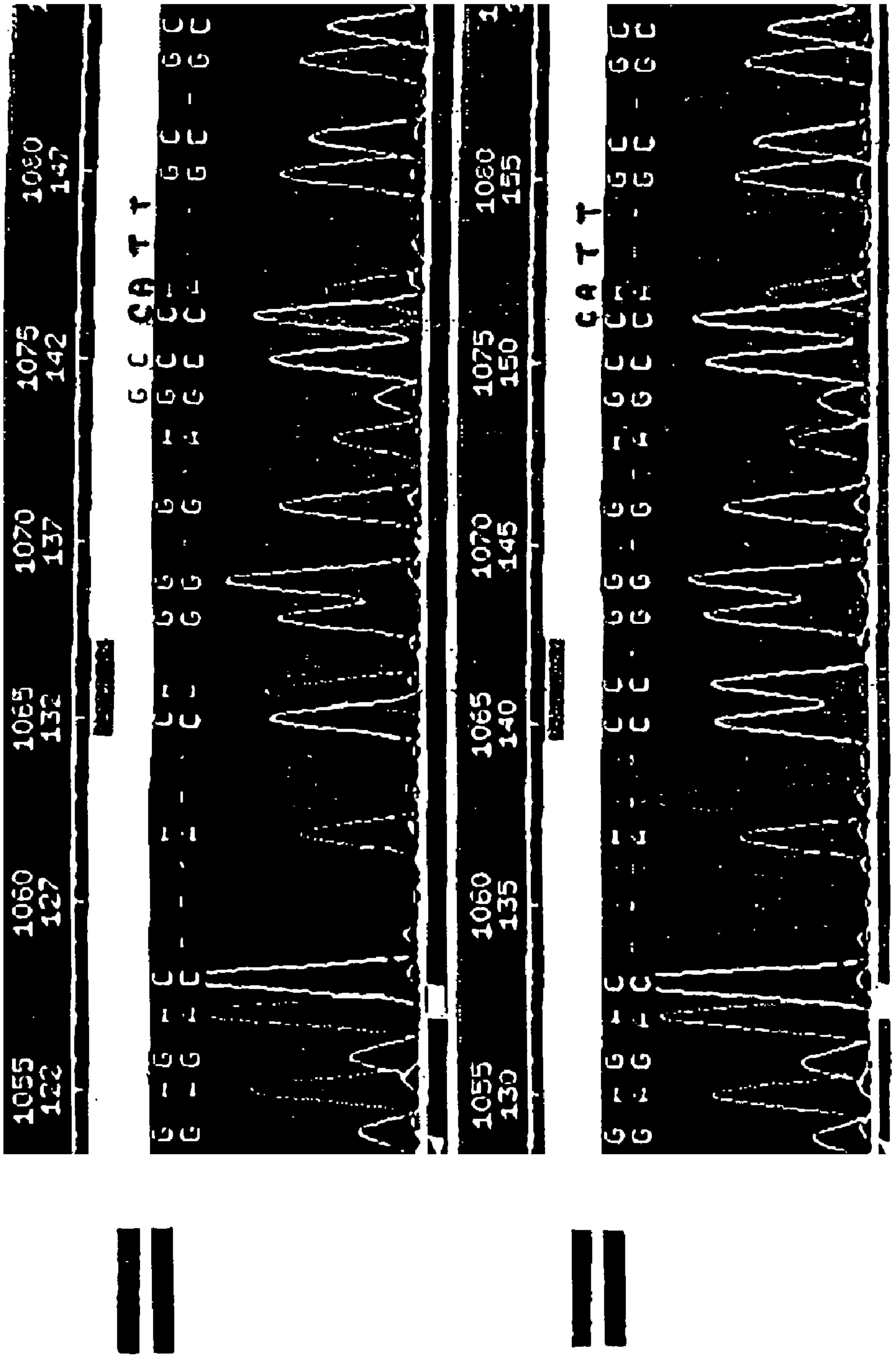
Figure 7C:
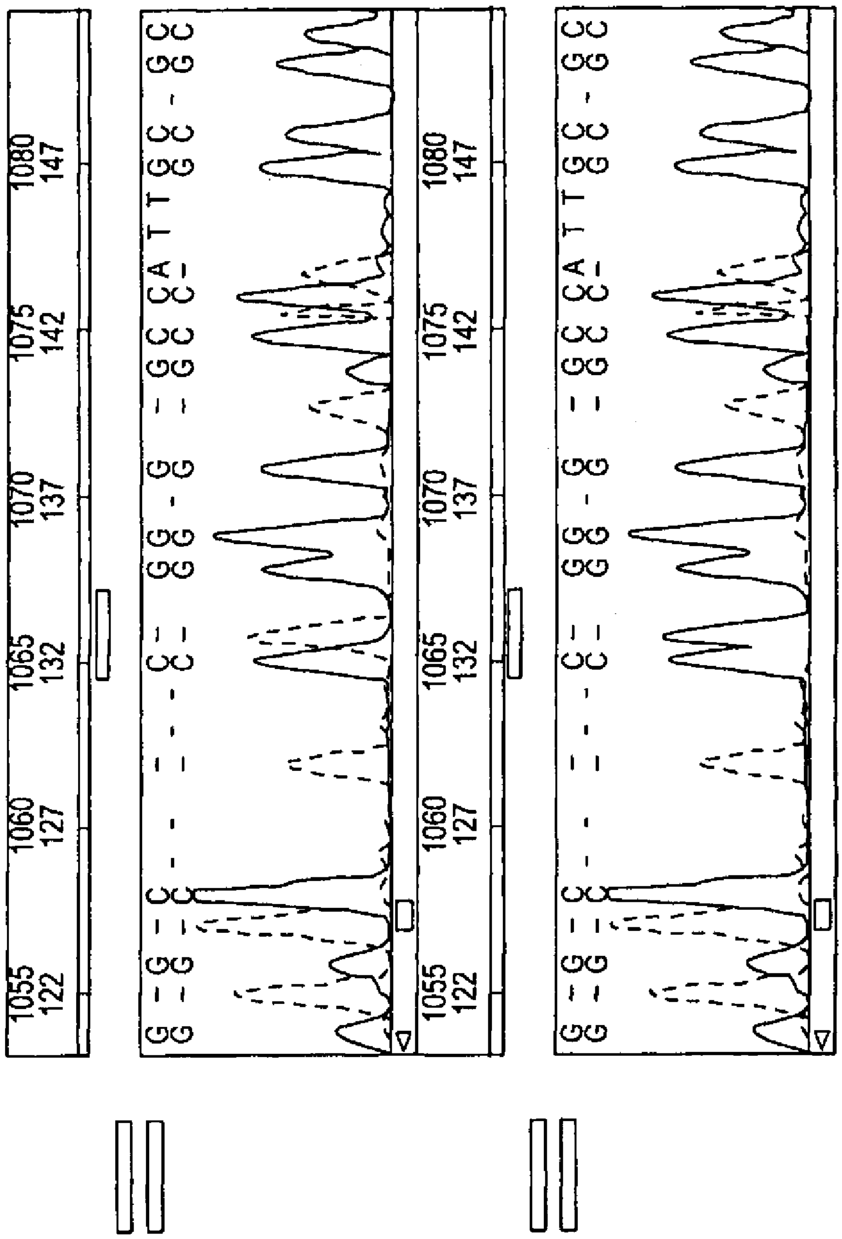

FIG. 7C. Sequencing of amplified DNA from the C3H/HeJ, C3H/HeN, SWR, C57BL/6, and DBA-2 mice genomes.

Figure 8A:
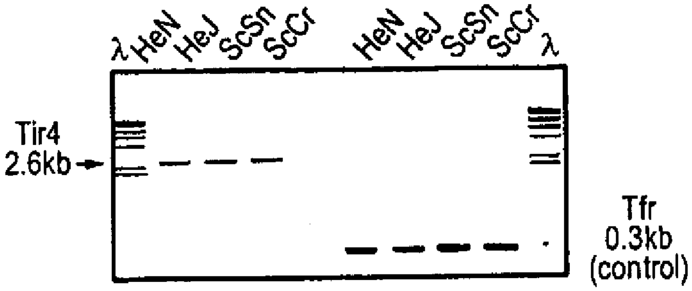

FIG. 8A. Amplification of low abundance control cDNAs from HeN, HeJ, ScSn, ScCr, HeN, HeJ, ScSn and ScCr.

Figure 8B:
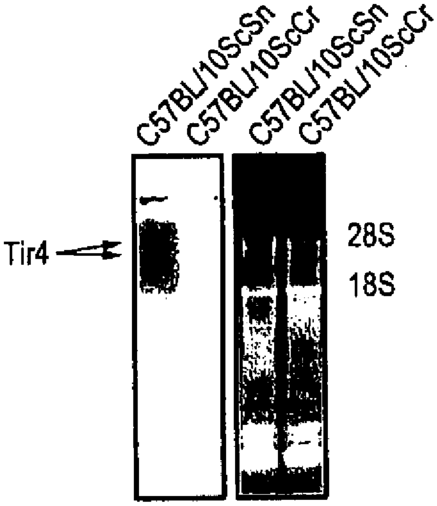
Figure 9:
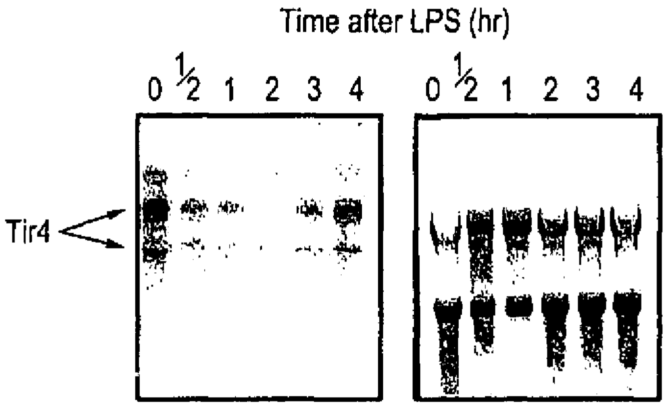
Figure 10:
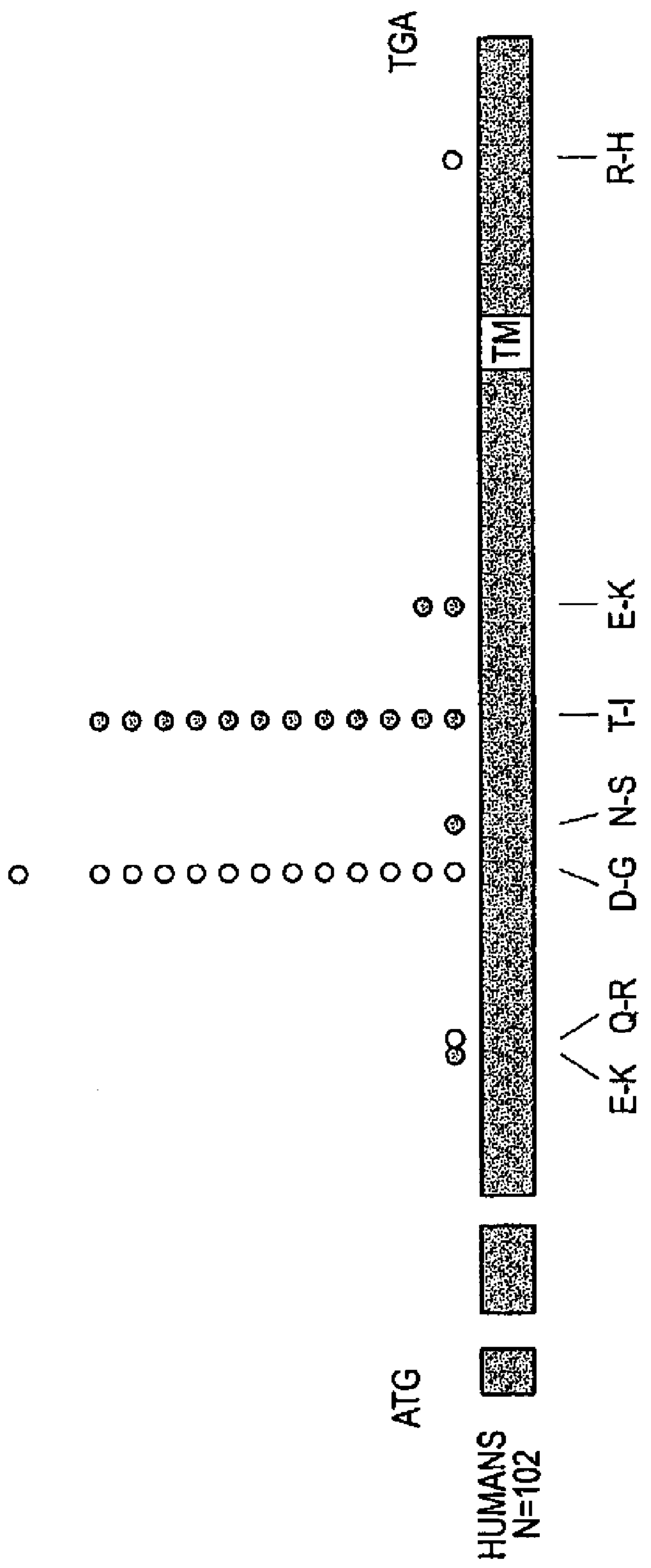
Figure 11:
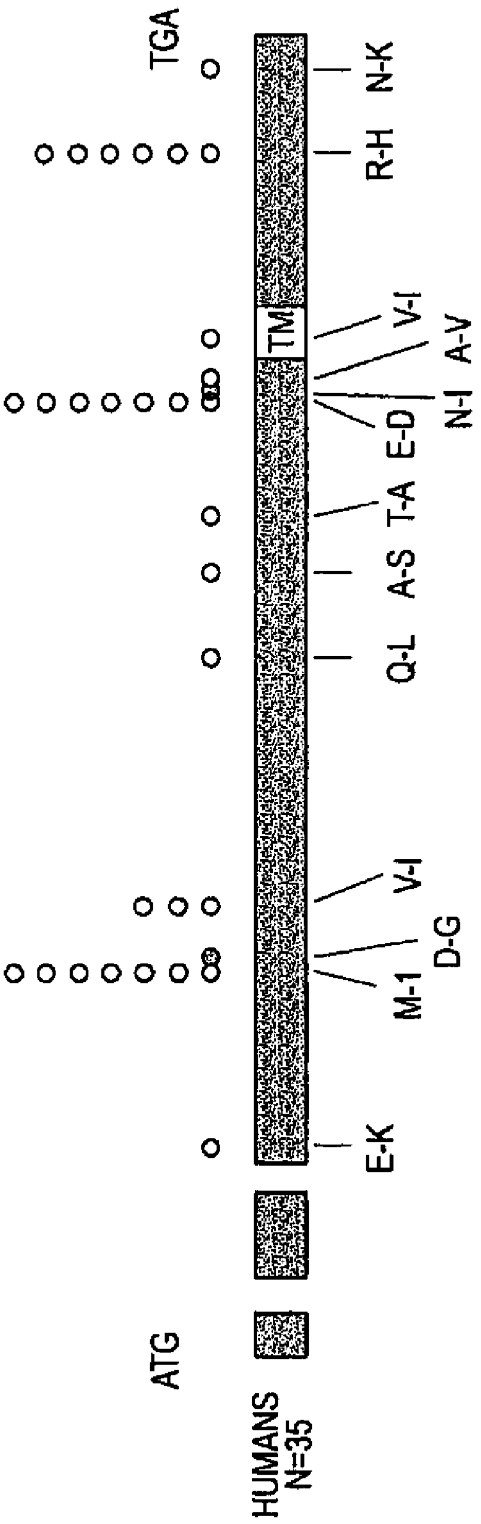
Figure 12:
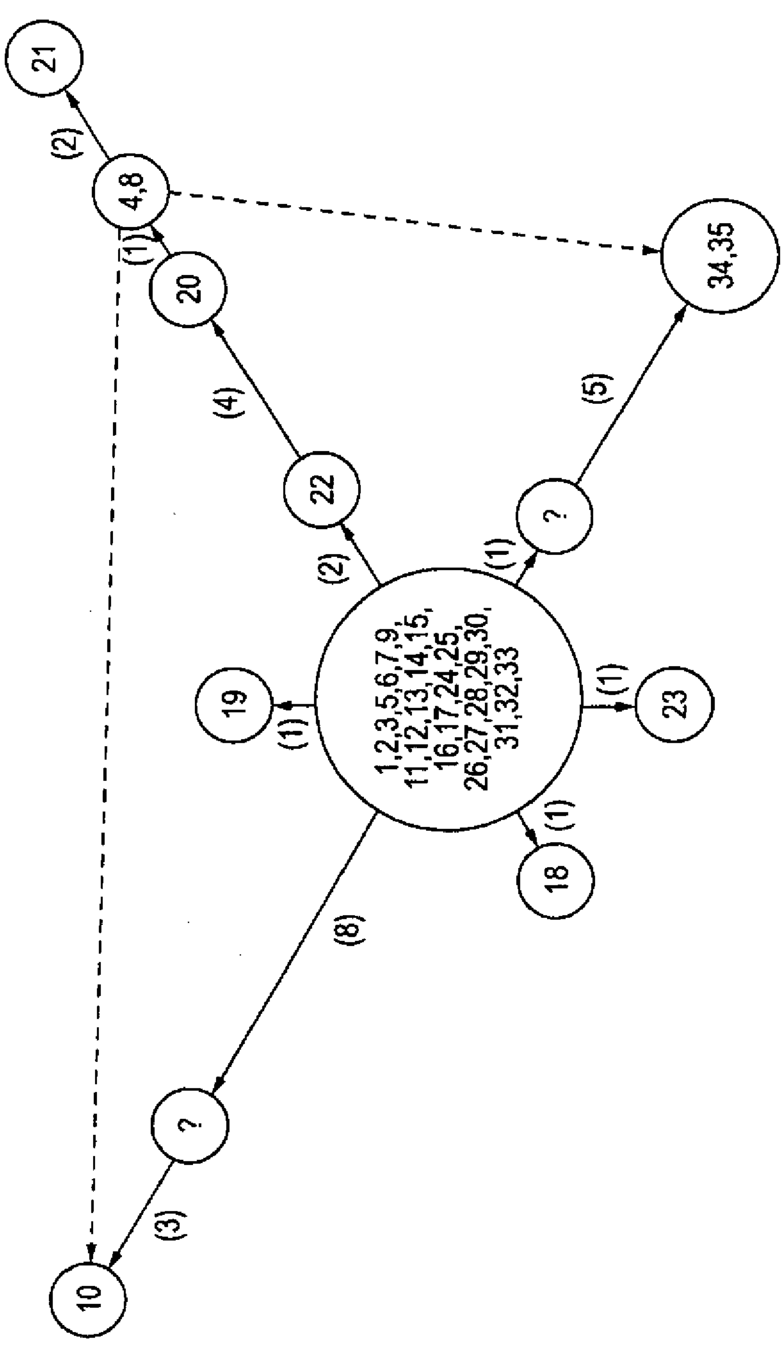
Figure 13:
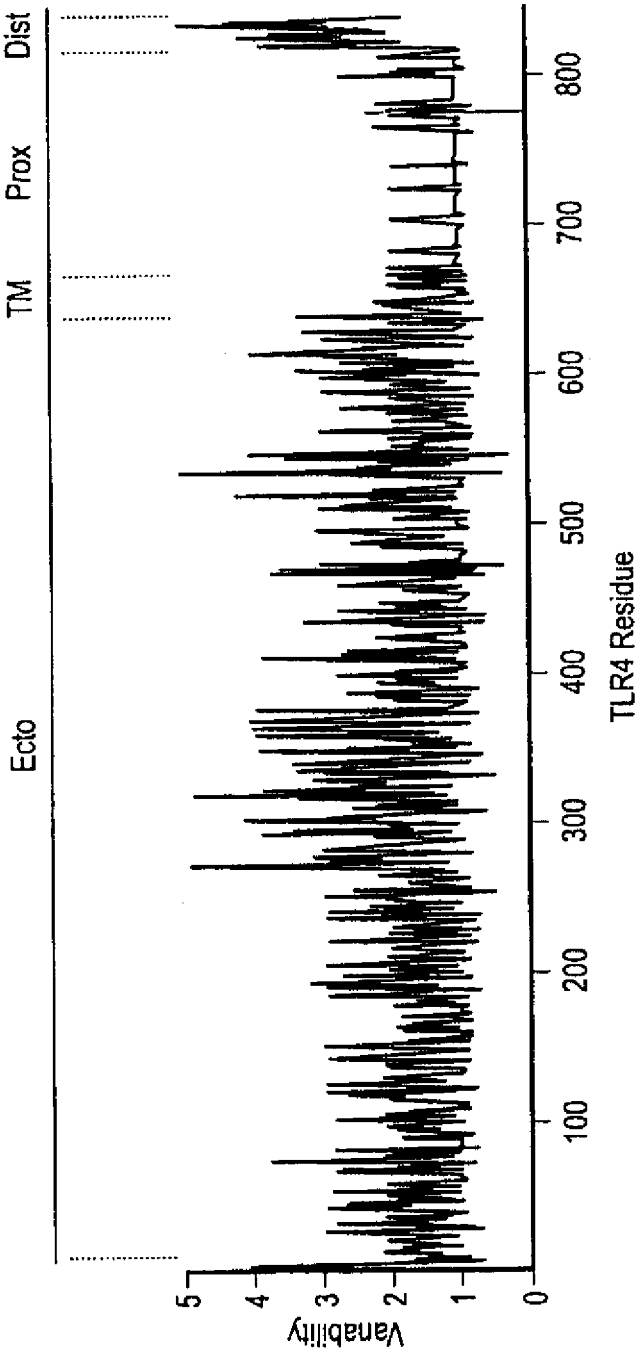
Figure 14:
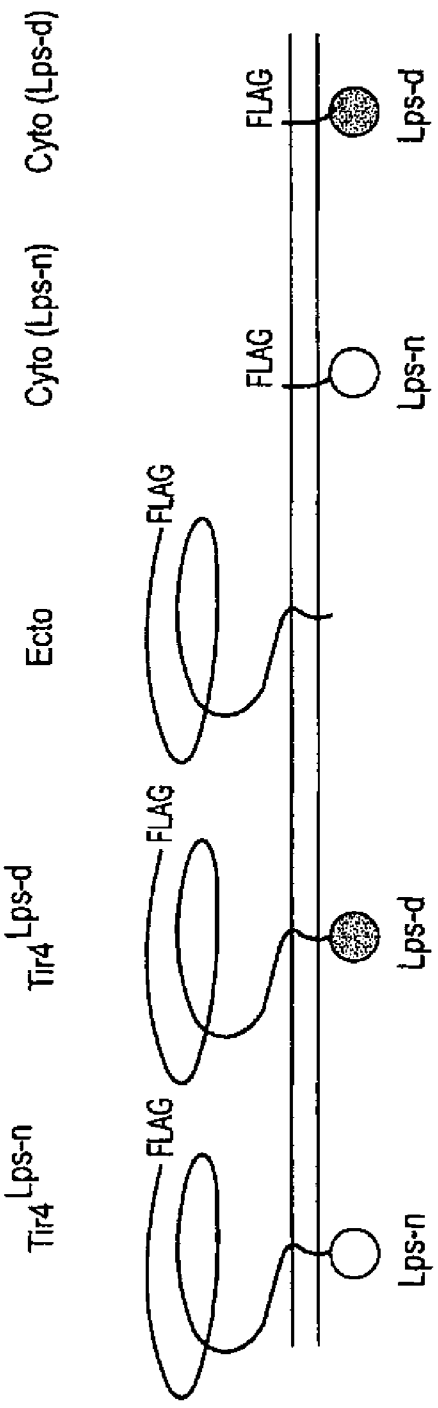

FIG. 8B. TLR-4 mRNA detected by Northern blots using total RNA from macrophages.

Figure 9:
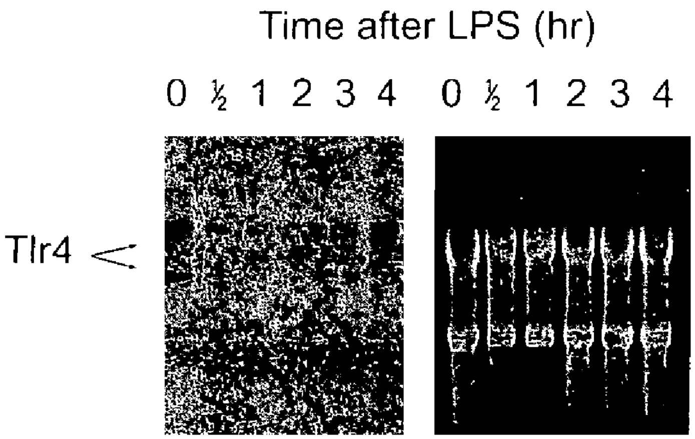

FIG. 9. TLR-4 mRNA induced by LPS in lymphoid tissues.

Figure 10:
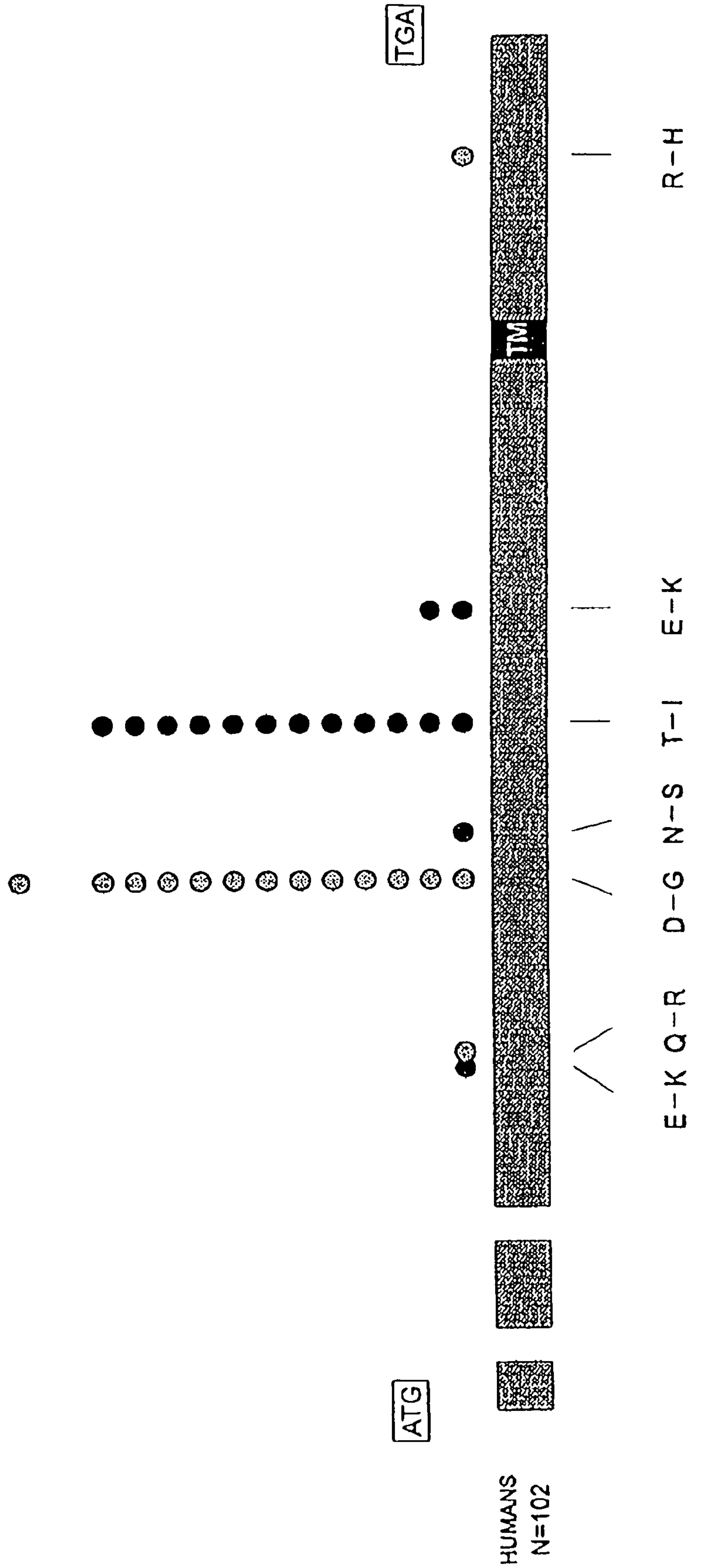

FIG. 10. Spatially conserved representation of coding mutations found in TLR4 of 102 human subjects. Each lightly shaded dot refers to a mutation affecting a residue that is relatively conserved (either invariant among six mammalian species, or extant in two forms). Each black dot refers to a less conserved residue (three or more variants among species). Twelve individuals were found to be heterozygous for a double amino acid substitution. One individual was found to be heterozygous at only one of the mutant sites. Introns are shortened, and non-coding regions are not shown, but the coding region of the three principal human exons is drawn to an equivalent scale at all points in the illustration.

Figure 11:
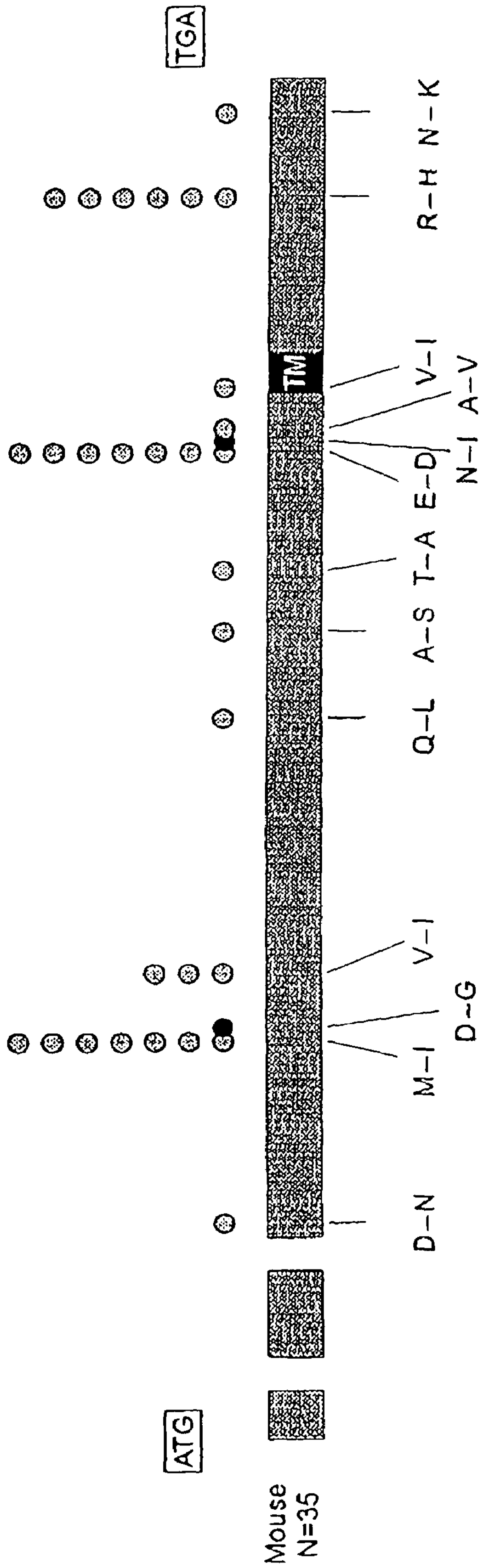

FIG. 11. Spatially conserved representation of coding mutations found in Tlr4 of 35 *Mus musculus* strains. As in FIG. 10, each lightly shaded dot refers to a mutation that is relatively conserved, and each black dot refers to a less conserved mutation.

Figure 12:
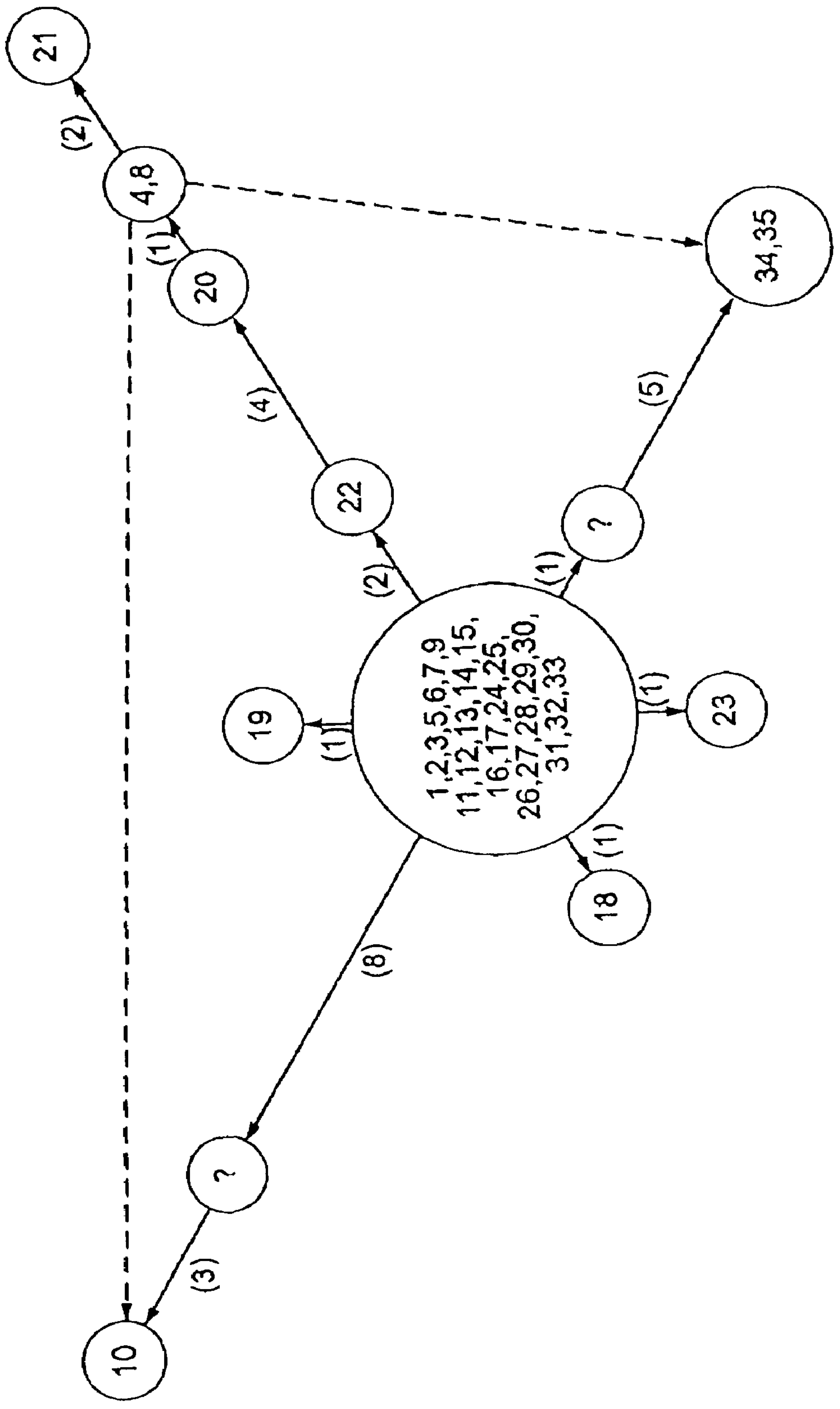

FIG. 12. Genetic distance and probable ancestral relationships among Tlr4 genes of 35 *Mus musculus* strains. Numbers within circles denote strains, in accordance with the legend of Table IV. Numbers within parentheses indicate the mutational distance (number of mutations separating each strain from its presumed ancestor), with reference to both coding and non-coding substitutions listed in Table IV. Arrows point in the direction of descent, and in length are proportionate to distance. Dashed arrows suggest that mice of a given genotype evidently contributed genetic information to mice of another strain, given the similarity of the mutations observed, though unique mutations are also observed in the latter latter strain, and not all of the mutations observed in the former strain are present. The symbol "?" denotes the likelihood of an intermediate form prior to interbreeding of strains.

Figure 13:
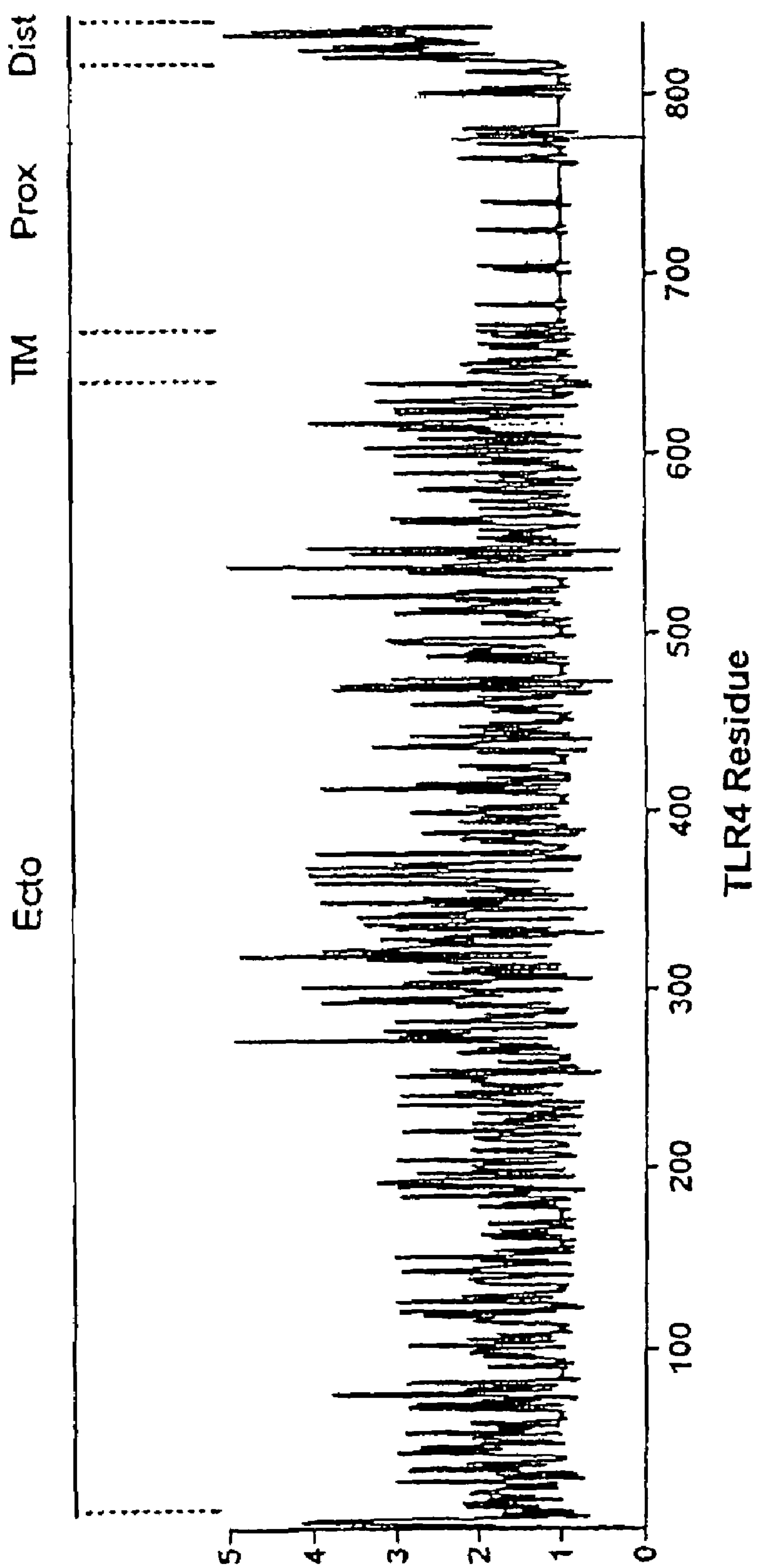

FIG. 13. Spline curve illustrating interspecific sequence variation across the Tlr4 protein. A multiple alignment of Tlr4 sequences from three rodent species (mouse, rat, and hamster) and three primate species (human, chimpanzee, and baboon) was generated using the GCG program pileup. The number of amino acids observed at each residue was plotted using the program Prism 3.0 (a value of 1 was assigned if a single amino acid was observed among the six species; a value of 5 was assigned if five forms were observed among the six species; etc). The points were then connected using a cubic spline curve. Ecto, the extracellular domain; TM, the transmembrane domain; Prox, the proximal cytoplasmic domain; Dist, the distal cytoplasmic domain. Numbering refers to the human sequence. Where a deletion was introduced by pileup, a single mismatch was assumed. Where the sequence was truncated, each absent residue was tabulated as a separate mismatch.

Figure 14:
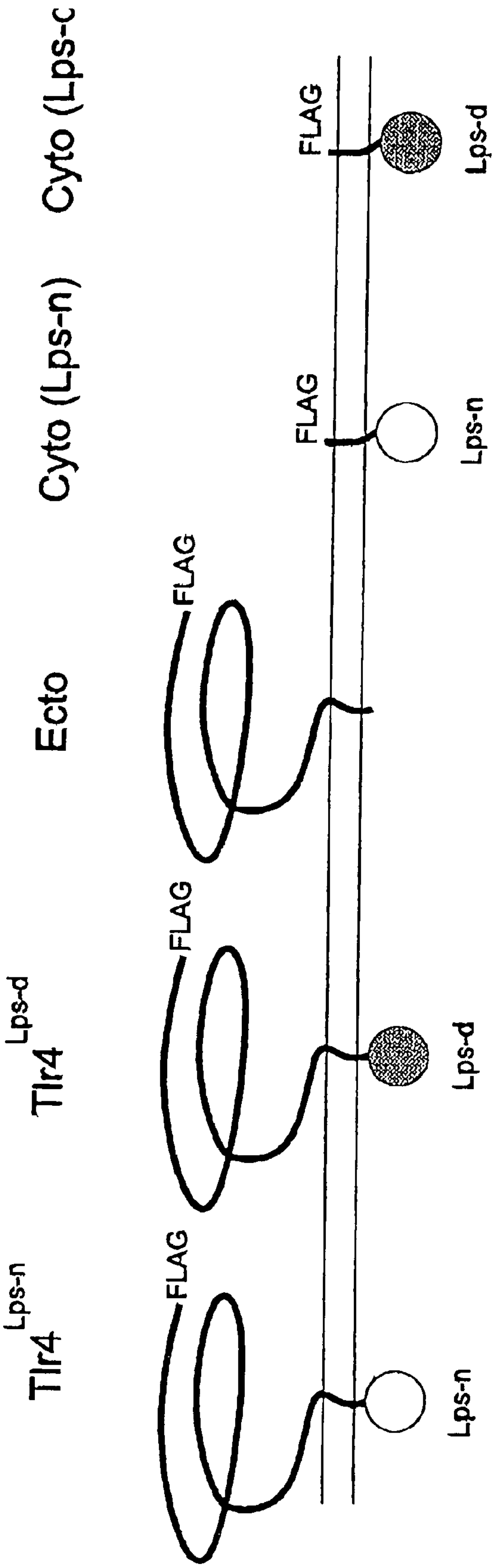

FIG. 14. Schematic illustration of recombinant proteins expressed in RAW 264.7 cells. Constructs were made by PCR, using cDNA derived from C3H/HeJ and C3H/HcN mice. The primers (5'_3'):

ATC GAT ACC AGG AGG CTT GAA TCC C (SEQ ID NO: 100) and

TAG CGA TAC CAG GCT TGA ATC CC (SEQ ID NO: 101)

were used to generate the full-length amplified products, which were cloned into the vector pFLAG-CMV-1 (Sigma) using ClaI and KpnI sites. The native signal peptide was thus removed, and an alternative signal peptide, followed by the flag sequence, was provided by the vector. The ectodomain construct was produced using the downstream primer (5'_3'):

CAG GGT ACC TCA CAG GTG AAA ATA GAA GTG GTA T (SEQ ID NO: 102), whereas the two cytoplasmic domain constructs were produced using the upstream primers (5'_3'):

GCC GAA TTC AAT GTA CAA GAC AAT CAT CAG T (SEQ ID NO: 103).

The latter two constructs were cloned into pFLAG-CMV-1 using EcoRI and KnpI sites. All constructs were verified by DNA sequencing on both strands. All expression constructs were shown to yield products of anticipated size in COS cells, after Western blot detection with M2 monoclonal antibody (not shown).

Figure 15E:
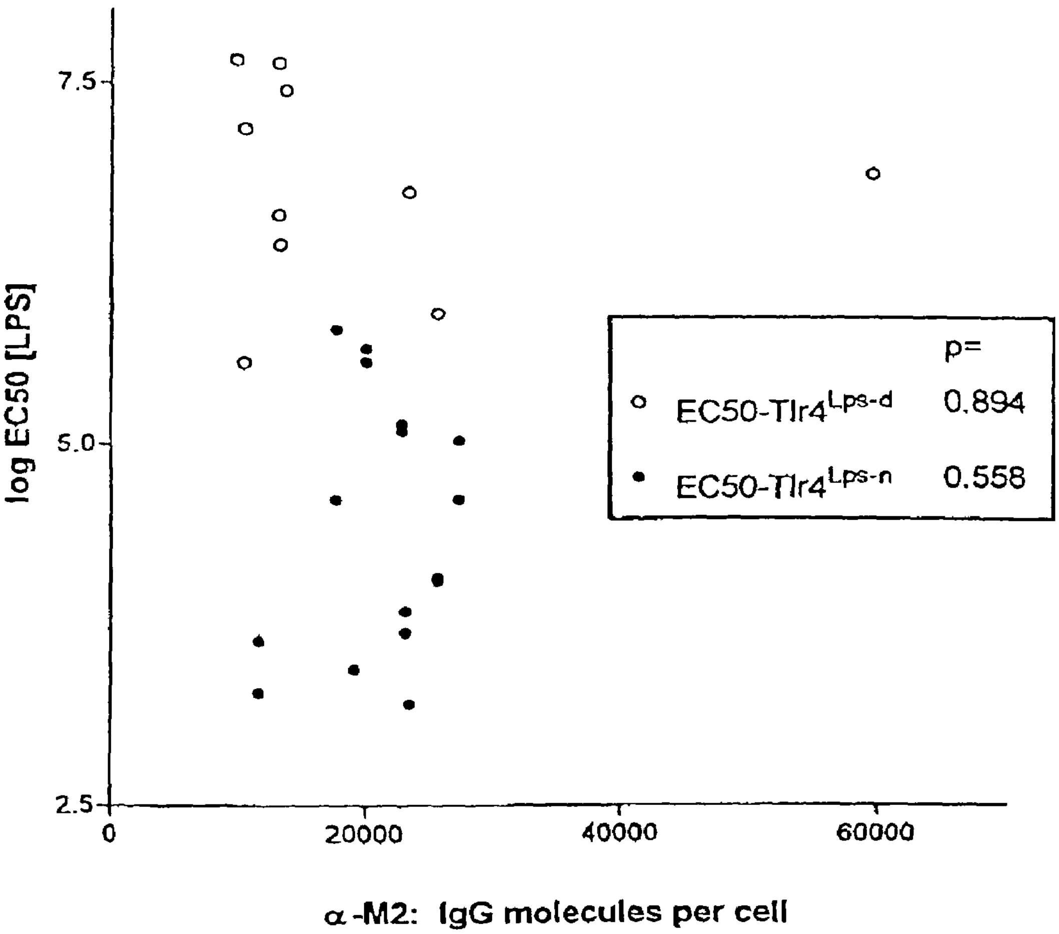
Figure 1:
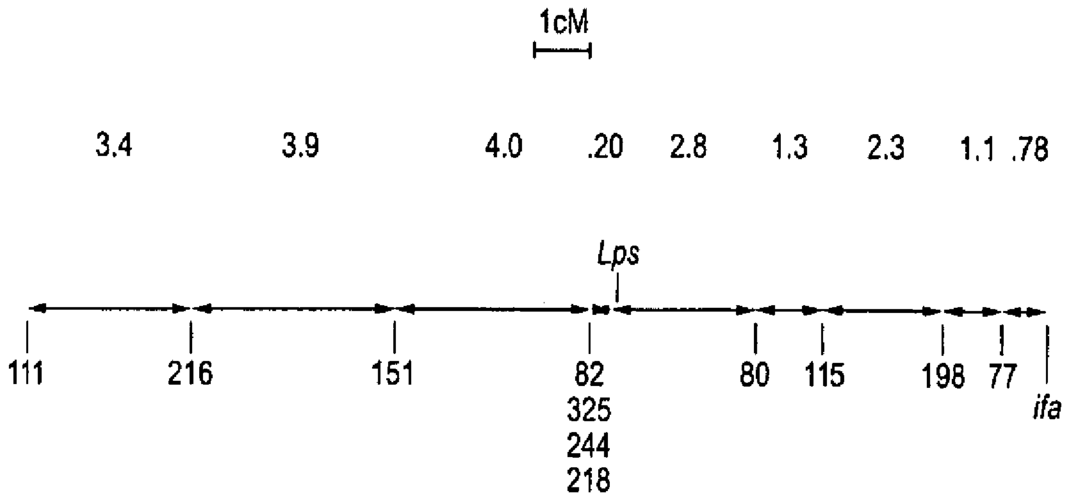
Figure 15A:
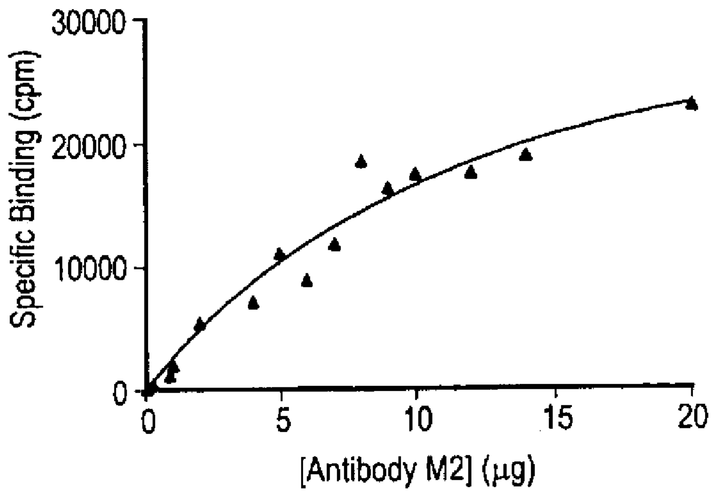

FIG. 15A. Saturation isotherm of monoclonal antibody M2 binding to a single clone of RAW 264.7 cells transfected with an expression vector encoding $Tlr4^{Lps-d}$. M2 antibody was labeled to a specific activity of $3.0\times10^6$ cpM/·g using $^{125}I$, by means of the iodogen technique[35]. Labeled antibody (concentration range 50 ng/ml to 20·g/ml) was added in a volume of 1.0 ml to monolayers of $2.0\times10^6$ cells in Hank's balanced salt solution, supplemented with 10% fetal bovine serum and buffered with 50 mM HEPES, pH 7.4. The cells were maintained at 0_C for a period of 4 hours. Performed as such, 56.4% saturation of the surface receptor was achieved at equilibrium using the highest concentration of antibody. Nonlinear regression analysis, based on the assumption of hyperbolic binding kinetics, suggested a Kd of $1.0\times10^{-7}$ Å $3.0\times10^{-8}$ $M^{-1}$ and the presence of $2.81\times10^4$ Å $4.99\times10^3$ binding sites per cell. $R^2$ for the analysis was 0.9576. Controls, performed for all plates, included the addition of the flag peptide to the system at a 10~M concentration in order to block specific binding, and only specific binding (in general, approximately 80% of total binding) is presented here. Mathematical analysis was performed using using the program Prism 3.0 (GraphPad Software Inc).

Figure 15B:
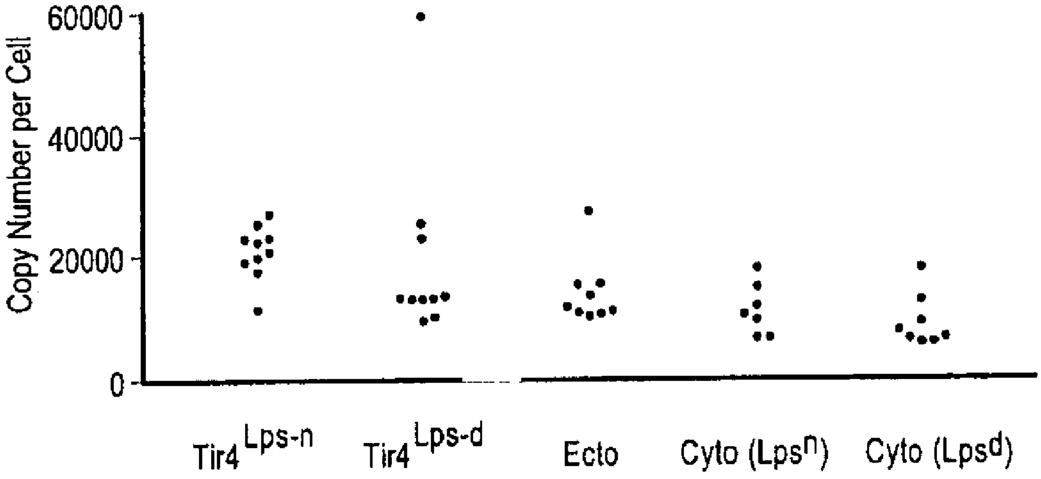

FIG. 15B. The expression level of each construct (copy number per cell) was determined by direct measurement of equilibrium M2 monoclonal antibody binding at a fixed concentration, with reference to the nonlinear regression analysis of saturation isotherms presented in FIG. 15A. Each point represents the result of duplicate determinations of specific binding. Cells transfected with vector alone had zero specific binding (not shown).

Figure 15C:
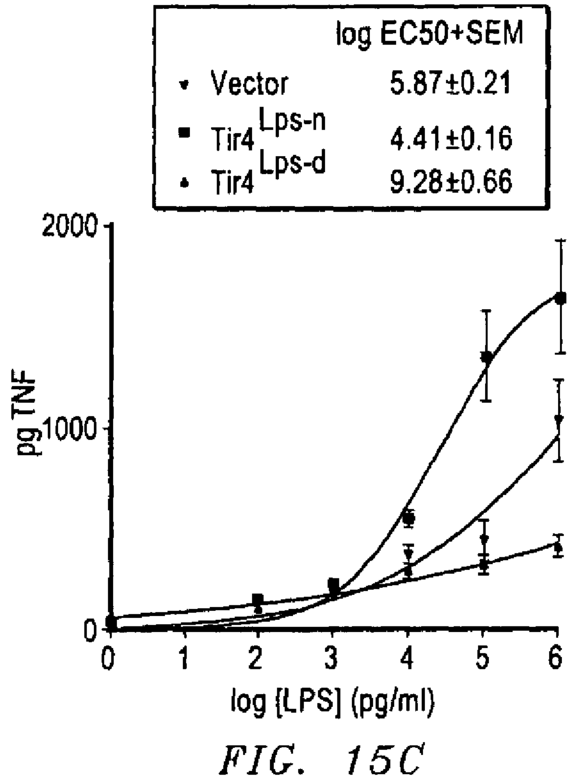

FIG. 15C. Composite analysis of the shift in EC50 caused by expression of $Tlr4^{Lps-n}$ and $Tlr4^{Lps-d}$ in RAW 264.7 cells. Each point represents an EC50 determination performed on ten independent clones at the stated LPS concentration. For each clone, four replicate assays were performed at each concentration. Hence, each curve represents the composite analysis of 240 assays. Transfected macrophages were plated in 24 well plates at a density of $5\times10^5$ cells per well, and covered with 1.0 ml of DMEM supplemented with 10% FBS. LPS was added to each well at the concentration indicated. After 15 hours of incubation the medium was harvested, and TNF concentration was assayed in the standard L-929 cytotoxicity system[36], using cycloheximide at a concentration of 100·g/ml to potentiate killing. After 15 hours of exposure to diluted macrophage medium or to mouse TNF applied at a range of 8 standard concentrations, the number of viable cells was determined by staining with crystal violet. A standard curve relating % cytotoxicity to TNF concentration (not shown) was generated using Prism 3.0, and was based on an assumption of sigmoidicity. Variance among replicate samples was typically beneath 5% of the mean, and departures of individual samples from the sigmoid plot were typically smaller still. Linear estimates of TNF concentration in unknown samples were based on non-linear interpolation from the standard curve (also performed using Prism 3.0). The curves shown were generated assuming sigmoidicity of response with variable slope for each curve, and further assigning a maximum response value of 1760 pg TNF, which yielded an optimal fit for the most responsive curve. Error bars indicate standard deviation among clones at each LPS concentration. Log EC50 values and standard error values are shown in the inset table.

Figure 15D:
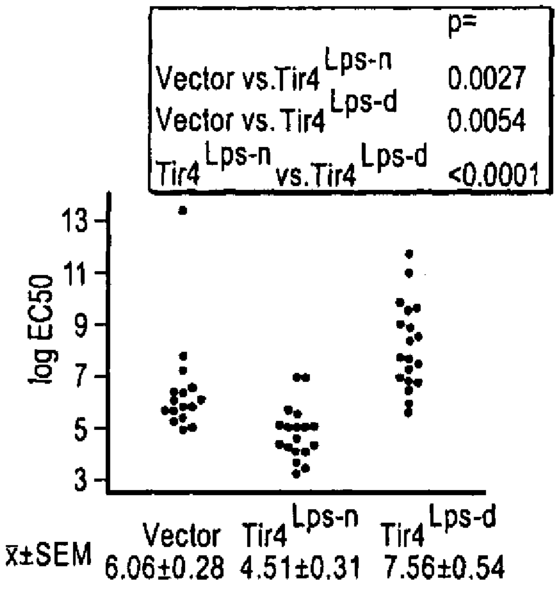
Figure 15E:
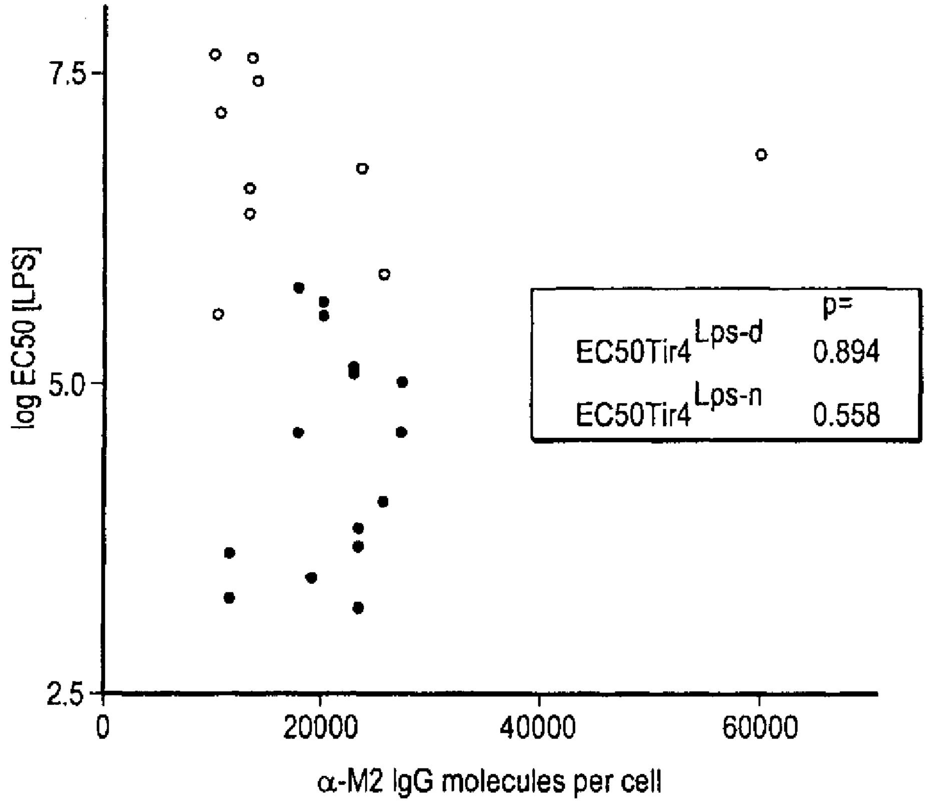

FIG. 15D. Shifts of the log EC50, determined for individual clones. A more conservative approach, in which log EC50 values were determined for individual clones transfected with vector alone, or with the $Tlr4^{Lps-n}$ or $Tlr4^{Lps-d}$ constructs. The log EC50 data were then represented as a scatter plot, in which each point represents the log EC50 determination of a single clone (confidence limits not shown for the sake of simplicity), and is derived from 24 separate TNF assays performed on samples stimulated over a $10^4$-fold range of LPS concentration (100 pg/ml to 1·g/ml, as well as an unstimulated control). In most instances, two determinations of log EC50 were made independently for each clone. The mean and standard error of each cluster is shown in the inset, together with p values defining the likelihood that the EC50 displacements are attributable to chance. Data were analyzed by means of a one-tailed t test, using Welch's correction for unequal variance.

FIG. 15E. Lack of correlation between level of recombinant receptor expression and the magnitude of effect on EC50. Plotting the EC50 of $Tlr4^{Lps-n}$ transfected cells (nine clones; duplicate assays) and $Tlr4^{Lps-d}$ transfected cells (eight clones; duplicate assays) vs. the receptor number measured for each clone (shown separately in FIGS. 2*b* and 2*d*), it is apparent that no correlation exists over the range of receptor number surveyed. Inset: p values calculated to assess the significance of departure of the slope (determined by linear regression for each set of points) from zero.

Figure 16A:
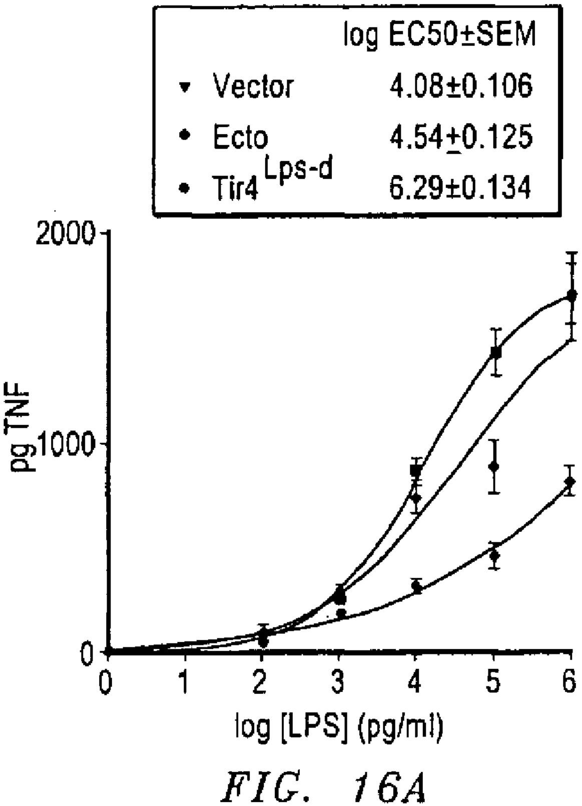

FIG. 16A. Over-expression of the Tlr4 ectodomain fails to inhibit LPS signaling. Composite analysis of the shift in EC50 caused by expression of the Tlr4 ectodomain (no cytoplasmic domain) or the full-length $Tlr4^{Lps-d}$ protein in RAW 264.7 cells. Control cells were transfected with the empty vector. Analysis was carried out in a manner identical to that described in FIG. 2*c*. Inset: log EC50 for each curve, and standard error.

Figure 16B:
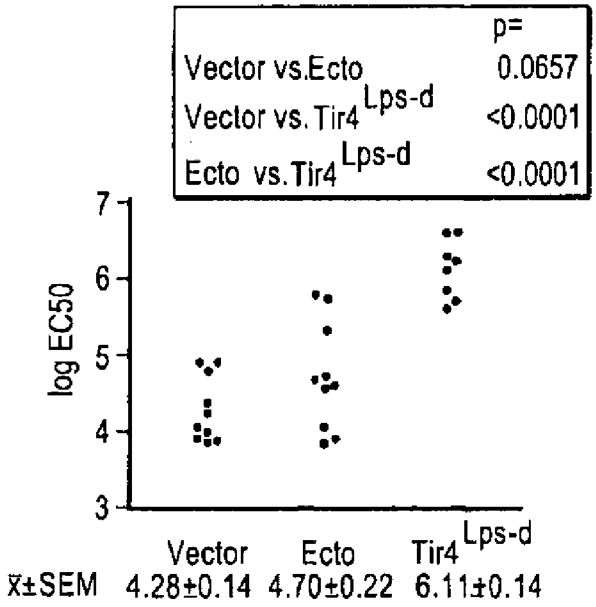

FIG. 16B. Distribution of individual log EC50 data for clones expressing the Tlr4 ecotodomain, the full-length $Tlr4^{Lps-d}$ protein, or no recombinant receptor (transfected with empty vector). Inset: the mean and standard error of each cluster, together with p values defining the likelihood that the EC50 displacements are attributable to chance. Data were analyzed by means of a t test, using Welch's correction for unequal variance.

Figure 17A:
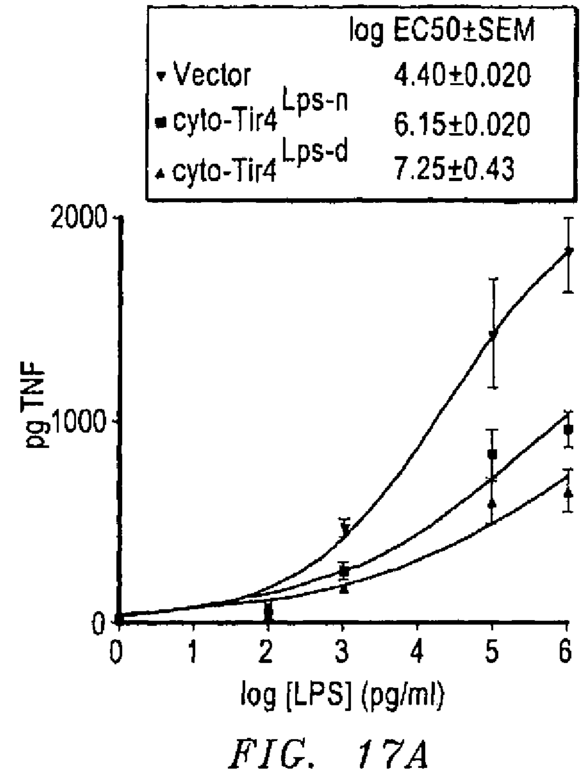

FIG. 17A. Over-expression of the Tlr4 cytoplasmic domain, either with or without the Lps-d mutation, impairs signal transduction in RAW 264.7 cells. Composite analysis of the shift in EC50 caused by expression of the Tlr4 ectodomain (no cytoplasmic domain) or the full-length $Tlr4^{Lps-d}$ protein in RAW 264.7 cells. Control cells were transfected with the empty vector. Analysis was carried out in a manner identical to that described in FIG. 2*c*. Inset: log EC50 for each curve, and standard error.

Figure 17B:
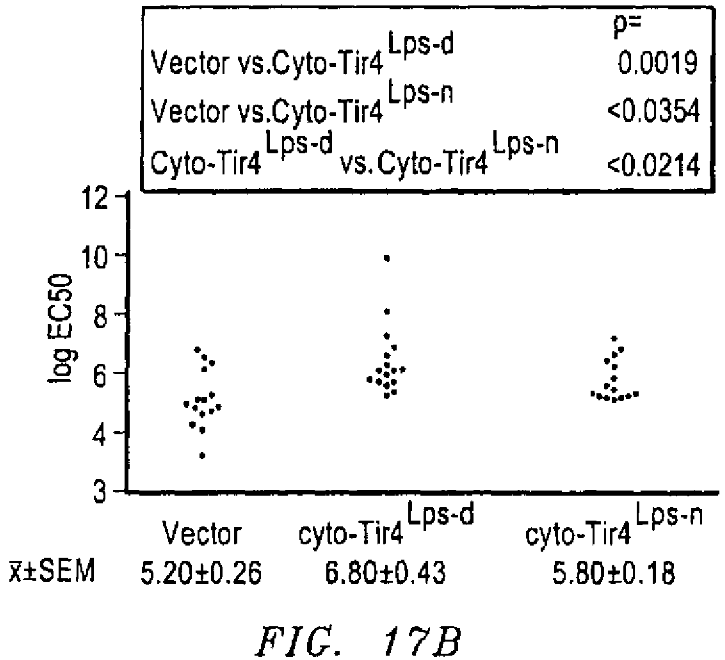

FIG. 17B. Distribution of individual log EC50 data for clones expressing the cytoplasmic domain of the $Tlr4^{Lps-d}$ protein, the $Tlr4^{Lps-n}$ protein, or no recombinant protein (transfected with empty vector). Inset: the mean and standard error of each cluster, together with p values defining the likelihood that the EC50 displacements are attributable to chance. Data were analyzed by means of a t test, using Welch's correction for unequal variance.

DESCRIPTION OF ILLUSTRATIVE EMBODIMENTS

Bacterial infections represent a significant challenge in the treatments of a wide variety of disease. Structurally disparate LPS molecules, produced by many different species of Gram-negative bacteria, are engaged on the macrophage surface by CD14 and ultimately trigger the release of cytokines such as tumor necrosis factor (TNF) and interleukin-1 (IL-1). These cytokines orchestrate the inflammatory response, with its attendant beneficial and harmful effects.

Given the ubiquitous presence of Gram-negative bacteria and the high incidence of Gram-negative mediated infections, certain individuals are at high risk to develop endotoxic shock even if adequate antimicrobial therapy is instituted. Methods for diagnosing patients at high risk for Gram-negative bacterial infections and sepsis in advance of its onset would be beneficial. Further, there is a need to determine whether a particular individual may be susceptible to Gram-negative bacterial infection, in determining the course of treatment for any number of diseases. For example, it will be beneficial to test individuals who are candidates for immuno-suppressive drug therapy, for susceptibility to Gram-negative bacteria in order to assess the risks of immunosuppressive treatment. Such diagnostic methods to predict the risk of infection as well as the clinical course of sepsis could be reasonably applied to most hospitalized patients. The present invention is directed towards addressing these needs.

The claimed invention also provides methods of identifying agents which stimulate endotoxin signaling such that TNF and other cytokines are released from macrophages. It is envisioned that such agents will be of therapeutic use in the treatment of individuals who are insensitive to endotoxin, either through genetic defect, disease or other condition, and whose immune system requires external stimulation to recognize infection from Gram-negative bacteria.

A. The Present Invention

In broad aspects, the present invention provides methods for screening for susceptibility to infection. On the basis of 2093 meioses analyzed in two separate intraspecific backcrosses, the location of the mouse $Lps^d$ mutation has been circumscribed to a genetic interval 0.9 cM in size. To identify gene candidates, nearly 40,000 sequencing runs were performed across the critical region. Selective hybridization and exon trapping were also employed to identify genes throughout the "zero" region. These studies revealed that only a single intact gene was identified within the entire critical region. This gene encodes the TLR-4 receptor, a member of the IL-1 family of receptors. Thus, the present inventors demonstrate that there is a mutation in the TLR-4-encoding gene that appears to provide a predisposition to infection.

In these studies a total of 19 genetic markers that lie in close proximity to the mutation were examined in mapping. Most of these were previously unpublished polymorphic microsatellites, identified by fragmentation of YAC and BAC clones spanning the region of interest. $Lps^d$ was found to be inseparable from the microsatellite marker D4MIT178, and from three novel polymorphic microsatellites identified near D4MIT178. The mutation was confined between two novel microsatellite markers, herein designated "B" and "83.3." B lies centromeric to the mutation, and was separated by four crossovers in a panel of 1600 mice; 83.3 lies distal to the mutation and was separated by three crossovers in a panel of 493 mice. 66 BAC clones and one YAC clone were assembled to cover >95% of the critical region. Estimates based on pulsed field gel electrophoresis and fluorescence in situ hybridization indicate that the B→83.3 interval is about 3.2 Mb in length. A minimal area of zero recombinational distance from $Lps^d$ was also assigned, and found to occupy approximately 1.2 Mb of physical size.

It was found that in the macrophages of mice that are susceptible to bacterial infection there is a genetic mutation in the lps locus. Specifically, there is a mutation in the TLR-4 receptor that is expressed by the macrophages of these compromised mice and this mutation leads to a reduced recognition of endotoxin. As the endotoxin is not recognized by these defense cells, there is a lack of immune response mounted against the invading bacteria which results in the deleterious effect of the infection. The present invention suggest that similar mechanisms work in other mammalian cells and as such in a broad sense the present invention provides methods of preventing a bacterial infection of a host comprising ensuring that the macrophages of the host express a function TLR-4 or Toll-like receptor. By providing such a functional receptor, the present invention ensures that the endotoxin signal is recognized by the immune system of the host. Conversely, in those instances in which widespread activation of macrophages by endotoxin results in the overproduction of TNF leading to the development of septic shock, it may be desirable to down-regulate the TLR-4 receptor.

Thus, the present invention also provides a method of treating gram-negative bacterial infections comprising administration of an agent that stimulates the recognition of endotoxin. In specific circumstances such an agent is likely to by a candidate substance that stimulates the expression, activity or function of the TLR-4 receptor that is expressed by the macrophages of the host. Similarly, methods and compositions for treating endotoxin related symptoms comprising administration of an agent that reduces the recognition of endotoxin also are provided by the present invention. A useful compound that may be identified by the present invention is one which inhibits endotoxin signaling by binding to a TLR-4 receptor and competing with endotoxin for the binding. Particularly preferred agents would be those that modulate the stimulation of TNF and cytokine secretion. Such a modulation may be an increase in secretion in circumstances where the endotoxin has not been recognized or a decrease in secretion in circumstances where there has been a deleterious production of TNF and/or other cytokines.

Thus, as outlined above and described in detail herein below, the TLR4 sequence will find utility in a variety of applications in bacterial infection susceptibility detection, diagnosis, prognosis and treatment. Examples of such applications within the scope of the present invention include amplification of markers of LPS mediated infections using specific primers; detection of markers of TLR-4 by hybridization with oligonucleotide probes; incorporation of isolated nucleic acids into vectors and expression of vector-incorporated nucleic acids as RNA and protein; development of immunologic reagents corresponding to gene encoded products; and therapeutic treatment for the identified infection using these reagents as well as, anti-sense nucleic acids, or other inhibitors specific for the identified disease. The present invention further discloses screening assays for compounds to upregulate gene expression or to combat the effects of the mutant TLR-4 genes.

B. LPS Mutation is Responsible for Susceptibility to Bacterial Infection

The Lps is an important susceptibility locus, influencing the propensity to develop a disseminated Gram negative infection, or the outcome of such an infection. Hence, C3H/HeJ mice, while highly resistant to LPS, show exaggerated susceptibility to infection by Gram negative organisms (O'Brien et al., 1980; Macela et al., 1996). In birds, resistance to *Salmonella typhimurium* is linked to a polymorphism at the tenascin locus (Hu et al., 1997); tenascin is closely linked to the Lps gene, and it may be assumed that a mutation of the avian Lps locus lies in linkage disequilibrium with the tenascin marker, yielding the reported association. From these investigations it is likely that mutations at the equivalent locus in humans also will influence the course of Gram negative infection.

The Lps critical region is remarkably gene-poor. While the average megabase of mammalian DNA contains approximately 30 genes, only one authentic gene (and a portion of a second gene) have been detected within 2.6 Mb of DNA flanking Lps. As virtually all of the Lps critical region was sequenced herein, and no other plausible candidates were found, it must be considered that the lone candidate, encoding the toll-like receptor 4 (TLR-4; Tlr-4; TIL4) of mice, very likely represents the Lps locus. Moreover, the inventors suggest that a specific mutation of this gene is responsible for the endotoxin-unresponsive phenotype witnessed in C3H/HeJ mice.

The toll family of receptors (Chaudhary et al., 1998; Rock et al., 1998) is defined by homology to the *Drosophila* toll protein, a plasma membrane receptor which engages an extracellular mediator encoded by späzle, leading to activation of a rel gene family member, by inducing its dissociation from cactus. This sequence of events is important for induction of the drosomycin antifungal response in *Drosophila* (Rosetto et al., 1995; Lemaitre et al., 1996). The mammalian IL-1 receptor is a member of the toll family of proteins, and four other mammalian family members (Toll-like receptors 1 through 4) have been identified by molecular cloning, though their function is uncertain. IL-1 signaling involves, among other events, the activation of NF-κB, which like dorsal, is a member of the rel family. LPS signaling also entails activation of NF-κB. As such, it is plausible to consider that LPS signaling might involve transduction via a toll family member. The present invention, for the first time shows that TLR-4 is the receptor for LPS.

Further evidence consistent with this hypothesis may be seen in the clinical observation of Kuhns and coworkers, who determined that a profound immunodeficiency results from a conjoint defect in responses to IL-1 and LPS (Kuhns et al., 1997). In view of the inventor's findings, the fact that a single mutation may block signal transduction initiated by both IL-1 and LPS may be taken to indicate that a common (proximal) mediator serves both the IL-1 receptor and the LPS receptor. This, in turn, would suggest the existence of structural similarity between the IL-1 and LPS receptors. While the details of signal transduction via toll family members have not been fully elucidated, the involvement of MyD88, IRAK, and TRAF6 has recently been proposed in the case of the TLR-4 receptor (Muzio et al., 1998).

The $Lps^d$ mutation has a codominant character, and attempts to identify the product of Lps through expression cDNA cloning in C3H/HeJ macrophages were unsuccessful. Blockade of endotoxin signal transduction in the C3H/HeJ mice may therefore reflect the expression of a protein with dominant negative characteristics. As CD14 serves as the physical receptor for LPS on the cell surface yet lacks a transmembrane domain, it would seem likely that CD14 engages TLR-4, and that the latter protein acts to transduce the LPS signal across the membrane. It is possible that the $Lps^d$ mutation leads to unproductive interaction between CD14 and an TLR-4, preventing signal transduction through other components of the signaling pathway. Alternatively, the mutation may merely abolish signal transduction through TLR-4 itself. Examination of these hypotheses will depend upon the demonstration of a mutational difference between the TLR-4 gene in C3H/HeJ mice and in C3H/HeN animals.

C. TLR-4 Polypeptides

TLR-4 may be obtained according to various standard methodologies that are known to those of skill in the art. For example, antibodies specific for TLR-4 may be used in immunoaffinity protocols to isolate TLR-4 from cells. Antibodies are advantageously bound to supports, such as columns or beads, and the immobilized antibodies can be used to pull the TLR-4 target out of the cell lysate. Size fractionation (chromatography, centrifugation), ion exchange or affinity chromatograph, and even gel purification may be used for purification as well.

TLR-4, according to the present invention, may advantageously be cleaved into fragments for use in further structural or functional analysis, or in the generation of reagents such as TLR-4-related polypeptides and TLR-4-specific antibodies. This can be accomplished by treating purified or unpurified TLR4 with a peptidase such as endoproteinase glu-C (Boehringer, Indianapolis, Ind.). Treatment with CNBr is another method by which TLR-4 fragments may be produced from natural TLR-4. Recombinant techniques also can be used to produce specific fragments of TLR-4.

In addition to the peptidyl compounds described herein, the inventors also contemplate that other sterically similar compounds may be formulated to mimic the key portions of the peptide structure, called peptidomimetics. Mimetics are peptide-containing molecules which mimic elements of protein secondary structure. See, for example, Johnson et al. (1993). The underlying rationale behind the use of peptide mimetics is that the peptide backbone of proteins exists chiefly to orient amino acid side chains in such a way as to facilitate molecular interactions, such as those of receptor and ligand.

Successful applications of the peptide mimetic concept have thus far focused on mimetics of β-turns within proteins. Likely β-turn structures within TLR-4 can be predicted by computer-based algorithms as discussed above. Once the component amino acids of the turn are determined, mimetics can be constructed to achieve a similar spatial orientation of the essential elements of the amino acid side chains, as discussed in Johnson et al. (1993).

D. DNA Segments

Important aspects of the present invention concern isolated DNA segments and recombinant vectors encoding TLR-4, and the creation and use of recombinant host cells through the application of DNA technology, that express TLR-4 for the purposes of increasing the recognition of endotoxin by a host cell. The present invention shows that the long sought after gene at the lps locus is TLR-4. The TLR-4 a receptor for LPS and is thus the protein that binds to and recognizes LPS from the bacteria cell wall. It is recognition of the endotoxin by the TLR-4 that allows an animal to mount an immune response against the invading bacteria. If the TLR-4 peptide is mutated such that it is unable to recognize the LPS the animal will not be able to mount an immune response.

TLR-4 is a member of the IL-1 family of receptors. U.S. Pat. No. 5,786,331; U.S. Pat. No. 5,776,731; U.S. Pat. No. 5,767,234; U.S. Pat. No. 5,767,064; U.S. Pat. No. 5,726,148; U.S. Pat. No. 5,608,035; U.S. Pat. No. 5,508,262; U.S. Pat. No. 5,488,032; U.S. Pat. No. 5,464,937 each specifically incorporated herein by reference, describe the IL-1 receptor and methods and compositions related to modulating the activity thereof. The present invention contemplates using techniques and compositions similar to those described in these patents for use with the TLR-4 receptor of the present invention.

DNA segments, recombinant vectors, recombinant host cells and expression methods using sequences of the human TLR-4 (SEQ ID NO:1, SEQ ID NO:3 and SEQ ID NO:47), rat (SEQ ID NO:5) and mouse (SEQ ID NO:45, SEQ ID NO:46 and SEQ ID NO:48) also are provided. These sequences express human polypeptides of SEQ ID NO:2, SEQ ID NO:4 and SEQ ID NO:98, rat polypeptide of SEQ ID NO:6, and mouse polypeptide of SEQ ID NO:99, respectively. Each of the foregoing genes are included within all aspects of the following description. The present invention concerns DNA segments, isolatable from mammalian and human cells, that are free from total genomic DNA and that are capable of expressing a functional TLR-4 protein. As used herein, the term "DNA segment" refers to a DNA molecule that has been isolated free of other genomic DNA of a particular species. Therefore, a DNA segment encoding a TLR-4 protein refers to a DNA segment that contains TLR-4 protein coding sequences yet is isolated away from, or purified free from, total mammalian or human genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified TLR-4 protein or subunit gene refers to a DNA segment including purified TLR-4 protein or subunit protein coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, complementary DNA (cDNA) sequences and smaller engineered gene segments that express, or may be adapted to express, TLR-4 proteins, polypeptides, domains, peptides, fusion proteins and mutants.

"Isolated substantially away from other coding sequences" means that the gene of interest, in this case a TLR-4 protein gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode a TLR-4 protein or subunit that includes within its amino acid sequence a contiguous amino acid sequence in accordance with, or essentially as set forth in, SEQ ID NO:2, SEQ ID NO:4, SEQ ID NO:6, SEQ ID NO:98 or SEQ ID NO:99 corresponding to TLR-4 in humans, rat and mouse, respectively. Moreover, in other particular embodiments, the invention concerns isolated DNA segments and recombinant vectors that encode a TLR-4 protein or subunit that includes within its amino acid sequence the substantially full length protein sequence of SEQ ID NO:2, SEQ ID NO:4, SEQ ID NO:6, SEQ ID NO:98 or SEQ ID NO:99.

The term "a sequence essentially as set forth in SEQ ID NO:2, SEQ ID NO:4, SEQ ID NO:6, SEQ ID NO:98 or SEQ ID NO:99" means that the sequence substantially corresponds to a portion of SEQ ID NO:2, SEQ ID NO:4, SEQ ID NO:6, SEQ ID NO:98 or SEQ ID NO:99 and has relatively few amino acids that are not identical to, or a biologically functional equivalent of, the amino acids of SEQ ID NO:2, SEQ ID NO:4, SEQ ID NO:6, SEQ ID NO:98 or SEQ ID NO:99. The term "biologically functional equivalent" is well understood in the art and is further defined in detail herein. Accordingly, sequences that have between about 85% and about 90%; or more preferably, between about 91% and about 95%; or even more preferably, between about 96% and about 99%; of amino acids that are identical or functionally equivalent to the amino acids of SEQ ID NO:2, SEQ ID NO:4, SEQ ID NO:6, SEQ ID NO:98 or SEQ ID NO:99 will be sequences that are "essentially as set forth in SEQ ID NO:2, SEQ ID NO:4, SEQ ID NO:6, SEQ ID NO:98 or SEQ ID NO:99", provided the biological activity of the protein is maintained.

In certain other embodiments, the invention concerns isolated DNA segments and recombinant vectors that include within their sequence a nucleic acid sequence essentially as set forth in SEQ ID NO:1, SEQ ID NO:3, SEQ ID NO:5, SEQ ID NO:45, SEQ ID NO:46, SEQ ID NO:47 and SEQ ID NO:48. The term "essentially as set forth in SEQ ID NO:1, SEQ ID NO:3, SEQ ID NO:5, SEQ ID NO:45, SEQ ID NO:46, SEQ ID NO:47 and SEQ ID NO:48" is used in the same sense as described above and means that the nucleic acid sequence substantially corresponds to a portion of SEQ ID NO:1, SEQ ID NO:3, SEQ ID NO:5, SEQ ID NO:45, SEQ ID NO:46, SEQ ID NO:47 or SEQ ID NO:48 and has relatively few codons that are not identical, or functionally equivalent, to the codons of SEQ ID NO:1, SEQ ID NO:3, SEQ ID NO:5, SEQ ID NO:45, SEQ ID NO:46, SEQ ID NO:47 or SEQ ID NO:48. Again, DNA segments that encode TLR-4 or related proteins or subunits will be most preferred.

The term "functionally equivalent codon" is used herein to refer to codons that encode the same amino acid, such as the six codons for arginine or serine, and also refers to codons that encode biologically equivalent amino acids (see Codon Table, below).

CODON TABLE

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |

-continued

| CODON TABLE | | | | | | | | | |
|---|---|---|---|---|---|---|---|---|---|
| Amino Acids | | | Codons | | | | | | |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have between about 75% and about 79%; or more preferably, between about 80% and about 89%; or even more preferably, between about 90% and about 99%; of nucleotides that are identical to the nucleotides of SEQ ID NO:1, SEQ ID NO:3, SEQ ID NO:5, SEQ ID NO:45 or SEQ ID NO:46 will be sequences that are "essentially as set forth in SEQ ID NO:1, SEQ ID NO:3, SEQ ID NO:5, SEQ ID NO:45, SEQ ID NO:46, SEQ ID NO:47 or SEQ ID NO:48."

Sequences that are essentially the same as those set forth in SEQ ID NO:1, SEQ ID NO:3, SEQ ID NO:5, SEQ ID NO:45, SEQ ID NO:46, SEQ ID NO:47 or SEQ ID NO:48 may also be functionally defined as sequences that are capable of hybridizing to a nucleic acid segment containing the complement of SEQ ID NO:1, SEQ ID NO:3, SEQ ID NO:5, SEQ ID NO:45, SEQ ID NO:46, SEQ ID NO:47 or SEQ ID NO:48 under relatively stringent conditions. Suitable relatively stringent hybridization conditions will be well known to those of skill in the art.

Suitable standard hybridization conditions for the present invention include, for example, hybridization in 50% formamide, 5× Denhardts' solution, 5×SSC, 25 mM sodium phosphate, 0.1% SDS and 100 μg/ml of denatured salmon sperm DNA at 42° C. for 16 hours followed by 1 hour sequential washes with 0.1×SSC, 0.1% SDS solution at 60° C. to remove the desired amount of background signal. Lower stringency hybridization conditions for the present invention include, for example, hybridization in 35% formamide, 5× Denhardts' solution, 5×SSC, 25 mM sodium phosphate, 0.1% SDS and 100 μg/ml denatured salmon sperm DNA or *E. coli* DNA at 42° C. for 16 hours followed by sequential washes with 0.8×SSC, 0.1% SDS at 55° C. Those of skill in the art will recognize that conditions can be readily adjusted to obtain the desired level of stringency.

Naturally, the present invention also encompasses DNA segments that are complementary, or essentially complementary, to the sequence set forth in SEQ ID NO:1, SEQ ID NO:3, SEQ ID NO:5, SEQ ID NO:45, SEQ ID NO:46, SEQ ID NO:47 or SEQ ID NO:48. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1, SEQ ID NO:3, SEQ ID NO:5, SEQ ID NO:45, SEQ ID NO:46, SEQ ID NO:47 or SEQ ID NO:48, under relatively stringent conditions such as those described immediately above.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a short contiguous stretch identical to or complementary to SEQ ID NO:1, SEQ ID NO:3, SEQ ID NO:5, SEQ ID NO:45, SEQ ID NO:46, SEQ ID NO:47 or SEQ ID NO:48, such as about 22–27 or about 32–36 nucleotides, and that are up to about 30,000 or 20,000, or about 10,000, or about 5,000 base pairs in length, with segments of about 3,000 being preferred in certain cases. DNA segments with total lengths of about 1,000, about 500, about 200, about 100 and about 50 base pairs in length (including all intermediate lengths) are also contemplated to be useful.

It will be readily understood that "intermediate lengths," in these contexts, means any length between the quoted ranges, such as 22, 23, 24, 25, 26, 27, 28, 29, etc; 30, 31, 32, 33, 34, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002, 15,000, 20,000, 30,000 and the like.

The various probes and primers designed around the disclosed nucleotide sequences of the present invention may be of any length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 25-mer, the probes correspond to bases 1 to 25, 2 to 26, 3 to 27 . . . and so on. For a 30-mer, the probes correspond to bases 1 to 30, 2 to 31, 3 to 32 . . . and so on. For a 35-mer, the probes correspond to bases 1 to 35, 2 to 36, 3 to 37 . . . and so on.

It will also be understood that this invention is not limited to the particular nucleic acid and amino acid sequences of SEQ ID NO:1, SEQ ID NO:3, SEQ ID NO:5, SEQ ID NO:45, SEQ ID NO:46, SEQ ID NO:47 or SEQ ID NO:48. Recombinant vectors and isolated DNA segments may therefore variously include these coding regions themselves, coding regions bearing selected alterations or modifications in the basic coding region, or they may encode larger polypeptides that nevertheless include such coding regions or may encode biologically functional equivalent proteins or peptides that have variant amino acids sequences.

The DNA segments of the present invention encompass biologically functional equivalent TLR-4 proteins. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine transcription, elongation or Tat binding activity at the molecular level.

One may also prepare fusion proteins and peptides, e.g., where the TLR-4 protein coding regions are aligned within the same expression unit with other proteins or peptides having desired functions, such as for purification or immunodetection purposes (e.g., proteins that may be purified by affinity chromatography and enzyme label coding regions, respectively).

Encompassed by the invention are DNA segments encoding relatively small peptides, such as, for example, peptides of from about 15 to about 50 amino acids in length, and more preferably, of from about 15 to about 30 amino acids in length; and also larger polypeptides up to and including proteins corresponding to the full-length sequences set forth in SEQ ID NO:2, SEQ ID NO:4, SEQ ID NO:6, SEQ ID NO:98 and SEQ ID NO:99 6.

It is proposed that the DNA segments of the present invention may be employed for a variety of applications. For example, a particularly useful application concerns the recombinant production of the individual subunits or proteins or peptides whose structure is derived from that of the subunits, or in the recombinant production of the holoenzyme following co-expression of the two subunits. Additionally, the TLR-4-encoding DNA segments of the present invention can also be used in the preparation of nucleic acid probes or primers, which can, for example, be used in the identification and cloning of TLR-4 genes or related genomic sequences, or in the study of subunit(s) expression, and the like.

E. Immunologic Detection Methods

In one embodiment, the diagnostic approach will be immunologic. The reagents will include antibodies to the TLR-4 and TLR-4 mutants, or fragments thereof, and will further include reagents capable of detecting an antibody immunoreactive with an such compound. Detection methods include, but are not limited to ELISA, RIA and immunoblots, as discussed elsewhere in the specification.

Antibodies against TLR-4 and TLR-4 mutants isolated using the methodology described will be useful in the present invention, primarily in assays for the detection of of individuals suspectible to Gram-negative infection. Means for preparing and characterizing antibodies are well known in the art (see, e.g., Antibodies: A Laboratory Manual, Cold Spring Harbor Laboratory, 1988; incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat.

Immunogenic compositions of the invention include TLR-4, TLR-4 mutants or fragments and the like. As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a compound to a carrier protein are well known in the art and include glutaraldehyde, m-maleimidobenzoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages, but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate.

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid. Radioimmunoassays, enzyme immunoassays, cytotoxicity assays, plaque assays, dot immunobinding assays, and the like, may be used.

Where one desires to generate an antibody with defined activity, one would generally screen the candidate hybridomas to identify those hybridomas that produce antibodies that have the desired inhibitory or stimulatory properties. Any selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Certain aspects of the present invention relates to the detection of TLR-4 and mutants thereof. One method of detecting such compounds uses immunoassays for agents of the present invention. Antibodies that recognize TLR-4 or TLR-4 mutants of the present invention are contemplated to be useful in these immunoassays.

Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful.

In one exemplary ELISA, the antibodies of the invention are immobilized onto a selected surface exhibiting protein affinity, such as a well in a polystyrene microtiter plate. Then, a test composition suspected of containing the desired antigen, such as a clinical sample, is added to the wells. After binding and washing to remove non-specifically bound immune complexes, the bound antigen may be detected. Detection is generally achieved by the addition of another antibody, specific for the desired antigen, that is linked to a detectable label. This type of ELISA is a simple "sandwich ELISA". Detection may also be achieved by the addition of a second antibody specific for the desired antigen, followed by the addition of a third antibody that has binding affinity for the second antibody, with the third antibody being linked to a detectable label.

In another exemplary ELISA, the samples suspected of containing the desired antigen are immobilized onto the well surface and then contacted with the antibodies of the invention. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

Antigen or antibodies may also be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of the antigen or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. Washing often includes washing with a solution of PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation, e.g., incubation for 2 hours at room temperature in a PBS-containing solution such as PBS-Tween.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid (ABTS) and $H_2O_2$, in the case of peroxidase as the enzyme label. Quantification is then achieved by measuring the degree of color generation, e.g., using a visible spectra spectrophotometer.

Alternatively, the label may be a chemiluminescent one. The use of such labels is described in U.S. Pat. Nos. 5,310,687, 5,238,808 and 5,221,605.

Assays for TLR-4 and TLR-4 mutants of the present invention also can determine normal/abnormal tissue distribution for diagnostic purposes. Methods for in vitro and in situ analysis are well known and involve assessing binding of antigen-specific antibodies to tissues, cells or cell extracts. These are conventional techniques well within the grasp of those skilled in the art. For example, the antibodies of the present invention may be used in conjunction with both fresh-frozen and formalin-fixed, paraffin-embedded tissue blocks prepared for study by immunohistochemistry (IHC). Each tissue block may consist of 50 mg of residual "pulverized" prostate tumor. The method of preparing tissue blocks from these particulate specimens has been successfully used in previous IHC studies of various prognostic factors, e.g., in breast cancer, and is well known to those of skill in the art. (Abbondanzo et al., 1990; Allred et al., 1990; Brown et al., 1990).

Briefly, frozen-sections may be prepared by rehydrating 50 ng of frozen pulverized tumor at room temperature in PBS in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections containing an average of about 500 remarkably intact tumor cells.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

F. Nucleic Acid Detection

In addition to their use in directing the expression of the TLR-4 protein, the nucleic acid sequences disclosed herein also have a variety of other uses. For example, they also have utility as probes or primers in nucleic acid hybridization embodiments.

i. Hybridization

The use of a hybridization probe of between 20 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production. These chemical means can include PCR™ technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For certain applications, for example, substitution of nucleotides by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a low stringency hybridization conditions for the present invention of hybridization in 35% formamide, 5× Denhardts' solution, 5×SSC, 25 mM sodium phosphate, 0.1% SDS and 100 μg/ml denatured salmon sperm DNA or *E. coli* DNA at 42° C. for 16 hours followed by sequential washes with 0.8×SSC, 0.1% SDS at 55° C. allows for cross-species hybridization to homologous proteins to occur. Thus, hybridization conditions can be readily manipulated depending on the desired results.

In other embodiments, hybridization may be achieved under conditions of, for example, 50% formamide, 5× Denhardts' solution, 5×SSC, 25 mM sodium phosphate, 0.1% SDS and 100 μg/ml of denatured salmon sperm DNA at 42° C. for 16 hours followed by 1 hour sequential washes with 0.1×SSC, 0.1% SDS solution at 60° C. to remove the desired amount of background signal.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

ii. Amplification and PCR™

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a cDNA.

Pairs of primers that selectively hybridize to nucleic acids corresponding to a TLR-4 protein or a mutant thereof are contacted with the isolated nucleic acid under conditions that permit selective hybridization. The term "primer", as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and each incorporated herein by reference in entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ (RT-PCR™) amplification procedure may be performed in order to quantify the amount of mRNA amplified or to prepare cDNA from the desired mRNA. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio] -triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., PCT Application WO 88/10315, incorporated herein by reference. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990, incorporated by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

All the essential materials and reagents required for detecting TLR-4 protein markers in a biological sample may be assembled together in a kit. This generally will comprise preselected primers for specific markers. Also included may be enzymes suitable for amplifying nucleic acids including various polymerases (RT, Taq, etc.), deoxynucleotides and buffers to provide the necessary reaction mixture for amplification.

Such kits generally will comprise, in suitable means, distinct containers for each individual reagent and enzyme as well as for each marker primer pair. Preferred pairs of primers for amplifying nucleic acids are selected to amplify the sequences specified in SEQ ID NO:1, SEQ ID NO:3, SEQ ID NO:5, SEQ ID NO:45, SEQ ID NO:46, SEQ ID NO:47 or SEQ ID NO:48.

In another embodiment, such kits will comprise hybridization probes specific for TLR-4 protein chosen from a group including nucleic acids corresponding to the sequences specified in SEQ ID NO:1, SEQ ID NO:3, SEQ ID NO:5, SEQ ID NO:45, SEQ ID NO:46, SEQ ID NO:47 or SEQ ID NO:48. Such kits generally will comprise, in suitable means, distinct containers for each individual reagent and enzyme as well as for each marker hybridization probe.

iii. Other Assays

Other methods for genetic screening to accurately detect genetic changes which may be caused by disease, such as bacterial infections that alter normal cellular production and processing, in genomic DNA, cDNA or RNA samples may be employed, depending on the specific situation.

For example, one method of screening for genetic variation is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as +.

Currently available RNase mismatch cleavage assays, including those performed according to U.S. Pat. No. 4,946,773, require the use of radiolabeled RNA probes. Myers and Maniatis in U.S. Pat. No. 4,946,773 describe the detection of base pair mismatches using RNase A. Other investigators have described the use of *E. coli* enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase protection assay was first used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations. In this type of RNase A mismatch cleavage assay, radiolabeled RNA probes transcribed in vitro from wild type sequences, are hybridized to complementary target regions derived from test samples. The test target generally comprises DNA (either genomic DNA or DNA amplified by cloning in plasmids or by PCR™), although RNA targets (endogenous mRNA) have occasionally been used. If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches.

G. Recombinant Vectors, Host Cells and Expression

Recombinant vectors form important further aspects of the present invention. The term "expression vector or construct" means any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense constructs.

Particularly useful vectors are contemplated to be those vectors in which the coding portion of the DNA segment, whether encoding a full length protein or smaller peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control" or "under transcriptional control" means that the promoter is in the correct location and orientation in relation to the nucleic acid to control RNA polymerase initiation and expression of the gene.

The promoter may be in the form of the promoter that is naturally associated with a TLR-4 protein gene, as may be obtained by isolating the 5' non-coding sequences located upstream of the coding segment or exon, for example, using recombinant cloning and/or PCR™ technology, in connection with the compositions disclosed herein (PCR™ technology is disclosed in U.S. Pat. No. 4,683,202 and U.S. Pat. No. 4,682,195, each incorporated herein by reference). Additionally, the toll-like receptors from *Drosophila* are well known to those of skill in the art. The promoter regions of these nucleic acids may be useful herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a TLR-4 protein gene in its natural environment. Such promoters may include promoters normally associated with other genes, and/or promoters isolated from any other bacterial, viral, eukaryotic, or mammalian cell.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989), incorporated herein by reference. The promoters employed may be constitutive, or inducible, and can be used under the appropriate conditions to direct high level expression of the introduced DNA segment, such as is advantageous in the large-scale production of recombinant proteins or peptides.

At least one module in a promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Preferred promoters include those derived from HSV, including the HNF1$\alpha$ promoter. Another preferred embodiment is the tetracycline controlled promoter.

In various other embodiments, the human cytomegalovirus (CMV) immediate early gene promoter, the Simian virus 40 (SV40) early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. The following tables list several elements/promoters which may be employed, in the context of the present invention, to regulate the expression of TLR-4 protein or subunit gene. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

PROMOTER TABLE

| PROMOTER | REFERENCES |
|---|---|
| Immunoglobulin Heavy Chain | Hanerji et al., 1983; Gilles et al., 1983; Grosschedl and Baltimore, 1985; Imler et al., 1987; Weinberger et al., 1988; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRα | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, 1990 |
| α-Fetoprotein | Godbout et al., 1988 |
| τ-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $\alpha_{1\text{-Antitrypain}}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; deVilliers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a,b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |

-continued

PROMOTER TABLE

| PROMOTER | REFERENCES |
|---|---|
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

ENHANCER TABLE

| | Inducer | References |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987; Karin ®, 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Fonta et al., 1985; Sakai et al., 1986 |
| β-Interferon | poly(rI)X poly(rc) | Tavernier et al., 1983 |
| Adenovirus 5 E2 | Ela | Imperiale and Nevins, 1984 |
| Collagenase | Phorbol Ester (TPA) | Angle et al., 1987a |
| Stromelysin | Phorbol Ester (TPA) | Angle et al., 1987b |
| SV40 | Phorbol Ester (TFA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2kb | Interferon | Blanar et al., 1989 |
| HSP70 | Ela, SV40 Large T Antigen | Taylor et al., 1989; Taylor and Kingston, 1990a,b |
| Proliferin | Phorbol Ester-TPA | Mordacq and Linzer, 1989 |
| Tumor Necrosis Factor | FMA | Hensel et al., 1989 |
| Thyroid Stimulating Hormone α Gene | Thyroid Hormone | Chatterjee et al., 1989 |

Turning to the expression of the TLR-4 proteins of the present invention, once a suitable clone or clones have been obtained, whether they be cDNA based or genomic, one may proceed to prepare an expression system. The engineering of DNA segment(s) for expression in a prokaryotic or eukaryotic system may be performed by techniques generally known to those of skill in recombinant expression. It is believed that virtually any expression system may be employed in the expression of the proteins of the present invention.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the possibility of employing a genomic version of a particular gene where desired is not excluded.

In expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

As used herein, the terms "engineered" and "recombinant" cells are intended to refer to a cell into which an exogenous DNA segment or gene, such as a cDNA or gene encoding a TLR-4 protein has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant TLR-4 protein, whether mutant or wild-type, in accordance with the present invention one would prepare an expression vector that comprises a TLR-4 protein-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, the like.

Promoters that are most commonly used in recombinant DNA construction include the b-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

The following details concerning recombinant protein production in bacterial cells, such as *E. coli*, are provided by way of exemplary information on recombinant protein production in general, the adaptation of which to a particular recombinant expression system will be known to those of skill in the art.

Bacterial cells, for example, *E. coli*, containing the expression vector are grown in any of a number of suitable media, for example, LB. The expression of the recombinant protein may be induced, e.g., by adding IPTG to the media or by switching incubation to a higher temperature. After culturing the bacteria for a further period, generally of between 2 and 24 hours, the cells are collected by centrifugation and washed to remove residual media.

The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents, such as β-mercaptoethanol or DTT (dithiothreitol).

Under some circumstances, it may be advantageous to incubate the protein for several hours under conditions suitable for the protein to undergo a refolding process into a conformation which more closely resembles that of the native protein. Such conditions generally include low protein concentrations, less than 500 mg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE, or with antibodies specific for the native molecule (which can be obtained from animals vaccinated with the native molecule or smaller quantities of recombinant protein). Following refolding, the protein can then be purified further and separated from the refolding mixture by chromatography on any of several supports including ion exchange resins, gel permeation resins or on a variety of affinity columns.

For expression in *Saccharomyces*, the plasmid YRp7, for example, is commonly used. This plasmid already contains the trp1 gene which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to microorganisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more Toll protein coding sequences.

In a useful insect system, *Autograph californica* nuclear polyhidrosis virus (AcNPV) is used as a vector to express foreign genes. The virus grows in *Spodoptera frugiperda* cells. The TLR-4 protein coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051, Smith, incorporated herein by reference).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein.

Different host cells have characteristic and specific mechanisms for the post-translational processing and modification of proteins. Appropriate cells lines or host systems can be chosen to ensure the correct modification and processing of the foreign protein expressed.

Expression vectors for use in mammalian such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired TLR-4 protein gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing TLR-4 proteins in infected hosts.

Specific initiation signals may also be required for efficient translation TLR-4 protein coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly-A addition site is placed about 30 to 2000 nucleotides "downstream" of the termination site of the protein at a position prior to transcription termination.

For long-term, high-yield production of recombinant TLR-4 proteins, stable expression is preferred. For example, cell lines that stably express constructs TLR-4 proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus (HSV) tk, hypoxanthine-guanine phosphoribosyltransferase (hgprt) and adenine phosphoribosyltransferase genes (aprt), in tk-, hgprt- or aprt-cells, respectively. Also, antimetabolite resistance can be used as the basis of selection for dhfr, that confers resistance to methotrexate; gpt, that confers resistance to mycophenolic acid; neo, that confers resistance to the aminoglycoside G-418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the TLR-4 protein of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural cells is indicative of overexpression, as is a relative abundance of the specific protein in relation to the other proteins produced by the host cell and, e.g., visible on a gel.

H. Kits

All the essential materials and reagents required for detecting TLR-4 polynucleotides or polypeptides may be assembled together in a kit. When the components of the kit are provided in one or more liquid solutions, the liquid solution preferably is an aqueous solution, with a sterile aqueous solution being particularly preferred. Each component preferably is supplied in a separate container.

For therapeutic uses, a polynucleotide or candidate substance, as identified according to the methods disclosed herein, may be formulated into a single or separate pharmaceutically acceptable syringeable composition. In this case, the container means may itself be an inhalant, syringe, pipette, eye dropper, or other such like apparatus, from which the formulation may be applied to an infected area of the body, injected into an animal, or even applied to and mixed with the other components of the kit.

The components of these kits may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of active compounds or explaining assays for detecting TLR-4 or TLR-4 mutants in samples.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle. Other instrumentation includes devices that permit the reading or monitoring of reactions in vitro.

I. Biological Functional Equivalents

As will be understood by those of skill in the art, modification and changes may be made in the structure of the TLR-4 protein and subunits and still obtain a molecule having like or otherwise desirable characteristics. For example, certain amino acids may be substituted for other amino acids in a protein structure without appreciable loss of interactive binding capacity. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. It is thus contemplated that various changes may be made in the sequence of TLR-4 proteins or subunits (or underlying DNA) without appreciable loss of their biological utility or activity.

Equally, the same considerations may be employed to create a TLR-4 protein or subunit with counterveiling (e.g., antagonistic) properties. This is relevant to the present invention in which TLR-4 analogues without endotoxin recognition activity are contemplated to be useful in inhibiting the secretion of TNF.

In terms of functional equivalents, it is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. In particular, where small peptides are concerned, less amino acids may be changed. Of course, a plurality of distinct proteins/peptides with different substitutions may easily be made and used in accordance with the invention.

It is also well understood that where certain residues are shown to be particularly important to the biological or structural properties of a protein or peptide, e.g., residues in the active site of an enzyme or to maintain protein function.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented hereinabove for use in such embodiments, as well as for other uses, such as in the design of probes and primers and the like.

i. Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

J. Inhibitors, Stimulators and Screening Assays

In still further embodiments, the present invention provides methods for identifying new TLR-4 inhibitory or stimulatory compounds, which may be termed as "candidate substances." It is contemplated that such screening techniques will prove useful in the general identification of any compound that will serve the purpose of inhibiting or stimulating TLR-4 directed signaling of TNF secretion, and in preferred embodiments, will provide candidate compounds.

It is further contemplated that useful compounds in this regard will in no way be limited to proteinaceous or peptidyl compounds. In fact, it may prove to be the case that the most useful pharmacological compounds for identification through application of the screening assays will be non-peptidyl in nature and, e.g., which will serve to inhibit TNF secretion through a tight binding or other chemical interaction. Candidate substances may be obtained from libraries of synthetic chemicals, or from natural samples, such as rain forest and marine samples.

i. Assay Formats

The present invention provides methods of screening for modulators of LPS mediated response by monitoring the standard activity profile of TLR-4 in the presence and absence of the candidate substance and comparing such results. It is contemplated that this screening technique will prove useful in the general identification of a compound that will serve the purpose of promoting, augmenting or increasing the activity of TLR-4 of a macrophage cell. Such compounds will be useful in the treatment of various bacterial infections.

In these embodiments, the present invention is directed to a method for determining the ability of a candidate substance to stimulate the wild-type TLR-4 of cells that either naturally express TLR-4 or have been engineered to express TLR-4 as described herein. The method including generally the steps of:

(i) providing a cell expressing a TLR-4 polypeptide;
(ii) determining the activity of said TLR-4 polypeptide; and
(iii) contacting said cell with a candidate substance; and
(iv) comparing the TLR-4 activity of the cell in step (iii) with the TLR-4 activity observed when said candidate substance is not added, wherein an alteration in the activity indicates that said candidate substance is a modulator of said apoptotic activity.

To identify a candidate substance as being capable of stimulating TLR-4 in the assay above, one would measure or determine the activity in the absence of the added candidate substance. One would then add the candidate substance to the cell and determine the activity in the presence of the candidate substance. A candidate substance which increases the activity or capacity relative to activity observed in its absence is indicative of a candidate substance with stimulatory capability.

In particular embodiments, any compound that stimulates the production of IFN or related cytokines and mediates the inflammatory response to LPS or LPS containing moieties (e.g., Gram negative bacteria). As stated above, a "candidate substance" refers to any molecule that is capable of modulating the activity of TLR-4. The candidate substance may be a protein or fragment thereof, a small molecule inhibitor, or even a nucleic acid molecule. Accordingly, the active compounds may include fragments or parts of naturally-occurring compounds or may be found as active combinations of known compounds which are otherwise inactive.

Accordingly, the present invention provides screening assays to identify agents which stimulate a cellular immune and/or response, it is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

Thus, it is understood that the candidate substance identified by the present invention may be polypeptide, polynucleotide, small molecule inhibitors or any other compounds that may be designed through rational drug design starting from known stimulators of immune and/or inflammatory response. For example, Barrett et al., describe peptides and compounds that bind the IL-1 receptor (U.S. Pat. No. 5,786,331, specifically incorporated herein by reference) and U.S. Pat. No. 5,508,262 describes an IL-1 receptor agonist. It may be that, as TLR-4 is an analogue of the IL-1 receptor, agonists of IL-1 may also be agonists of TLR-4. Alternatively, known modulators of IL-1 receptors may prove to be a useful starting point in a rational drug design strategy that will yield experimentally, therapeutically or clinically relevant compounds that modulate the activity of TLR-4 and the immune response that TLR-4 mediates.

The candidate screening assays are simple to set up and perform. Thus, in assaying for a candidate substance, after obtaining a cell expressing functional TLR-4, one will admix a candidate substance with the cell, under conditions which would allow measurable TNF secretion to occur. In this fashion, one can measure the ability of the candidate substance to stimulate the TNF secretory response of the cell in the absence of the candidate substance. One would then measure the response in the presence of the candidate substance and determine the effect of the candidate substance.

"Effective amounts" in certain circumstances are those amounts effective to reproducibly stimulate the TNF secretory (inflammatory) response from the cell in comparison to their normal levels. Compounds that achieve significant appropriate changes in activity will be used.

Significant changes in inflammatory response, e.g., as measured TNF production, splenocyte activity and the like are represented by an increase/decrease in the response of at least about 30%–40%, and most preferably, by changes of at least about 50%, with higher values of course being possible.

It will, of course, be understood that all the screening methods of the present invention are useful in themselves notwithstanding the fact that effective candidates may not be found. The invention provides methods for screening for such candidates, not solely methods of finding them.

ii. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for TLR-4 or a fragment thereof. This could be accomplished by x-ray crystallograph, computer modeling or by a combination of both approaches. An alternative approach, "alanine scan," involves the random replacement of residues throughout molecule with alanine, and the resulting affect on function determined.

It also is possible to isolate a specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have activity as stimulators, inhibitors, agonists, antagonists of TLR-4 or molecules affected by TLR-4 function. Such rational drug design may start with lead compounds already known to those of skill in the art. By virtue of the availability of cloned TLR-4 sequences, sufficient amounts of these proteins can be produced to perform crystallographic studies. In addition, knowledge of the polypeptide sequences permits computer employed predictions of structure-function relationships. Particularly useful agents that may be found by the present invention will be those agents that stimulate the TLR-4 receptor response to LPS and therefore increase the immune attack against LPS. Such agents may bind to the TLR-4.

K. Formulations and Routes for Administration to Patients

Where clinical applications are contemplated, it will be necessary to prepare the expression vectors or candidate substances of the present invention as pharmaceutical compositions, i.e., in a form appropriate for in vivo applications. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds may be administered via any suitable route, including parenterally or by injection. Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

In this connection, sterile aqueous media which can be employed will be known to those of skill in the art in light of the present disclosure. For example, a unit dose could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

L. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials And Methods

Mice

[SWR×C3H/HeJ]×C3H/HeJ F2 animals. SWR mice were obtained from Jackson Laboratories, and maintained in the Animal Resource Center of the University of TX, Southwestern Medical Center. C3H/HeJ mice were also obtained from Jackson Laboratories (Bar Harbor, Me.). F1 mice obtained by the cross of C3H/HeJ males to SWR females were backcrossed at eight weeks of age to C3H/HeJ animals of both sexes. 493 F2 animals were used at six to eight weeks of age for analysis of LPS response phenotype and preparation of genomic DNA. In this panel of animals, both splenocyte responses and macrophage TNF production were assayed as endpoints of endotoxin response determination.

[C57BL/6×C3H/HeJ]×C3H/HeJ F2 animals. 1600 F2 mice were produced at the Jackson Laboratories, and shipped to the Animal Resource Center of the University of TX, Southwestern Medical center at 5 to 8 weeks of age. Animals were immediately ear-tagged for identification and tail cuttings were taken for identification. For this panel of animals, selection of individuals with recombination between markers D4MIT164 and D4MIT27 was made by PCR analysis. All but a few non-recombinants were sacrificed; the remaining non-recombinants were used as controls (obligate $Lps^d$ heterozygotes or homozygotes with representative genetic variability at other loci) with each assay series. In this panel of animals, macrophage TNF production was used as the sole endpoint of endotoxin response determination.

Preparation of Genomic DNA

Tail fragments approximately 5 mm in length were placed in 1.5 ml microcentrifuge tubes containing 650 μl of SSTE buffer, in which proteinase K had been dissolved at a concentration of 1 mg/ml. SSTE buffer was made by bringing 10 ml of 10% SDS, 2 ml of 5 M NaCl, 5 ml of 1M tris, pH 8.0, and 3 ml of 0.5 M EDTA, pH 8.0 to a final volume of 100 ml with distilled water. The tissue was digested overnight at 55° C. 30 μl of RNase T1 (5 U/μl) was then added to each tube, and a second incubation was carried out at 37° C. for one hour. DNA was then extracted with phenol, 1:1 phenol/chloroform solution, and finally chloroform. After addition of 1/10 volume of 3M sodium acetate solution, samples were precipitated with two volumes of ethanol. Pellets were dried and redissolved in 300 μl of TE solution.

Assays for LPS Responsiveness

Splenocyte proliferation assays were used to type all 493 animals produced by the backcross of C3H/HeJ mice to SWR mice, and were performed by harvesting 30 to 40 million spleen cells from each animal. Erythrocytes were lysed with ammonium chloride, and the remaining cell population, predominantly lymphocytes, were plated at a density of 1 million cells per well, in triplicate, in round bottom 96-well plates. Cells were stimulated with Con A as a control for viability, and also with LPS at two concentrations (1.0 μg/ml and 5.0 μg/ml) for a period of 72 hours, in the presence of tritiated thymidine. All samples showing Con A responses that exceeded 100,000 CPM were retained for analysis; those occasional samples that had smaller Con A responses were discarded from consideration. A cell harvester was used to collect the lymphocytes, and measurements of thymidine incorporation were made. An index of LPS responsiveness (I) was calculated for each sample as follows:

$$I=[\text{mean } CPM \text{ of } LPS\text{-induced splenocytes}]/[\text{mean } CPM \text{ of non-induced splenocytes}]$$

For simplicity, only the data pertaining to stimulation with 5 μg/ml LPS are reported in this paper.

TNF production by peritoneal macrophages was used to type all 1600 animals produced by the backcross of C3H/HeJ mice to C57BL/6 mice. TNF mediated cytolytic activity is released by LPS-responsive cells following endotoxin stimulation in vitro, and was used to quantitate LPS sensitivity. Eight-week-old mice were injected intraperitoneally with sterile Brewer's thioglycollate broth (3.0 ml). 4 days later, peritoneal exudate macrophages were harvested by peritoneal lavage. $2\times10^5$ cells from each mouse were plated in 24 well plates, and after adherence, stimulated by LPS at concentrations of 0.01 and 0.5 μg/ml. After 16 hours, the medium was harvested and assayed for TNF content. TNF assays were performed using the L929 cell method, in which cells were plated in 96 well plates, exposed to the macrophage medium, and after rinsing, stained with crystal violet. The intensity of staining, measured in a microplate reader at 590 nm, corresponded to the fraction of surviving cells (Cseh and Beutler, 1989). Results were expressed as % cytotoxicity, defined as:

$$[1-OD_{[sample\ well]}/OD_{[control]}]\times100$$

Both the splenocyte proliferation assay and the macrophage response assay permitted unambiguous discrimination between responders (heterozygotes for the $Lps^d$ allele) and nonresponders (homozygotes for the $Lps^d$ allele), but the macrophage response assay showed less day-to-day variability and was more convenient to perform.

Contig Assembly.

YACs were isolated from the Research Genetics mouse YAC library by PCR-based screening of a matrix consisting of superpools, pools, and plates. The probes initially employed in this process were the map-pair markers: D4MIT82, D4MIT218, D4MIT325, D4MIT244, D4MIT25, NdS9, D4MIT178, D4MIT7, D4MIT132, and D4MIT83. A total of 20YACs were isolated in this manner. All were sized by pulsed-field gel electrophoresis. The ends of all of the YACs were checked by sequencing. In some cases, continuity with adjoining BACs was immediately established. When highly repetitive sequence was present, internal sequences were determined by cloning rather large fragments of the YAC that contained the end. If when no overlap was established, additional YACs were isolated using the end sequence. In several instances, after two such cycles of chromosome walking, it was concluded that the original YACs were chimeric.

Unique sequences derived from shotgun cloning of YACs, as well as the above mentioned D4MIT markers, were used to identify BAC clones, chiefly by screening the Research Genetics mouse BAC library. Two additional clones (BACs 84C8 and 389F15) were obtained by screening BAC libraries maintained at Genome Systems (St. Louis, Mo.). A contiguous span of BACs crossing most of the interval was produced, as in the case of the YAC contig, by chromosome walking. Among the BACs that were isolated, only two proved to be chimeric; the chimeric BACs are not presented in any of the Figures.

Novel Marker Identification.

YACs were fragmented by ultrasonic shearing and subcloned for internal sequence analysis. Both random, non-repetitive sequences and novel microsatellite repeats were isolated in this manner. More than 100 such markers were identified across the region in question. These markers were used for PCR-based screening of a mouse BAC library from Research Genetics (Birmingham, Ala.), and permitted the isolation of BAC clones. The PCR primers defining all markers relevant to the Figures are presented in Table I.

TABLE I

PCR primers defining relevant markers

| Marker designation* | Polymorphism HeJ vs. SWR | Polymorphism HeJ vs. C57BL/6 | Primer pairs |
|---|---|---|---|
| D4MIT164 | ND | + | 1. tgaacacatatataccaaggcagc (SEQ ID NO:7)<br>2. accagagggtcattctccaa (SEQ ID NO:8) |
| D4MIT244 | + | − | 1. caaaatatctgacaaaaacaagtgtg (SEQ ID NO:9)<br>2. ggtgtcatcaccatgatgga (SEQ ID NO:10) |
| D4MIT218 | + | − | 1. agtaagcaatgttcactccaacc (SEQ ID NO:11)<br>2. tcccagcattgatgctcac (SEQ ID NO:12) |
| D4MIT82 | + | − | 1. atgtgtgccattttgcatgt (SEQ ID NO:13)<br>2. agtattgcttgataaatttgcatg (SEQ ID NO:14) |
| D4MIT325 | + | − | 1. gttccgtttctttttacaactatgg (SEQ ID NO:15)<br>2. atttgcctattttattttcatttgtg (SEQ ID NO:16) |
| 25.5 | + | − | 1. ggaaggttgaagcaagac (SEQ ID NO:17)<br>2. gactcatgatttgataactgac (SEQ ID NO:18) |
| 25.15 | + | − | 1. gccaagaaagagcaaatag (SEQ ID NO:19)<br>2. cgattcctatggctcagcc (SEQ ID NO:20) |
| 9.2 | + | − | 1. agtaattcagcttctcccaa (SEQ ID NO:21)<br>2. cagatccatgatacagatatgc (SEQ ID NO:22) |
| C | ND | + | 1. cctccagcacagtgtacaatg (SEQ ID NO:23)<br>2. gtgtgtgtgtgtgtaagcttg (SEQ ID NO:24) |
| C' | ND | + | 1. tagaaagtggaaacatctgac (SEQ ID NO:25)<br>2. atgtaactcaatcacagaactc (SEQ ID NO:26) |
| B | ND | + | 1. tcaagatccataacctagac |

TABLE I-continued

PCR primers defining relevant markers

| Marker designation* | Polymorphism HeJ vs. SWR | Polymorphism HeJ vs. C57BL/6 | Primer pairs |
|---|---|---|---|
| | | | (SEQ ID NO:27) 2. agacagacagatagacagaaag (SEQ ID NO:28) |
| D4MIT178 | – | + | 1. gccctgaaggtaaatcagtaact (SEQ ID NO:29) 2. gctcaggaggtacattgcct (SEQ ID NO:30) |
| A | ND | + | 1. tcagtttgcttgcattctc (SEQ ID NO:31) 2. aagtatggatgtgtgtgtaag (SEQ ID NO:32) |
| D | ND | + | 1. tgctaagattgtgatgactg (SEQ ID NO:33) 2. gactaggtgagagaaacagac (SEQ ID NO:34) |
| E | ND | + | 1. ttgggctgatagtacaatatac (SEQ ID NO:35) 2. ggagatttctaatgcttgg (SEQ ID NO:36) |
| 7.1 | + | – | 1. tggacaaacaccacataaca (SEQ ID NO:37) 2. cagactatcagatgactga (SEQ ID NO:38) |
| 7.3 | + | – | 1. acattagaatcatttcctgca (SEQ ID NO:39) 2. gcaaagtcttgtgagtct (SEQ ID NO:40) |
| 7.11 | + | – | 1. cttaactggagaggaaagatc (SEQ ID NO:41) 2. cagttctgtctttgtatctctg (SEQ ID NO:42) |
| 83.3 | + | – | 1. agagagtgagcctcagtct (SEQ ID NO:43) 2. ttgggtgatgattgtgaac (SEQ ID NO:44) |

*Presented in centromeric to telomeric order

Shotgun Sequencing.

Using a minimal contig containing 24 BACs and one YAC, which together encompassed >95% of the interval between markers B and 83.3, approximately 20 million bases of high-quality sequence were obtained, from bidirectional reads of approximately 20,000 fragments of DNA (i.e., approximately 40,000 reads in all). In this process, all BACs and the YAC clone 100E4 were fragmented by ultrasonic shearing, repaired to a blunt-ended state using Klenow fragment or mung bean nuclease, and subcloned into the vector pBluescript, which was been cut with SmaI and treated with calf intestine alkaline phosphatase to prevent self ligation. The average fragment size was about 1.5 kb. Automated sequencing was performed using ABI model 377A sequencers, and chain termination chemistry was used by all four of these sequencing laboratories.

Bioinformatic Analysis.

All sequences were hand-edited or processed by Phred and Phrap (obtained from Brent Ewing and Phil Green, respectively; University of Washington Genome Center) to remove vector, and to assemble as completely as possible. Individual reads were stored as a growing database in a single large directory, and subjected to the following tests, all of which were carried out using Genetics Computing Group (GCG) software, or via web or e-mail servers:

1. All sequences were periodically compared to all other sequences in the database using the Fasta search algorithm, in order to establish and display regions of overlap and homology.
2. All sequences were masked to hide common repetitive elements from consideration prior to searches against the large sequence databases listed below. Censoring was usually carried out using the program RepeatMasker (obtained from Arian Smit, University of Washingtion).
3. All sequences, in censored and uncensored form, were subjected to blastn analysis using the genembl, dbest, and HCD databases, the latter at levels I and II.
4. All sequences, in censored (masked) and uncensored form, were subjected to blastx analysis using the genembl and HCD databases, the latter at levels I and II.
5. In some select instances, sequences were studied locally using the framesearch algorithm to detect open reading frames with homology to components of the Swissprot database.
6. All sequences were analyzed for rare peptide motifs by translating them in all six frames and subjecting them to a local Motif search.
7. All sequences were, at various stages, aligned with others using the GCG program Gelmerge, or using the program Phrap. In this manner, long contiguous sequences were obtained and unambiguous overlap between adjacent BACs, as well as the approximate extent of overlap, could be inferred.
8. Individual sequencing reads, or when possible, contigs of reads, were subjected to analysis by GRAIL 2 in order to identify putative exons.

Exon Trapping.

A total of 169 exons were trapped from the "zero area" of the critical region: Exon trapping was performed using the vector pSPL3 (Burn et al., 1995). Digested genomic DNA was ligated into the vector, and pooled clones (generally 20 to 100 at one time) were transfected into COS-7 cells, obtained from the ATCC. Capture of putative exons was accomplished by PCR.

Shotgun Sequencing.

Using a minimal contig containing 24 BACs and one YAC, which together encompassed >95% of the interval between markers B and 83.3, approximately 20 million bases of high-quality sequence were obtained, from bidirectional reads of approximately 20,000 fragments of DNA (i.e., approximately 40,000 reads in all). In this process, all BACs and the YAC clone 100E4 were fragmented by ultrasonic shearing, repaired to a blunt-ended state using Klenow fragment or mung bean nuclease, and subcloned into the vector pBluescript, which was been cut with SmaI and treated with calf intestine alkaline phosphatase to prevent self ligation. The average fragment size was about 1.5 kb. Automated sequencing was performed using ABI model 377A sequencers, and chain termination chemistry was used by all four of these sequencing laboratories.

Bioinformatic Analysis.

All sequences were hand-edited or processed by Phred and Phrap (obtained from Brent Ewing and Phil Green, respectively; University of Washington Genome Center) to remove vector, and to assemble as completely as possible. Individual reads were stored as a growing database in a single large directory, and subjected to the following tests, all of which were carried out using Genetics Computing Group (GCG) software, or via web or e-mail servers:

1. All sequences were periodically compared to all other sequences in the database using the Fasta search algorithm, in order to establish and display regions of overlap and homology.
2. All sequences were masked to hide common repetitive elements from consideration prior to searches against the large sequence databases listed below. Censoring was usually carried out using the program RepeatMasker (obtained from Arian Smit, University of Washingtion).
3. All sequences, in censored and uncensored form, were subjected to blastn analysis using the genembl, dbest, and HCD databases, the latter at levels I and II.
4. All sequences, in censored (masked) and uncensored form, were subjected to blastx analysis using the genembl and HCD databases, the latter at levels I and II.
5. In some select instances, sequences were studied locally using the framesearch algorithm to detect open reading frames with homology to components of the Swissprot database.
6. All sequences were analyzed for rare peptide motifs by translating them in all six frames and subjecting them to a local Motif search.
7. All sequences were, at various stages, aligned with others using the GCG program Gelmerge, or using the program Phrap. In this manner, long contiguous sequences were obtained and unambiguous overlap between adjacent BACs, as well as the approximate extent of overlap, could be inferred.
8. Individual sequencing reads, or when possible, contigs of reads, were subjected to analysis by GRAIL 2 in order to identify putative exons.

Exon Trapping.

A total of 169 exons were trapped from the "zero area" of the critical region. Exon trapping was performed using the vector pSPL3 (Burn et al., 1995). Digested genomic DNA was ligated into the vector, and pooled clones (generally 20 to 100 at one time) were transfected into COS-7 cells, obtained from the ATCC. Capture of putative exons was accomplished by PCR.

Hybridization Selection of Expressed cDNAs Using BACs.

This method was carried out as described by Rommens et al. (1998), using cDNA from RAW 264.7 cells (obtained from the ATCC). A total of 538 selected clones from the "zero area" were examined in the course of the present study.

Fluorescence In Situ Hybridization.

Six separate distance measurements were made at Genome Systems, Inc., using interphase nuclei of mouse cells. The measurements included distances between the following BACs, which were used as probes:

[L22 and O12], [O12 and N13], [N13 and B6], [B6 and B22], [B22 and K4], [B22 and L15].

The minimum distance that may be measured through this approach is 0.2 Mb, and the maximum distance that may be measured is 1.6 Mb. A 10% margin of error is certified for all measurements.

Genetic Computation.

A 500 Mhz DECA computer (DCG Viper EV-56) equipped with 63 Gb of hard drive space and 256 Mb of RAM was used in all of these studies. Programs were run under a Digital UNIX operating system. For the design of primer pairs to be used in PCR and sequence extension, the program Gene Runner was used (Hastings Software, Inc). The graphics program used in depiction of the contig was Hijaak Draw (Inset Graphics, Inc). Each of the latter two programs was run under Windows95 using a Pentium Pro computer from Gateway, Inc.

Example 2

LPS Response Assays and Validation Thereof

Both splenocyte proliferation assays and assays of TNF production were used to distinguish LPS nonresponder mice ($Lps^d$ homozygotes) LPS responders ($Lps^d$ heterozygotes) were used in analysis of the [SWR×C3H/HeJ]F1×C3H/HeJ panel. Both assays were carried out using two separate LPS concentrations. When splenocyte proliferation was used as an endpoint, a simultaneous assay of proliferation occurring in response to concanavalin A was used as a means of controlling for cell viability. In the [SWR×C3H/HeJ]F1×C3H/HeJ panel, conflict between the two assays was rarely observed, and mice that were felt to be ambiguous in their responsiveness to LPS were discarded from further consideration.

Experience with the two assays of LPS response showed that measurement of TNF production occurring at low (10 ng/ml) concentrations of LPS was a more reliable index of responsiveness than measurement of splenocyte proliferation. Therefore, this assay was used exclusively in analysis of the [C57BL/6×C3H/HeJ]F1×C3H/HeJ backcross panel. Since not all of the potential recombinants were assayed for LPS responsiveness on the same day, and since day-to-day variability in TNF measurement might confuse interpretation of the results, a series of obligate $Lps^d$ allele homozygotes and heterozygotes were identified by analysis of flanking markers, and included as controls with each assay performed. The distinction between responder and non-responder control groups was in every instance clear and unambiguous. Similarly, the designation of each individual recombinant as homozygous or heterozygous with respect to the Lps locus was accomplished without ambiguity.

EXAMPLE 3

[SWR×C3H/HeJ]×C3H/HeJ Backcross

Figure 1:
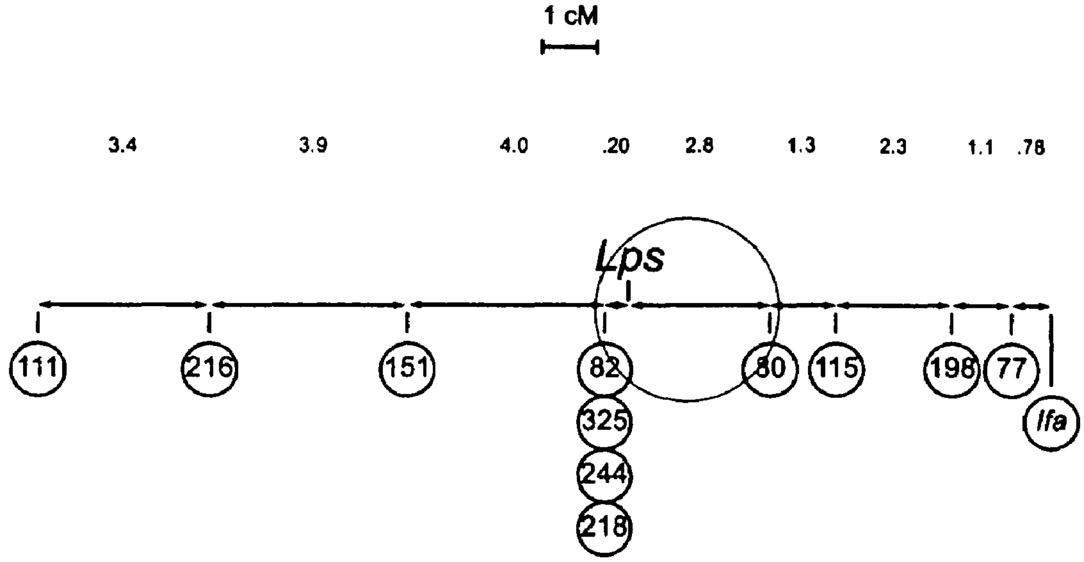
FIG. 1. Coarse genetic map of the Lps locus with respect to D4MIT markers. 493 meioses from an (SWR×C3H/HeJ)× C3H/HeJ backcross were examined, and crossovers used to map the locus with respect to eleven markers, including the D4MIT markers shown and a single marker derived from the interferon-α locus. Numbers above double arrows indicate centimorgan distances. The gene was confined to a region between a cluster of four inseparable markers (D4MIT244, 218,82, and 325) and the single marker D4MIT80.

In initial efforts to confine the $Lps^d$ mutation to a point between two markers, animals of the [SWR×C3H/HeJ]×C3H/HeJ backcross were examined. Raw data are not presented as this was essentially a range-finding study. A total of eleven D4MIT markers flanking the gene could be used for genotypic analysis, as the two parental genotypes could be distinguished on the basis of length differences. The crossover frequency between each of these markers and the Lps gene in a panel of 493 mice is illustrated in FIG. 1. A cluster of four markers (D4MIT82, 325, 218, and 244) which underwent no recombination with one another each exhibited a single crossover event with the Lps mutation. This cluster of markers lay centromeric to the mutation. On the distal side of the mutation, D4MIT80 was separated from $Lps^d$ by 14 recombination events.

Figure 2A:
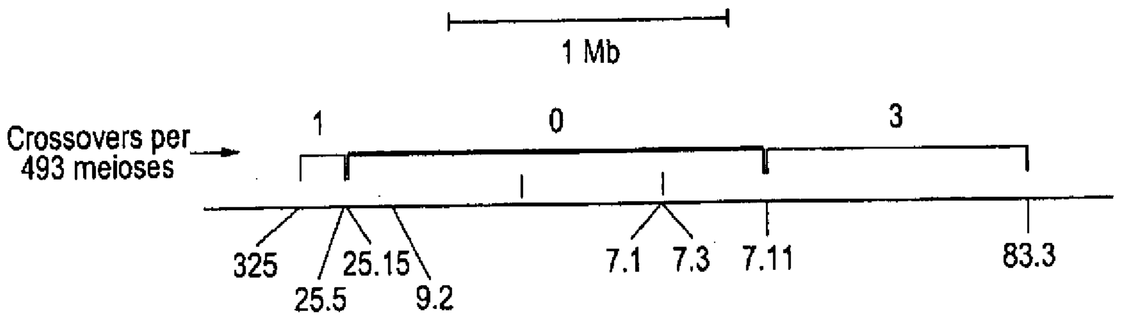
FIG. 2A and FIG. 2B. Identification of novel microsatellite markers, and mapping of the Lps locus with respect to these markers.
Figure 2B:
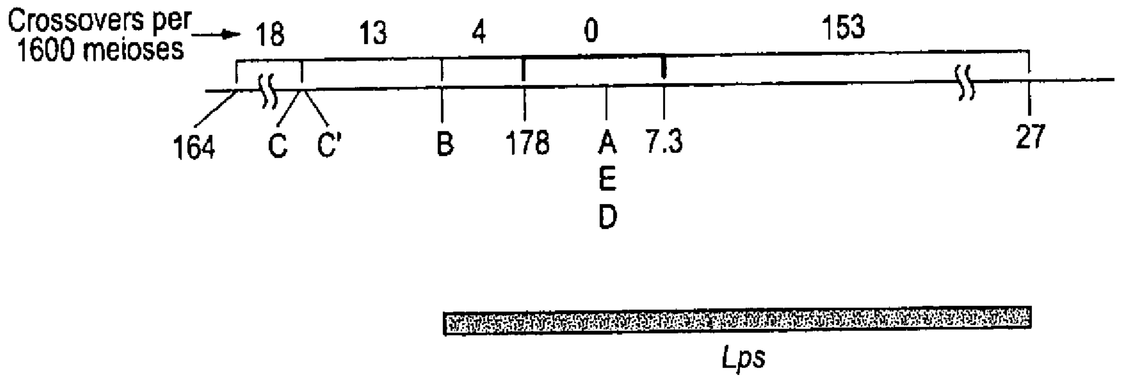

From the fact that only a single crossover event was observed between D4MIT82 and $Lps^d$, it was inferred that the mutation might well lie within the proximal half of the D4MIT82→D4MIT80 interval. Partial ordering of microsatellite markers between D4MIT82 and D4MIT80 was achieved by Bell, et al., who employed a series of deletion mutants to map markers in the region of the b locus (Bell et al., 1995). A YAC clone containing D4MIT83 (which was mapped to the middle portion of the interval) was isolated, fragmented, and used to identify fresh microsatellite repeat polymorphisms. One of these, designated CA83.3, lay distal to the mutation and was separated from it by only six crossover events. Moreover a total of six polymorphic microsatellites (designated CA25.5, CA25.15, CA9.2, CA7.1, CA7.3, and CA7.11) were identified in three other YAC clones which were isolated using the markers D4MIT25, NdS9, and D4MIT7. These six new markers all co-localized with the mutation (FIG. 2). When physical mapping (detailed below) revealed that some of the new markers were separated from others of the group by as much as 1.6 Mb of DNA, it appeared certain that a second backcross would be required to narrow the interval.

Example 4

[C57BL/6×C3H/HeJ]×C3H/HeJ Cross

A total of 1600 F2 mice made by crossing C57BL/6×C3H/HeJ and backcrossing to C3H/HeJ were analyzed for recombination in the region of the Lps gene. Those mice that showed such recombination were further analyzed for LPS responsiveness, and fine mapping of the recombination events was accomplished using novel microsatellite markers. The inventors examined markers over a relatively broad range in a screen for crossover events. This range spanned the interval D4MIT164 to D4MIT27, and included D4MIT178.

Figure 3A:
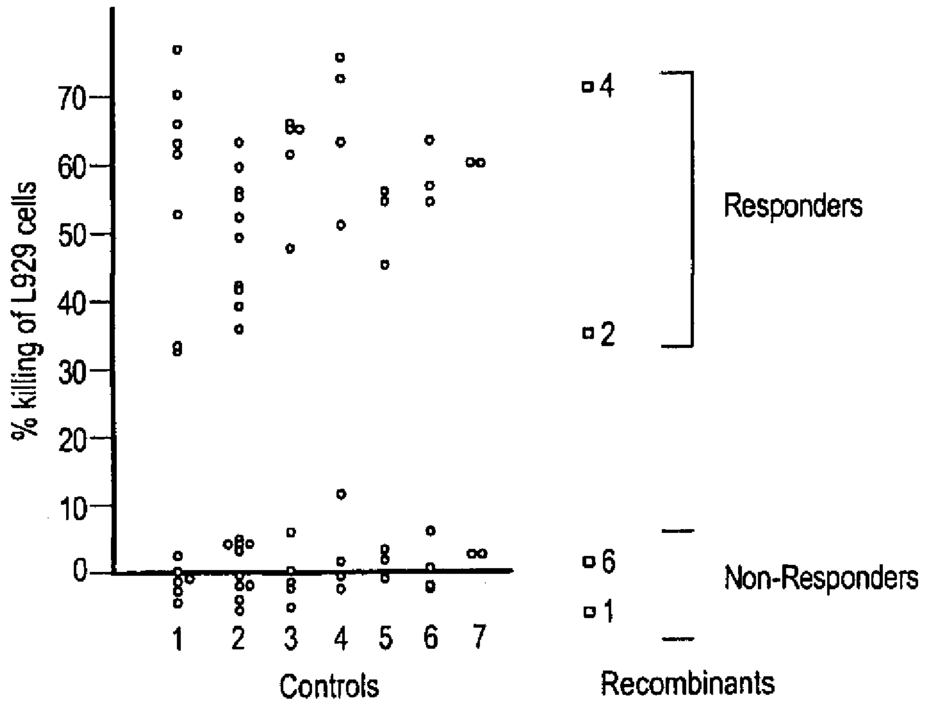
FIG. 3A and FIG. 3B. Primary biological assay data used in defining crossovers between $Lps^d$ and B (FIG. 3A), and between $Lps^d$ and 83.3 (FIG. 3B). Assays of LPS response were performed on seven separate days. On each of these days, control assays of TNF production by macrophages (FIG. 3A) or splenocyte proliferation (FIG. 3B) from obligate heterozygotes and obligate homozygotes for the $Lps^d$ allele were performed in parallel with assays performed on samples from the seven mice known to have recombination in the interval between B and 83.3. Results of assays performed on obligate heterozygotes are shown as blue circles; obligate homozygote results are shown as red circles. The LPS responses of the seven mice with a recombination event between markers B and 83.3 are represented as black squares. Four of these mice (FIG. 3A) showed recombination between B and $Lps^d$, and three mice (FIG. 3B) showed recombination occurred between $Lps^d$ and 83.3. No overlap was apparent between the range of values obtained with obligate homozygotes and obligate heterozygotes, and the mice bearing recombination could be unambiguously categorized as responders or nonresponders. Each point represents the mean of four replicate cytotoxicity assays (FIG. 3A) or splenocyte proliferation assays (FIG. 3B). Error bars are omitted for simplicity, but were generally in the range of 10% of the mean value.
Figure 3B:
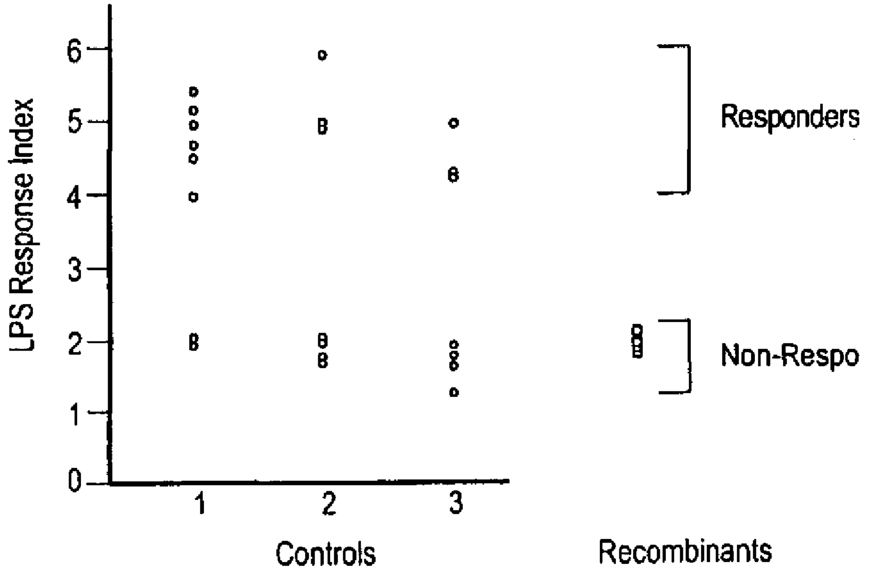

A total of 192 crossovers were observed between D4MIT164 and D4MIT27 in the 1600 meioses studied. 157 of these crossovers occurred between D4MIT178 and D4MIT27, while 35 crossovers occurred between D4MIT164 and D4MIT178. The location of these events could be further assigned based on the identification of six novel polymorphisms within the D4MIT164→ D4MIT27 interval (FIG. 2). Five novel markers (designated A, D, E, 7.3 and 7.11) still co-localized with the $Lps^d$ mutation, as did marker D4MIT178. The physical separation between all four of these microsatellite markers (which were isolated from two overlapping BAC clones) was approximately 1.2 Mb, corresponding to the "zero region" of the critical area. Four crossovers were observed between $Lps^d$ and marker B. In terms of physical size, the B→83.3 interval corresponds to approximately 2.6 Mb. Because the crossovers between B and 83.3 are essential to confinement of $Lps^d$, the primary assay data for each of the seven critical meioses are presented in FIG. 3.

Example 5

The Physical Map

Figure 4A:
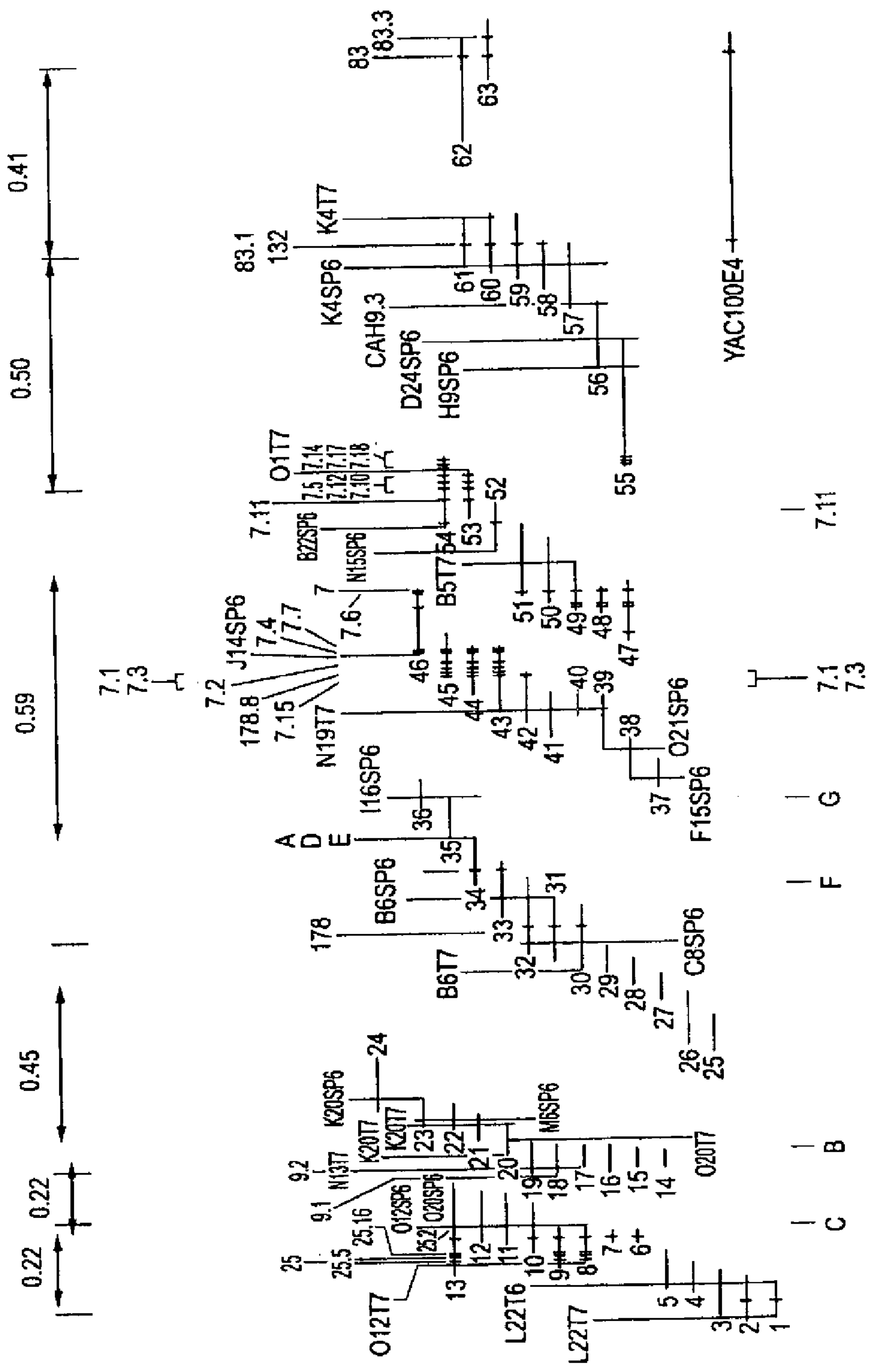
FIG. 4A and FIG. 4B.
Figure 4B:
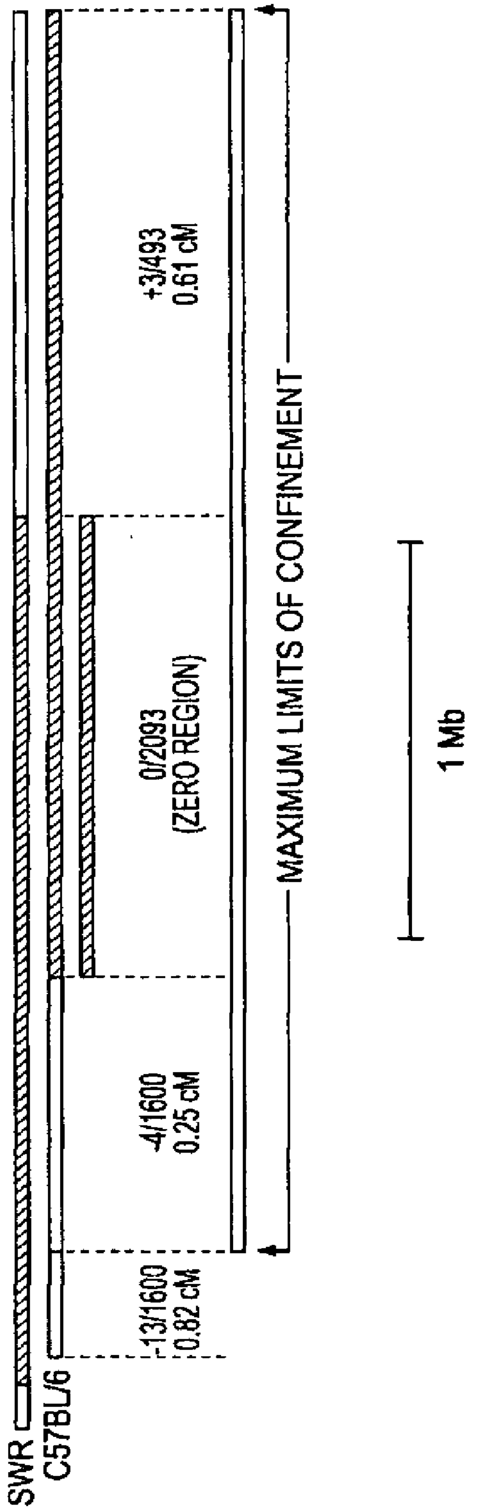
Figure 5:
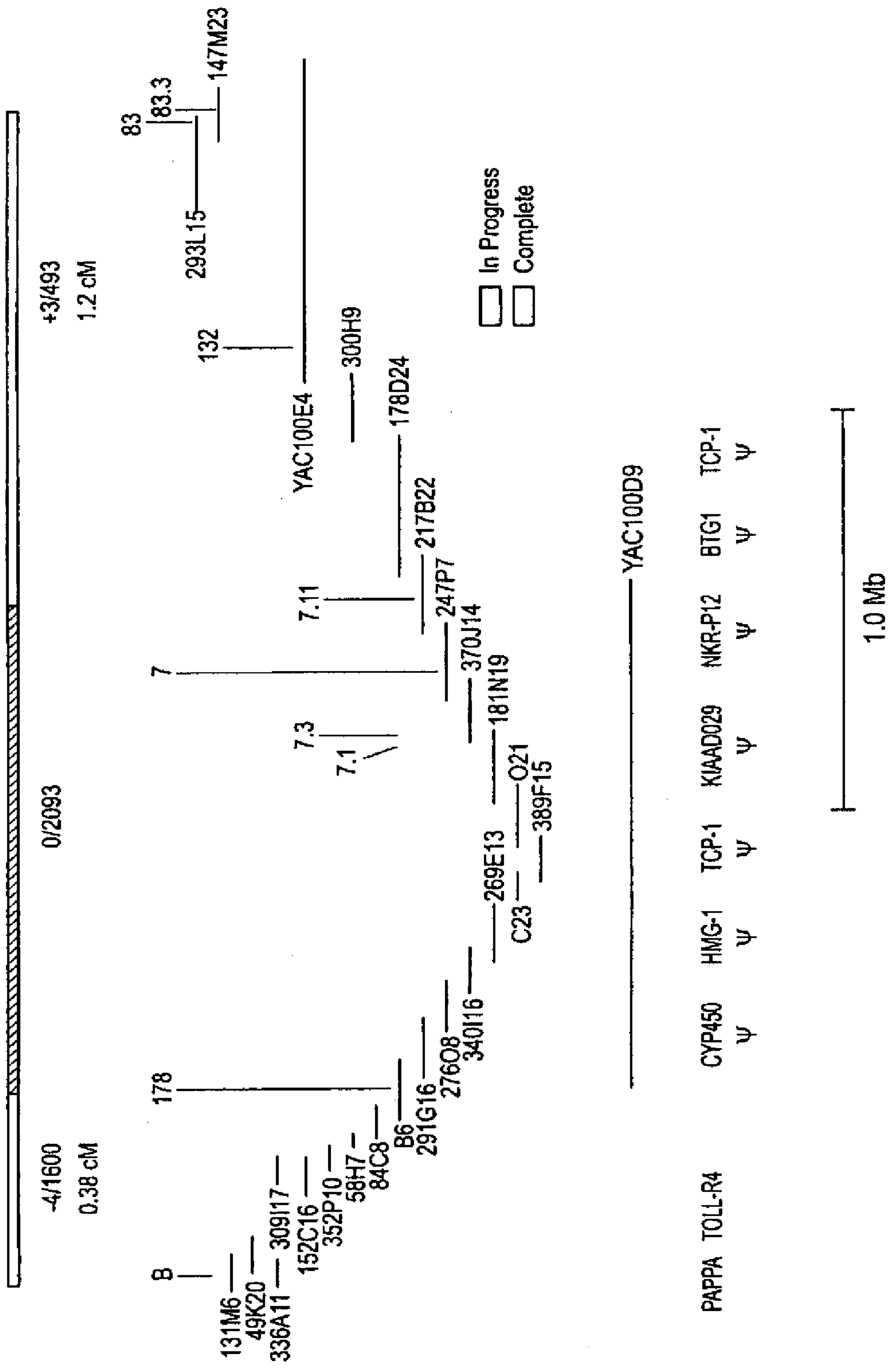
Figure 6:
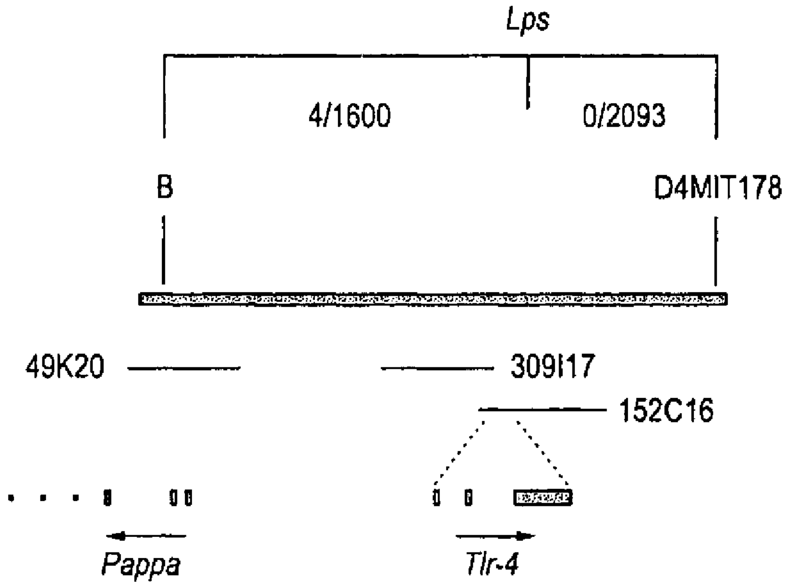

A map of the entire interval between D4MIT325 and marker 83.3 is shown in FIG. 4. A total of 63 BAC clones and 20YAC clones (only one of which is shown, in red) were isolated to span the critical region. Each YAC and BAC clone is drawn to scale according to analysis by pulsed-field gel electrophoresis. A FISH map is drawn above the assembly, and is in approximate agreement with the electrophoretic map. The black bar in FIG. 4 indicates the region of zero recombination determined on the basis of 493 meioses analyzed by the cross [SWR×C3H/HeJ]×C3H/HeJ and 1600 meioses analyzed by the cross [C57BL/6×C3H/HeJ]×C3H/HeJ. This "zero area" is approximately 1.2 Mb in length. The critical region, known with certainty to contain the $Lps^d$ mutation, extends over a distance of approximately 2.6 Mb, circumscribed by markers "B" and D4MIT83.3.

Example 6

Gene Identification 169 putative exons were identified throughout the "zero area" of the contig, and in selected portions that lay beyond the zero area, by exon trapping. 538 clones were isolated from the zero area and beyond by hybridization/selection. Some of each of these represented fragments of known genes and pseudogenes, including Pappa, HMG-I and KIAA0029 (detected by both exon trapping and hybridization selection). TCP-1 and BTG-1 were detected by hybridization selection, though not by exon trapping. Most of the sequences identified by the two methods could not be shown to encode authentic, expressed genes despite exhaustive analysis through northern blotting and other techniques.

High density sequence analysis was carried out over an interval containing 24 minimally overlapping BACs and one YAC clone. These BACs are depicted in FIG. 5. BACs shown in blue were sequenced either to completion or to the point of finishing (i.e., only a few gaps remain between large assemblies of sequence). BACs shown in red were sequenced with to a high density (several hundred reads each) but not to the point of finishing, and are still considered "in progress." YAC 100E4 was analyzed with nearly 1000 reads. The genes and pseudogenes detected within the region by homology searches are indicated as well.

A large number of exons were predicted by GRAIL analysis. However, many of these were of retroviral origin (e.g., exons within L1, B1, Bam5, and IAP repeats). Among those that were not, some belonged to known genes such as Pappa. Among all GRAIL-predicted, non-repetitive exons with ratings of "good" to "excellent," none could be demonstrated to encode authentic macrophage-expressed transcripts when used as probes on northern blots.

Pseudogenes encoding fragments of TCP-1, BTG-1, NKR-P12, KIAA0029, HMG-1, and cytochrome P450 were identified within the contig. However, all of these genes were either fragmentary or contained nonsense mutations. Only two authentic genes were identified within the contig. These were the classical marker gene Pappa, encoding a plasma metalloproteinase, and the mouse homolog of TLR-4, encoding a transmembrane protein homologous to the IL-1 receptor. The TLR-4 gene resides in BAC clones 309I17 and 152C16. Its sequence (5'→3') corresponds to a proximal→distal orientation along the chromosome. The complete size and intron-exon boundaries of the gene remain to be determined.

Example 7

Identification of the $Lps^d$ Mutation that Alters the TLR-4 Protein Cytoplasmic Domain Mutations of the Lps gene selectively impede lipopolysaccharide (LPS) signal transduction in C3H/HeJ and C57BL/10ScCR mice. Homozygotes display a phenotype characterized by resistance to all biological effects of endotoxin and exaggerated susceptibility to overwhelming gram-negative infection. The codominant $Lps^d$ mutation of C3H/HeJ mice was confined to a 0.9 centiMorgan genetic interval, based on the analysis of 2093 meioses.

A minimal contig, consisting of 20 BAC clones and one YAC clone, was subjected to sequence analysis. Approximately 40,000 sequencing reads were obtained from shotgun-cloned genomic DNA, bringing over 1.6 Mb of the central contig to a near-contiguous state and yielding rather dense coverage of >95% of the entire critical region. BLAST searches performed on masked versions of the sequence disclosed dozens of high-scoring homologies with published expressed sequence tags (ESTs), but these were excluded from consideration as they could not be cloned from macrophage or fetal cDNA libraries of trusted complexity. Several pseudogenes were observed, but dismissed because they were found to be fragmentary. GRAIL analyses, performed on long contiguous sequences of the central contig using X-GRAIL software, revealed an abundance of retroviral repeats and scattered non-retroviral exons, most of which proved to be derived from pseudogenes.

Two authentic genes (a portion of the Pappa locus and the entire TLR-4 receptor locus) were identified in the entire region, by both BLAST and GRAIL analysis. The orientation and location of these genes, with respect to the nearest genetic markers, is presented in FIG. 6. Both genes lie at the centromeric end of the critical region, and at most, only a small 5' fragment of Pappa lies distal to marker B.

Pappa encodes a secreted metalloproteinase, which lacks any evidence of a transmembrane domain. It is expressed by placental tissue, but not by primary macrophages or macrophage cell lines (not shown), and for these reasons, as well as its extreme proximity to marker B (which is separated from $Lps^d$ by four crossovers in a panel of 1600 meioses), it is considered a poor candidate.

In contrast, the TLR-4 locus seemed a particularly attractive candidate, both on the grounds of map position, and because the pro-inflammatory IL-1 receptor is also a member of the toll receptor family. Further, a human mutation causing co-resistance to LPS and IL-1 attests to the likelihood that the IL-1 and LPS signal transduction proteins share a common downstream intermediate. A priori, it would therefore seem likely that the IL-1 and LPS transducers are structurally related. Finally, the pro-inflammatory signaling potential of TLR-4 is suggested by studies in which chimeric versions of human TLR-4, bearing a CD4 sequence in place of the native extracellular domain, were shown to be capable of activating NF-6B in human mononuclear cells.

Accordingly, the TLR-4 cDNAs from C3H/HeJ mRNA, and from the mRNA of several LPS-responsive strains of mice (including C3H/HeN) were cloned, by reverse transcription and polymerase chain reaction, using primers derived from the genomic sequence. The amplified product was fragmented by sonication, shotgun cloned into the vector pBluescript, and sequenced using an Applied Biosystems model 373 DNA sequencer. 100 reads were aligned using the programs phred and phrap (obtained from Brent Ewing and Phil Green, University of Washington Genome Center).

A single mutation was observed in the 835 aa coding region of the TLR-4 cDNA derived from C3H/HeJ mice. At position 712 (within the cytoplasmic domain), a histidine is predicted rather than the proline that resides in mouse TLR-4 from C3H/HeN mice, SWR mice, or C57BL/6 mice. Furthermore, the residue is invariant across species, in that endotoxin-responsive mice, rats and humans all display a proline in the relevant position (FIG. 7*a*). The same mutation was identified in DNA amplified from the C3H/HeJ genome and directly sequenced. It was not observed in DNA amplified from the C3H/HeN genome, nor in DNA from SWR, C57BL/6, 129, or DBA-2 mice (FIG. 7*b*). No other difference in sequence has ever been observed on comparison of any genomic interval from C3H/HeN and C3H/HeJ mice, which were, until recently, a single strain. In FIG. 7A the sequence identified as J-toll is the mutant protein sequence in which the PRO at residue 712 is mutated to HIS.

While the TLR-4 cDNA was readily amplified by RT-PCR from macrophage RNA derived from C3H/HeJ, C3H/HeN, and C57BL/10ScN mice, it could not be amplified from macrophage RNA derived from C57BL/10ScCR mice. On the other hand, several low-abundance control cDNAs could be amplified from all strains without difficulty (FIG. 8*a*). Moreover, though the toll mRNA is relatively scarce, it could be detected on Northern blots prepared using total RNA derived from macrophages of the three former strains; it could not be detected in total RNA obtained from C57BL/10ScCR mice (FIG. 8*b*). Thus, a cis-acting mutation—yet to be defined at the genomic level—prevents the expression of processed toll mRNA in C57BL/10ScCR mice.

Since a definable mutation exists within TLR-4 in C3H/HeJ mice, and a severe deficiency or complete absence of TLR-4 mRNA expression is observed in C57BL/10ScCR mice, it is clear that Lps is, in fact, the TLR-4 gene.

The $Lps^d$ mutation of C3H/HeJ mice was originally described as codominant, in the sense that $Lps^d/Lps^n$ heterozygotes show intermediate levels of endotoxin response. The point mutation [$^{732}$ (pro6 his)] that we have identified exerts a dominant negative effect on LPS signal transduction. Supporting this conclusion, the functionally null (i.e., non-expressed) Lps allele represented in C57BL/10ScCR mice is strictly recessive. Since the TLR-4 molecule functions in a dimeric state, it is likely that the $Lps^d$ mutation renders interplay between normal and abnormal subunits unproductive; hence the codominant phenotype. Alternatively, the mutation may cause sequestration of a downstream signaling molecule.

Insofar as the Cross:

$$C3H/HeJ \times C57BL/10ScCR$$

yields mice that are profoundly unresponsive to LPS, it may also be inferred that a single copy of the $Lps^d$ allele (i.e., the genotype $Lps^d$/-) corresponds to a phenotype as unresponsive as that conferred by $Lps^d/Lps^d$. This observation supports the notion that signal transduction proceeds directly through the TLR-4 molecule, and tends to detract from the hypothesis that TLR-4 undergoes interaction with a second plasma membrane protein that acts, in turn, as a primary LPS transducer.

TLR-4 mRNA is expressed predominantly in lymphoid tissues, and the TLR-4 mRNA is induced by LPS (FIG. 9), suggesting that up-regulation of TLR-4 mRNA may perpetuate cell activation by LPS. Moreover, the well-known phenomenon of endotoxin tolerance is not likely to result from down-regulation of TLR-4.

In *Drosophila*, several Toll homologs are now known to exist (including 18-wheeler. Toll itself engages an extracellular protein ligand, spätzle, which promotes signal transduction via tub and pelle gene products, leading to dissociation of the cytoplasmic inhibitor encoded by cactus from a yet-unidentified member of the rel family of transcription factors. This pathway culminates in activation of the drosomycin gene, and is required for effective protection against fungal infection.

The mammalian ligand for TLR-4 has not yet been identified, and while an endogenous ligand may exist, it is equally possible that LPS recognition is the raison d'etre for TLR-4. CD14, the best characterized cell surface receptor for LPS, is also a member of the toll superfamily, and it is likely that it directly engages TLR-4 upon interaction with LPS, inducing signal transduction through the latter protein.

TLR-4 signal transduction is believed to proceed through activation of MyD88, a cytoplasmic protein bearing homology both to the cytoplasmic domain of toll itself and to a pair of death domain motifs, originally described in the TNF receptor family. In addition, the interleukin-1 receptor associated kinase (IRAK) and TNF-receptor associated factor (TRAF-6) lie on the TLR-4 signaling pathway, leading to the activation of AP-1 and NF-6B. It has been known for some time that NF-6B activation is essential for transcriptional activation of the mouse TNF gene, and that TNF subserves many of the effects of LPS, including the lethal effect.

It has recently been reported that human toll-2 cDNA, transfected into 293 cells, can promote LPS signal transduction, given co-expression of CD14. It was also noted that LPS is directly bound by soluble dimerized versions of toll-2, and that toll-2 mutants bearing truncations in the cytoplasmic domain exert a dominant inhibitory effect on LPS signaling. LPS signal transduction via TLR-4 has never been reported. However, the demonstration that Lps is identical to TLR-4 leaves no room for doubt that TLR-4 is essential for LPS signaling. In mice lacking functional TLR-4, toll-2 does not make a substantial contribution to LPS signal transduction; hence C3H/HeJ and C57BL/10ScCR mice are entirely refractory to LPS. Though it is possible that toll-2, or other members of the toll family, might also be required for LPS signaling, the data in hand do not sustain this conclusion. Recently, it was demonstrated that Chinese hamsters lacking a fucntional copy of a toll-2 gene, still were responsive to endotoxin (Heine et al., 1999), indicating that toll-2 is not essential in LPS signalling.

Several mammalian toll homologs have now been identified, and several more may exist undiscovered. The phenotypic consequences of mutations in genes encoding other members of the family remain to be seen. Remarkably, C3H/HeJ and C57BL/10ScCR mice are developmentally and phenotypically intact, aside from their inability to effectively respond to LPS, and to gram-negative infection. Their response to products of gram-positive organisms and most other microbes is intact. This fact would suggest that TLR-4 has been retained in evolution principally for the purpose of serving the LPS response pathway. Malo and coworkers have recently adduced evidence to suggest that, in birds, distinct allelic forms of Lps may influence survival during gram-negative infection. As such, polymorphisms associated with the tenascin locus predict outcome following infection of outbred chickens with *Salmonella typhimurium*. In mice, and presumably in birds, the tenascin locus is closely linked to Lps. It is entirely possible that mutations of the human TLR-4 gene also influence susceptibility to gram-negative infection, or its clinical outcome. As two independent mutations of TLR-4 have thus far become fixed in mice, it is likely that human populations have also retained TLR-4 mutations. A search for such mutations is currently in progress.

Example 8

Genetic Variation at the TLR-4 Locus

Materials and Methods

Determination of the Complete Mouse (Tlr4) and Human (TLR4) Genomic Sequences.

The mouse BAC 152C16 (from the 129/J strain; Research Genetics), was earlier shown by the inventors to contain the Tlr4 gene in entirety, and a small fraction of Tlr4 was also found to reside in the overlapping BAC 309I17 (Poltorak et al., 1998). Human TLR4 was identified in BAC 110P15 (Genome Systems) by hybridization screening. All three BACs were fragmented by ultrasound, shotgun cloned into the vector pBluescript-KS, and sequenced extensively using ABI model 373 and 377 sequencers. 959 reads were obtained from 390I17, 1503 reads from 110P15, and 2731 reads from 152C16. The average read length was approximately 700 nt. To concentrate data acquisition efforts on the Tlr4 and TLR4 genes themselves, PCR primers were fashioned to match regions flanking each gene. A 16 kb fragment was amplified from the mouse BAC 152C16, and a 12 kb fragment was amplified from the human BAC 110P15, each containing all exons of the respective gene. These fragments were also shotgun cloned, and sequenced extensively, so that the depth of sequence reached an average of 12 reads over the area of greatest interest. Assembly was performed using the programs phred and Phrap (obtained from Brent Ewing and Phil Green, University of Washington Genome Center). Interpretation of repetitive elements was achieved with the program RepeatMasker (obtained from Arian Smit, University of Washington Genome Center). A contiguous high-quality sequence 18974 bp in length containing TLR4 was obtained from the human BAC, and a contig 91748 bp in length containing Tlr4 was obtained from the mouse BAC. Over these intervals, the error rate was estimated at <1 per $10^4$ bp. The sequences have been posted to Genbank in annotated form (accession number AF177767 for the murine sequence, SEQ ID NO:48, and accession number AF177765 for the human sequence, SEQ ID NO:47). All data related to mutations are presented with reference to these sequences.

Sequencing DNA from Individual Human, Mouse, Chimpanzee, and Baboon Samples.

Human DNA samples were obtained from blood anticoagulated with EDTA, obtained from healthy laboratory personnel and from non-selected visitors to the Aston Center outpatient clinic in Dallas, Tex. The samples, 102 in all, were from a population of mixed ethnicity, but were predominantly obtained from Caucasian donors. Samples were prepared using the Wizard Genomic DNA Purification kit (Prornega). Mouse DNA, obtained from animals of 35 *Mus musculus* strains, was ordered from the Jackson Laboratories. Chimpanzee and baboon DNA were obtained from Dr. Kurt Benirschke (U. of CA, San Diego) and Dr. Gregory Delzoppo (Scripps Research Institute), respectively.

The three principal exons of Tlr4 and TLR4 were amplified independently from all human and mouse genomic DNA samples, leaving a margin of approximately 50 bp to each side of the exons so as to identify intronic mutations that might alter splicing. An alternative second exon, apparent in the cDNA sequence has been reported (Rock et al., 1998) (Gb accession number U88880) that specifies a truncated and presumably inactive product. It was not analyzed in the population survey.

All exons of the chimpanzee were amplified and sequenced using the same primers used to amplify and sequence the human exons. For the baboon, the first two exons were also amplified using these same primers; however, the third exon of the baboon was amplified with a substituted primer at the 5' end.

The PCR products were isolated by agarose gel electrophoresis. Exons 1 and 2 were sequenced using the same primers that were used for amplification. Exon 3 was sequenced using the flanking primers, as well as a collection of eight internal primers. In this manner, the entire coding region and all splice junctions of the human and mouse sequences could be covered with a total of 14 sequencing reads, given that all reads were of high quality. All primers used for amplification and sequencing are presented in Table II.

TABLE II

Oligonucleotide primers used to amplify and mouse and human Tlr4 genes.
↑, primer matches ⊕ strand; ↓, primer matches ⊖ strand.

| | MOUSE | SEQ. ID NO. | HUMAN | SEQ. ID NO. |
|---|---|---|---|---|
| AMPLIFICATION | | | | |
| EXON 1 | ↑ CAGTCGGTCAGCAAACGCCTTCTTC | 49 | ↑ GCTCGGTAAACGGTGATAG | 55 |
| | ↓ CAAGGCAGGCTAGCAGGAAAGGGTG | 50 | ↓ TGAGAAGTTCTGGGCAGAAG | 56 |
| EXON 2 | ↑ TTATTCATCTTTGGAGAGGAGTGG | 51 | ↑ TCTCTGGTCTAGGAGAGG | 57 |
| | ↓ AAGGAAGTTTAGTTAGAACCACCTTG | 52 | ↓ CCAGTCCAATAATGAAATG | 58 |
| EXON 3 | ↑ TCTCCTGCTCACACCATCATCACCTG | 53 | ↑ CCATCACATCTGTATGAAGAGCTGGATGAC | 59 |
| | ↓ CATGTGTTCCATGGGCTCTCGGTC | 54 | ↓ TGACTTTCTTTGTCATGGGTTCCTTGACTG | 60 |
| SEQUENCING | | | | |
| EXON 1 SAME AS ABOVE | | | | |
| EXON 2 SAME AS ABOVE | | | | |
| EXON 3 | 1 ↓ ATGCCATGCCTTGTCTTC | 61 | 3.1 ↑ GAGCTGGATGACTAGGATTAATATTC | 74 |
| | 2 ↓ TTTAAATTCTCCCAAG | 62 | 3.1 ↓ TCAAATTGCACAGGCCCTCTAG | 75 |
| | 3 ↓ CAGCTCTTCTAGACC | 63 | 3.2 ↑ CAATCTCTCTTTAGACCTGTCC | 76 |
| | 4 ↑ TGTGAACATCAGAAATTCCT | 64 | 3.2 ↓ AATACTTTAGGCTGGTTGTCCC | 77 |
| | 5 ↑ TGAGATTGCTCAAACATGG | 65 | 3.3 ↑ GAAGTTGATCTACCAAGCCTTG | 78 |
| | 6 ↑ TTGAAACAATTGAAGACAAGGC | 66 | 3.3 ↓ GGAAGTCATTATGTGATTGAGAC | 79 |
| | 7 ↑ CCTGGCTGGTTTACACGTC | 67 | 3.4 ↑ CTTCCTGGACCTCTCTCAGTGTCAAC | 80 |
| | 8 ↑ TTTCATGGGTCTAGAAGAGCTG | 68 | 3.4 ↓ GAAGGCAGAGCTGAAATGGAGG | 81 |
| | 9 ↓ AAGAACTGCTTCTGTTCC | 69 | 3.5 ↑ TCAGATGAATAAGACCATCATTGGTG | 82 |
| | 10 ↓ TCAGAAACTGCCATGTTTG | 70 | 3.5 ↓ AACAAGTGTTGGACCCAG | 83 |
| EXON 3 | 5' ↑ TGAGCTGGTAAAGAATTTAG | 71 | 1 ↑ GTAAATTTGGACAGTTTCC | 84 |
| Secondary | 7' ↑ CTGACGAACCTAGTACATGTG | 72 | 2 ↑ TTCAGTATTCCTATCACTCAG | 85 |
| | 9' ↓ ATGTCAAGTTTGTTGTGTT | 73 | 3 ↑ TTATAAGTGTCTGAACTCCC | 86 |
| | | | 4 ↑ TCGGTCCTCAGTGTGCTTG | 87 |
| | | | 5 ↑ GTGTCCCAGCACTTCATC | 88 |
| | | | 6 ↑ AACCTCCTGAGGCATTTC | 89 |
| | | | 7 ↓ GTTTCAAATTGGAATGCTG | 90 |
| | | | 8 ↓ AAGGAAACGTATCCAATG | 91 |
| | | | 9 ↓ AAGCACACTGAGGACCGAC | 92 |
| | | | 10 ↓ GATGAAGTGCTGGGACAC | 93 |
| | | | 11 ↓ TCCTCTTCAGATAGATGTTG | 94 |
| | | | 12 ↓ TTTCTTTGTCATGGGTTC | 95 |
| | | | 0 ↑ TTTAGGTTCTTATTCAGCAG | 96 |
| | | | 0 ↓ GCTCTAGATTGGTCAGATTAG | 97 |

Independent assembly of each sample was required as a condition for further analysis, and if such assembly failed, additional reads were executed using a secondary collection of primers. Thereafter, mutations were identified en mass, by pooling all of the reads from 25 to 30 samples at a time and reassembling with the program polyphred, using the phred-PhrapPoly script (obtained from Natalie Kolker, University of Washington Genome Center). Consed_alpha (obtained from David Gordon, University of Washington Genome Center) was used to visualize reads and mutations.

The annotated chimpanzee exon sequences have been submitted to Genbank with the accession numbers AF179218, AF179219, and AF179220. The baboon sequences have been submitted with the accession numbers [pending]. For the purpose of genetic comparisons, rat and hamster Tlr4 sequences were also used; their Genbank accession numbers are AF057025 and AF153676, respectively.

Genetic Computation

A 500 MHz DEC-alpha system equipped with 256 Mbytes of memory was used for direct analysis of sequence data as described above. In addition to the programs already mentioned, the GCG software (version 9.0) was used for alignment analysis. The windows-based program Generunner 3.0 (Hastings Software) was used for the design of oligonucleotide primers. A spline curve describing heterogeneity of the Tlr4 polypeptide sequence from different species was produced using the program Prism 3.0 (Graphpad Software, Inc). Sequences were prepared for submission with the use of the program Sequin 2.90 (obtained from NCBI).

Results

Overall Structure of TLR4 and Tlr4.

The mouse Tlr4 gene is somewhat longer than its human counterpart, owing to the greater length of intronic sequence (15337 bp from beginning to end of transcribed sequence in the mouse, SEQ ID NO:48, as compared to 11467 bp in the human, SEQ ID NO:47). There are three exons in Tlr4, and each corresponds to a homologous sequence in the human gene. A human cDNA sequence (Genbank accession number U88880) that includes a fourth exon, positioned between the "normal" first and second intron has been reported (Rock et al., 1998). When included in the processed transcript, however, this exon specifies early termination of the polypeptide chain. While it is possible that translation is initiated distal to the added stop codon, and that a shorter product results in the human than in the mouse, such a situation would be unusual given the length of the 5'UTR that would then exist, and the presence of multiple upstream initiation codons.

Moreover, there is no murine sequence homologous to the alternative second exon of the human gene. The biological significance of this exon is therefore unclear, and in all likelihood, its inclusion in the mRNA leads to the formation of a nonfunctional protein product.

Neither the human nor the mouse gene display a TATA element or CAAT box in the proximal promoter region. A number of conserved promoter and enhancer motifs are apparent on alignment of the murine and human 5' flanking sequences. Both Tlr4 and TLR4 lie in the midst of repetitive sequences of retroviral origin, and no other genes may be detected in close communication with either of them, using homology searches or the gene prediction algorithm GRAL.

Genetic Variation at the Human TLR4 Locus

In total, 204 human TLR4 alleles were sequenced in entirety. As such, all but the rarest alleles have likely been encountered. According to the formula:

$$(1-p)=(1-x)^N,$$

where p is the probability of detecting an allele, x is the actual frequency of the allele in population surveyed, and N is the number of alleles examined, there is a 95% chance that any allele with a frequency exceeding 1.46% was detected through sequencing this population.

In all, 12 mutable sites were found in human TLR4 (Table III, FIG. 10). Of these, most were confined to exon 3, though some were also placed in the second intron. Five changes observed in the coding region were silent (i.e., did not produce an amino acid substitution). Five changes did cause amino acid substitutions, one of which affected the cytoplasmic domain, and four of which affected the ectodomain.

The most common allele in the human population exists at a frequency of 86.3%, and 74.5% of the population is homozygous for this allele. The most common TLR4 polymorphism (designated TLR4-B; Genbank accession number AF177766) exists at an allelic frequency of 6%, and consists of a double amino acid substitution (residues 299 and 399 of the human polypeptide chain; nts 12874 and 13174 of the gene), one of which (residue 299) affects an aspartic acid residue conserved in mice, rats, hamsters, and chimpanzees (though differing in the baboon sequence). Though the mutations are almost always co-inherited, and hence, must lie in cis with one another, a single instance of mutation at the 12874 site was observed in the absence of the 13174 mutation. This would suggest that the double mutation may have arisen from an ancestral allele that is now very rare, and conceivably, it may confer an advantage to carriers.

Of the other mutations observed, 3 modified relatively conserved amino acid residues, whereas 4 modified relatively variable residues.

Genetic Variation at the Mouse Tlr4 Locus.

Among 35 strains of *Mus musculus,* 10 different alleles were identified, based on mutations occurring at 22 sites with respect to the reference sequence, 13 of which create amino acid substitutions (Table IV; FIG. 11). Hence, greater variation was observed among mice than among humans, with the most common murine allele represented at a frequency of only 69%. To a far greater extent in mice than in humans, the ancestry of different Tlr4 alleles may be traced, as many deviations from the reference allele occur in conduction with one another. A plausible arrangement of strain relationships is presented in FIG. 12. Some strains have accumulated many more mutations than others. For example, the P/J strain Tlr4 gene exhibits eleven mutations that distinguish it from the most common haplotype, six of them specifying changes in the Tlr4 amino acid sequence; the SEA/GnJ strain differs by nine mutations, and the strains NZW/J and VM/Dk, which are identical to one another, differ at six sites. Shared mutations suggest that interbreeding of some strains took place after their initial mutational separation had occurred, leading to the introduction of groups of mutations by genetic recombination. Hence, mice of the P/J, NZW/J, and VM/Dk strains have several mutations that are observed in the A/J and BALB/c strains, but

TABLE III

POLYMORPHISM OF THE HUMAN TLR4 LOCUS IN NORMAL INDIVIDUALS OF A MULTI-ETHNIC POPULATION — DALLAS, TX[§]

| Control | Nucleotide (Genomic) | Exon/ Intron[#] | AA | Receptor Domain* | Conserved | Allele Frequency |
|---|---|---|---|---|---|---|
| 12 | 8612 G → A | Intron 2 | — | — | | 0.01 |
| 57[†] | 12399 C → T | Exon 3 | — | — | No | 0.01 |
| | 12510 G → A | | (178) E → K | | | |
| 19, 42, 99 | 12413 C → A | Exon 3 | — | — | | 0.03 |
| 56[†] | 12413 C → A | Exon 3 | — | — | Yes | 0.01 |
| | 14266 G → A | | (763) R → H | Cyto | | |
| 89 | 12541 A → G | Exon 3 | (188) Q → R | Ecto | Yes | 0.01 |
| 2, 4, 11, 29, 31, | 12874 A → G | Exon 3 | (299) D → G | Ecto | Yes | 0.12 |
| 43, 62, 65, 70, | 13174 C → T | | (399) T → I | | No | |
| 78, 87, 93[‡] | | | | | | |
| 18 | 12874 A → G | Exon 3 | (299) D → G | Ecto | Yes | 0.01 |
| 55 | 12964 A → G | Exon 3 | (329) N → S | Ecto | No | 0.01 |
| 17, 67 | 13398 G → A | Exon 3 | (474) E → K | Ecto | No | 0.02 |
| 68 | 13769 G → A | Exon 3 | — | — | | 0.01 |
| 94 | 13937 G → A | Exon 3 | — | — | | 0.01 |
| 75 | 14266 G → A | Exon 3 | (763) R → H | Cyto | Yes | 0.01 |

[§]The complete exonic coding sequence of TLR4, including splice junctions, was determined using samples obtained from 102 anonymous individuals.
[†]It is unclear whether the mutations in these individuals lie in cis or in trans from one another.
[‡]With one exception (control 18), these mutations constitute a single allele and are always co-inherited.
*Transmembrane domain extends between residues 636 and 662.
[#]Coding limits within exons: Exon 1: (ATG) 4325→4417; Exon 2: 8414→8580; Exon 3: 12239→15625 (14498 = TGA). Alternative Exon 2: 8050–8169.

also lack some of the mutations of the latter strains, and have unique mutations of their own.

TABLE IV

POLYMORPHISM OF THE Tlr4 Among Mice

| Mouse[1] | Nucleotide (Genomic) | Exon/ Intron | AA | Receptor Domain* | Con-served |
|---|---|---|---|---|---|
| 10 | 26400 A → G | Exon 2 | — | — | |
| 4, 8, 21, 22 | 37685: $(T)_{10}$ | Intron 2 | — | — | |
| 34, 35 | 37685: $(T)_{12}$ | Intron 2 | — | — | |
| 23 | 37754 G → A | Exon 3 | 94 D → N | Ecto | Yes |
| 4, 8, 10, 20, 21, 34, 35 | 38101 G → A | Exon 3 | 209 M → I | Ecto | No |
| 21 | 38130 A → G | Exon 3 | 219 D → G | Ecto | No |
| 4, 8, 21 | 38234 G → A | Exon 3 | 254 V → I | Ecto | Yes |
| 10 | 38584 A → G | Exon 3 | — | — | |
| 21 | 38742 A → T | Exon 3 | 423 Q → L | Ecto | No |
| 10 | 38794 G → A | Exon 3 | — | — | |
| 10 | 38903 G → T | Exon 3 | 477 A → S | Ecto | Yes |
| 18 | 39020 A → G | Exon 3 | 516 T → A | Ecto | No |
| 4, 8, 10, 20, 21, 22, 34, 35 | 39199 C → T | Exon 3 | — | — | |
| 4, 8, 10, 20, 21, 34, 35 | 39253 A → C | Exon 3 | 593 E → D | Ecto | No |
| 23 | 39273 A → T | Exon 3 | 600 N → I | Ecto | No |
| 10 | 39383 G → A | Exon 3 | 637 V → I | TM | Yes |
| 19 | 39604 T → C | Exon 3 | — | — | |
| 4, 8, 20, 21, 34, 35 | 39631 C → T | Exon 3 | — | — | |
| 4, 8, 20, 21, 34, 35 | 39756 G → A | Exon 3 | 761 R → H | Cyto | Yes |
| 18 | 39826 T → C | Exon 3 | — | — | |
| 10 | 39907 T → G | Exon 3 | 811 N → K | Cyto | No |

As in the human TLR4 gene, most of the murine mutations reside within exon 3, and only two substitutions are noted to modify the cytoplasmic domain (FIG. 12). Of these, however, one mutation (R761H), is fairly common among the strains surveyed, and corresponds exactly to the human mutation (R763H), observed in one individual out of the 102 surveyed. The same residue has been reported as an H in the hamster. A single conservative substitution (V637I) was noted within the transmembrane domain of the P/J strain.

Anthropoid ape and Lower Primate TLR4 Sequences, and their Relationship to the Human and Rodent Sequences The human and chimpanzee amino acid sequences are nearly identical over the interval studied, distinguished only by three amino acid substitutions. The baboon sequence is 93.5% identical to the human in the ectodomain, differs in the transmembrane domain by one substitution out of 30 residues, and differs in the proximal cytoplasmic domain by only 1 residue in 155. At the C-terminus, however, homology is badly disrupted, so that 16 of the last 21 human residues are not replicated in the baboon protein, which is 13 amino acids shorter than the human protein. Similarly, among rodents, the C-terminus of the protein is the least conserved. Overall, the order of conservation with respect to domain is:

proximal cytoplasmic domain>transmembrane domain>ectodomain>distal cytoplasmic domain.

Indeed, interspecific comparisons of complete Tlr4 amino acid sequence confirm the existence of a hypervariable region at the distal end of the Tlr4 cytoplasmic domain (Table V, FIG. 13).

TABLE V

| | Human | Chimp | Baboon | Rat | Mouse | Hamster |
|---|---|---|---|---|---|---|
| | | | ECTO | | | |
| Human | 100% | | | | | |
| Chimp | 99.6% | 100% | | | | |
| Baboon | 91.5% | 91.5% | 100% | | | |
| Rat | 61.3% | 60.7% | 59.4% | 100% | | |
| Mouse | 61.9% | 62.0% | 60.1% | 82.9% | 100% | |
| Hamster | 64.3% | 64.2% | 62.5% | 73.8% | 74.8% | 100% |
| | | | TM | | | |
| Human | 100% | | | | | |
| Chimp | 100% | 100% | | | | |
| Baboon | 97.1% | 97.1% | 100% | | | |
| Rat | 67.7% | 67.7% | 67.7% | 100% | | |
| Mouse | 70.6% | 70.6% | 70.6% | 91.2% | 100% | |
| Hamster | 73.5% | 73.5% | 73.5% | 79.4% | 79.4% | 100% |
| | | | PROXIMAL | | | |
| Human | 100% | | | | | |
| Chimp | 99.4% | 100% | | | | |
| Baboon | 99.4% | 98.7% | 100% | | | |
| Rat | 91.7% | 91.0% | 91.0% | 100% | | |
| Mouse | 90.4% | 89.7% | 89.7% | 98.1% | 100% | |
| Hamster | 91.7% | 91.0% | 91.0% | 97.4% | 95.5% | 100% |
| | | | DISTAL | | | |
| Human | 100% | | | | | |
| Chimp | 100% | 100% | | | | |
| Baboon | 50% | 50% | 100% | | | |
| Rat | 38.1% | 38.1% | NS | 100% | | |
| Mouse | 26.3% | 26.3% | NS | 63.2% | 100% | |
| Hamster | 40.9% | 40.9% | NS | 40.9% | 45.5% | 100% |

Homology among functional domains of Tlr4 from six species. Percentages refer to identity on Fast-A comparison. Ecto, residues 1–631; TM, residues 632–662; Proximal, residues 663–819; Distal, residues 820–839.

TABLE VI

POLYMORPHISM OF THE HUMAN TLR4 LOCUS IN PATIENTS WITH SYSTEMIC LUPUS ERYTHEMATOSUS — CONNECTICUT

| Patient | Nucleotide (Genomic) | Exon/ Intron# | AA | Receptor Domain | Conserved | Allele Frequency |
|---|---|---|---|---|---|---|
| 22, 5, 3 | 12874 A → G | Exon 3 | (299) D → G | Ecto | Yes | 0.12 |
| 22, 3 | 13174 C → T | Exon 3 | (399) T → I | Ecto | No | 0.08 |
| 24 | 13398 G → A | Exon 3 | (474) E → K | Ecto | No | 0.04 |
| 19, 20 | 14266 G → A | Exon 3 | (763) R → H | Cyto | Yes | 0.08 |

#Coding limits within exons: Exon 1: (ATG) 4325→4417; Exon 2: 8414→8580; Exon 3: 12239→15625 (14498 = TGA). Alternative Exon 2: 8050–8169.

TABLE VII

POLYMORPHISM OF THE HUMAN TLR4 LOCUS IN PATIENTS WITH MENINGOCOCCAL SEPSIS — HOLLAND, UK, USA

| Patient | Nucleotide (Genomic) | Exon/ Intron | AA | Receptor Domain | Conserved | Allele Frequency |
|---|---|---|---|---|---|---|
| 121, 122, 146 | 8457 A → G | Exon 2 | (46) Y → C | Ecto | No | .017 |
| 98 | 8631 A → G | Intron 2 | — | — | — | .006 |
| 86 | 12228 ΔT | Intron 2 | — | — | | .006 |
| 28 | 12245 A → G | Exon 3 | — | — | Yes | .006 |
| | Δ 14453 → 14461 | | Δ (827–829) VGT | Cyto | | .006 |
| 86 | 12293 T → C | Exon 3 | — | — | — | .006 |
| 69, 76, 97, 102, 107, 115, 125, 136 | 12413 C → A | Exon 3 | — | — | — | .045 |
| ??136 | 12412 C → A | Exon 3 | (145) P → H | Ecto | No | .006 |
| 17 | 12820 G → A | Exon 3 | (281) C → Y | Ecto | Yes | .006 |
| 64, 143 | 12874 A → G | Exon 3 | (299) D → G | Ecto | Yes | .011 |
| 11, 75, 113, 116, 120 | 12874 A → G<br>13174 C → T | Exon 3 | (299) D → G<br>(399) T → I | Ecto | Yes<br>No | .028 |
| 70, 138 | 13174 C → T | Exon 3 | (399) T → I | Ecto | No | .011 |
| 150 | 13848 A → C | Exon 3 | (624) N → H | Ecto | Yes | .006 |
| 62, 85 | 13937 G → A | Exon 3 | — | — | — | .011 |

#Coding limits within exons: Exon 1: (ATG) 4325→4417; Exon 2: 8414→8580; Exon 3: 12239→15625 (14498 = TG A). Alternative Exon 2: 8050–8169.
*locus-equivalents sequenced

Example 9

Tlr4-Mediated LPS Signal Transduction in Macroprages

The mammalian LPS sensor is formed by a complex array of proteins, some of which may as yet be unknown. Complexes of LPS and LBP are initially engaged at the cell surface by CD14, a glycosphosphoinositol-linked protein with no cytoplasmic domain (Wright et al., 1990). The biological relevance of CD14 in LPS signaling, originally deduced from binding and transfection studies (Wright, 1990; Kirkland et al., 1990), is supported by gene knockout data, which revealed that CD14 expression is required for normal sensitivity to LPS (Haziot et al., 1996. However, it was assumed that a second, membrane-spanning protein must ultimately transduce the LPS signal, since CD14 lacks a cytoplasmic domain.

The protein that likely fulfills this role was identified through studies of mice, wherein mutations of a single gene (Lps) have long been known to abolish LPS signal transduction (Sultzer, 1968; Watson et al., 1978). The $Lps^d$ allele, represented in C3H/HeJ mice, is codominant in the sense that $Lps^d/Lps^n$ heterozygotes exhibit intermediate sensitivity to LPS (Rosenstreich et al., (1978), and their macrophages display intermediate levels of TNF production in response to LPS. The innominate non-responder allele represented in C57BL/10ScCr mice is recessive to the wild-type allele, in that heterozygotes display normal responses to LPS (Coutinho and Meo, 1978). Using positional methods, the inventors have determined that Lps encodes the toll-like receptor 4 (Tlr4), a single-spanning transmembrane protein with a leucine-rich ectodomain and a "Toll-like" cytoplasmic domain (Poltorak et al., 1998a; Poltorak et al., 1998b). The $Lps^d$ allele bears a missense mutation (2342 C_A; P712H) which lies within the cytoplasmic domain of the polypeptide chain. The mutation in C57BL/10ScCr mice is a null allele. Relying on these data (Qureshi et al., 1999a), other workers confirmed the presence of the mutations (Qureshi et al., 1999b). Moreover, Hoshino and colleagues demonstrated that a Tlr4 knockout produces an excellent phenocopy of the naturally occurring Tlr4 mutations (Hoshino et al., 1999).

In order to directly examine the role of Tlr4 as a transducer of the LPS signal in macrophages, the inventors expressed the normal mouse protein—and various mutant forms—in RAW 264.7 macrophages have been expressed (FIG. 14; Table VIII). These cells of murine origin are highly responsive to LPS, and are known to express the Tlr4 mRNA (Poltorak et al, 1998b). Unlike cell lines of non-myeloid origin (i.e., 293 cells or CHO cells), they express all proteins required for the elicitation of a biologically relevant response to LPS (e.g., TNF production). As such, they may be used to determine whether Tlr4 is a limiting factor in the initiation of an LPS signal, and to examine the mechanism by which the $Tlr4^{Lps-d}$ allele exerts its dominant inhibitory effect on signaling. This was determined by performing more than 3,000 assays of TNF production, induced over an extensive range of LPS concentrations in numerous stable clones, since individual clones show considerable background variability in LPS responses. Moreover, because culture conditions can affect the sensitivity of the TNF assay and production of TNF by LPS-stimulated cells, all transfected and control clones were induced and assayed in parallel. Statistical analyses of shifts in the EC50 values determined for individual clones were then applied in order to determine the influence of recombinant protein expression.

RAW 264.7 cells were first cotransfected with cDNAs derived from the $Tlr4^{Lps-n}$ and $Tlr4^{Lps-d}$ alleles and with a vector encoding neo. The amino terminus of each protein was flag-tagged to permit measurement of expression at the cell surface using the monoclonal antibody M2 (obtained from Sigma). After G418 selection, stable clones expressing each Tlr4 isoform or transfected with vector alone were examined for LPS signal transduction. The binding isotherm from one such clone, transfected with the $Tlr4^{Lps-n}$ construct, is displayed in FIG. 15A, and the flag copy number for clones bearing each construct is displayed in FIG. 15B. Despite the use of a strong promoter, the mean copy number rarely exceeded $3\times10^4$ per cell, and the range of expression among all clones spanned less than an order of magnitude. The relatively low copy number achieved is consistent with the possibility that surface expression may be limited by the level of co-expression of other proteins (e.g. MD-2 (Shimazu et al., 1999)), and the lower copy number in clones bearing truncated constructs as compared with full-length constructs may reflect diminished stability.

Composite EC50 analysis revealed strong augmentation of the LPS response (a 30-fold leftward shift of the curve) resulting from modest over-expression of the normal protein; even stronger suppression (a 2600-fold shift to the right) was observed with expression of the mutant isoform. Hence, with respect to the over-expression of $Tlr4^{Lps-n}$ and $Tlr4^{Lps-d}$ proteins, a 74,000-fold difference in the mean response is apparent at the EC50 point (FIG. 15C). A more conservative approach, based on measurement of the LPS EC50 for each individual clone, also revealed that the $Tlr4^{Lps-n}$ isoform strongly enhances LPS sensitivity, while the $Tlr4^{Lps-d}$ isoform strongly suppresses it (FIG. 15D). According to this method of estimation, the composite range of the responsiveness (mean EC50 of $Tlr4^{Lps-d}$ transfected clones/mean EC50 of $Tlr4^{Lsp-n}$ transfected clones) was 1120-fold. Taking the dimension of receptor number into account (FIG. 15E), and excluding the statistical contribution of the clones transfected with vector alone, no significant correlation was observed between LPS signal intensity and the absolute number of recombinant Tlr4 molecules on the cell surface. This suggests that the number of artificial receptors expressed (usually ~$1–2\times10^4$) is well in excess of the number of native receptors, and that maximum augmentation of LPS response is achieved in each clone transfected with $Tlr4^{Lps-n}$, with variation attributable to other factors. It is interesting in this regard that, on a linear scale, the inhibitory effect of $Tlr4^{Lps-d}$ over-expression vastly exceeds the augmenting effect of $Tlr4^{Lps-n}$ expression. In fact, most of the macrophage clones were rendered virtually unresponsive to LPS through over-expression of $Tlr4^{Lps-d}$ (LPS EC50>10 μg/ml).

Several conclusions can be drawn from these results. First, the dominant effect of the $Tlr4^{Lps-d}$ allele may be directly demonstrated through transfection-based expression of the protein at moderate levels in an LPS-responsive macrophage cell line. Second, since over-expression of $Tlr4^{Lps-n}$ augments the LPS response, the intensity of the LPS signal is normally limited by the quantity of Tlr4 protein on the macrophage membrane. Third, since there appears to be little correlation between the absolute number of recombinant receptors expressed and the magnitude of augmentation or inhibition achieved, it may be inferred that saturation of another component of the signaling cascade, either proximal or distal to Tlr4, occurs when the level of Tlr4 expression exceeds a certain threshold: perhaps in the range of several thousand copies per cell. By the same token, the level of endogenous Tlr4 expression is probably very low: perhaps lower than 10 (Michalek et al., 1980) copies per cell (a finding consistent with the fact that Tlr4 mRNA is of very low abundance (Poltorak et al., 1998b), but nonetheless remarkable in view of the global effects wrought by activation of the receptor). Fourth, and perhaps most important of all, since rather modest changes in the level of normal Tlr4 protein expression or the expression of a dominant negative Tlr4 isoform can shift LPS sensitivity over a range that spans three to four orders of magnitude, one may infer that Tlr4 is of preponderant importance in LPS signal transduction: there is little room for the belief that independent pathways act to transduce the LPS signal as well. This last point is fully supported by the observation that mutation or deletion of the Tlr4 locus can completely abrogate LPS signaling (Sultzer, 1968; Coutinho and Meo, 1978; Poltorak et al., 1998b).

In one model, the dominant suppressive effect of $Tlr4^{Lps-d}$ might be ascribed to the postulated multimeric structure of the Tlr4 protein (Schneider et al., 1991; Medzhitov et al., 1997), given that unproductive association between normal and abnormal subunits yields inhibition of signaling. If association between subunits is principally dependent upon ectodomain contacts, one would predict that any mutation that disrupts function of the Tlr4 cytoplasmic domain might impede signal transduction in a dominant fashion, just as observed with $Tlr4^{Lps-d}$. To examine this hypothesis, the inventors expressed a truncated version of the Tlr4 protein, lacking the entire cytoplasmic domain. This protein was well expressed on the cell surface, but had only a weak inhibitory effect on LPS signaling, which fell short of significance according to the more stringent method of analysis (FIG. 16A and FIG. 16B). Hence, the $Tlr4^{Lps-d}$ isoform exerts a strong dominant effect whereas deletion of the entire cytoplasmic domain does so weakly at most. The inventors conclude that, if the model of dominant inhibition based on multimeric structure is correct, cytoplasmic domain contacts, in addition to ectodomain contacts, must serve to maintain the holoprotein in a multimeric state. Given free exchange between subunits, mutant Tlr4 proteins lacking a cytoplasmic domain would predictably be excluded from the signaling complex in favor of intact subunits that interact more strongly with one another.

The biological consequence of interactions between normal and mutant cytoplasmic domains and the intact Tlr4 protein were tested directly. Upon expressing membrane-associated versions of the Tlr4 cytoplasmic domain (with either the normal or mutant sequence and an exteriorized flag peptide, but lacking the entire ectodomain), the inventors observed that the all-cytoplasmic $Tlr4^{Lps-d}$ isoform inhibited LPS signaling (rightward EC50 shift of 39-fold; p=0.0019). The $Tlr4^{Lps-n}$ isoform was a significantly weaker inhibitor than the $Tlr4^{Lps-d}$ isoform (p=0.0214), though it also blocked signaling when overexpressed (rightward EC50 shift of 4-fold; p=0.035). These results suggest that the $Tlr4^{Lps-d}$ mutation not only permits interaction between normal and mutant subunits, but actually enhances the interaction, or actively engages downstream signaling molecules, thus blocking the LPS response (FIG. 17A and FIG. 17B).

The primacy of Tlr4 in LPS signal transduction was originally suggested by positional cloning data (Poltorak et al., 1998a; Poltorak et al., 1998b). Direct confirmation of Tlr4's function as the transmembrane signaling component of the LPS receptor complex has lagged, due largely to the difficulties inherent in transiently transfecting macrophage lines with high efficiency. Rather, there has been a tendency to utilize non-macrophage lines (e.g., HEK 293 cells) in transfection-based studies of LPS signaling. However, these cells do not replicate the biological response phenotype of authentic macrophages. In particular, they do not produce TNF in response to LPS; hence, a surrogate endpoint of response (nuclear translocation of NF-B, measured using a transcriptional reporter) has been adopted in most such studies. However, it is quite clear that NF-B translocation cannot be equated with an LPS response, since many stimuli that elicit NF-B Translocation yield effects that have little or nothing in common with the LPS response in other respects. Moreover, it has recently been shown that mutational inactivation of MyD88, which is known to engage Tlr4, leads to a state of profound LPS unresponsiveness, though permitting NF-B Translocation. Finally, given that a response of any kind is observed in non-macrophage cell lines, there exists no standard for comparison. It has never been clear, for example, that the magnitude of the NF-B response approaches that witnessed in a normal macrophage over an identical range of LPS concentrations, nor is it known what effect this might have in a macrophage. These technical issues have, to date, confounded interpretation of which molecule actually does transduce the LPS signal, a role previously ascribed to Tlr2 (Yang et al., 1998; Kirschning et al., 1998) but now clearly attributable to Tlr4.

The present data reveal that Tlr4 is the limiting factor in LPS signal transduction in LPS responsive macrophages. Over-expression of Tlr4 in cells that already express it augments the LPS response, by about 30-fold on average. The relationship between the level of Tlr4 expression and biological response indicates that, although other proteins fulfill indispensable functions in LPS signal transduction both upstream (Wright et al., 1990) and downstream (Kawai et al., 1999; Muzio et al., 1998; Medzhitov et al., 1998) from Tlr4, the quantity of Tlr4 expressed is an important limiting factor in the intensity of the signal that is evoked. Hence, sensitivity to LPS is likely controlled through modulation of Tlr4 biosynthesis or activity. Priming by interferon (Pace et al., 1985; Lau and Livesey, 1989; Hayes and Zoon, 1993) or by treatment with facultative intracellular pathogens (Vogel et al., 1980; Haranaka et al., 1984; Matsuura and Galanos, 1990) can greatly enhance sensitivity to LPS, while corticosteroids create a state of LPS resistance (Beutler et al., 1986). Such modulation may be achieved through alteration of Tlr4 structure or expression, or alternatively, through changes in sensitivity to the signal that Tlr4 initiates, or changes in the intensity of the signal that Tlr4 receives.

The over-expression of a membrane-anchored Tlr4 ectodomain (lacking any of the wild-type cytoplasmic domain) inhibited the LPS response only weakly, if at all. This failure of the overexpressed ectodomain to block signaling by a competitive mechanism implies that upstream components of the signal transduction pathway must either exist in excess with respect to Tlr4, or must interact with Tlr4 at very low affinity. There is now good reason to doubt the proposal (Modlin et al., 1999) that the expression of soluble Tlr4 might prove an effective means of interdicting the LPS signal in vivo, particularly in view of the fact that a membrane-anchored form of the protein would be sterically positioned to exert such an effect with maximum efficiency, while a soluble form would not be. It is, for example, possible to calculate the local concentration of Tlr4 ectodomain achieved through over-expression of a membrane-associated version of the protein. Assuming that the Tlr4 ectodomain resides within a space that is 100 Å "deep" from its most apical point to the surface of the membrane, and further assuming that the macrophage is a spherical body with a 15 µM radius, the expression of $2\times10^4$ receptors per cell corresponds to a protein concentration of $1.2\times10^{-6}$ M, or 840 µg of ectodomain per ml. While it might be possible to achieve such concentrations of soluble ectodomain in vivo, it would not be easy to do so, and at that, little or no attenuation of the LPS signal would be anticipated. On the other hand, interventions that inhibit contact between Tlr4 subunits would be likely to have a pronounced impact on signal transduction.

TABLE VIII

| Construct | Residues expressed | Copies/cell | Å SD | n |
|---|---|---|---|---|
| $Tlr4^{Lps-n}$ | 22–835 | $2.1\times10^4$ | $4.1\times10^3$ | 10 |
| $Tlr4^{Lps-d}$ | 22–835 (P712H) | $2.0\times10^4$ | $1.4\times10^4$ | 10 |
| $Tlr4^{Lps-n}$ Cyt. Dom. | 630–835 | $1.2\times10^4$ | $3.8\times10^3$ | 7 |
| $Tlr4^{Lps-d}$ Cyt. Dom. | 630–835 (P712H) | $9.9\times10^3$ | $4.0\times10^3$ | 8 |
| Ectodomain | 22–660 | $1.4\times10^4$ | $5.1\times10^3$ | 9 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,464,937
U.S. Pat. No. 5,488,032
U.S. Pat. No. 5,508,262
U.S. Pat. No. 5,608,035
U.S. Pat. No. 5,726,148
U.S. Pat. No. 5,767,064
U.S. Pat. No. 5,767,234
U.S. Pat. No. 5,776,731
U.S. Pat. No. 5,786,331
U.S. Pat. No. 4,215,051,
U.S. Pat. No. 4,554,101
U.S. Pat. No. 4,603,102
U.S. Pat. No. 4,683,195
U.S. Pat. No. 4,683,202
U.S. Pat. No. 4,683,202
U.S. Pat. No. 4,800,159,
U.S. Pat. No. 4,883,750
U.S. Pat. No. 4,682,195
WO 90/07641
Angle et al., *Cell.* 49(6): 729–739, 1987
Angle et al., *Mol Cell Biol.* 7(6): 2256–2266, 1987a
Apte et al., *J. Cell. Physiol.* 89, 313–323, 1976
Apte, et al., *J. Immunol.* 119, 1898 1977
Banerji et al., *Cell;* 27(2 Pt 1): 299–308, 1981
Bell, et al., *Mammalian Genome.* 6, 389–395, 1995
Berkhout et al., *Cell;* 59(2): 273–282, 1989
Beutler et al., *J. Immunol.,* 135:3972–3977, 1985a.
Beutler et al., *Science,* 229:869–871, 1985b.
Beutler et al., *Science,* 232:977–980, 1986.
Beutler, Krochin, Milsark, Luedke, Cerami, *Science,* 232: 977–980, 1986.
Beutler, Milsark, Cerami, *Science,* 229:869–871, 1985.

Blanar et al., *Mol Cell Biol.* 1989 February; 9(2): 844–846, 1989
Bodine and Ley, *EMBO J.* 6(10): 2997–3004, 1987
Boshart et al., *Cell.* 1985 June; 41(2): 521–530, 1985
Bosze et al., *EMBO J.* 1986 July; 5(7): 1615–1623, 1986
Braddock et al., *Cell.* 1989 Jul. 28; 58(2): 269–279, 1989
Bulla and Siddiqui, Virology. 1989 May; 170(1): 251–260, 1989
Burn et al., *Gene.* 161, 183–187, 1995
Campbell and Villarreal, *Mol Cell Biol.* 1988 May; 8(5): 1993–2004, 1988
Campo et al., Nature. 1983 May 5; 303(5912): 77–80, 1983
Celander and Haseltine, J. Virol. 61(2): 269–275, 1987
Celander et al., J. Virol. 62(4): 1314–1322, 1988
Chandler et al., Cell. 1983 June; 33(2): 489–499, 1983
Chang et al., Mol Cell Biol. 1989 May; 9(5): 2153–2162, 1989
Chatterjee et al., Proc Natl Acad Sci U S A. 1989 December; 86(23): 9114–9118, 1989
Chaudhary et al., *Blood.* 91, 4020–4027, 1998
Chedid et al., *Infec. Immun.* 13, 722–727, 1976
Chol et al., Eur J. Biochem. August 1; 239(3): 579–587, 1996
Cohen et al., 1987
Costa et al., Mol Cell Biol. 8(1): 81–90, 1988
Coutinho and Meo, *Immunogenetics,* 7:17–24, 1978.
Coutinho et al., *Eur. J. Immunol.* 7, 325–328, 1977
Coutinho et al., *Immunogenetics.* 7, 17–24, 1978
Cripe et al., EMBO J. 6(12): 3745–3753, 1987
Cseh and Beutler, *J. Biol. Chem.* 264, 16256–16260, 1989
Cseh and Beutler, *J. Biol. Chem.,* 264:16256–16260, 1989.
Culotta and Hamer, Mol Cell Biol; 9(3): 1376–1380, 1989
Dandolo et al., J. Virol. 47(1): 55–64, 1983
Davey et al., EPA No. 329 822
Deschamps et al., 1985
deVilliers et al., Nature. 1984 Nov. 15; 312(5991): 242–246, 1984
Edbrooke et al., Mol Cell Biol. 1989 May; 9(5): 1908–1916, 1989
Edlund et al., Science. 1985 Nov. 22; 230(4728): 912–916, 1985
EPA No. 320 308
Feng and Holland, Nature. 1988 Jul. 14; 334(6178): 165–167, 1988
Firak and Subramanian, Mol Cell Biol. 1986 November; 6(11): 3667–3676, 1986
Foecking and Hofstetter, Gene. 1986; 45(1): 101–105, 1986
Fonta et al., Neuroreport. 1995 Mar. 27; 6(5): 745–749, 1985
Fraker and Speck, *Biochem. Biophys. Res. Commun.,* 80:849–857, 1978.
Freudenberg, Keppler, Galanos, *Infec. Immun.,* 51:891–895, 1986.
Frohman, M. A., In: *PCR™ PROTOCOLS: A GUIDE TO METHODS AND APPLICATIONS*, Academic Press, N.Y., 1990
Fujita et al., Cell. 1987 May 8; 49(3): 357–367, 1987
Geppert et al, *Mol. Med.,* 1:93–103, 1994.
Gerard, *Nature,* 395:217–219, 1998.
Gilles et al., *Nucleic Acids Res.* 1983 Nov. 25; 11(22): 7981–7997, 1983
Gloss et al., *EMBO J.* 1987 Dec. 1; 6(12): 3735–3743, 1987
Glue et al., 1988
Godbout et al., Genes Dev. 1988 August; 2(8): 949–956, 1988
Goodbourn and Maniatis, Cell. 1985 June; 41(2): 509–520, 1985
Goodbourn et al., Cell. 1986 May 23; 45(4): 601–610, 1986
Greene et al., Adv Exp Med Biol. 1989; 254: 55–60, 1989
Grosschedl and Baltimore, Cell. 1985 July; 41(3): 885–897, 1985
Han et al., *J. Exp. Med.,* 171:465–475, 1990.
Han, Brown, Beutler, *J. Exp. Med.,* 171:465–475, 1990.
Haranaka, Satomi, Sakurai, Haranaka, *Cancer Immunol. Immunother.,* 18:87–90, 1984.
Haslinger and Karin, Proc Natl Acad Sci USA. 1985 December; 82(24): 8572–8576, 1985
Hauber and Cullan, 1988
Hayes and Zoon, *Infec. Immun.,* 61:3222–3227, 1993.
Haziot, Ferrero, Kontgen et al., *Immunity,* 4:407–414, 1996.
Heine et al., *J. Immunology,* 162:6971–6975, 1999.
Hen et al., Nature. 1986 May 15; 321(6067): 249–251, 1986
Hensel et al., 1989
Herr and Clarke, 1986
Hirochika et al., J. Virol. 1987 August; 61(8): 2599–2606, 1987
Hirsch et al., Mol Cell Biol. 1990 May; 10(5): 1959–1968, 1990
Hoffmann et al., *J. Exp. Med.* 146, 1640–1647, 1977
Holbrook et al., Virology. 1987 March; 157(1): 211–219, 1987
Horlick and Benfield, Mol Cell Biol. 1989 June; 9(6): 2396–2413, 1989
Hoshino, Takeuchi, Kawai et al., *Journal of Immunology,* 162:3749–3752, 1999.
Hu et al., *Genome Research.* 7, 693–704, 1997
Huang et al., 1981
Hwang et al., 1990
Imagawa et al., Cell. 1987 Oct. 23; 51(2): 251–260, 1987
Imbra and Karin, Nature. 1986 Oct. 9; 323(6088): 555–558, 1986
Imler et al., Mol Cell Biol. 1987 July; 7(7): 2558–2567, 1987
Imperiale and Nevins, Mol Cell Biol. 1984 May; 4(5): 875–882, 1984
Jakobovits et al., Mol Cell Biol. 1988 December; 8(12): 5549–5554, 1988
Jameel and Siddiqui, Mol Cell Biol. 1986 February; 6(2): 710–715, 1986
Jaynes et al., Mol Cell Biol. 1988 January; 8(1): 62–70, 1988
Johnson et al., Mol Cell Biol. 1989 August; 9(8): 3393–3399, 1989a
Kadesch and Berg, Mol Cell Biol. 1986 July; 6(7): 2593–2601, 1986
Karin et al., Mol Cell Biol. 1987 February; 7(2): 606–613, 1987
Katinka et al., Cell. 1980 June; 20(2): 393–399, 1980,
Katinka et al., Nature. 1981 Apr. 23; 290(5808): 720–722, 1981
Kawai, Adachi, Ogawa, Takeda, Akira, *Immunity,* 11(1): 115–122, 1999.
Kawamoto et al., Mol Cell Biol. 1988 January; 8(1): 267–272, 1988
Kirkland, Virca, Kuus-Reichel et al., *J. Biol. Chem.,* 265: 9520–9525, 1990.
Kirschning, Wesche, Merrill, Rothe, *J. Exp. Med.,* 188: 2091–2097, 1998.
Kruys, Kemmer, Shakhov, Jongeneel, Beutler, *Proc. Natl. Acad. Sci. USA,* 89:673–677, 1992.
Kuhns et al., *J. Immunol.* 158, 3959–3964, 1997
Kyte and Doolittle, *J. Mol. Biol.,* 157(1):105–132, 1982.
Lau and Livesey, *J. Clin. Invest.,* 84:738–743, 1989.
Lemaitre et al., *Cell.* 86, 973–983, 1996
Macela et al., *FEMS Immunol. Med. Microbiol.* 13, 235–238, 1996

Matsuura and Galanos, *Infec. Immun.*, 58:935–937, 1990.
Medzhitov, Preston-Hurlburt, Janeway, *Nature*, 388:394–397, 1997.
Medzhitov, Preston-Hurlburt, Kopp et al., *Molecular Cell*, 2:253–258, 1998.
Michalek, Moore, McGhee, Rosenstreich, Mergenhagen, *J. Infec. Dis.*, 141:55–63, 1980.
Miller et al., PCT Application WO 89/06700
Modlin, Brightbill, Godowski, *N. Engl. J. Med.*, 340:1834–1835, 1999.
Muzio et al., *J. Exp. Med.* 187, 2097–2101, 1998
Muzio, Natoli, Saccani, Levrero, Mantovani, *J. Exp. Med.*, 187:2097–2101, 1998.
O'Brien et al., *J. Immunol.* 124, 20–24, 1980.
Pace, Russell, LeBlanc, Murasko, *J. Immunol.*, 134:977–989, 1985.
Poltorak et al., "Endotoxin, Lipopolysaccharide, c. Positional, Shock, Inflammation, and Sepsis," *Blood Cells Molecules & Diseases* 24:340–355, 1998.
Poltorak, He, Smirnova et al., *Science*, 282:2085–2088, 1998b.
Poltorak, Smirnova, He et al., *Blood Cells Mol. Dis.*, 24:340–355, 1998a.
Qureshi et al., 10*th International Mouse Genome Conference*. 311, 1996(Abstract)
Qureshi, Lariviere, Leveque et al., *J. Exp. Med.*, 189:1519, 1999.
Qureshi, Lariviere, Leveque et al., *J. Exp. Med.*, 189: 615–625, 1999.
Rock et al., "A family of human receptors structurally related to *Drosophila* Toll," *Proc. Natl. Acad. Sci. U.S.A.* 95, 588–593, 1998.
Rommens et al., In: Hochgeschwender, U., Gardiner, K., eds., *Identification of Transcribed Sequences*, New York, N.Y., Plenum Press, 1998, p. 65
Rosenstreich et al., *J. Immunol.* 121, 1664–1670, 1978
Rosenstreich et al., *J. Infec. Dis.* 136, S239–S2451977
Rosenstreich, Vogel, Jacques, Wahl, Oppenheim, *J. Immunol.*, 121:1664–1670, 1978.
Rosetto et al., *Biochem. Biophys. Res. Commun.* 209, 111–116, 1995
Ryan et al., *Nature*. 269, 153–155, 1977
Sambrook et al., *In: Molecular Cloning: A Laboratory Manual*, Cold Spring Harbor Laboratory Press, Cold Spring Harbor, N.Y., 1989.
Schneider, Hudson, Lin, Anderson, *Genes Dev.*, 5:797–807, 1991.
Shimazu, Akashi, Ogata et al., *J. Exp. Med.*, 189(11): 1777–1782, 1999.
Sultzer, *Nature*, 219:1253–1254, 1968.
Sultzer, *Nature*. 219, 1253–1254, 1968
Tracey et al., *Science*, 234:470–474, 1986.
Tracey, Beutler, Lowry et al., *Science*, 234:470–474, 1986.
Truffa-Bachi et al., *Cell. Immunol.* 30, 1–11, 1977
Vogel and Fultz, *Microbiol. Immunol.* 137, 165–170, 1988
Vogel et al., *Infect. Immun.* 62, 4454–4459, 1994
Vogel, Moore, Sipe, Rosenstreich, *J. Immunol.*, 124:2004–2009, 1980.
Von Jeney et al., *Infec. Immun.* 15, 26–33, 1977
Watson et al., *J. Immunol.* 118, 2088–2093, 1977
Watson et al., *J. Immunol.* 120, 422–424, 1978
Watson, Kelly, Largen, Taylor, *J. Immunol.*, 120:422–424, 1978.
Wright et al., *Science*, 249:1431–1433, 1990.
Wright, Ramos, Tobias, Ulevitch, Mathison, *Science*, 249: 1431–1433, 1990.
Yang et al., *Nature*, 395:284–288, 1998.
Yang, Mark, Gray et al., *Nature*, 395:284–288, 1998.

What is claimed is:

1. A method of screening for modulators of a lipopolysaccharide mediated response comprising the steps of:

a) obtaining a cell expressing a TLR-4 polypeptide, wherein the TLR-4 polypeptide has the amino acid sequence of SEQ ID NO:2, SEQ ID NO:4, SEQ ID NO:6, SEQ ID NO:98 or SEQ ID NO:99, or is encoded by a nucleic acid sequence comprising SEQ ID NO:1, SEQ ID NO:3, SEQ ID NO:5, SEQ ID NO:46, SEQ ID NO:47 or SEQ ID NO:48;

b) measuring a lipopolysaccharide mediated response mediated by the TLR-4 polypeptide;

c) contacting the TLR-4 polypeptide with a putative modulator;

d) assaying for a change in the lipopolysaccharide mediated response; and e) comparing the lipopolysaccharide mediated responses mediated by the TLR-4 polypeptide obtained in steps b) and d) above wherein a difference in the lipopolysaccharide mediated responses indicates that the putative modulator is a modulator of a lipopolysaccharide mediated response.

2. The method of claim 1, wherein the lipopolysaccharide mediated response mediated by the TLR-4 polypeptide is determined by determining the ability of the TLR-4 polypeptide to stimulate transcription of a reporter gene, the reporter gene operatively positioned under control of a nucleic acid segment comprising a promoter from a TLR-4 gene.

3. The method of claim 1, wherein the TLR-4 polypeptide has the amino acid sequence of SEQ ID NO:2.

4. The method of claim 1, wherein the TLR-4 polypeptide has the amino acid sequence of SEQ ID NO:4.

5. The method of claim 1, wherein the TLR-4 polypeptide has the amino acid sequence of SEQ ID NO:6.

6. The method of claim 1, wherein the TLR-4 polypeptide has the amino acid sequence of SEQ ID NO:98.

7. The method of claim 1, wherein the TLR-4 polypeptide has the amino acid sequence of SEQ ID NO:99.

8. The method of claim 1, wherein said putative modulator is effective in altering the mediation of the lipopolysaccharide mediated response by TLR-4.

9. The method of claim 8, wherein said putative modulator is an agonist of the lipopolysaccharide mediated response.

10. The method of claim 8, wherein said putative modulator is an antagonist of the lipopolysaccharide mediated response.

11. The method of claim 8, wherein said putative modulator affects the transcription of TLR-4.

12. The method of claim 8, wherein said putative modulator affects the translation of TLR-4.

13. The method of claim 1, wherein said putative modulator inhibits TLR-4 directed signaling of TNF secretion.

14. The method of claim 1, wherein said putative modulator stimulates TLR-4 directed signaling of TNF secretion.

15. The method of claim 1, wherein said putative modulator to be screened is obtained from a library of synthetic chemicals.

16. The method of claim 1, wherein said putative modulator to be screened is obtained from a natural source.

17. The method of claim 16, wherein said natural source is selected from the group consisting of animals, bacteria, fungi, plant sources, and living marine samples.

18. The method of claim 1, wherein said putative modulator to be screened is a protein or peptide.

19. The method of claim 1, wherein said putative modulator to be screened is a nucleic acid molecule.

20. The method of claim 1, wherein said putative modulator to be screened is a stimulator of an immune response.

21. The method of claim 20, wherein said stimulator of an immune response is a cytokine.

22. The method of claim 20, wherein said stimulator of an immune response is an interferon.

23. The method of claim 1, wherein said putative modulator to be screened is an IL-1 receptor antagonist.

24. The method of claim 1, wherein said putative modulator to be screened is a small molecule.

25. The method of claim 24, wherein said small molecule inhibits TLR-4 mediation of the lipopolysaccharide mediated response.

26. The method of claim 24, wherein said small molecule inhibits the lipopolysaccharide mediated response.

* * * * *

UNITED STATES PATENT AND TRADEMARK OFFICE

CERTIFICATE OF CORRECTION

PATENT NO. : 7,029,861 B1
APPLICATION NO. : 09/396985
DATED : April 18, 2006
INVENTOR(S) : Beutler et al.

It is certified that error appears in the above-identified patent and that said Letters Patent is hereby corrected as shown below:

The drawing sheets, consisting of Figs. 1-22, should be deleted to be replaced with the drawing sheets, consisting of Figs. 1-22 as shown on the attached pages.

Signed and Sealed this

Seventh Day of December, 2010

David J. Kappos
*Director of the United States Patent and Trademark Office*

```
         1                                                 50
jtoll    MMPPWLLART LIMAL.FFSC LTPGSLNPCI EVVPNITYQC MDQKLSKVPD
ntoll    MMPPWLLART LIMAL.FFSC LTPGSLNPCI EVVPNITYQC MDQKLSKVPD
rattlr4  MMPLLHLAGT LIMAL.FLSC LRPGSLNPCI EVLPNITYQC MDQKLSKIPH
humtlr4  MMSASRLAGT LIPAMAFLSC VRPESWEPCV EVVPNITYQC MELNFYKIPD
         51                                               100
jtoll    DTPSSTKNID LSFNPLKILK SYSFSNFSEL QWLDLSRCEI ETIEDKAWHG
ntoll    DTPSSTKNID LSFNPLKILK SYSFSNFSEL QWLDLSRCEI ETIEDKAWHG
rattlr4  DIPYSTKNLD LSFNPLKILR SYSFTNFSQL QWLDLSRCEI ETIEDKAWHG
humtlr4  NLPFSTKNLD LSFNPLRHLG SYSFFSFPEL QVLDLSRCEI QTIEDGAYQS
         101                                              150
jtoll    LHHLSNLILT GNPIQSFSPG SFSGLTSLEN LVAVETKLAS LESFPIGQLI
ntoll    LHHLSNLILT GNPIQSFSPG SFSGLTSLEN LVAVETKLAS LESFPIGQLI
rattlr4  LNQLSTLVLT GNPIKSFSPG SFSGLTNLEN LVAVETKMTS LEGFHIGQLI
humtlr4  LSHLSNLILT GNPIQSLALG AFSGLSSLQK LVAVETNLAS LENFPIGQLI
         151                                              200
jtoll    TLKKLNVAHN FIGSCKLPAY FSNLTNLVHV DLSYNYIQTI TVNDLQFLRE
ntoll    TLKKLNVAHN FIGSCKLPAY FSNLTNLVHV DLSYNYIQTI TVNDLQFLRE
rattlr4  SLKKLNVAHN LIHSFKLPEY FSNLTNLEHV DLSYNYIQTI SVKDLQFLRE
humtlr4  TLKELNVAHN LIQSFKLPEY FSNLTNLEHL DLSSNKIQSI YCTDLRVLHQ
         201                                              250
jtoll    NPQVNLSLDM SLNPIDFIQD QAFQGIKLHE LTLRGNFNSS NIMKTCLQNL
ntoll    NPQVNLSLDM SLNPIDFIQD QAFQGIKLHE LTLRGNFNSS NIMKTCLQNL
rattlr4  NPQVNLSLDL SLNPIDSIQA QAFQGIRLHE LTLRSNFNSS NVLKMCLQNM
humtlr4  MPLLNLSLDL SLNPMNFIQP GAFKEIRLHE LTLRNNFDSL NVMKTCIQGL
         251                                              300
jtoll    AGLHVHRLIL GEFKDERNLE IFEPSIMEGL CDVTIDEFRL TYTNDFSDDI
ntoll    AGLHVHRLIL GEFKDERNLE IFEPSIMEGL CDVTIDEFRL TYTNDFSDDI
rattlr4  TGLHVHRLIL GEFKNERNLE SFDRSVMEGL CNVSIDEFRL TYINHFSDDI
humtlr4  AGLEVHRLVL GEFRNEGNLE KFDKSALEGL CNTLIEEFRL AYLDYYSDDI
         301                                              350
jtoll    VK.FHCLANV SAMSLAGVSI KYLEDVPKHF KWQSLSIIRC QLKQFPTLDL
ntoll    VK.FHCLANV SAMSLAGVSI KYLEDVPKHF KWQSLSIIRC QLKQFPTLDL
rattlr4  YN.LNCLANI SAMSFTGVHI KHIADVPKHF KWQSLSIIRC HLKPFPKLSL
humtlr4  IDLFNCLTNV SSFSLVSVTI ERVKDFSYNF GWQHLELVNC KFGQFPTLKL
         351                                              400
jtoll    PFLKSLTLTM NKGSISFKKV ALPSLSYLDL SRNALSFSGC CSYSDLGTNS
ntoll    PFLKSLTLTM NKGSISFKKV ALPSLSYLDL SRNALSFSGC CSYSDLGTNS
rattlr4  PLFKSWTLTT NREDISFGQL ALPSLRYLDL SRNAMSFRGC CSYSDFGTNN
humtlr4  KSLKRLTFTS NKGGNAFSEV DLPSLEFLDL SRNGLSFKGC CSQSDFGTTS
         401                                              450
jtoll    LRHLDLSFNG AIIMSANFMG LEELQHLDFQ HSTLKRVTEF SAFLSLEKLL
ntoll    LRHLDLSFNG AIIMSANFMG LEELQHLDFQ HSTLKRVTEF SAFLSLEKLL
rattlr4  LKYLDLSFNG VILMSANFMG LEELEYLDFQ HSTLKKVTEF SVFLSLEKLL
humtlr4  LKYLDLSFNG VITMSSNFLG LEQLEHLDFQ HSNLKQMSEF SVFLSLRNLI
```

*FIG. 7A*

```
         451                                                    500
   jtoll YLDISYTNTK IDFDGIFLGL TSLNTLKMAG NSFKDNTLSN VFANTTNLTF
   ntoll YLDISYTNTK IDFDGIFLGL TSLNTLKMAG NSFKDNTLSN VFANTTNLTF
rattlr4  YLDISYTNTK IDFDGIFLGL ISLNTLKMAG NSFKDNTLSN VFTNTTNLTF
humtlr4  YLDISHTHTR VAFNGIFLGL SSLEVLKMAG NSFQENFLPD IFTELRNLTF
         501                                                    550
   jtoll LDLSKCQLEQ ISWGVFDTLH RLQLLNMSHN NLLFLDSSHY NQLYSLSTLD
   ntoll LDLSKCQLEQ ISWGVFDTLH RLQLLNMSHN NLLFLDSSHY NQLYSLSTLD
rattlr4  LDLSKCQLEQ ISRGVFDTLY RLQLLNMSHN NLLFLDPSHY KQLYSLRTLD
humtlr4  LDLSQCQLEQ LSPTAFNSLS SLQVLNMSHN NFFSLDTFPY KCLNSLQVLD
         551                                                    600
   jtoll CSFNRIETS. KGILQHFPKS LAFENLTNNS VACICEHQKF LQWVKEQKQF
   ntoll CSFNRIETS. KGILQHFPKS LAFENLTNNS VACICEHQKF LQWVKEQKQF
rattlr4  CSFNRIETS. KGILQHFPKS LAVFNLTNNS VACICEYQNF LQWVKDQKMF
humtlr4  CSFNRIETS. KQELQHFPKS LAFLNLTQND FACTCEHQSF LQWIKDQRQL
         601                                                    650
   jtoll LVNVEQMTCA TPVEMNTSLV LDFNNSTCYM YKTIISVSVV SVIVVSTVAF
   ntoll LVNVEQMTCA TPVEMNTSLV LDFNNSTCYM YKTIISVSVV SVIVVSTVAF
rattlr4  LVNVEQMKCA SPIDMKASLV LDFTNSTCYI YKTIISVSVV SVLVVATVAF
humtlr4  LVEVERMECA TPSDKQGMPV LSL.NITCQM NKTIIGVSVL SVLVVSVVAV
         651                                                    700
   jtoll LIYHFYFHLI LIAGCKKYSR GESIYDAFVI YSSQNEDWVR NELVKNLEEG
   ntoll LIYHFYFHLI LIAGCKKYSR GESIYDAFVI YSSQNEDWVR NELVKNLEEG
rattlr4  LIYHFYFHLI LIAGCKKYSR GESIYDAFVI YSSQNEDWVR NELVKNLEEG
humtlr4  LVYKFYFHLM LLAGCIKYGR GENIYDAFVI YSSQDEDWVR NELVKNLEEG
         701                                                    750
   jtoll VPRFHLCLHY RDFIHGVAIA ANTIQEGFHK SRKVIVVVSR HFIQSRWCIF
   ntoll VPRFHLCLHY RDFIHGVAIA ANTIQEGFHK SRKVIVVVSR HFIQSRWCIF
rattlr4  VPRFQLCLHY RDFIPGVAIA ANTIQEGFHK SRKVIVVVSR HFIQSRWCIF
humtlr4  VPPFQLCLHY RDFIPGVAIA ANTIHEGFHK SRKVIVVVSQ HFIQSRWCIF
         751                                                    800
   jtoll EYEIAQTWQF LSSRSGIIFI VLEKVEKSLL RQQVELYRLL SRNTYLEWED
   ntoll EYEIAQTWQF LSSRSGIIFI VLEKVEKSLL RQQVELYRLL SRNTYLEWED
rattlr4  EYEIAQTWQF LSSRSGIIFI VLEKVEKSLL RQQVELYRLL SRNTYLEWED
humtlr4  EYEIAQTWQF LSSRAGIIFI VLQKVEKTLL RQQVELYRLL SRNTYLEWED
         801                                         840
   jtoll NPLGRHIFWR RLKNALLDGK ASNPEQTAEE EQETATWT~~
   ntoll NPLGRHIFWR RLKNALLDGK ASNPEQTAEE EQETATWT~~
rattlr4  NALGRHIFWR RLKKALLDGK ALNPDETSEE EQEATTLT~~
humtlr4  SVLGRHIFWR RLRKALLDGK SWNPEGTVGT GCNWQEATSI
```

Fig 7b